(12) United States Patent
Katagiri et al.

(10) Patent No.: US 11,447,554 B2
(45) Date of Patent: *Sep. 20, 2022

(54) ANTI-ALK2 ANTIBODY

(71) Applicants: Saitama Medical University, Saitama (JP); Daiichi Sankyo Company, Limited, Tokyo (JP)

(72) Inventors: Takenobu Katagiri, Saitama (JP); Kenji Osawa, Saitama (JP); Sho Tsukamoto, Saitama (JP); Shinnosuke Tsuji, Tokyo (JP); Yoshirou Kawaguchi, Tokyo (JP); Kensuke Nakamura, Tokyo (JP)

(73) Assignees: Saitama Medical University, Saitama (JP); Daiichi Sankyo Company, Limited, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/511,357

(22) Filed: Oct. 26, 2021

(65) Prior Publication Data

US 2022/0041738 A1 Feb. 10, 2022

Related U.S. Application Data

(62) Division of application No. 16/543,991, filed on Aug. 19, 2019, which is a division of application No. 15/547,231, filed as application No. PCT/JP2016/052602 on Jan. 29, 2016, now Pat. No. 10,428,148.

(30) Foreign Application Priority Data

Jan. 30, 2015 (JP) .................. 2015-017882

(51) Int. Cl.
| | |
|---|---|
| *A61K 39/395* | (2006.01) |
| *A61K 39/00* | (2006.01) |
| *C07K 16/28* | (2006.01) |
| *A61P 7/06* | (2006.01) |
| *A61P 19/08* | (2006.01) |
| *A61P 35/00* | (2006.01) |
| *A61K 45/06* | (2006.01) |

(52) U.S. Cl.
CPC ...... *C07K 16/2863* (2013.01); *A61K 39/3955* (2013.01); *A61K 45/06* (2013.01); *A61P 7/06* (2018.01); *A61P 19/08* (2018.01); *A61P 35/00* (2018.01); *A61K 2039/505* (2013.01); *C07K 2317/21* (2013.01); *C07K 2317/24* (2013.01); *C07K 2317/31* (2013.01); *C07K 2317/54* (2013.01); *C07K 2317/55* (2013.01); *C07K 2317/56* (2013.01); *C07K 2317/565* (2013.01); *C07K 2317/622* (2013.01); *C07K 2317/71* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 9,334,331 B2 | 5/2016 | Igawa et al. | |
| 10,421,807 B2 | 9/2019 | Gonzales et al. | |
| 10,428,148 B2 * | 10/2019 | Katagiri ............ | C07K 16/2863 |
| 2012/0164159 A1 | 6/2012 | Dellacasagrande | |
| 2013/0129739 A1 | 5/2013 | Ottto et al. | |

FOREIGN PATENT DOCUMENTS

| | | |
|---|---|---|
| JP | 2012-531922 A | 12/2012 |
| JP | 2013-513361 A | 4/2013 |
| WO | WO 2007/123896 A2 | 11/2007 |
| WO | WO 2008/030611 A2 | 3/2008 |
| WO | WO-2011/112671 A2 | 9/2011 |
| WO | WO 2014/051109 A1 | 4/2014 |
| WO | WO 2014/078306 A1 | 5/2014 |
| WO | WO 2019/172165 A1 | 9/2019 |

OTHER PUBLICATIONS

Al Qaraghuli et al. (2020, Nature Scientific Reports 10:13969).*
Casset et al. (Biochem Biophys Res Comm. 2003; 307:198-205).*
Vajdos et al. (J Mol Biol. 2002; 320(2):415-428).*
Holm et al. (Mol Immunol. 2007; 44(6):1075-1084).*
"Activin receptor type-1 A (ALK2) antibody. Datasheet sc-73676," Online catalogue of Santa Cruz Biotechnologies, Jan. 1, 2015, XP55477645, https://datasheets.scbt.com/sc-73676.pdf, retrieved on May 23, 2018.
"ACTR-I (C-5): sc-374523," Santa Cruz online catalogue, Jan. 1, 2014, 1 page.
"ACTR-I (N-a5): sc-5671," Santa Cruz online catalogue, Jan. 1, 2014, 1 page.
"Human Activin RIA/ALK2 antibody," R&D Systems online catalogue, Feb. 7, 2018, 1 page, XP55478125.
Al Qaraghuli et al., "Antibody-protein binding and conformational changes: identifying allosteric signalling pathways to engineer a better effector response," Nature Scientific Reports, 2020, 10:13969.
Casset et al., "A peptide mimetic of an anti-CD4 monoclonal antibody by rational design," Biochemical and Biophysical Research Communications, 2003, 307:198-205.
Chaikaud et al., "Structure of the Bone Morphogenetic Protein Receptor ALK2 and Implications for Fibrodysplasia Ossificans Progressiva," J. Biol. Chem., 2012, 287:36990-36998.

(Continued)

*Primary Examiner* — Elizabeth C. Kemmerer
(74) *Attorney, Agent, or Firm* — Foley & Lardner LLP

(57) ABSTRACT

This application provides: an antibody which specifically binds to an ALK2 protein and has an activity of inhibiting BMP signal transduction mediated by ALK2; a method for producing the antibody; and a pharmaceutical composition comprising the antibody, for treating and/or preventing ectopic ossification and/or bone dysplasia, anemia, or diffuse intrinsic pontine glioma (DIPG).

27 Claims, 53 Drawing Sheets

Specification includes a Sequence Listing.

(56) References Cited

OTHER PUBLICATIONS

Chen et al., "Selection and Analysis of an Optimized Anti-VEGF Antibody: Crystal Structure of an Affinity-matured Fab in Complex with Antigen," J. Mol. Biol., 1999, 293:865-881.

Da Silveira et al., "Regulation of ACVR1 and ID2 by cell-secreted exosomes during follicle maturation in the mare," Reproductive Biology and Endocrinology, May 26, 2014, 12(1):44, 1-9.

Edwards et al., "The Remarkable Flexibility of the Human Antibody Repertoire; Isolation of Over One Thousand Different Antibodies to a Single Protein, BLyS", J. Mol. Biol., Sep. 24, 2003, 334(1):103-118.

Fukuda et al., "Constitutively Activated ALK2 and Increased SMAD1/5 Cooperatively Induce Bone Morphogenetic Protein Signaling in Fibrodysplasia Ossificans Progressiva," J. Biol. Chem., 2009, 284:7149-7156.

Goel et al., "Plasticity within the Antigen-Combining Site May Manifest as Molecular Mimicry in the Humoral Immune Response," 2004, 173:7358-7367.

Hatsell et al., "ACVR1R206H receptor mutation causes fibrodysplasia ossificans progressiva by imparting responsiveness to activin A," Science Translational Medicine, Sep. 2, 2015, 7(303):303ra137, 13 pages.

Holm et al., "Functional mapping and single chain construction of the anti-cytokeratin 8 monoclonal antibody TS1," Molecular Immunology, 2007, 44:1075-1084.

International Search Report dated Apr. 12, 2016, in PCT/JP2016/052602.

Kaplan et al., "From mysteries to medicines: drug development for fibrodysplasia ossificans progressiva," Expert Opinion on Orphan Drugs, Jul. 25, 2013, 1(8):637-649.

Kaplan et al., "When one skeleton is enough: approaches and strategies for the treatment of fibrodysplasia ossificans progressiva (FOP)," Drug Discov. Today Ther. Strateg., 2008, 5(4):255-262.

Katagiri et al., "The unique activity of bone morphogenetic proteins in bone: a critical role of the Smad signaling pathway," Biol. Chem., 2013, 394(6)703-714.

Katagiri, Takenobu, "Heterotopic Bone Formation Induced by Bone Morphogenetic Protein Signaling: Fibrodysplasia Ossificans Progressiva," J. Oral Biosci., 2010, 52(1):33-41.

Katagiri, Takenobu, "Recent topics in fibrodysplasia ossificans progressive," Journal of Oral Biosciences, 2012, 54:119-123.

Khan et al., "Adjustable Locks and Flexible keys: Plasticity of Epitope-Paratope Interactions in Germline Antibodies," J. Immunology, 2014, 192:5398-5405.

Lai et al., "Activin Receptor-like Kinase 2 Can Mediate Atrioventricular Cushion Transformation," Developmental Biology, Jun. 2000, 222:1-11.

Lloyd et al., "Modelling the human immune response: performance of a 10″ human antibody repertoire against a broad panel of therapeutically relevant antigens", Protein Engineering, Design & Selection, 2009, 22(3):159-168.

MacCallum et al., "Antibody-antigen Interactions: Contact Analysis and Binding Site Topography," J. Mol. Biol., 1996, 262:732-745.

Office Action dated Feb. 10, 2020, in EP 16743511.4.

Office Action dated Jun. 26, 2018, in CA 2,975,376.

Paul, William E., M.D., Fundamental Immunology, 3rd Ed., Raven Press, New York, Chapter 8, 1993, 292-295.

Poorsarla et al., "Computational De Novo Design of Antibodies Binding to a Peptide with High Affinity," Biotechn. Bioeng., 2017, 114(6):1331-1342.

Sakabe et al., "ROCK1 expression is regulated by TGFbeta3 and ALK2 during valvuloseptal endocardial cushion formation," Anat. Rec. (Hoboken), Jul. 2008, 291(7):845-857, Abstract.

Shore et al. "A recurrent mutation in the BMP type I receptor ACVR1 causes inherited and sporadic fibrodysplasia ossificans progressive," Nature Genetics, May 2006, 38(5):525-527.

Supplementary European Search Report dated Jun. 12, 2018, in EP 16743511.4.

Vajdos et al., "Comprehensive Functional Maps of the Antigen-binding Site of an Anti-ErbB2 Antibody Obtained with Shotgun Scanning Mutagenesis," J. Mol. Biol., 2002, 320:415-428.

Xu et al., "BMP7 Signaling via BMPR1 A, BMPR1B Inhibits the Proliferation of Lung Large Carcinoma NCI-H460 Cell," Chin. J. Lung Cancer, Jul. 1, 2010, 659-664, XP55664709.

Office Action dated Aug. 26, 2021 in TW 109125515.

Arduin et al., "Highly reduced binding to high and low affinity mouse Fc gamma receptors by L234A/L235A and N297A Fc mutations engineered into mouse IgG2a," Molecular Immunology, Feb. 1, 2015, 63(2):456-463.

Macias-Silva et al., "Specific Activation of Smad1 Signaling Pathways by the BMP7 Type 1 Receptor, ALK2," The Journal of Biological Chemistry, Oct. 2, 1998, 273(40):25628-25636.

Office Action dated May 11, 2022 in EP 16743511.4.

Shen et al., "Removal of a C-terminal serine residue proximal to the inter-chain disulfide bond of a human IgG1 lambda light chain mediates enhanced antibody stability and antibody dependent cell-mediated cytotoxicity," mAbs, May 1, 2013, 5(3):418-431.

* cited by examiner

FIG. 11

SEQ ID NO:59: Amino acid sequence of A2-15A CDRH1
GFTFSHYYMA

SEQ ID NO:60: Amino acid sequence of A2-15A CDRH2
SITNSGGSINYRDSVKG

SEQ ID NO: 61: Amino acid sequence of A2-15A CDRH3
EGGENYGGYPPFAY

SEQ ID NO:62: Amino acid sequence of A2-15A CDRL1
RANQGVSLSRYNLMH

SEQ ID NO:63: Amino acid sequence of A2-15A CDRL2
RSSNLAS

SEQ ID NO:64: Amino acid sequence of A2-15A CDRL3
QQSRESPFT

SEQ ID NO:71: Amino acid sequence of humanized hA2-15A-L6 CDRL2
RSSNLAQ

FIG. 12

SEQ ID NO:65: Amino acid sequence of A2-27D CDRH1
GSTFSNYGMK

SEQ ID NO:66: Amino acid sequence of A2-27D CDRH2
SISRSSTYIYYADTVKG

SEQ ID NO:67: Amino acid sequence of A2-27D CDRH3
AISTPFYWYFDF

SEQ ID NO:68: Amino acid sequence of A2-27D CDRL1
LASSSVSYMT

SEQ ID NO:69: Amino acid sequence of A2-27D CDRL2
GTSNLAS

SEQ ID NO:70: Amino acid sequence of A2-27D CDRL3
LHLTSYPPYT

FIG. 13

SEQ ID NO:72: Amino acid sequence of A2-11E CDRH1
GFTFSNYYMY

SEQ ID NO:73: Amino acid sequence of A2-11E CDRH2
SINTDGGSTYYPDSVKG

SEQ ID NO:74: Amino acid sequence of A2-11E CDRH3
STPNIPLAY

SEQ ID NO:75: Amino acid sequence of A2-11E CDRL1
KASQNIYKYLN

SEQ ID NO:76: Amino acid sequence of A2-11E CDRL2
YSNSLQT

SEQ ID NO:77: Amino acid sequence of A2-11E CDRL3
FQYSSGPT

FIG. 14

SEQ ID NO:78: Amino acid sequence of A2-25C CDRH1
GFTFSYYAMS

SEQ ID NO:79: Amino acid sequence of A2-25C CDRH2
SISRGGDNTYYRDTVKG

SEQ ID NO:80: Amino acid sequence of A2-25C CDRH3
LNYNNYFDY

SEQ ID NO:81: Amino acid sequence of A2-25C CDRL1
QASQDIGNWLS

SEQ ID NO:82: Amino acid sequence of A2-25C CDRL2
GATSLAD

SEQ ID NO:83: Amino acid sequence of A2-25C CDRL3
LQAYSAPFT

FIG. 15

SEQ ID NO:27: Nucleotide sequence of humanized hA2-15A-H1
ATGAAACACCTGTGGTTCTTCCTCCTGCTGGTGGCAGCTCCCAGATGGGTGCTGAGCGAAGTGCAGCTGGTGG
AATCTGGCGGCGGACTGGTGCAGCCTGGCGGATCTCTGAGACTGAGCTGTGCCGCCAGCGGCTTCACCTTCAG
CCACTACTACATGGCCTGGGTGCGCCAGGCCCCTGGCAAAGGACTGGAATGGGTGGCCAGCATCACCAACAGC
GGCGGCAGCATCAACTACCGGGACAGCGTGAAGGGCCGGTTCACCATCAGCCGGGACAACAGCAAGAACACCC
TGTACCTGCAGATGAACAGCCTGCGGGCCGAGGACACCGCCGTGTACTATTGTGCCAGAGAGGGCGGCGAGAA
CTACGGCGGCTATCCCCCTTTTGCCTACTGGGGCCAGGGCACCCTCGTGACCGTCAGCTCAGCCTCCACCAAG
GGCCCAAGCGTCTTCCCCCTGGCACCCTCCTCCAAGAGCACCTCTGGCGGCACAGCCGCCCTGGGCTGCCTGG
TCAAGGACTACTTCCCCGAACCCGTGACCGTGAGCTGGAACTCAGGCGCCCTGACCAGCGGCGTGCACACCTT
CCCCGCTGTCCTGCAGTCCTCAGGACTCTACTCCCTCAGCAGCGTGGTGACCGTGCCCTCCAGCAGCTTGGGC
ACCCAGACCTACATCTGCAACGTGAATCACAAGCCCAGCAACACCAAGGTGGACAAGAGAGTTGAGCCCAAAT
CTTGTGACAAAACTCACACATGCCCACCCTGCCCAGCACCTGAACTCCTGGGGGGACCCTCAGTCTTCCTCTT
CCCCCCAAAACCCAAGGACACCCTCATGATCTCCCGGACCCCTGAGGTCACATGCGTGGTGGTGGACGTGAGC
CACGAAGACCCTGAGGTCAAGTTCAACTGGTACGTGGACGGCGTGGAGGTGCATAATGCCAAGACAAAGCCCC
GGGAGGAGCAGTACAACAGCACGTACCGGGTGGTCAGCGTCCTCACCGTCCTGCACCAGGACTGGCTGAATGG
CAAGGAGTACAAGTGCAAGGTCTCCAACAAAGCCCTCCCAGCCCCCATCGAGAAAACCATCTCCAAAGCCAAA
GGCCAGCCCCGGGAACCACAGGTGTACACCCTGCCCCCATCCCGGGAGGAGATGACCAAGAACCAGGTCAGCC
TGACCTGCCTGGTCAAAGGCTTCTATCCCAGCGACATCGCCGTGGAGTGGGAGAGCAATGGCCAGCCCGAGAA
CAACTACAAGACCACCCCTCCCGTGCTGGACTCCGACGGCTCCTTCTTCCTCTACAGCAAGCTCACCGTGGAC
AAGAGCAGGTGGCAGCAGGGCAACGTCTTCTCATGCTCCGTGATGCATGAGGCTCTGCACAACCACTACACCC
AGAAGAGCCTCTCCCTGTCTCCCGGCAAA
Signal sequence (1-57), Variable region (58-426), Constant region (427-1416)

SEQ ID NO:28: Amino acid sequence of humanized hA2-15A-H1
MKHLWFFLLLVAAPRWVLSEVQLVESGGGLVQPGGSLRLSCAASGFTFSHYYMAWVRQAPGKGLEWVASITNS
GGSINYRDSVKGRFTISRDNSKNTLYLQMNSLRAEDTAVYYCAREGGENYGGYPPFAYWGQGTLVTVSSASTK
GPSVFPLAPSSKSTSGGTAALGCLVKDYFPEPVTVSWNSGALTSGVHTFPAVLQSSGLYSLSSVVTVPSSSLG
TQTYICNVNHKPSNTKVDKRVEPKSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGKEYKCKVSNKALPAPIEKTISKAK
GQPREPQVYTLPPSREEMTKNQVSLTCLVKGFYPSDIAVEWESNGQPENNYKTTPPVLDSDGSFFLYSKLTVD
KSRWQQGNVFSCSVMHEALHNHYTQKSLSLSPGK
Signal sequence (1-19), Variable region (20-142), Constant region (143-472)

FIG. 16

SEQ ID NO:29: Nucleotide sequence of humanized hA2-15A-H4
ATGAAACACCTGTGGTTCTTCCTCCTGCTGGTGGCAGCTCCCAGATGGGTGCTGAGCGAAGTGCAGCTGGTGG
AATCTGGCGGCGGACTGGTGCAGCCTGGCGGATCTCTGAGACTGAGCTGTGCCGCCAGCGGCTTCACCTTCAG
CCACTACTACATGGCCTGGGTGCGCCAGGCCCCTGGCAAAGGACTGGAATGGGTGGCCAGCATCACCAACAGC
GGCGGCAGCATCAACTACCGGGACAGCGTGAAGGGCCGGTTCACCATCAGCCGGGACAACGCCAAGAGCACCC
TGTACCTGCAGATGAACAGCCTGCGGGCCGAGGACACCGCCACCTACTACTGTACAAGAGAGGGCGGCGAGAA
CTACGGCGGCTACCCTCCTTTTGCCTACTGGGGCCAGGGCACCCTCGTGACCGTCAGCTCAGCCTCCACCAAG
GGCCCAAGCGTCTTCCCCCTGGCACCCTCCTCCAAGAGCACCTCTGGCGGCACAGCCGCCCTGGGCTGCCTGG
TCAAGGACTACTTCCCCGAACCCGTGACCGTGAGCTGGAACTCAGGCGCCCTGACCAGCGGCGTGCACACCTT
CCCCGCTGTCCTGCAGTCCTCAGGACTCTACTCCCTCAGCAGCGTGGTGACCGTGCCCTCCAGCAGCTTGGGC
ACCCAGACCTACATCTGCAACGTGAATCACAAGCCCAGCAACACCAAGGTGGACAAGAGAGTTGAGCCCAAAT
CTTGTGACAAAACTCACACATGCCCACCCTGCCCAGCACCTGAACTCCTGGGGGGACCCTCAGTCTTCCTCTT
CCCCCCAAAACCCAAGGACACCCTCATGATCTCCCGGACCCCTGAGGTCACATGCGTGGTGGTGGACGTGAGC
CACGAAGACCCTGAGGTCAAGTTCAACTGGTACGTGGACGGCGTGGAGGTGCATAATGCCAAGACAAAGCCCC
GGGAGGAGCAGTACAACAGCACGTACCGGGTGGTCAGCGTCCTCACCGTCCTGCACCAGGACTGGCTGAATGG
CAAGGAGTACAAGTGCAAGGTCTCCAACAAAGCCCTCCCAGCCCCCATCGAGAAAACCATCTCCAAAGCCAAA
GGCCAGCCCCGGGAACCACAGGTGTACACCCTGCCCCCATCCCGGGAGGAGATGACCAAGAACCAGGTCAGCC
TGACCTGCCTGGTCAAAGGCTTCTATCCCAGCGACATCGCCGTGGAGTGGGAGAGCAATGGCCAGCCCGAGAA
CAACTACAAGACCACCCCTCCCGTGCTGGACTCCGACGGCTCCTTCTTCCTCTACAGCAAGCTCACCGTGGAC
AAGAGCAGGTGGCAGCAGGGCAACGTCTTCTCATGCTCCGTGATGCATGAGGCTCTGCACAACCACTACACCC
AGAAGAGCCTCTCCCTGTCTCCCGGCAAA
Signal sequence (1-57), Variable region (58-426), Constant region (427-1416)

SEQ ID NO:30: Amino acid sequence of humanized hA2-15A-H4
MKHLWFFLLLVAAPRWVLSEVQLVESGGGLVQPGGSLRLSCAASGFTFSHYYMAWVRQAPGKGLEWVASITNS
GGSINYRDSVKGRFTISRDNAKSTLYLQMNSLRAEDTATYYCTREGGENYGGYPPFAYWGQGTLVTVSSASTK
GPSVFPLAPSSKSTSGGTAALGCLVKDYFPEPVTVSWNSGALTSGVHTFPAVLQSSGLYSLSSVVTVPSSSLG
TQTYICNVNHKPSNTKVDKRVEPKSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGKEYKCKVSNKALPAPIEKTISKAK
GQPREPQVYTLPPSREEMTKNQVSLTCLVKGFYPSDIAVEWESNGQPENNYKTTPPVLDSDGSFFLYSKLTVD
KSRWQQGNVFSCSVMHEALHNHYTQKSLSLSPGK
Signal sequence (1-19), Variable region (20-142), Constant region (143-472)

FIG. 17

SEQ ID NO:31: Nucleotide sequence of DNA fragment comprising sequences encoding humanized hA2-15A-L1
ccagcctccggactctagagccaccATGGTGCTGCAGACCCAGGTGTTCATCAGCCTGCTGCTGTGGATCAGC
GGCGCCTACGGCGACATCGTGATGACCCAGAGCCCTGACAGCCTGGCCGTGTCTCTGGGAGAGAGGGCCACCA
TCAACTGCAGAGCCAACCAGGGCGTGTCCCTGAGCCGGTACAACCTGATGCACTGGTATCAGCAGAAGCCCGG
CCAGCCCCCCAAGCTGCTGATCTACAGAAGCTCCAACCTGGCCAGCGGCGTGCCCGATAGATTTTCTGGCAGC
GGCTCCGGCACCGACTTCACCCTGACAATCAGCTCCCTGCAGGCCGAGGACGTGGCCGTGTACTACTGCCAGC
AGAGCAGAGAGAGCCCCTTCACCTTTGGCCAGGGCACCAAGGTGGAAATCAAGCGGGCTGTGGCCGCTCCCTC
CGTGTTCATCTTTCCACCCAGCGACGAGCAGCTGAAGTCTGGCACAGCCAGCGTCGTGTGCCTGCTGAACAAC
TTCTACCCCCGCGAGGCCAAGGTGCAGTGGAAGGTGGACAATGCCCTGCAGAGCGGCAACTCCCAGGAAAGCG
TGACCGAGCAGGACAGCAAGGACTCCACCTACAGCCTGAGCAGCACCCTGACCCTGAGCAAGGCCGACTACGA
GAAGCACAAGGTGTACGCCTGCGAAGTGACCCACCAGGGCCTGTCTAGCCCCGTGACCAAGAGCTTCAACCGG
GGCGAGTGTtgagttttaaacgggggaggctaact
Signal sequence (26-85), Variable region (86-424), Constant region (425-739)

SEQ ID NO:32: Amino acid sequence of humanized hA2-15A-L1
MVLQTQVFISLLLWISGAYGDIVMTQSPDSLAVSLGERATINCRANQGVSLSRYNLMHWYQQKPGQPPKLLIY
RSSNLASGVPDRFSGSGSGTDFTLTISSLQAEDVAVYYCQQSRESPFTFGQGTKVEIKRAVAAPSVFIFPPSD
EQLKSGTASVVCLLNNFYPREAKVQWKVDNALQSGNSQESVTEQDSKDSTYSLSSTLTLSKADYEKHKVYACE
VTHQGLSSPVTKSFNRGEC
Signal sequence (1-20), Variable region (21-133), Constant region (134-238)

FIG. 18

SEQ ID NO:33: Nucleotide sequence of DNA fragment comprising sequences encoding humanized hA2-15A-L4
ccagcctccggactctagagccaccATGGTGCTGCAGACCCAGGTGTTCATCAGCCTGCTGCTGTGGATCAGC
GGCGCCTACGGCGATATCGTGCTGACCCAGAGCCCTGACAGCCTGGCCGTGTCTCTGGGAGAGAGGGCCACCA
TCAACTGCAGAGCCAACCAGGGCGTGTCCCTGAGCCGGTACAACCTGATGCACTGGTATCAGCAGAAGCCCGG
CCAGAAGCCCAAGCTGCTGATCTACCGGTCCAGCAACCTGGCCTCTGGCATCCCCGCCAGATTTTCTGGCAGC
GGCTCCGGCACCGACTTCACCCTGACAATCAGCAGCGTGCAGGCCGACGACATTGCCGTGTACTACTGCCAGC
AGAGCAGAGAGAGCCCCTTCACCTTTGGCCAGGGCACCAAGCTGGAACTGAAGAGAGCCGTGGCCGCTCCCTC
CGTGTTCATCTTCCCACCTAGCGACGAGCAGCTGAAGTCTGGCACAGCCAGCGTCGTGTGCCTGCTGAACAAC
TTCTACCCCCGCGAGGCCAAGGTGCAGTGGAAGGTGGACAATGCCCTGCAGAGCGGCAACAGCCAGGAAAGCG
TGACCGAGCAGGACAGCAAGGACTCCACCTACAGCCTGAGCAGCACCCTGACCCTGAGCAAGGCCGACTACGA
GAAGCACAAGGTGTACGCCTGCGAAGTGACCCACCAGGGCCTGTCTAGCCCCGTGACCAAGAGCTTCAACCGG
GGCGAGTGTtgagtttaaacgggggaggctaact
Signal sequence (26-85), Variable region (86-424), Constant region (425-739)

SEQ ID NO:34: Amino acid sequence of humanized hA2-15A-L4
MVLQTQVFISLLLWISGAYGDIVLTQSPDSLAVSLGERATINCRANQGVSLSRYNLMHWYQQKPGQKPKLLIY
RSSNLASGIPARFSGSGSGTDFTLTISSVQADDIAVYYCQQSRESPFTFGQGTKLELKRAVAAPSVFIFPPSD
EQLKSGTASVVCLLNNFYPREAKVQWKVDNALQSGNSQESVTEQDSKDSTYSLSSTLTLSKADYEKHKVYACE
VTHQGLSSPVTKSFNRGEC
Signal sequence (1-20), Variable region (21-133), Constant region (134-238)

FIG. 19

SEQ ID NO:35: Nucleotide sequence of DNA fragment comprising sequences encoding humanized hA2-15A-L6
ccagcctccggactctagagccaccATGGTGCTGCAGACCCAGGTGTTCATCAGCCTGCTGCTGTGGATCAGC
GGCGCCTACGGCGATATCGTGCTGACCCAGAGCCCTGACAGCCTGGCCGTGTCTCTGGGAGAGAGGGCCACCA
TCAACTGCAGAGCCAACCAGGGCGTGTCCCTGAGCCGGTACAACCTGATGCACTGGTATCAGCAGAAGCCCGG
CCAGAAGCCCAAGCTGCTGATCTACCGGTCCAGCAACCTGGCCCAGGGCATCCCTGCCAGATTTTCTGGCAGC
GGCTCCGGCACCGACTTCACCCTGACAATCAGCAGCGTGCAGGCCGACGACATTGCCGTGTACTACTGCCAGC
AGAGCAGAGAGAGCCCCTTCACCTTTGGCCAGGGCACCAAGCTGGAACTGAAGAGAGCCGTGGCCGCTCCCTC
CGTGTTCATCTTCCCACCTAGCGACGAGCAGCTGAAGTCTGGCACAGCCAGCGTCGTGTGCCTGCTGAACAAC
TTCTACCCCCGCGAGGCCAAGGTGCAGTGGAAGGTGGACAATGCCCTGCAGAGCGGCAACAGCCAGGAAAGCG
TGACCGAGCAGGACAGCAAGGACTCCACCTACAGCCTGAGCAGCACCCTGACCCTGAGCAAGGCCGACTACGA
GAAGCACAAGGTGTACGCCTGCGAAGTGACCCACCAGGGCCTGTCTAGCCCCGTGACCAAGAGCTTCAACCGG
GGCGAGTGTtgagtttaaacggggggaggctaact
Signal sequence (26-85), Variable region (86-424), Constant region (425-739)

SEQ ID NO:36: Amino acid sequence of humanized hA2-15A-L6
MVLQTQVFISLLLWISGAYGDIVLTQSPDSLAVSLGERATINCRANQGVSLSRYNLMHWYQQKPGQKPKLLIY
RSSNLAQGIPARFSGSGSGTDFTLTISSVQADDIAVYYCQQSRESPFTFGQGTKLELKRAVAAPSVFIFPPSD
EQLKSGTASVVCLLNNFYPREAKVQWKVDNALQSGNSQESVTEQDSKDSTYSLSSTLTLSKADYEKHKVYACE
VTHQGLSSPVTKSFNRGEC
Signal sequence (1-20), Variable region (21-133), Constant region (134-238)

FIG. 20

SEQ ID NO:37: Nucleotide sequence of DNA fragment comprising sequences encoding humanized hA2-15A-L7
ccagcctccggactctagagccaccATGGTGCTGCAGACCCAGGTGTTCATCAGCCTGCTGCTGTGGATCAGC
GGCGCCTACGGCGATATCGTGCTGACCCAGAGCCCTGACAGCCTGGCCGTGTCTCTGGGAGAGAGGGCCACCA
TCAACTGCAGAGCCAACCAGGGCGTGTCCCTGAGCCGGTACAACCTGATGCACTGGTATCAGCAGAAGCCCGG
CCAGAAGCCCAAGCTGGCCATCTACAGAAGCAGCAACCTGGCCAGCGGCATCCCCGCCAGATTTTCTGGCAGC
GGCTCCGGCACCGACTTCACCCTGACAATCAGCAGCGTGCAGGCCGACGACATTGCCGTGTACTACTGCCAGC
AGAGCAGAGAGAGCCCCTTCACCTTTGGCCAGGGCACCAAGCTGGAACTGAAGAGAGCCGTGGCCGCTCCCTC
CGTGTTCATCTTCCCACCTAGCGACGAGCAGCTGAAGTCTGGCACAGCCAGCGTCGTGTGCCTGCTGAACAAC
TTCTACCCCCGCGAGGCCAAGGTGCAGTGGAAGGTGGACAATGCCCTGCAGAGCGGCAACAGCCAGGAAAGCG
TGACCGAGCAGGACAGCAAGGACTCCACCTACAGCCTGAGCAGCACCCTGACCCTGAGCAAGGCCGACTACGA
GAAGCACAAGGTGTACGCCTGCGAAGTGACCCACCAGGGCCTGTCTAGCCCCGTGACCAAGAGCTTCAACCGG
GGCGAGTGTtgagtttaaacggggaggctaact
Signal sequence (26-85), Variable region (86-424), Constant region (425-739)

SEQ ID NO:38: Amino acid sequence of humanized hA2-15A-L7
MVLQTQVFISLLLWISGAYGDIVLTQSPDSLAVSLGERATINCRANQGVSLSRYNLMHWYQQKPGQKPKLAIY
RSSNLASGIPARFSGSGSGTDFTLTISSVQADDIAVYYCQQSRESPFTFGQGTKLELKRAVAAPSVFIFPPSD
EQLKSGTASVVCLLNNFYPREAKVQWKVDNALQSGNSQESVTEQDSKDSTYSLSSTLTLSKADYEKHKVYACE
VTHQGLSSPVTKSFNRGEC
Signal sequence (1-20), Variable region (21-133), Constant region (134-238)

FIG. 21

SEQ ID NO:39: Nucleotide sequence of humanized hA2-27D-H1
ATGAAACACCTGTGGTTCTTCCTCCTGCTGGTGGCAGCTCCCAGATGGGTGCTGAGCGAAGTGCAGCTGGTGG
AATCTGGCGGCGGACTGGTGCAGCCTGGCGGATCTCTGAGACTGAGCTGTGCCGCCAGCGGCAGCACCTTCAG
CAACTACGGCATGAAATGGGTGCGCCAGGCCCCTGGCAAGGGACTGGAATGGGTGTCCAGCATCAGCAGAAGC
AGCACCTACATCTACTACGCCGACACCGTGAAGGGCCGGTTCACCATCAGCCGGGACAACAGCAAGAACACCC
TGTACCTGCAGATGAACAGCCTGCGGGCCGAGGACACCGCCGTGTACTATTGTGCCAGAGCCATCAGCACCCC
CTTCTACTGGTACTTCGACTTCTGGGGCCAGGGCACCCTCGTGACCGTCAGCTCAGCCTCCACCAAGGGCCCA
AGCGTCTTCCCCCTGGCACCCTCCTCCAAGAGCACCTCTGGCGGCACAGCCGCCCTGGGCTGCCTGGTCAAGG
ACTACTTCCCCGAACCCGTGACCGTGAGCTGGAACTCAGGCGCCCTGACCAGCGGCGTGCACACCTTCCCCGC
TGTCCTGCAGTCCTCAGGACTCTACTCCCTCAGCAGCGTGGTGACCGTGCCCTCCAGCAGCTTGGGCACCCAG
ACCTACATCTGCAACGTGAATCACAAGCCCAGCAACACCAAGGTGGACAAGAGAGTTGAGCCCAAATCTTGTG
ACAAAACTCACACATGCCCACCCTGCCCAGCACCTGAACTCCTGGGGGGACCCTCAGTCTTCCTCTTCCCCCC
AAAACCCAAGGACACCCTCATGATCTCCCGGACCCCTGAGGTCACATGCGTGGTGGTGGACGTGAGCCACGAA
GACCCTGAGGTCAAGTTCAACTGGTACGTGGACGGCGTGGAGGTGCATAATGCCAAGACAAAGCCCCGGGAGG
AGCAGTACAACAGCACGTACCGGGTGGTCAGCGTCCTCACCGTCCTGCACCAGGACTGGCTGAATGGCAAGGA
GTACAAGTGCAAGGTCTCCAACAAAGCCCTCCCAGCCCCCATCGAGAAAACCATCTCCAAAGCCAAAGGCCAG
CCCCGGGAACCACAGGTGTACACCCTGCCCCCATCCCGGGAGGAGATGACCAAGAACCAGGTCAGCCTGACCT
GCCTGGTCAAAGGCTTCTATCCCAGCGACATCGCCGTGGAGTGGGAGAGCAATGGCCAGCCCGAGAACAACTA
CAAGACCACCCCTCCCGTGCTGGACTCCGACGGCTCCTTCTTCCTCTACAGCAAGCTCACCGTGGACAAGAGC
AGGTGGCAGCAGGGCAACGTCTTCTCATGCTCCGTGATGCATGAGGCTCTGCACAACCACTACACCCAGAAGA
GCCTCTCCCTGTCTCCCGGCAAA
Signal sequence (1-57), Variable region (58-420), Constant region (421-1410)

SEQ ID NO:40: Amino acid sequence of humanized hA2-27D-H1
MKHLWFFLLLVAAPRWVLSEVQLVESGGGLVQPGGSLRLSCAASGSTFSNYGMKWVRQAPGKGLEWVSSISRS
STYIYYADTVKGRFTISRDNSKNTLYLQMNSLRAEDTAVYYCARAISTPFYWYFDFWGQGTLVTVSSASTKGP
SVFPLAPSSKSTSGGTAALGCLVKDYFPEPVTVSWNSGALTSGVHTFPAVLQSSGLYSLSSVVTVPSSSLGTQ
TYICNVNHKPSNTKVDKRVEPKSCDKTHTCPPCPAPELLGGPSVFLFPPKPKDTLMISRTPEVTCVVVDVSHE
DPEVKFNWYVDGVEVHNAKTKPREEQYNSTYRVVSVLTVLHQDWLNGKEYKCKVSNKALPAPIEKTISKAKGQ
PREPQVYTLPPSREEMTKNQVSLTCLVKGFYPSDIAVEWESNGQPENNYKTTPPVLDSDGSFFLYSKLTVDKS
RWQQGNVFSCSVMHEALHNHYTQKSLSLSPGK
Signal sequence (1-19), Variable region (20-140), Constant region (141-470)

FIG. 22

SEQ ID NO:41: Nucleotide sequence of humanized hA2-27D-H2
ATGAAACACCTGTGGTTCTTCCTCCTGCTGGTGGCAGCTCCCAGATGGGTGCTGAGCGAAGTGCAGCTGGTGG
AATCTGGCGGCGGACTGGTGCAGCCTGGCGGATCTCTGAGACTGAGCTGTGCCGCCAGCGGCAGCACCTTCAG
CAACTACGGCATGAAGTGGATCCGGCAGGCCCCTGGCAAGGGCCTGGAATGGGTGTCCAGCATCAGCAGAAGC
AGCACCTACATCTACTACGCCGACACCGTGAAGGGCCGGTTCACCATCAGCCGGGACAACAGCAAGAACACCC
TGTACCTGCAGATGAACAGCCTGCGGGCCGAGGACACCGCCGTGTACTATTGTGCCGCCGCTATCAGCACCCC
CTTCTACTGGTACTTCGACTTCTGGGGCCAGGGCACCCTCGTGACCGTCAGCTCAGCCTCCACCAAGGGCCCA
AGCGTCTTCCCCCTGGCACCCTCCTCCAAGAGCACCTCTGGCGGCACAGCCGCCCTGGGCTGCCTGGTCAAGG
ACTACTTCCCCGAACCCGTGACCGTGAGCTGGAACTCAGGCGCCCTGACCAGCGGCGTGCACACCTTCCCCGC
TGTCCTGCAGTCCTCAGGACTCTACTCCCTCAGCAGCGTGGTGACCGTGCCCTCCAGCAGCTTGGGCACCCAG
ACCTACATCTGCAACGTGAATCACAAGCCCAGCAACACCAAGGTGGACAAGAGAGTTGAGCCCAAATCTTGTG
ACAAAACTCACACATGCCCACCCTGCCCAGCACCTGAACTCCTGGGGGGACCCTCAGTCTTCCTCTTCCCCCC
AAAAACCCAAGGACACCCTCATGATCTCCCGGACCCCTGAGGTCACATGCGTGGTGGTGGACGTGAGCCACGAA
GACCCTGAGGTCAAGTTCAACTGGTACGTGGACGGCGTGGAGGTGCATAATGCCAAGACAAAGCCCCGGGAGG
AGCAGTACAACAGCACGTACCGGGTGGTCAGCGTCCTCACCGTCCTGCACCAGGACTGGCTGAATGGCAAGGA
GTACAAGTGCAAGGTCTCCAACAAAGCCCTCCCAGCCCCCATCGAGAAAACCATCTCCAAAGCCAAAGGCCAG
CCCCGGGAACCACAGGTGTACACCCTGCCCCCATCCCGGGAGGAGATGACCAAGAACCAGGTCAGCCTGACCT
GCCTGGTCAAAGGCTTCTATCCCAGCGACATCGCCGTGGAGTGGGAGAGCAATGGCCAGCCCGAGAACAACTA
CAAGACCACCCCTCCCGTGCTGGACTCCGACGGCTCCTTCTTCCTCTACAGCAAGCTCACCGTGGACAAGAGC
AGGTGGCAGCAGGGCAACGTCTTCTCATGCTCCGTGATGCATGAGGCTCTGCACAACCACTACACCCAGAAGA
GCCTCTCCCTGTCTCCGGCAAA
Signal sequence (1-57), Variable region (58-420), Constant region (421-1410)

SEQ ID NO:42: Amino acid sequence of humanized hA2-27D-H2
MKHLWFFLLLVAAPRWVLSEVQLVESGGGLVQPGGSLRLSCAASGSTFSNYGMKWIRQAPGKGLEWVSSISRS
STYIYYADTVKGRFTISRDNSKNTLYLQMNSLRAEDTAVYYCAAAISTPFYWYFDFWGQGTLVTVSSASTKGP
SVFPLAPSSKSTSGGTAALGCLVKDYFPEPVTVSWNSGALTSGVHTFPAVLQSSGLYSLSSVVTVPSSSLGTQ
TYICNVNHKPSNTKVDKRVEPKSCDKTHTCPPCPAPELLGGPSVFLFPPKPKDTLMISRTPEVTCVVVDVSHE
DPEVKFNWYVDGVEVHNAKTKPREEQYNSTYRVVSVLTVLHQDWLNGKEYKCKVSNKALPAPIEKTISKAKGQ
PREPQVYTLPPSREEMTKNQVSLTCLVKGFYPSDIAVEWESNGQPENNYKTTPPVLDSDGSFFLYSKLTVDKS
RWQQGNVFSCSVMHEALHNHYTQKSLSLSPGK
Signal sequence (1-19), Variable region (20-140), Constant region (141-470)

FIG. 23

SEQ ID NO:43: Nucleotide sequence of humanized hA2-27D-H3
ATGAAACACCTGTGGTTCTTCCTCCTGCTGGTGGCAGCTCCCAGATGGGTGCTGAGCGAAGTGCAGCTGGTGG
AATCTGGCGGCGGACTGGTGCAGCCTGGCGGATCTCTGAGACTGAGCTGTGCCGCCAGCGGCAGCACCTTCAG
CAACTACGGCATGAAGTGGATCCGGCAGGCCCCTGGCAAGGGCCTGGAATGGGTGGCCAGCATCAGCAGAAGC
AGCACCTACATCTACTACGCCGACACCGTGAAGGGCCGGTTCACCATCAGCCGGGACAACAGCAAGAACACCC
TGTACCTGCAGATGAACAGCCTGCGGGCCGAGGACACCGCCGTGTACTATTGTGCCGCCGCTATCAGCACCCC
CTTCTACTGGTACTTCGACTTCTGGGGCCAGGGCACCCTCGTGACCGTCAGCTCAGCCTCCACCAAGGGCCCA
AGCGTCTTCCCCCTGGCACCCTCCTCCAAGAGCACCTCTGGCGGCACAGCCGCCCTGGGCTGCCTGGTCAAGG
ACTACTTCCCCGAACCCGTGACCGTGAGCTGGAACTCAGGCGCCCTGACCAGCGGCGTGCACACCTTCCCCGC
TGTCCTGCAGTCCTCAGGACTCTACTCCCTCAGCAGCGTGGTGACCGTGCCCTCCAGCAGCTTGGGCACCCAG
ACCTACATCTGCAACGTGAATCACAAGCCCAGCAACACCAAGGTGGACAAGAGAGTTGAGCCCAAATCTTGTG
ACAAAACTCACACATGCCCACCCTGCCCAGCACCTGAACTCCTGGGGGGACCCTCAGTCTTCCTCTTCCCCCC
AAAACCCAAGGACACCCTCATGATCTCCCGGACCCCTGAGGTCACATGCGTGGTGGTGGACGTGAGCCACGAA
GACCCTGAGGTCAAGTTCAACTGGTACGTGGACGGCGTGGAGGTGCATAATGCCAAGACAAAGCCCCGGGAGG
AGCAGTACAACAGCACGTACCGGGTGGTCAGCGTCCTCACCGTCCTGCACCAGGACTGGCTGAATGGCAAGGA
GTACAAGTGCAAGGTCTCCAACAAAGCCCTCCCAGCCCCCATCGAGAAAACCATCTCCAAAGCCAAAGGCCAG
CCCCGGGAACCACAGGTGTACACCCTGCCCCCATCCCGGGAGGAGATGACCAAGAACCAGGTCAGCCTGACCT
GCCTGGTCAAAGGCTTCTATCCCAGCGACATCGCCGTGGAGTGGGAGAGCAATGGCCAGCCCGAGAACAACTA
CAAGACCACCCCTCCCGTGCTGGACTCCGACGGCTCCTTCTTCCTCTACAGCAAGCTCACCGTGGACAAGAGC
AGGTGGCAGCAGGGCAACGTCTTCTCATGCTCCGTGATGCATGAGGCTCTGCACAACCACTACACCCAGAAGA
GCCTCTCCCTGTCTCCGGCAAA
Signal sequence (1-57), Variable region (58-420), Constant region (421-1410)

SEQ ID NO:44: Amino acid sequence of humanized hA2-27D-H3
MKHLWFFLLLVAAPRWVLSEVQLVESGGGLVQPGGSLRLSCAASGSTFSNYGMKWIRQAPGKGLEWVASISRS
STYIYYADTVKGRFTISRDNSKNTLYLQMNSLRAEDTAVYYCAAAISTPFYWYFDFWGQGTLVTVSSASTKGP
SVFPLAPSSKSTSGGTAALGCLVKDYFPEPVTVSWNSGALTSGVHTFPAVLQSSGLYSLSSVVTVPSSSLGTQ
TYICNVNHKPSNTKVDKRVEPKSCDKTHTCPPCPAPELLGGPSVFLFPPKPKDTLMISRTPEVTCVVVDVSHE
DPEVKFNWYVDGVEVHNAKTKPREEQYNSTYRVVSVLTVLHQDWLNGKEYKCKVSNKALPAPIEKTISKAKGQ
PREPQVYTLPPSREEMTKNQVSLTCLVKGFYPSDIAVEWESNGQPENNYKTTPPVLDSDGSFFLYSKLTVDKS
RWQQGNVFSCSVMHEALHNHYTQKSLSLSPGK
Signal sequence (1-19), Variable region (20-140), Constant region (141-470)

FIG. 24

SEQ ID NO:45: Nucleotide sequence of humanized hA2-27D-H4
ATGAAACACCTGTGGTTCTTCCTCCTGCTGGTGGCAGCTCCCAGATGGGTGCTGAGCGAAGTGCAGCTGGTGG
AATCTGGCGGCGGACTGGTGCAGCCTGGCGGATCTCTGAGACTGAGCTGTGCCGCCAGCGGCAGCACCTTCAG
CAACTACGGCATGAAGTGGATCCGGCAGGCCCCTGGCAAGGGCCTGGAATGGGTGGCCAGCATCAGCAGAAGC
AGCACCTACATCTACTACGCCGACACCGTGAAGGGCCGGTTCACCATCAGCCGGGACAACAGCAAGAACACCC
TGTACCTGCAGATGAACAGCCTGCGGGCCGAGGACACCGCCCTGTACTATTGTGCCGCCGCTATCAGCACCCC
CTTCTACTGGTACTTCGACTTCTGGGGCCCTGGCACCCTCGTGACCGTCAGCTCAGCCTCCACCAAGGGCCCA
AGCGTCTTCCCCCTGGCACCCTCCTCCAAGAGCACCTCTGGCGGCACAGCCGCCCTGGGCTGCCTGGTCAAGG
ACTACTTCCCCGAACCCGTGACCGTGAGCTGGAACTCAGGCGCCCTGACCAGCGGCGTGCACACCTTCCCCGC
TGTCCTGCAGTCCTCAGGACTCTACTCCCTCAGCAGCGTGGTGACCGTGCCCTCCAGCAGCTTGGGCACCCAG
ACCTACATCTGCAACGTGAATCACAAGCCCAGCAACACCAAGGTGGACAAGAGAGTTGAGCCCAAATCTTGTG
ACAAAACTCACACATGCCCACCCTGCCCAGCACCTGAACTCCTGGGGGGACCCTCAGTCTTCCTCTTCCCCCC
AAAACCCAAGGACACCCTCATGATCTCCCGGACCCCTGAGGTCACATGCGTGGTGGTGGACGTGAGCCACGAA
GACCCTGAGGTCAAGTTCAACTGGTACGTGGACGGCGTGGAGGTGCATAATGCCAAGACAAAGCCCCGGGAGG
AGCAGTACAACAGCACGTACCGGGTGGTCAGCGTCCTCACCGTCCTGCACCAGGACTGGCTGAATGGCAAGGA
GTACAAGTGCAAGGTCTCCAACAAAGCCCTCCCAGCCCCCATCGAGAAAACCATCTCCAAAGCCAAAGGCCAG
CCCCGGGAACCACAGGTGTACACCCTGCCCCCATCCCGGGAGGAGATGACCAAGAACCAGGTCAGCCTGACCT
GCCTGGTCAAAGGCTTCTATCCCAGCGACATCGCCGTGGAGTGGGAGAGCAATGGCCAGCCCGAGAACAACTA
CAAGACCACCCCTCCCGTGCTGGACTCCGACGGCTCCTTCTTCCTCTACAGCAAGCTCACCGTGGACAAGAGC
AGGTGGCAGCAGGGCAACGTCTTCTCATGCTCCGTGATGCATGAGGCTCTGCACAACCACTACACCCAGAAGA
GCCTCTCCCTGTCTCCCGGCAAA
Signal sequence (1-57), Variable region (58-420), Constant region (421-1410)

SEQ ID NO:46: Amino acid sequence of humanized hA2-27D-H4
MKHLWFFLLLVAAPRWVLSEVQLVESGGGLVQPGGSLRLSCAASGSTFSNYGMKWIRQAPGKGLEWVASISRS
STYIYYADTVKGRFTISRDNSKNTLYLQMNSLRAEDTALYYCAAAISTPFYWYFDFWGPGTLVTVSSASTKGP
SVFPLAPSSKSTSGGTAALGCLVKDYFPEPVTVSWNSGALTSGVHTFPAVLQSSGLYSLSSVVTVPSSSLGTQ
TYICNVNHKPSNTKVDKRVEPKSCDKTHTCPPCPAPELLGGPSVFLFPPKPKDTLMISRTPEVTCVVVDVSHE
DPEVKFNWYVDGVEVHNAKTKPREEQYNSTYRVVSVLTVLHQDWLNGKEYKCKVSNKALPAPIEKTISKAKGQ
PREPQVYTLPPSREEMTKNQVSLTCLVKGFYPSDIAVEWESNGQPENNYKTTPPVLDSDGSFFLYSKLTVDKS
RWQQGNVFSCSVMHEALHNHYTQKSLSLSPGK
Signal sequence (1-19), Variable region (20-140), Constant region (141-470)

FIG. 25

SEQ ID NO:47: Nucleotide sequence of humanized hA2-27D-H5
ATGAAACACCTGTGGTTCTTCCTCCTGCTGGTGGCAGCTCCCAGATGGGTGCTGAGCGAAGTGCAGCTGGTGG
AATCTGGCGGCGGACTGGTGCAGCCTGGCGGATCTCTGAGACTGAGCTGTGCCGCCAGCGGCAGCACCTTCAG
CAACTACGGCATGAAGTGGATCCGGCAGGCCCCTGGCAAGGGCCTGGAATGGGTGGCCAGCATCAGCAGAAGC
AGCACCTACATCTACTACGCCGACACCGTGAAGGGCCGGTTCACCATCTCCCGGGACAACGCCAAGAACACCC
TGTACCTGCAGATGAACAGCCTGCGGAGCGAGGACACCGCCCTGTACTATTGTGCCGCCGCTATCAGCACCCC
CTTCTACTGGTACTTCGACTTCTGGGGCCCTGGCACCCTCGTGACCGTCAGCTCAGCCTCCACCAAGGGCCCA
AGCGTCTTCCCCCTGGCACCCTCCTCCAAGAGCACCTCTGGCGGCACAGCCGCCCTGGGCTGCCTGGTCAAGG
ACTACTTCCCCGAACCCGTGACCGTGAGCTGGAACTCAGGCGCCCTGACCAGCGGCGTGCACACCTTCCCCGC
TGTCCTGCAGTCCTCAGGACTCTACTCCCTCAGCAGCGTGGTGACCGTGCCCTCCAGCAGCTTGGGCACCCAG
ACCTACATCTGCAACGTGAATCACAAGCCCAGCAACACCAAGGTGGACAAGAGAGTTGAGCCCAAATCTTGTG
ACAAAACTCACACATGCCCACCCTGCCCAGCACCTGAACTCCTGGGGGGACCCTCAGTCTTCCTCTTCCCCCC
AAAACCCAAGGACACCCTCATGATCTCCCGGACCCCTGAGGTCACATGCGTGGTGGTGGACGTGAGCCACGAA
GACCCTGAGGTCAAGTTCAACTGGTACGTGGACGGCGTGGAGGTGCATAATGCCAAGACAAAGCCCCGGGAGG
AGCAGTACAACAGCACGTACCGGGTGGTCAGCGTCCTCACCGTCCTGCACCAGGACTGGCTGAATGGCAAGGA
GTACAAGTGCAAGGTCTCCAACAAAGCCCTCCCAGCCCCCATCGAGAAAACCATCTCCAAAGCCAAAGGCCAG
CCCCGGGAACCACAGGTGTACACCCTGCCCCCATCCCGGGAGGAGATGACCAAGAACCAGGTCAGCCTGACCT
GCCTGGTCAAAGGCTTCTATCCCAGCGACATCGCCGTGGAGTGGGAGAGCAATGGCCAGCCCGAGAACAACTA
CAAGACCACCCCTCCCGTGCTGGACTCCGACGGCTCCTTCTTCCTCTACAGCAAGCTCACCGTGGACAAGAGC
AGGTGGCAGCAGGGCAACGTCTTCTCATGCTCCGTGATGCATGAGGCTCTGCACAACCACTACACCCAGAAGA
GCCTCTCCCTGTCTCCCGGCAAA
Signal sequence (1-57), Variable region (58-420), Constant region (421-1410)

SEQ ID NO:48: Amino acid sequence of humanized hA2-27D-H5
MKHLWFFLLLVAAPRWVLSEVQLVESGGGLVQPGGSLRLSCAASGSTFSNYGMKWIRQAPGKGLEWVASISRS
STYIYYADTVKGRFTISRDNAKNTLYLQMNSLRSEDTALYYCAAAISTPFYWYFDFWGPGTLVTVSSASTKGP
SVFPLAPSSKSTSGGTAALGCLVKDYFPEPVTVSWNSGALTSGVHTFPAVLQSSGLYSLSSVVTVPSSSLGTQ
TYICNVNHKPSNTKVDKRVEPKSCDKTHTCPPCPAPELLGGPSVFLFPPKPKDTLMISRTPEVTCVVVDVSHE
DPEVKFNWYVDGVEVHNAKTKPREEQYNSTYRVVSVLTVLHQDWLNGKEYKCKVSNKALPAPIEKTISKAKGQ
PREPQVYTLPPSREEMTKNQVSLTCLVKGFYPSDIAVEWESNGQPENNYKTTPPVLDSDGSFFLYSKLTVDKS
RWQQGNVFSCSVMHEALHNHYTQKSLSLSPGK
Signal sequence (1-19), Variable region (20-140), Constant region (141-470)

FIG. 26

SEQ ID NO:49: Nucleotide sequence of DNA fragment comprising sequences encoding humanized hA2-27D-L1
ccagcctccggactctagagccaccATGGTGCTGCAGACCCAGGTGTTCATCAGCCTGCTGCTGTGGATCAGC
GGCGCCTACGGCGAGATCGTGCTGACACAGAGCCCTGGCACCCTGAGCCTGTCTCCAGGCGAAAGAGCCACCC
TGTCCTGTCTGGCCAGCAGCAGCGTGTCCTACATGACCTGGTATCAGCAGAAGCCCGGCCAGGCCCCCAGACT
GCTGATCTACGGCACAAGCAATCTGGCCTCCGGCATCCCCGACAGATTTTCCGGCTCTGGCAGCGGCACCGAC
TTCACCCTGACCATCAGCAGACTGGAACCCGAGGACTTCGCCGTGTACTACTGCCTGCACCTGACCAGCTACC
CCCCCTACACATTTGGCCAGGGCACCAAGGTGGAAATCAAGCGGGCTGTGGCCGCTCCCTCCGTGTTCATCTT
TCCACCCAGCGACGAGCAGCTGAAGTCCGGCACAGCTAGCGTCGTGTGCCTGCTGAACAACTTCTACCCCCGC
GAGGCCAAGGTGCAGTGGAAGGTGGACAATGCCCTGCAGAGCGGCAACTCCCAGGAAAGCGTGACCGAGCAGG
ACAGCAAGGACTCCACCTACAGCCTGAGCAGCACCCTGACACTGAGCAAGGCCGACTACGAGAAGCACAAGGT
GTACGCCTGCGAAGTGACCCACCAGGGCCTGTCTAGCCCCGTGACCAAGAGCTTCAACCGGGGCGAGTGTtga
gtttaaacgggggaggctaact
Signal sequence (26-85), Variable region (86-412), Constant region (413-727)

SEQ ID NO:50: Amino acid sequence of humanized hA2-27D-L1
MVLQTQVFISLLLWISGAYGEIVLTQSPGTLSLSPGERATLSCLASSSVSYMTWYQQKPGQAPRLLIYGTSNL
ASGIPDRFSGSGSGTDFTLTISRLEPEDFAVYYCLHLTSYPPYTFGQGTKVEIKRAVAAPSVFIFPPSDEQLK
SGTASVVCLLNNFYPREAKVQWKVDNALQSGNSQESVTEQDSKDSTYSLSSTLTLSKADYEKHKVYACEVTHQ
GLSSPVTKSFNRGEC
Signal sequence (1-20), Variable region (21-129), Constant region (130-234)

FIG. 27

SEQ ID NO:51: Nucleotide sequence of DNA fragment comprising sequences encoding humanized hA2-27D-L2
ccagcctccggactctagagccaccATGGTGCTGCAGACCCAGGTGTTCATCAGCCTGCTGCTGTGGATCAGC
GGCGCCTACGGCGAGATCGTGCTGACACAGAGCCCTGGCACCCTGAGCCTGTCTCCAGGCGAAAGAGCCACCC
TGTCCTGTCTGGCCAGCAGCAGCGTGTCCTACATGACCTGGTATCAGCAGAAGCCCGGCCAGAGCCCCAGACT
GTGGATCTACGGCACCAGCAATCTGGCCTCCGGCGTGCCCGATAGATTTTCCGGCTCTGGCAGCGGCACCGAC
TTCACCCTGACCATCAGCAGACTGGAACCCGAGGACTTCGCCGTGTACTACTGCCTGCACCTGACCAGCTACC
CCCCCTACACATTTGGCCAGGGCACCAAGGTGGAAATCAAGCGGGCTGTGGCCGCTCCCTCCGTGTTCATCTT
TCCACCCAGCGACGAGCAGCTGAAGTCCGGCACAGCTAGCGTCGTGTGCCTGCTGAACAACTTCTACCCCCGC
GAGGCCAAGGTGCAGTGGAAGGTGGACAATGCCCTGCAGAGCGGCAACTCCCAGGAAAGCGTGACCGAGCAGG
ACAGCAAGGACTCCACCTACAGCCTGAGCAGCACCCTGACACTGAGCAAGGCCGACTACGAGAAGCACAAGGT
GTACGCCTGCGAAGTGACCCACCAGGGCCTGTCTAGCCCCGTGACCAAGAGCTTCAACCGGGGCGAGTGTtga
gtttaaacggggaggctaact
Signal sequence (26-85), Variable region (86-412), Constant region (413-727)

SEQ ID NO:52: Amino acid sequence of humanized hA2-27D-L2
MVLQTQVFISLLLWISGAYGEIVLTQSPGTLSLSPGERATLSCLASSSVSYMTWYQQKPGQSPRLWIYGTSNL
ASGVPDRFSGSGSGTDFTLTISRLEPEDFAVYYCLHLTSYPPYTFGQGTKVEIKRAVAAPSVFIFPPSDEQLK
SGTASVVCLLNNFYPREAKVQWKVDNALQSGNSQESVTEQDSKDSTYSLSSTLTLSKADYEKHKVYACEVTHQ
GLSSPVTKSFNRGEC
Signal sequence (1-20), Variable region (21-129), Constant region (130-234)

FIG. 28

SEQ ID NO:53: Nucleotide sequence of DNA fragment comprising sequences encoding humanized hA2-27D-L3
ccagcctccggactctagagccaccATGGTGCTGCAGACCCAGGTGTTCATCAGCCTGCTGCTGTGGATCAGC
GGCGCCTACGGCGAGATCGTGCTGACACAGAGCCCTGGCACCCTGAGCCTGTCTCCAGGCGAAAGAGCCACCC
TGTCCTGTCTGGCCAGCAGCAGCGTGTCCTACATGACCTGGTATCAGCAGAAGCCAGGCGCCAGCCCCAGACT
GTGGATCTACGGCACAAGCAACCTGGCCAGCGGCGTGCCCGATAGATTTTCTGGCAGCGGCTCCGGCACCGAC
TACACCCTGACAATCAGCAGACTGGAACCCGAGGACTTCGCCACCTACTACTGCCTGCACCTGACCAGCTACC
CCCCCTACACATTTGGAGCCGGCACCAAGGTGGAAATCAAGCGGGCTGTGGCCGCTCCCTCCGTGTTCATCTT
TCCACCCAGCGACGAGCAGCTGAAGTCTGGCACAGCCAGCGTCGTGTGCCTGCTGAACAACTTCTACCCCCGC
GAGGCCAAGGTGCAGTGGAAGGTGGACAATGCCCTGCAGAGCGGCAACTCCCAGGAAAGCGTGACCGAGCAGG
ACAGCAAGGACTCCACCTACAGCCTGAGCAGCACACTGACCCTGAGCAAGGCCGACTACGAGAAGCACAAGGT
GTACGCCTGCGAAGTGACCCACCAGGGCCTGTCTAGCCCCGTGACCAAGAGCTTCAACCGGGGCGAGTGTtga
gtttaaacgggggaggctaact
Signal sequence (26-85), Variable region (86-412), Constant region (413-727)

SEQ ID NO:54: Amino acid sequence of humanized hA2-27D-L3
MVLQTQVFISLLLWISGAYGEIVLTQSPGTLSLSPGERATLSCLASSSVSYMTWYQQKPGASPRLWIYGTSNL
ASGVPDRFSGSGSGTDYTLTISRLEPEDFATYYCLHLTSYPPYTFGAGTKVEIKRAVAAPSVFIFPPSDEQLK
SGTASVVCLLNNFYPREAKVQWKVDNALQSGNSQESVTEQDSKDSTYSLSSTLTLSKADYEKHKVYACEVTHQ
GLSSPVTKSFNRGEC
Signal sequence (1-20), Variable region (21-129), Constant region (130-234)

FIG. 29

SEQ ID NO:55: Nucleotide sequence of DNA fragment comprising sequences encoding humanized hA2-27D-L4
ccagcctccggactctagagccaccATGGTGCTGCAGACCCAGGTGTTCATCAGCCTGCTGCTGTGGATCAGC
GGCGCCTACGGCGAGATCGTGCTGACACAGAGCCCTGGCACCATGTCTGCCAGCCCTGGCGAGAGAGTGACCC
TGAGCTGTCTGGCCAGCTCCAGCGTGTCCTACATGACCTGGTATCAGCAGAAGCCAGGCGCCAGCCCCAGACT
GTGGATCTACGGCACAAGCAACCTGGCCAGCGGCGTGCCCGATAGATTTTCTGGCAGCGGCTCCGGCACCGAC
TACACCCTGACCATCAGCCGGATGGAACCCGAGGACTTCGCCACCTACTACTGCCTGCACCTGACCAGCTACC
CCCCCTACACATTTGGAGCCGGCACCAAGCTGGAACTGAAGAGAGCCGTGGCTGCCCCCTCCGTGTTCATCTT
CCCACCTAGCGACGAGCAGCTGAAGTCTGGCACAGCCAGCGTCGTGTGCCTGCTGAACAACTTCTACCCCCGC
GAGGCCAAGGTGCAGTGGAAGGTGGACAATGCCCTGCAGAGCGGCAACAGCCAGGAAAGCGTGACCGAGCAGG
ACAGCAAGGACTCCACCTACAGCCTGAGCAGCACCCTGACACTGAGCAAGGCCGACTACGAGAAGCACAAGGT
GTACGCCTGCGAAGTGACCCACCAGGGCCTGTCTAGCCCCGTGACCAAGAGCTTCAACCGGGGCGAGTGTtga
gtttaaacgggggaggctaact
Signal sequence (26-85), Variable region (86-412), Constant region (413-727)

SEQ ID NO:56: Amino acid sequence of humanized hA2-27D-L4
MVLQTQVFISLLLWISGAYGEIVLTQSPGTMSASPGERVTLSCLASSSVSYMTWYQQKPGASPRLWIYGTSNL
ASGVPDRFSGSGSGTDYTLTISRMEPEDFATYYCLHLTSYPPYTFGAGTKLELKRAVAAPSVFIFPPSDEQLK
SGTASVVCLLNNFYPREAKVQWKVDNALQSGNSQESVTEQDSKDSTYSLSSTLTLSKADYEKHKVYACEVTHQ
GLSSPVTKSFNRGEC
Signal sequence (1-20), Variable region (21-129), Constant region (130-234)

FIG. 30

SEQ ID NO:57: Nucleotide sequence of DNA fragment comprising sequences encoding humanized hA2-27D-L5
ccagcctccggactctagagccaccATGGTGCTGCAGACCCAGGTGTTCATCAGCCTGCTGCTGTGGATCAGC
GGCGCCTACGGCGAGATCGTGCTGACACAGAGCCCTGGCACCATGTCTGCCAGCCCTGGCGAGAGAGTGACCC
TGAATTGTCTGGCCAGCAGCAGCGTGTCCTACATGACCTGGTATCAGCAGAAGTCCGGCGCCAGCCCCAAACT
GTGGATCTACGGCACCAGCAACCTGGCCAGCGGCGTGCCCAATAGATTTTCCGGCAGCGGCTCCGGCACCTCC
TACACCCTGACCATCAGCCGGATGGAACCCGAGGACTTCGCCACCTACTACTGCCTGCACCTGACCAGCTACC
CCCCTACACATTTGGAGCCGGCACCAAGCTGGAACTGAAGAGAGCCGTGGCCGCTCCCTCCGTGTTCATCTT
CCCACCTAGCGACGAGCAGCTGAAGTCTGGCACAGCCAGCGTCGTGTGCCTGCTGAACAACTTCTACCCCCGC
GAGGCCAAGGTGCAGTGGAAGGTGGACAATGCCCTGCAGAGCGGCAACAGCCAGGAAAGCGTGACCGAGCAGG
ACAGCAAGGACTCCACCTACAGCCTGAGCAGCACCCTGACACTGAGCAAGGCCGACTACGAGAAGCACAAGGT
GTACGCCTGCGAAGTGACCCACCAGGGCCTGTCTAGCCCCGTGACCAAGAGCTTCAACCGGGGCGAGTGTtga
gtttaaacgggggaggctaact Signal sequence (26-85), Variable region (86-412), Constant region (413-727)

SEQ ID NO:58: Amino acid sequence of humanized hA2-27D-L5
MVLQTQVFISLLLWISGAYGEIVLTQSPGTMSASPGERVTLNCLASSSVSYMTWYQQKSGASPKLWIYGTSNL
ASGVPNRFSGSGSGTSYTLTISRMEPEDFATYYCLHLTSYPPYTFGAGTKLELKRAVAAPSVFIFPPSDEQLK
SGTASVVCLLNNFYPREAKVQWKVDNALQSGNSQESVTEQDSKDSTYSLSSTLTLSKADYEKHKVYACEVTHQ
GLSSPVTKSFNRGEC Signal sequence (1-20), Variable region (21-129), Constant region (130-234)

FIG. 32

SEQ ID NO:104: Nucleotide sequence of humanized hA2-15A-H4 IgG2 type
ATGAAACACCTGTGGTTCTTCCTCCTGCTGGTGGCAGCTCCCAGATGGGTGCTGAGCGAAGTGCAGCTGGTGG
AATCTGGCGGCGGACTGGTGCAGCCTGGCGGATCTCTGAGACTGAGCTGTGCCGCCAGCGGCTTCACCTTCAG
CCACTACTACATGGCCTGGGTGCGCCAGGCCCCTGGCAAAGGACTGGAATGGGTGGCCAGCATCACCAACAGC
GGCGGCAGCATCAACTACCGGGACAGCGTGAAGGGCCGGTTCACCATCAGCCGGGACAACGCCAAGAGCACCC
TGTACCTGCAGATGAACAGCCTGCGGGCCGAGGACACCGCCACCTACTACTGTACAAGAGAGGGCGGCGAGAA
CTACGGCGGCTACCCTCCTTTTGCCTACTGGGGCCAGGGCACCCTCGTGACCGTCAGCTCAGCCAGCACCAAG
GGCCCTTCCGTGTTCCCTCTGGCCCCTTGTAGCCGTTCCACCAGCGAGTCCACCGCCGCCCTTGGCTGTCTGG
TGAAGGACTACTTCCCTGAGCCTGTGACCGTGAGCTGGAACTCCGGAGCCCTTACCAGCGGCGTGCACACCTT
CCCTGCCGTGCTGCAGTCCAGCGGCCTTTACTCCCTGAGCTCCGTGGTGACCGTGCCTAGCTCCAACTTCGGC
ACCCAAACCTACACCTGTAACGTGGACCACAAGCCTAGCAACACCAAGGTGGACAAGACCGTGGAGCGTAAGT
GTTGTGTGGAGTGTCCTCCTTGTCCTGCCCCTCCTGTGGCCGGACCTTCCGTGTTCCTTTTCCCTCCTAAGCC
TAAGGACACCCTGATGATCAGCCGTACCCCTGAGGTGACCTGTGTGGTGGTGGACGTGTCCCACGAGGACCCT
GAGGTGCAGTTCAACTGGTACGTGGACGGCGTGGAGGTGCACAACGCCAAGACCAAGCCTCGTGAGGAGCAAT
TCAACAGCACCTTCCGTGTGGTGTCCGTGCTTACCGTGGTGCACCAAGACTGGCTGAACGGCAAGGAGTACAA
GTGTAAGGTGAGCAACAAGGGACTTCCTGCCCCTATCGAGAAGACCATCTCCAAGACCAAGGGCCAACCTCGT
GAGCCTCAAGTGTACACCCTTCCTCCTAGCCGTGAGGAGATGACCAAGAACCAAGTGTCCCTTACCTGTCTGG
TGAAGGGCTTCTACCCTAGCGACATCGCCGTGGAGTGGGAGTCCAACGGACAACCTGAGAACAACTACAAGAC
CACCCCTCCTATGCTTGACAGCGACGGCTCCTTCTTCCTGTACAGCAAGCTGACCGTGGACAAGTCCCGTTGG
CAACAAGGCAACGTGTTCAGCTGTTCCGTGATGCACGAGGCCCTGCACAACCACTACACCCAAAAGAGCCTTT
CCCTGAGCCCTGGAAAG
Signal sequence (1-57), Variable region (58-426), Constant region (427-1404)

SEQ ID NO:105: Amino acid sequence of humanized hA2-15A-H4 IgG2 type
MKHLWFFLLLVAAPRWVLSEVQLVESGGGLVQPGGSLRLSCAASGFTFSHYYMAWVRQAPGKGLEWVASITNS
GGSINYRDSVKGRFTISRDNAKSTLYLQMNSLRAEDTATYYCTREGGENYGGYPPFAYWGQGTLVTVSSASTK
GPSVFPLAPCSRSTSESTAALGCLVKDYFPEPVTVSWNSGALTSGVHTFPAVLQSSGLYSLSSVVTVPSSNFG
TQTYTCNVDHKPSNTKVDKTVERKCCVECPPCPAPPVAGPSVFLFPPKPKDTLMISRTPEVTCVVVDVSHEDP
EVQFNWYVDGVEVHNAKTKPREEQFNSTFRVVSVLTVVHQDWLNGKEYKCKVSNKGLPAPIEKTISKTKGQPR
EPQVYTLPPSREEMTKNQVSLTCLVKGFYPSDIAVEWESNGQPENNYKTTPPMLDSDGSFFLYSKLTVDKSRW
QQGNVFSCSVMHEALHNHYTQKSLSLSPGK
Signal sequence (1-19), Variable region (20-142), Constant region (143-468)

FIG. 33

SEQ ID NO:106: Nucleotide sequence of humanized hA2-27D-H2-LALA
ATGAAACACCTGTGGTTCTTCCTCCTGCTGGTGGCAGCTCCCAGATGGGTGCTGAGCGAAGTGCAGCTGGTGG
AATCTGGCGGCGGACTGGTGCAGCCTGGCGGATCTCTGAGACTGAGCTGTGCCGCCAGCGGCAGCACCTTCAG
CAACTACGGCATGAAGTGGATCCGGCAGGCCCCTGGCAAGGGCCTGGAATGGGTGTCCAGCATCAGCAGAAGC
AGCACCTACATCTACTACGCCGACACCGTGAAGGGCCGGTTCACCATCAGCCGGGACAACAGCAAGAACACCC
TGTACCTGCAGATGAACAGCCTGCGGGCCGAGGACACCGCCGTGTACTATTGTGCCGCCGCTATCAGCACCCC
CTTCTACTGGTACTTCGACTTCTGGGGCCAGGGCACCCTCGTGACCGTCAGCTCAGCCTCCACCAAGGGCCCA
AGCGTCTTCCCCCTGGCACCCTCCTCCAAGAGCACCTCTGGCGGCACAGCCGCCCTGGGCTGCCTGGTCAAGG
ACTACTTCCCCGAACCCGTGACCGTGAGCTGGAACTCAGGCGCCCTGACCAGCGGCGTGCACACCTTCCCCGC
TGTCCTGCAGTCCTCAGGACTCTACTCCCTCAGCAGCGTGGTGACCGTGCCCTCCAGCAGCTTGGGCACCCAG
ACCTACATCTGCAACGTGAATCACAAGCCCAGCAACACCAAGGTGGACAAGAGAGTTGAGCCCAAATCTTGTG
ACAAAACTCACACATGCCCACCCTGCCCAGCACCTGAAGCCGCGGGGGGACCCTCAGTCTTCCTCTTCCCCCC
AAAACCCAAGGACACCCTCATGATCTCCCGGACCCCTGAGGTCACATGCGTGGTGGTGGACGTGAGCCACGAA
GACCCTGAGGTCAAGTTCAACTGGTACGTGGACGGCGTGGAGGTGCATAATGCCAAGACAAAGCCCCGGGAGG
AGCAGTACAACAGCACGTACCGGGTGGTCAGCGTCCTCACCGTCCTGCACCAGGACTGGCTGAATGGCAAGGA
GTACAAGTGCAAGGTCTCCAACAAAGCCCTCCCAGCCCCCATCGAGAAAACCATCTCCAAAGCCAAAGGCCAG
CCCCGGGAACCACAGGTGTACACCCTGCCCCCATCCCGGGAGGAGATGACCAAGAACCAGGTCAGCCTGACCT
GCCTGGTCAAAGGCTTCTATCCCAGCGACATCGCCGTGGAGTGGGAGAGCAATGGCCAGCCCGAGAACAACTA
CAAGACCACCCCTCCCGTGCTGGACTCCGACGGCTCCTTCTTCCTCTACAGCAAGCTCACCGTGGACAAGAGC
AGGTGGCAGCAGGGCAACGTCTTCTCATGCTCCGTGATGCATGAGGCTCTGCACAACCACTACACCCAGAAGA
GCCTCTCCCTGTCTCCCGGCAAA
Signal sequence (1-57), Variable region (58-420), Constant region (421-1410)

SEQ ID NO:107: Amino sequence of humanized hA2-27D-H2-LALA
MKHLWFFLLLVAAPRWVLSEVQLVESGGGLVQPGGSLRLSCAASGSTFSNYGMKWIRQAPGKGLEWVSSISRS
STYIYYADTVKGRFTISRDNSKNTLYLQMNSLRAEDTAVYYCAAAISTPFYWYFDFWGQGTLVTVSSASTKGP
SVFPLAPSSKSTSGGTAALGCLVKDYFPEPVTVSWNSGALTSGVHTFPAVLQSSGLYSLSSVVTVPSSSLGTQ
TYICNVNHKPSNTKVDKRVEPKSCDKTHTCPPCPAPEAAGGPSVFLFPPKPKDTLMISRTPEVTCVVVDVSHE
DPEVKFNWYVDGVEVHNAKTKPREEQYNSTYRVVSVLTVLHQDWLNGKEYKCKVSNKALPAPIEKTISKAKGQ
PREPQVYTLPPSREEMTKNQVSLTCLVKGFYPSDIAVEWESNGQPENNYKTTPPVLDSDGSFFLYSKLTVDKS
RWQQGNVFSCSVMHEALHNHYTQKSLSLSPGK
Signal sequence (1-19), Variable region (20-140), Constant region (141-470)

FIG. 34

SEQ ID NO:108: Nucleotide sequence of humanized hA2-27D-H3-LALA
ATGAAACACCTGTGGTTCTTCCTCCTGCTGGTGGCAGCTCCCAGATGGGTGCTGAGCGAAGTGCAGCTGGTGG
AATCTGGCGGCGGACTGGTGCAGCCTGGCGGATCTCTGAGACTGAGCTGTGCCGCCAGCGGCAGCACCTTCAG
CAACTACGGCATGAAGTGGATCCGGCAGGCCCCTGGCAAGGGCCTGGAATGGGTGGCCAGCATCAGCAGAAGC
AGCACCTACATCTACTACGCCGACACCGTGAAGGGCCGGTTCACCATCAGCCGGGACAACAGCAAGAACACCC
TGTACCTGCAGATGAACAGCCTGCGGGCCGAGGACACCGCCGTGTACTATTGTGCCGCCGCTATCAGCACCCC
CTTCTACTGGTACTTCGACTTCTGGGGCCAGGGCACCCTCGTGACCGTCAGCTCAGCCTCCACCAAGGGCCCA
AGCGTCTTCCCCCTGGCACCCTCCTCCAAGAGCACCTCTGGCGGCACAGCCGCCCTGGGCTGCCTGGTCAAGG
ACTACTTCCCCGAACCCGTGACCGTGAGCTGGAACTCAGGCGCCCTGACCAGCGGCGTGCACACCTTCCCCGC
TGTCCTGCAGTCCTCAGGACTCTACTCCCTCAGCAGCGTGGTGACCGTGCCCTCCAGCAGCTTGGGCACCCAG
ACCTACATCTGCAACGTGAATCACAAGCCCAGCAACACCAAGGTGGACAAGAGAGTTGAGCCCAAATCTTGTG
ACAAAACTCACACATGCCCACCCTGCCCAGCACCTGAAGCCGCGGGGGGACCCTCAGTCTTCCTCTTCCCCCC
AAAACCCAAGGACACCCTCATGATCTCCCGGACCCCTGAGGTCACATGCGTGGTGGTGGACGTGAGCCACGAA
GACCCTGAGGTCAAGTTCAACTGGTACGTGGACGGCGTGGAGGTGCATAATGCCAAGACAAAGCCCCGGGAGG
AGCAGTACAACAGCACGTACCGGGTGGTCAGCGTCCTCACCGTCCTGCACCAGGACTGGCTGAATGGCAAGGA
GTACAAGTGCAAGGTCTCCAACAAAGCCCTCCCAGCCCCCATCGAGAAAACCATCTCCAAAGCCAAAGGCCAG
CCCCGGGAACCACAGGTGTACACCCTGCCCCCATCCCGGGAGGAGATGACCAAGAACCAGGTCAGCCTGACCT
GCCTGGTCAAAGGCTTCTATCCCAGCGACATCGCCGTGGAGTGGGAGAGCAATGGCCAGCCCGAGAACAACTA
CAAGACCACCCCTCCCGTGCTGGACTCCGACGGCTCCTTCTTCCTCTACAGCAAGCTCACCGTGGACAAGAGC
AGGTGGCAGCAGGGCAACGTCTTCTCATGCTCCGTGATGCATGAGGCTCTGCACAACCACTACACCCAGAAGA
GCCTCTCCCTGTCTCCCGGCAAA
Signal sequence (1-57), Variable region (58-420), Constant region (421-1410)

SEQ ID NO:109: Amino sequence of humanized hA2-27D-H3-LALA
MKHLWFFLLLVAAPRWVLSEVQLVESGGGLVQPGGSLRLSCAASGSTFSNYGMKWIRQAPGKGLEWVASISRS
STYIYYADTVKGRFTISRDNSKNTLYLQMNSLRAEDTAVYYCAAAISTPFYWYFDFWGQGTLVTVSSASTKGP
SVFPLAPSSKSTSGGTAALGCLVKDYFPEPVTVSWNSGALTSGVHTFPAVLQSSGLYSLSSVVTVPSSSLGTQ
TYICNVNHKPSNTKVDKRVEPKSCDKTHTCPPCPAPEAAGGPSVFLFPPKPKDTLMISRTPEVTCVVVDVSHE
DPEVKFNWYVDGVEVHNAKTKPREEQYNSTYRVVSVLTVLHQDWLNGKEYKCKVSNKALPAPIEKTISKAKGQ
PREPQVYTLPPSREEMTKNQVSLTCLVKGFYPSDIAVEWESNGQPENNYKTTPPVLDSDGSFFLYSKLTVDKS
RWQQGNVFSCSVMHEALHNHYTQKSLSLSPGK
Signal sequence (1-19), Variable region (20-140), Constant region (141-470)

FIG. 38

SEQ ID NO:110: Nucleotide sequence of humanized hA2-11E-H3
ATGAAACACCTGTGGTTCTTCCTCCTGCTGGTGGCAGCTCCCAGATGGGTGCTGAGCGAAGTGCAGCTGGTGG
AATCTGGCGGCGGACTGGTGCAGCCTGGCGGATCTCTGAGACTGAGCTGTGCCGCCAGCGGCTTCACCTTCAG
CAACTACTACATGTACTGGATCCGGCAGGCCCCTGGCAAGGGCCTGGAATGGGTGTCCAGCATCAACACCGAT
GGCGGCAGCACCTACTACGCCGACAGCGTGAAGGGCCGGTTCACCATCAGCCGGGACAACAGCAAGAACACCG
TGTACCTGCAGATGAACAGCCTGCGGGCCGAGGACACCGCCGTGTACTACTGTGCCAAGAGCACCCCCAACAT
CCCCCTGGCCTATTGGGGCCAGGGAACCCTCGTGACCGTCAGCTCAGCCTCCACCAAGGGCCCAAGCGTCTTC
CCCCTGGCACCCTCCTCCAAGAGCACCTCTGGCGGCACAGCCGCCCTGGGCTGCCTGGTCAAGGACTACTTCC
CCGAACCCGTGACCGTGAGCTGGAACTCAGGCGCCCTGACCAGCGGCGTGCACACCTTCCCCGCTGTCCTGCA
GTCCTCAGGACTCTACTCCCTCAGCAGCGTGGTGACCGTGCCCTCCAGCAGCTTGGGCACCCAGACCTACATC
TGCAACGTGAATCACAAGCCCAGCAACACCAAGGTGGACAAGAGAGTTGAGCCCAAATCTTGTGACAAAACTC
ACACATGCCCACCCTGCCCAGCACCTGAACTCCTGGGGGGACCCTCAGTCTTCCTCTTCCCCCCAAAACCCAA
GGACACCCTCATGATCTCCCGGACCCCTGAGGTCACATGCGTGGTGGTGGACGTGAGCCACGAAGACCCTGAG
GTCAAGTTCAACTGGTACGTGGACGGCGTGGAGGTGCATAATGCCAAGACAAAGCCCCGGGAGGAGCAGTACA
ACAGCACGTACCGGGTGGTCAGCGTCCTCACCGTCCTGCACCAGGACTGGCTGAATGGCAAGGAGTACAAGTG
CAAGGTCTCCAACAAAGCCCTCCCAGCCCCCATCGAGAAAACCATCTCCAAAGCCAAAGGCCAGCCCCGGGAA
CCACAGGTGTACACCCTGCCCCCATCCCGGGAGGAGATGACCAAGAACCAGGTCAGCCTGACCTGCCTGGTCA
AAGGCTTCTATCCCAGCGACATCGCCGTGGAGTGGGAGAGCAATGGCCAGCCCGAGAACAACTACAAGACCAC
CCCTCCCGTGCTGGACTCCGACGGCTCCTTCTTCCTCTACAGCAAGCTCACCGTGGACAAGAGCAGGTGGCAG
CAGGGCAACGTCTTCTCATGCTCCGTGATGCATGAGGCTCTGCACAACCACTACACCCAGAAGAGCCTCTCCC
TGTCTCCCGGCAAA
Signal sequence (1-57), Variable region (58-411), Constant region (412-1401)

SEQ ID NO:111: Amino acid sequence of humanized hA2-11E-H3
MKHLWFFLLLVAAPRWVLSEVQLVESGGGLVQPGGSLRLSCAASGFTFSNYYMYWIRQAPGKGLEWVSSINTD
GGSTYYADSVKGRFTISRDNSKNTVYLQMNSLRAEDTAVYYCAKSTPNIPLAYWGQGTLVTVSSASTKGPSVF
PLAPSSKSTSGGTAALGCLVKDYFPEPVTVSWNSGALTSGVHTFPAVLQSSGLYSLSSVVTVPSSSLGTQTYI
CNVNHKPSNTKVDKRVEPKSCDKTHTCPPCPAPELLGGPSVFLFPPKPKDTLMISRTPEVTCVVVDVSHEDPE
VKFNWYVDGVEVHNAKTKPREEQYNSTYRVVSVLTVLHQDWLNGKEYKCKVSNKALPAPIEKTISKAKGQPRE
PQVYTLPPSREEMTKNQVSLTCLVKGFYPSDIAVEWESNGQPENNYKTTPPVLDSDGSFFLYSKLTVDKSRWQ
QGNVFSCSVMHEALHNHYTQKSLSLSPGK
Signal sequence (1-19), Variable region (20-137), Constant region (138-467)

FIG. 39

SEQ ID NO:112: Nucleotide sequence of humanized hA2-11E-H4
ATGAAACACCTGTGGTTCTTCCTCCTGCTGGTGGCAGCTCCCAGATGGGTGCTGAGCGAAGTGCAGCTGGTGG
AATCTGGCGGCGGACTGGTGCAGCCTGGCGGATCTCTGAGACTGAGCTGTGCCGCCAGCGGCTTCACCTTCAG
CAACTACTACATGTACTGGATCCGGCAGGCCCCTGGCAAGGGCCTGGAATGGATCAGCAGCATCAACACCGAC
GGCGGCAGCACCTACTACCCCGATAGCGTGAAGGGCCGGTTCACCATCAGCCGGGACAACAGCAAGAACACCG
TGTACCTGCAGATGAACAGCCTGCGGGCCGAGGACACCGCCGTGTACTACTGTGCCAAGAGCACCCCCAACAT
CCCCCTGGCCTATTGGGGCCAGGGAACCCTCGTGACCGTCAGCTCAGCCTCCACCAAGGGCCCAAGCGTCTTC
CCCCTGGCACCCTCCTCCAAGAGCACCTCTGGCGGCACAGCCGCCCTGGGCTGCCTGGTCAAGGACTACTTCC
CCGAACCCGTGACCGTGAGCTGGAACTCAGGCGCCCTGACCAGCGGCGTGCACACCTTCCCCGCTGTCCTGCA
GTCCTCAGGACTCTACTCCCTCAGCAGCGTGGTGACCGTGCCCTCCAGCAGCTTGGGCACCCAGACCTACATC
TGCAACGTGAATCACAAGCCCAGCAACACCAAGGTGGACAAGAGAGTTGAGCCCAAATCTTGTGACAAAACTC
ACACATGCCCACCCTGCCCAGCACCTGAACTCCTGGGGGGACCCTCAGTCTTCCTCTTCCCCCCAAAACCCAA
GGACACCCTCATGATCTCCCGGACCCCTGAGGTCACATGCGTGGTGGTGGACGTGAGCCACGAAGACCCTGAG
GTCAAGTTCAACTGGTACGTGGACGGCGTGGAGGTGCATAATGCCAAGACAAAGCCCCGGGAGGAGCAGTACA
ACAGCACGTACCGGGTGGTCAGCGTCCTCACCGTCCTGCACCAGGACTGGCTGAATGGCAAGGAGTACAAGTG
CAAGGTCTCCAACAAAGCCCTCCCAGCCCCCATCGAGAAAACCATCTCCAAAGCCAAAGGCCAGCCCCGGGAA
CCACAGGTGTACACCCTGCCCCCATCCCGGGAGGAGATGACCAAGAACCAGGTCAGCCTGACCTGCCTGGTCA
AAGGCTTCTATCCCAGCGACATCGCCGTGGAGTGGGAGAGCAATGGCCAGCCCGAGAACAACTACAAGACCAC
CCCTCCCGTGCTGGACTCCGACGGCTCCTTCTTCCTCTACAGCAAGCTCACCGTGGACAAGAGCAGGTGGCAG
CAGGGCAACGTCTTCTCATGCTCCGTGATGCATGAGGCTCTGCACAACCACTACACCCAGAAGAGCCTCTCCC
TGTCTCCCGGCAAA
Signal sequence (1-57), Variable region (58-411), Constant region (412-1401)

SEQ ID NO:113: Amino acid sequence of humanized hA2-11E-H4
MKHLWFFLLLVAAPRWVLSEVQLVESGGGLVQPGGSLRLSCAASGFTFSNYYMYWIRQAPGKGLEWISSINTD
GGSTYYPDSVKGRFTISRDNSKNTVYLQMNSLRAEDTAVYYCAKSTPNIPLAYWGQGTLVTVSSASTKGPSVF
PLAPSSKSTSGGTAALGCLVKDYFPEPVTVSWNSGALTSGVHTFPAVLQSSGLYSLSSVVTVPSSSLGTQTYI
CNVNHKPSNTKVDKRVEPKSCDKTHTCPPCPAPELLGGPSVFLFPPKPKDTLMISRTPEVTCVVVDVSHEDPE
VKFNWYVDGVEVHNAKTKPREEQYNSTYRVVSVLTVLHQDWLNGKEYKCKVSNKALPAPIEKTISKAKGQPRE
PQVYTLPPSREEMTKNQVSLTCLVKGFYPSDIAVEWESNGQPENNYKTTPPVLDSDGSFFLYSKLTVDKSRWQ
QGNVFSCSVMHEALHNHYTQKSLSLSPGK
Signal sequence (1-19), Variable region (20-137), Constant region (138-467)

FIG. 40

SEQ ID NO:114: Nucleotide sequence of humanized hA2-11E-L2
ATGGTGCTGCAGACCCAGGTGTTCATCTCCCTGCTGCTGTGGATCTCCGGCGCGTACGGCGACATCCAGATGA
CCCAGAGCCCTAGCAGCCTGAGCGCCAGCGTGGGCGACAGAGTGACCATCACATGCAAGGCCAGCCAGAACAT
CTACAAGTACCTGAACTGGTTCCAGCAGAAGCCCGGCAAGGCCCCCAAGCTGCTGATCTACTACAGCAACAGC
CTGCAGACCGGCGTGCCCAGCAGATTTTCTGGCAGCGGCTCCGGCACCGACTTCACCCTGACAATCAGCTCCC
TGCAGCCCGAGGACTTCGCCACCTACTACTGCTTCCAGTACAGCAGCGGCCCCACCTTTGGCCAGGGCACCAA
GGTGGAAATCAAGCGTACGGTGGCCGCCCCCTCCGTGTTCATCTTCCCCCCCTCCGACGAGCAGCTGAAGTCC
GGCACCGCCTCCGTGGTGTGCCTGCTGAATAACTTCTACCCCAGAGAGGCCAAGGTGCAGTGGAAGGTGGACA
ACGCCCTGCAGTCCGGGAACTCCCAGGAGAGCGTGACCGAGCAGGACAGCAAGGACAGCACCTACAGCCTGAG
CAGCACCCTGACCCTGAGCAAAGCCGACTACGAGAAGCACAAGGTGTACGCCTGCGAGGTGACCCACCAGGGC
CTGAGCTCCCCCGTCACCAAGAGCTTCAACAGGGGGGAGTGT
Signal sequence (1-60), Variable region (61-384), Constant region (385-699)

SEQ ID NO:115: Amino acid sequence of humanized hA2-11E-L2
MVLQTQVFISLLLWISGAYGDIQMTQSPSSLSASVGDRVTITCKASQNIYKYLNWFQQKPGKAPKLLIYYSNS
LQTGVPSRFSGSGSGTDFTLTISSLQPEDFATYYCFQYSSGPTFGQGTKVEIKRTVAAPSVFIFPPSDEQLKS
GTASVVCLLNNFYPREAKVQWKVDNALQSGNSQESVTEQDSKDSTYSLSSTLTLSKADYEKHKVYACEVTHQG
LSSPVTKSFNRGEC
Signal sequence (1-20), Variable region (21-128), Constant region (129-233)

FIG. 41

SEQ ID NO:116: Nucleotide sequence of humanized hA2-11E-L3
ATGGTGCTGCAGACCCAGGTGTTCATCTCCCTGCTGCTGTGGATCTCCGGCGCGTACGGCGACATCCAGATGA
CCCAGAGCCCTAGCAGCCTGAGCGCCAGCGTGGGCGACAGAGTGACCATCACATGCAAGGCCAGCCAGAACAT
CTACAAGTACCTGAACTGGTTCCAGCAGAAGCCCGGCAAGGCCCCCAAGCTGCTGATCTACTACAGCAACAGC
CTGCAGACCGGCATCCCCAGCAGATTTTCTGGCAGCGGCTCCGGCACCGACTTCACCCTGACAATCAGCTCCC
TGCAGCCCGAGGACTTCGCCACCTACTACTGCTTCCAGTACAGCAGCGGCCCCACCTTTGGCCAGGGCACCAA
GGTGGAAATCAAGCGTACGGTGGCCGCCCCCTCCGTGTTCATCTTCCCCCCCTCCGACGAGCAGCTGAAGTCC
GGCACCGCCTCCGTGGTGTGCCTGCTGAATAACTTCTACCCCAGAGAGGCCAAGGTGCAGTGGAAGGTGGACA
ACGCCCTGCAGTCCGGGAACTCCCAGGAGAGCGTGACCGAGCAGGACAGCAAGGACAGCACCTACAGCCTGAG
CAGCACCCTGACCCTGAGCAAAGCCGACTACGAGAAGCACAAGGTGTACGCCTGCGAGGTGACCCACCAGGGC
CTGAGCTCCCCCGTCACCAAGAGCTTCAACAGGGGGGAGTGT
Signal sequence (1-60), Variable region (61-384), Constant region (385-699)

SEQ ID NO:117: Amino acid sequence of humanized hA2-11E-L3
MVLQTQVFISLLLWISGAYGDIQMTQSPSSLSASVGDRVTITCKASQNIYKYLNWFQQKPGKAPKLLIYYSNS
LQTGIPSRFSGSGSGTDFTLTISSLQPEDFATYYCFQYSSGPTFGQGTKVEIKRTVAAPSVFIFPPSDEQLKS
GTASVVCLLNNFYPREAKVQWKVDNALQSGNSQESVTEQDSKDSTYSLSSTLTLSKADYEKHKVYACEVTHQG
LSSPVTKSFNRGEC
Signal sequence (1-20), Variable region (21-128), Constant region (129-233)

FIG. 42

SEQ ID NO:118: Nucleotide sequence of humanized hA2-11E-L4
ATGGTGCTGCAGACCCAGGTGTTCATCTCCCTGCTGCTGTGGATCTCCGGCGCGTACGGCGACATCCAGATGA
CCCAGAGCCCTAGCAGCCTGAGCGCCAGCGTGGGCGATAGAGTGACCATCAGCTGCAAGGCCAGCCAGAACAT
CTACAAGTACCTGAACTGGTTCCAGCAGAAGCCCGGCGAGGCCCCCAAGCTGCTGATCTACTACAGCAACAGC
CTGCAGACCGGCATCCCCAGCAGATTTTCTGGCAGCGGCTCCGGCACCGACTTCACCCTGACAATCAGCTCCC
TGCAGCCCGAGGACTTCGCTATCTACTTCTGTTTTCAATACTCCAGCGGCCCCACCTTCGGCCCTGGCACCAA
GGTGGAAATCAAGCGTACGGTGGCCGCCCCCTCCGTGTTCATCTTCCCCCCCTCCGACGAGCAGCTGAAGTCC
GGCACCGCCTCCGTGGTGTGCCTGCTGAATAACTTCTACCCCAGAGAGGCCAAGGTGCAGTGGAAGGTGGACA
ACGCCCTGCAGTCCGGGAACTCCCAGGAGAGCGTGACCGAGCAGGACAGCAAGGACAGCACCTACAGCCTGAG
CAGCACCCTGACCCTGAGCAAAGCCGACTACGAGAAGCACAAGGTGTACGCCTGCGAGGTGACCCACCAGGGC
CTGAGCTCCCCCGTCACCAAGAGCTTCAACAGGGGGGAGTGT
Signal sequence (1-60), Variable region (61-384), Constant region (385-699)

SEQ ID NO:119: Amino acid sequence of humanized hA2-11E-L4
MVLQTQVFISLLLWISGAYGDIQMTQSPSSLSASVGDRVTISCKASQNIYKYLNWFQQKPGEAPKLLIYYSNS
LQTGIPSRFSGSGSGTDFTLTISSLQPEDFAIYFCFQYSSGPTFGPGTKVEIKRTVAAPSVFIFPPSDEQLKS
GTASVVCLLNNFYPREAKVQWKVDNALQSGNSQESVTEQDSKDSTYSLSSTLTLSKADYEKHKVYACEVTHQG
LSSPVTKSFNRGEC
Signal sequence (1-20), Variable region (21-128), Constant region (129-233)

FIG. 43

SEQ ID NO:120: Nucleotide sequence of humanized hA2-25C-H3
ATGAAACACCTGTGGTTCTTCCTCCTGCTGGTGGCAGCTCCCAGATGGGTGCTGAGCGAAGTGCAGCTGGTGG
AATCTGGCGGCGGACTGGTGCAGCCTGGCGGATCTCTGAGACTGAGCTGTGCCGCCAGCGGCTTCACCTTCAG
CTACTACGCCATGAGCTGGGTGCGCCAGGCCCCTGGAAAAGGCCTGGAATGGGTGGCCAGCATCAGCAGAGGC
GGCGACAACACCTACTACCGGGACAGCGTGAAGGGCCGGTTCACCACCAGCCGGGACAACAGCAAGAACACCC
TGTACCTGCAGATGAACAGCCTGCGGGCCGAGGACACCGCCGTGTACTATTGCGCCAGACTGAACTACAACAA
CTACTTCGACTACTGGGGCCAGGGCACCCTCGTGACCGTCAGCTCAGCCTCCACCAAGGGCCCAAGCGTCTTC
CCCCTGGCACCCTCCTCCAAGAGCACCTCTGGCGGCACAGCCGCCCTGGGCTGCCTGGTCAAGGACTACTTCC
CCGAACCCGTGACCGTGAGCTGGAACTCAGGCGCCCTGACCAGCGGCGTGCACACCTTCCCCGCTGTCCTGCA
GTCCTCAGGACTCTACTCCCTCAGCAGCGTGGTGACCGTGCCCTCCAGCAGCTTGGGCACCCAGACCTACATC
TGCAACGTGAATCACAAGCCCAGCAACACCAAGGTGGACAAGAGAGTTGAGCCCAAATCTTGTGACAAAACTC
ACACATGCCCACCCTGCCCAGCACCTGAACTCCTGGGGGGACCCTCAGTCTTCCTCTTCCCCCCAAAACCCAA
GGACACCCTCATGATCTCCCGGACCCCTGAGGTCACATGCGTGGTGGTGGACGTGAGCCACGAAGACCCTGAG
GTCAAGTTCAACTGGTACGTGGACGGCGTGGAGGTGCATAATGCCAAGACAAAGCCCCGGGAGGAGCAGTACA
ACAGCACGTACCGGGTGGTCAGCGTCCTCACCGTCCTGCACCAGGACTGGCTGAATGGCAAGGAGTACAAGTG
CAAGGTCTCCAACAAAGCCCTCCCAGCCCCCATCGAGAAAACCATCTCCAAAGCCAAAGGCCAGCCCCGGGAA
CCACAGGTGTACACCCTGCCCCCATCCCGGGAGGAGATGACCAAGAACCAGGTCAGCCTGACCTGCCTGGTCA
AAGGCTTCTATCCCAGCGACATCGCCGTGGAGTGGGAGAGCAATGGCCAGCCCGAGAACAACTACAAGACCAC
CCCTCCCGTGCTGGACTCCGACGGCTCCTTCTTCCTCTACAGCAAGCTCACCGTGGACAAGAGCAGGTGGCAG
CAGGGCAACGTCTTCTCATGCTCCGTGATGCATGAGGCTCTGCACAACCACTACACCCAGAAGAGCCTCTCCC
TGTCTCCCGGCAAA
Signal sequence (1-57), Variable region (58-411), Constant region (412-1401)

SEQ ID NO:121: Amino acid sequence of humanized hA2-25C-H3
MKHLWFFLLLVAAPRWVLSEVQLVESGGGLVQPGGSLRLSCAASGFTFSYYAMSWVRQAPGKGLEWVASISRG
GDNTYYRDSVKGRFTTSRDNSKNTLYLQMNSLRAEDTAVYYCARLNYNNYFDYWGQGTLVTVSSASTKGPSVF
PLAPSSKSTSGGTAALGCLVKDYFPEPVTVSWNSGALTSGVHTFPAVLQSSGLYSLSSVVTVPSSSLGTQTYI
CNVNHKPSNTKVDKRVEPKSCDKTHTCPPCPAPELLGGPSVFLFPPKPKDTLMISRTPEVTCVVVDVSHEDPE
VKFNWYVDGVEVHNAKTKPREEQYNSTYRVVSVLTVLHQDWLNGKEYKCKVSNKALPAPIEKTISKAKGQPRE
PQVYTLPPSREEMTKNQVSLTCLVKGFYPSDIAVEWESNGQPENNYKTTPPVLDSDGSFFLYSKLTVDKSRWQ
QGNVFSCSVMHEALHNHYTQKSLSLSPGK
Signal sequence (1-19), Variable region (20-137), Constant region (138-467)

FIG. 44

SEQ ID NO:122: Nucleotide sequence of humanized hA2-25C-H4
ATGAAACACCTGTGGTTCTTCCTCCTGCTGGTGGCAGCTCCCAGATGGGTGCTGAGCGAAGTGCAGCTGGTGG
AATCTGGCGGCGGACTGGTGCAGCCTGGCGGATCTCTGAGACTGAGCTGTGCCGCCAGCGGCTTCACCTTCAG
CTACTACGCCATGAGCTGGGTGCGCCAGGCCCCTGGAAAAGGCCTGGAATGGGTGGCCAGCATCAGCAGAGGC
GGCGACAACACCTACTACCGGGACAGCGTGAAGGGCCGGTTCACCACCAGCCGGGACAACAGCAAGAACACCC
TGTACCTGCAGATGAACAGCCTGCGGGCCGAGGACACCGCCACCTACTATTGCGCCAGACTGAACTACAACAA
CTACTTCGACTACTGGGGCCAGGGCGTGCTCGTGACCGTCAGCTCAGCCTCCACCAAGGGCCCAAGCGTCTTC
CCCCTGGCACCCTCCTCCAAGAGCACCTCTGGCGGCACAGCCGCCCTGGGCTGCCTGGTCAAGGACTACTTCC
CCGAACCCGTGACCGTGAGCTGGAACTCAGGCGCCCTGACCAGCGGCGTGCACACCTTCCCCGCTGTCCTGCA
GTCCTCAGGACTCTACTCCCTCAGCAGCGTGGTGACCGTGCCCTCCAGCAGCTTGGGCACCCAGACCTACATC
TGCAACGTGAATCACAAGCCCAGCAACACCAAGGTGGACAAGAGAGTTGAGCCCAAATCTTGTGACAAAACTC
ACACATGCCCACCCTGCCCAGCACCTGAACTCCTGGGGGGACCCTCAGTCTTCCTCTTCCCCCCAAAACCCAA
GGACACCCTCATGATCTCCCGGACCCCTGAGGTCACATGCGTGGTGGTGGACGTGAGCCACGAAGACCCTGAG
GTCAAGTTCAACTGGTACGTGGACGGCGTGGAGGTGCATAATGCCAAGACAAAGCCCCGGGAGGAGCAGTACA
ACAGCACGTACCGGGTGGTCAGCGTCCTCACCGTCCTGCACCAGGACTGGCTGAATGGCAAGGAGTACAAGTG
CAAGGTCTCCAACAAAGCCCTCCCAGCCCCCATCGAGAAAACCATCTCCAAAGCCAAAGGCCAGCCCCGGGAA
CCACAGGTGTACACCCTGCCCCCATCCCGGGAGGAGATGACCAAGAACCAGGTCAGCCTGACCTGCCTGGTCA
AAGGCTTCTATCCCAGCGACATCGCCGTGGAGTGGGAGAGCAATGGCCAGCCCGAGAACAACTACAAGACCAC
CCCTCCCGTGCTGGACTCCGACGGCTCCTTCTTCCTCTACAGCAAGCTCACCGTGGACAAGAGCAGGTGGCAG
CAGGGCAACGTCTTCTCATGCTCCGTGATGCATGAGGCTCTGCACAACCACTACACCCAGAAGAGCCTCTCCC
TGTCTCCCGGCAAA
Signal sequence (1-57), Variable region (58-411), Constant region (412-1401)

SEQ ID NO:123: Amino acid sequence of humanized hA2-25C-H4
MKHLWFFLLLVAAPRWVLSEVQLVESGGGLVQPGGSLRLSCAASGFTFSYYAMSWVRQAPGKGLEWVASISRG
GDNTYYRDSVKGRFTTSRDNSKNTLYLQMNSLRAEDTATYYCARLNYNNYFDYWGQGVLVTVSSASTKGPSVF
PLAPSSKSTSGGTAALGCLVKDYFPEPVTVSWNSGALTSGVHTFPAVLQSSGLYSLSSVVTVPSSSLGTQTYI
CNVNHKPSNTKVDKRVEPKSCDKTHTCPPCPAPELLGGPSVFLFPPKPKDTLMISRTPEVTCVVVDVSHEDPE
VKFNWYVDGVEVHNAKTKPREEQYNSTYRVVSVLTVLHQDWLNGKEYKCKVSNKALPAPIEKTISKAKGQPRE
PQVYTLPPSREEMTKNQVSLTCLVKGFYPSDIAVEWESNGQPENNYKTTPPVLDSDGSFFLYSKLTVDKSRWQ
QGNVFSCSVMHEALHNHYTQKSLSLSPGK
Signal sequence (1-19), Variable region (20-137), Constant region (138-467)

FIG. 45

SEQ ID NO:124: Nucleotide sequence of humanized hA2-25C-L1
ATGGTGCTGCAGACCCAGGTGTTCATCTCCCTGCTGCTGTGGATCTCCGGCGCGTACGGCGACATCCAGATGA
CCCAGAGCCCTAGCAGCCTGAGCGCCAGCGTGGGCGACAGAGTGACCATTACCTGTCAGGCCAGCCAGGACAT
CGGCAACTGGCTGAGCTGGTATCAGCAGAAGCCCGGCAAGGCCCCCAAGCTGCTGATCTACGGCGCCACATCT
CTGGCCGATGGCGTGCCCAGCAGATTTTCTGGCAGCGGCTCCGGCACCGACTTCACCCTGACAATCAGCAGCC
TGCAGCCCGAGGACTTCGCCACCTACTACTGTCTGCAAGCCTACAGCGCCCCCTTCACCTTTGGCCAGGGCAC
CAAGGTGGAAATCAAGCGTACGGTGGCCGCCCCCTCCGTGTTCATCTTCCCCCCCTCCGACGAGCAGCTGAAG
TCCGGCACCGCCTCCGTGGTGTGCCTGCTGAATAACTTCTACCCCAGAGAGGCCAAGGTGCAGTGGAAGGTGG
ACAACGCCCTGCAGTCCGGGAACTCCCAGGAGAGCGTGACCGAGCAGGACAGCAAGGACAGCACCTACAGCCT
GAGCAGCACCCTGACCCTGAGCAAAGCCGACTACGAGAAGCACAAGGTGTACGCCTGCGAGGTGACCCACCAG
GGCCTGAGCTCCCCCGTCACCAAGAGCTTCAACAGGGGGGAGTGT
Signal sequence (1-60), Variable region (61-387), Constant region (388-702)

SEQ ID NO:125: Amino acid sequence of humanized hA2-25C-L1
MVLQTQVFISLLLWISGAYGDIQMTQSPSSLSASVGDRVTITCQASQDIGNWLSWYQQKPGKAPKLLIYGATS
LADGVPSRFSGSGSGTDFTLTISSLQPEDFATYYCLQAYSAPFTFGQGTKVEIKRTVAAPSVFIFPPSDEQLK
SGTASVVCLLNNFYPREAKVQWKVDNALQSGNSQESVTEQDSKDSTYSLSSTLTLSKADYEKHKVYACEVTHQ
GLSSPVTKSFNRGEC
Signal sequence (1-20), Variable region (21-129), Constant region (130-234)

FIG. 46

SEQ ID NO:126: Nucleotide sequence of humanized hA2-25C-L2
ATGGTGCTGCAGACCCAGGTGTTCATCTCCCTGCTGCTGTGGATCTCCGGCGCGTACGGCGACATCCAGATGA
CCCAGAGCCCTAGCAGCCTGAGCGCCAGCGTGGGCGACAGAGTGACCATTACCTGTCAGGCCAGCCAGGACAT
CGGCAACTGGCTGAGCTGGTATCAGCAGAAGCCCGGCAAGGCCCCCAAGCTGCTGATCTACGGCGCCACATCT
CTGGCCGATGGCGTGCCCAGCAGATTCAGCGGCAGCAGATCCGGCACCGACTACACCCTGACCATCAGCAGCC
TGCAGCCCGAGGACTTCGCCACCTACTACTGTCTGCAAGCCTACAGCGCCCCCTTCACCTTTGGCCAGGGCAC
CAAGGTGGAAATCAAGCGTACGGTGGCCGCCCCCTCCGTGTTCATCTTCCCCCCCTCCGACGAGCAGCTGAAG
TCCGGCACCGCCTCCGTGGTGTGCCTGCTGAATAACTTCTACCCCAGAGAGGCCAAGGTGCAGTGGAAGGTGG
ACAACGCCCTGCAGTCCGGGAACTCCCAGGAGAGCGTGACCGAGCAGGACAGCAAGGACAGCACCTACAGCCT
GAGCAGCACCCTGACCCTGAGCAAAGCCGACTACGAGAAGCACAAGGTGTACGCCTGCGAGGTGACCCACCAG
GGCCTGAGCTCCCCCGTCACCAAGAGCTTCAACAGGGGGGAGTGT
Signal sequence (1-60), Variable region (61-387), Constant region (388-702)

SEQ ID NO:127: Amino acid sequence of humanized hA2-25C-L2
MVLQTQVFISLLLWISGAYGDIQMTQSPSSLSASVGDRVTITCQASQDIGNWLSWYQQKPGKAPKLLIYGATS
LADGVPSRFSGSRSGTDYTLTISSLQPEDFATYYCLQAYSAPFTFGQGTKVEIKRTVAAPSVFIFPPSDEQLK
SGTASVVCLLNNFYPREAKVQWKVDNALQSGNSQESVTEQDSKDSTYSLSSTLTLSKADYEKHKVYACEVTHQ
GLSSPVTKSFNRGEC
Signal sequence (1-20), Variable region (21-129), Constant region (130-234)

FIG. 47

SEQ ID NO:128: Nucleotide sequence of humanized hA2-25C-L3
ATGGTGCTGCAGACCCAGGTGTTCATCTCCCTGCTGCTGTGGATCTCCGGCGCGTACGGCGACATCCAGATGA
CCCAGAGCCCTAGCAGCCTGAGCGCCAGCGTGGGCGACAGAGTGACCATTACCTGTCAGGCCAGCCAGGACAT
CGGCAACTGGCTGAGCTGGTATCAGCAGAAGCCCGGCAAGAGCCCCAAGCTGCTGATCTACGGCGCCACCTCT
CTGGCCGATGGCGTGCCAAGCAGATTCAGCGGCAGCAGATCCGGCACCCAGTACACCCTGACCATCAGCAGCC
TGCAGCCCGAGGACTTCGCCACCTACTACTGTCTGCAAGCCTACAGCGCCCCCTTCACCTTTGGCAGCGGCAC
CAAGGTGGAAATCAAGCGTACGGTGGCCGCCCCCTCCGTGTTCATCTTCCCCCCCTCCGACGAGCAGCTGAAG
TCCGGCACCGCCTCCGTGGTGTGCCTGCTGAATAACTTCTACCCCAGAGAGGCCAAGGTGCAGTGGAAGGTGG
ACAACGCCCTGCAGTCCGGGAACTCCCAGGAGAGCGTGACCGAGCAGGACAGCAAGGACAGCACCTACAGCCT
GAGCAGCACCCTGACCCTGAGCAAAGCCGACTACGAGAAGCACAAGGTGTACGCCTGCGAGGTGACCCACCAG
GGCCTGAGCTCCCCCGTCACCAAGAGCTTCAACAGGGGGGAGTGT
Signal sequence (1-60), Variable region (61-387), Constant region (388-702)

SEQ ID NO:129: Amino acid sequence of humanized hA2-25C-L3
MVLQTQVFISLLLWISGAYGDIQMTQSPSSLSASVGDRVTITCQASQDIGNWLSWYQQKPGKSPKLLIYGATS
LADGVPSRFSGSRSGTQYTLTISSLQPEDFATYYCLQAYSAPFTFGSGTKVEIKRTVAAPSVFIFPPSDEQLK
SGTASVVCLLNNFYPREAKVQWKVDNALQSGNSQESVTEQDSKDSTYSLSSTLTLSKADYEKHKVYACEVTHQ
GLSSPVTKSFNRGEC
Signal sequence (1-20), Variable region (21-129), Constant region (130-234)

FIG. 48
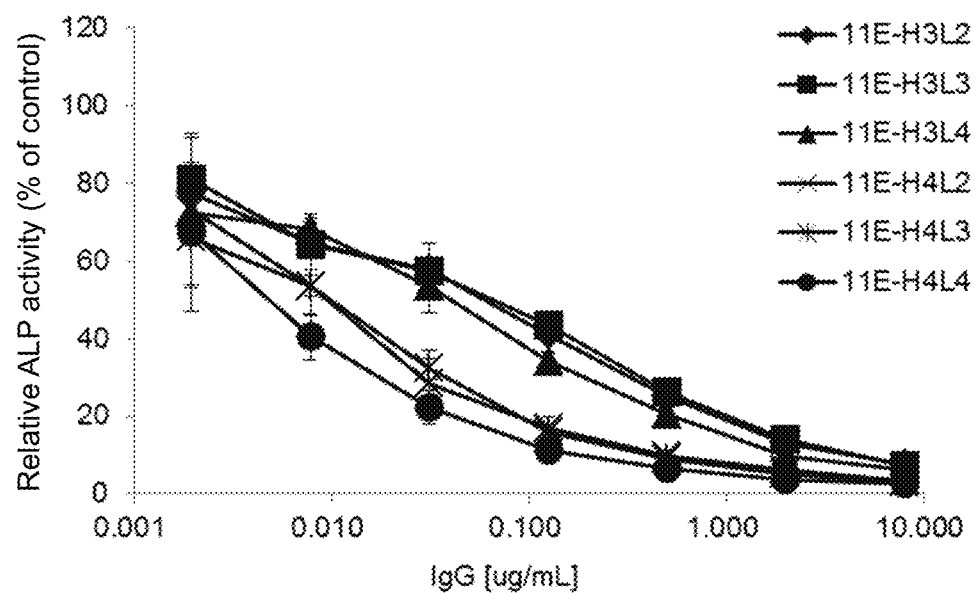
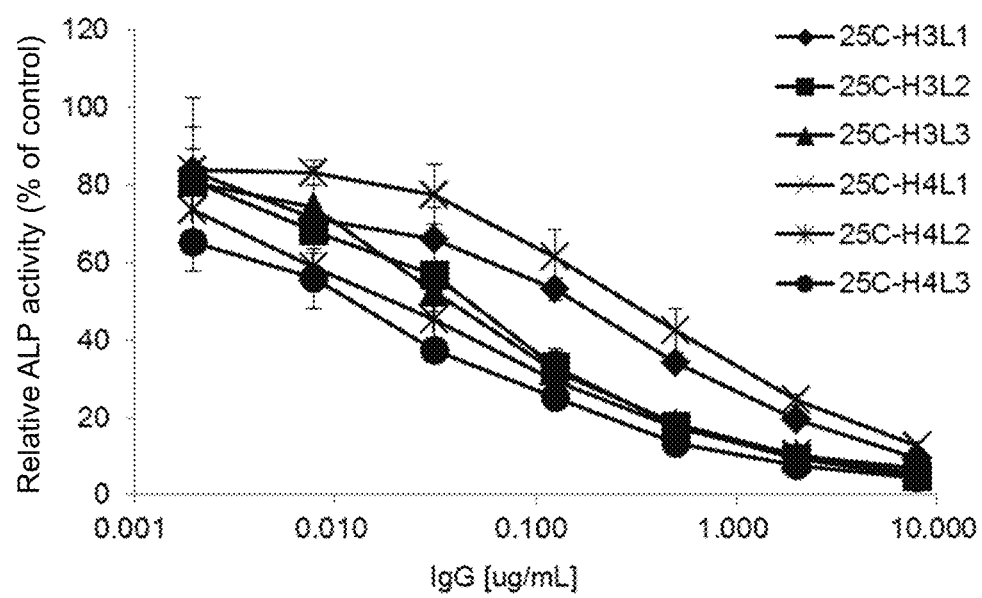

ANTI-ALK2 ANTIBODY

CROSS-REFERENCE TO RELATED APPLICATIONS

This application is a Divisional of U.S. application Ser. No. 16/543,991, filed Aug. 19, 2019, which is a Divisional of U.S. application Ser. No. 15/547,231, now U.S. Pat. No. 10,428,148, which is the U.S. National Stage application of PCT/JP2016/052602, filed Jan. 29, 2016, which claims priority from Japanese application JP 2015-017882, filed Jan. 30, 2015.

The instant application contains a Sequence Listing which has been submitted in ASCII format via EFS-WEB and is hereby incorporated by reference in its entirety. Said ASCII copy, created on Oct. 26, 2021, is named sequence.txt and is 202,712 bytes.

TECHNICAL FIELD

The present invention relates to a substance useful as a therapeutic and/or prophylactic drug for ectopic ossification and/or bone dysplasia, and to a method for treating and/or preventing ectopic ossification and/or bone dysplasia.

BACKGROUND ART

Fibrodysplasia ossificans progressiva (FOP) is a genetic disease which causes cartilage tissues or bone tissues to be ectopically formed in soft tissues, such as skeletal muscle, tendon, and ligament, where bone tissues are not normally formed (Non Patent Literatures 1 to 3). In this disease, ectopic ossification occurs throughout the entire body including the face so that ectopic bones and existing normal bones are fused to remarkably reduce the range of joint motion or to deform the body (Non Patent Literatures 1 to 3).

The ectopic ossification in FOP proceeds chronically with growth, whereas acute ectopic ossification is also known which proceeds while manifesting a symptom called flare-up caused by muscle injury, viral infection, or the like (Non Patent Literature 1). The flare-up is swelling with inflammatory response or sustained pain as principal symptoms. The flare-up is induced by bruise, falling, intramuscular injection, or the like, which causes muscle injury. In addition, sudden flare-ups with no clear cause are also known. For FOP, invasive medical acts such as biopsy and operation are contraindicated because ectopic bones are formed after flare-up. Thus, the ectopic bone tissues cannot be surgically removed. The ectopic bone tissues in FOP are consisted of normal cartilage cells or osteoblasts and bone metabolismee of heterotopic bones is the same as normal bone tissues. As such, only the ectopic bone tissues cannot be medically removed using drugs or the like.

Any fundamental therapy for suppressing the ectopic ossification in FOP has not yet been established, and only symptomatic treatment for pain or the like has been made. Thus, the ectopic bone tissues formed in FOP are very difficult to remove, and the development of a promising drug that can exert prophylactic effects before the onset of ectopic ossification has been expected.

Activin like kinase 2 (ALK2) gene encoding a receptor of bone morphogenetic proteins (BMPs) that induces ectopic bone formation in soft tissues including skeletal muscle tissues has been identified as a responsible gene for FOP (Non Patent Literature 4). The ALK2 gene is identical to activin A type I receptor 1 (ACVR1) gene. ALK2 having an amino acid substitution has been found from familial and sporadic FOP cases (Non Patent Literature 4).

Human or mouse ALK2 is a single-pass transmembrane protein consisting of 509 amino acids and having a signal peptide and functions as a transmembrane type of serine-threonine kinase receptor binding to BMPs (Non Patent Literatures 1 to 3). ALK2 binds to BMPs at its N-terminal extracellular region and activates the downstream intracellular signal transduction system through an intracellular serine-threonine kinase.

BMP receptors are classified based on their structures and functions into 2 types: type I receptors including ALK2; and type II receptors (Non Patent Literatures 1 to 3). The type II receptors are constitutively active enzymes that exhibit kinase activity even if not bound with BMP. On the other hand, the type I receptors including ALK2 are inactive enzymes in a state unbound with BMP and exhibit kinase activity in a manner dependent on binding to BMP. This is probably because upon binding to BMP, type II receptor kinase phosphorylates type I receptor intracellular domain as the substrate, which can change its conformation, and activates the type I receptor (Non Patent Literatures 1 to 3).

Type I receptors are known to be constitutive active independent of a type II receptor by substitution of a particular amino acid in the intracellular region (Non Patent Literatures 1 to 3). Overexpression of this constitutively active mutants of the type I receptors activate the intracellular signal transduction system without BMP stimulation. Thus, the type I receptors are considered as responsible molecules that transduce BMP signals from the outside to the inside of cells.

A mutation in ALK2 identified from familial and typical sporadic FOP patients was the R206H mutation in which Arg206 is substituted by His (Non Patent Literature 4). All of gene mutations previously identified from FOP cases have been reported to cause amino acid substitutions in the intracellular region of ALK2. Most of these mutations from FOP cases reside mainly in or around the ATP-binding region in the intracellular domain of ALK2 (Non Patent Literature 5).

Overexpression of the ALK2 mutants identified in FOP in cultured cells activates the intracellular signal transduction system of BMP without BMP stimulation (Non Patent Literature 6). Accordingly, for example, small molecular inhibitors for ALK2 kinase, RNAi or exon skipping methods which specifically suppress the expression of genetically mutated ALK2, downstream transcriptional factor inhibitors of ALK2 receptor, and inhibitors of BMP signal-mediated osteoblast differentiation are being developed as therapeutics for FOP (Patent Literature 1 and Non Patent Literatures 1 to 3).

All of small molecular compounds or nucleic acids currently under development as therapeutics for FOP are expected to inhibit intracellular ALK2 signal after they penetrate cell membranes. However, any effective drug delivery method has not yet been established for nucleic acid drugs. In addition, there still remain problems such as the low specificity of kinase inhibitors for other ALK receptor families with high similarity to ALK2. As such, it has been desired to develop novel therapeutics for FOP having high specificity for ALK2. Antibody drugs that act on the extracellular region of ALK2 and inhibit its signal are highly safe therapeutic approach that utilize the physiological immune system. The antibody drugs facilitate stable drug delivery via blood flow and are capable of specifically inhibiting ALK2 without acting on other ALK receptor families with high identity thereto. Furthermore, the antibody drugs can be expected to have inhibitory effect on wild-type ALK2 and various intracellular mutant ALK2s including novel unidentified mutants. The antibody drugs are expected not to inhibit ALK3 expressed in cells throughout the body. Therefore, unlike general osteoblast differentiation inhibitors, antibodies specifically inhibiting ALK2 can be expected to serve as drugs less likely to influence the growth, maintenance, and regeneration of normal skeletal tissues. However, any antibody that specifically binds to ALK2 and exhibits therapeutic effects on FOP has not been known so far.

PRIOR ART LITERATURE

Patent Literature

Patent Literature 1: International Publication No. WO2007/123896

Non Patent Literature

Non Patent Literature 1: T. Katagiri, J. Oral Biosci., 52, 33-41 (2010)
Non Patent Literature 2: T. Katagiri, J. Oral Biosci., 54, 119-123 (2012)
Non Patent Literature 3: T. Katagiri and S. Tsukamoto, Biol. Chem., 394, 703-714 (2013)
Non Patent Literature 4: E. M. Shore et al., Nat. Genet., 38, 525-527 (2006)
Non Patent Literature 5: A. Chaikuad et al., J. Biol. Chem., 287, 36990-36998 (2012)
Non Patent Literature 6: T. Fukuda et al., J. Biol. Chem., 284, 7149-7156 (2009)

SUMMARY OF INVENTION

Problem to be Solved by the Invention

An object of the present invention is to provide a substance useful as a therapeutic and/or prophylactic drug for ectopic ossification and/or bone dysplasia, and a method for treating and/or preventing ectopic ossification and/or bone dysplasia.

Means for Solution of the Problem

The present inventors have now conducted diligent studies to attain the object and consequently completed the present invention through successfully obtaining a novel antibody that specifically binds to ALK2 and has therapeutic and/or prophylactic effects on ectopic ossification and/or bone dysplasia.

Specifically, the present invention encompasses the following aspects:

(1) An antibody or an antigen-binding fragment thereof which specifically binds to a polypeptide sequence consisting of at least 7 amino acids in any one of the following amino acid sequences (a) to (e) and inhibits ALK2-mediated BMP signal transduction:
(a) the amino acid sequence of SEQ ID NO: 84;
(b) an amino acid sequence consisting of amino acid numbers 21 to 123 of the amino acid sequence of SEQ ID NO: 84;
(c) the amino acid sequence of SEQ ID NO: 86;
(d) an amino acid sequence consisting of amino acid numbers 21 to 123 of the amino acid sequence of SEQ ID NO: 86; and
(e) an amino acid sequence comprising a substitution(s), deletion(s), or addition(s) of one to several amino acid residues in any one of the amino acid sequences (a) to (d).

(2) An antibody or an antigen-binding fragment thereof which specifically binds to a polypeptide sequence consisting of at least 7 amino acids in an amino acid sequence encoded by any one of the following nucleotide sequences (f) to (j) and inhibits ALK2-mediated BMP signal transduction:
(f) the nucleotide sequence of SEQ ID NO: 85;
(g) a nucleotide sequence consisting of nucleotide numbers 728 to 1036 of the nucleotide sequence of SEQ ID NO: 85;
(h) the nucleotide sequence of SEQ ID NO: 87;
(i) a nucleotide sequence consisting of nucleotide numbers 728 to 1036 of the nucleotide sequence of SEQ ID NO: 87; and
(j) a nucleotide sequence of a polynucleotide hybridizing under stringent conditions to a polynucleotide consisting of the nucleotide sequence complementary to any one of the nucleotide sequences (f) to (i).

(3) The antibody or the antigen-binding fragment thereof according to (1) or (2), wherein the polypeptide sequence is a sequence in an ALK2 extracellular region.

(4) The antibody or the antigen-binding fragment thereof according to any one of (1) to (3), wherein the antibody binds to a wild-type ALK2 protein and a mutant ALK2 protein.

(5) The antibody or the antigen-binding fragment thereof according to any one of (1) to (4), wherein the antibody is a monoclonal antibody or a polyclonal antibody.

(6) The antibody or the antigen-binding fragment thereof according to any one of (1) to (5), wherein the antibody or the antigen-binding fragment is a chimeric antibody, a humanized antibody, a human antibody, a single-chain antibody, a bispecific antibody, or a multispecific antibody.

(7) The antibody or the antigen-binding fragment thereof according to any one of (1) to (6), wherein the antibody or the antigen-binding fragment cross-competes, for binding to the polypeptide, with at least any one antibody selected from the group consisting of an antibody comprising a heavy chain variable region consisting of the amino acid sequence of SEQ ID NO: 2 and a light chain variable region consisting of the amino acid sequence of SEQ ID NO: 4, an antibody comprising a heavy chain variable region consisting of the amino acid sequence of SEQ ID NO: 6 and a light chain variable region consisting of the amino acid sequence of SEQ ID NO: 8, an antibody comprising a heavy chain variable region consisting of the amino acid sequence of SEQ ID NO: 10 and a light chain variable region consisting of the amino acid sequence of SEQ ID NO: 12, and an antibody comprising a heavy chain variable region consisting of the amino acid sequence of SEQ ID NO: 14 and a light chain variable region consisting of the amino acid sequence of SEQ ID NO: 16.

(8) The antibody or the antigen-binding fragment thereof according to any one of (1) to (6), wherein the antibody or the antigen-binding fragment binds to an epitope that is bound by at least any one antibody selected from the group consisting of an antibody comprising a heavy chain variable region consisting of the amino acid sequence of SEQ ID NO: 2 and a light chain variable region consisting of the amino acid sequence of SEQ ID NO: 4, an antibody comprising a heavy chain variable region consisting of the amino acid sequence of SEQ ID NO: 6 and a light chain variable region consisting of the amino acid sequence of SEQ ID NO: 8, an antibody comprising a heavy chain variable region consisting of the amino acid sequence of SEQ ID NO: 10 and a light chain variable region consisting of the amino acid sequence of SEQ ID NO: 12, and an antibody comprising a heavy chain variable region consisting of the amino acid sequence of SEQ ID NO: 14 and a light chain variable region consisting of the amino acid sequence of SEQ ID NO: 16.

(9) The antibody or the antigen-binding fragment thereof according to any one of (1) to (6), wherein the antibody or the antigen-binding fragment binds to an epitope comprising each residue of glutamic acid (Glu) at position 18, glycine (Gly) at position 19, isoleucine (Ile) at position 39, asparagine (Asn) at position 40, aspartic acid (Asp) at position 41, glycine (Gly) at position 42, phenylalanine (Phe) at position 43, histidine (His) at position 44, valine (Val) at position 45, tyrosine (Tyr) at position 46, asparagine (Asn) at position 82, threonine (Thr) at position 84, glutamine (Gln) at position 86, and leucine (Leu) at position 87 in the amino acid sequence of SEQ ID NO: 84.

(10) The antibody or the antigen-binding fragment thereof according to any one of (1) to (6), having an interaction distance between the antibody or the antigen-binding fragment and each residue of glutamic acid (Glu) at position 18, glycine (Gly) at position 19, isoleucine (Ile) at position 39, asparagine (Asn) at position 40, aspartic acid (Asp) at position 41, glycine (Gly) at position 42, phenylalanine (Phe) at position 43, histidine (His) at position 44, valine (Val) at position 45, tyrosine (Tyr) at position 46, asparagine (Asn) at position 82, threonine (Thr) at position 84, glutamine (Gln) at position 86, and leucine (Leu) at position 87 in the amino acid sequence of SEQ ID NO: 84.

(11) The antibody or the antigen-binding fragment thereof according to any one of (1) to (6), wherein the antibody or the antigen-binding fragment binds to an epitope comprising each residue of glutamic acid (Glu) at position 18, glycine (Gly) at position 19, leucine (Leu) at position 20, isoleucine (Ile) at position 39, aspartic acid (Asp) at position 41, glycine (Gly) at position 42, phenylalanine (Phe) at position 43, histidine (His) at position 44, valine (Val) at position 45, tyrosine (Tyr) at position 46, and threonine (Thr) at position 84 in the amino acid sequence of SEQ ID NO: 84.

(12) The antibody or the antigen-binding fragment thereof according to any one of (1) to (6), having an interaction distance between the antibody or the antigen-binding fragment and each residue of glutamic acid (Glu) at position 18, glycine (Gly) at position 19, leucine (Leu) at position 20, isoleucine (Ile) at position 39, aspartic acid (Asp) at position 41, glycine (Gly) at position 42, phenylalanine (Phe) at position 43, histidine (His) at position 44, valine (Val) at position 45, tyrosine (Tyr) at position 46, and threonine (Thr) at position 84 in the amino acid sequence of SEQ ID NO: 84.

(13) The antibody or the antigen-binding fragment thereof according to (10) or (12), wherein the interaction distance is 6 angstroms or smaller.

(14) The antibody or the antigen-binding fragment thereof according to (10) or (12), wherein the interaction distance is 4 angstroms or smaller.

(15) The antibody or the antigen-binding fragment thereof according to any one of (1) to (8), wherein
the heavy chain sequence comprises a variable region having CDRH1, CDRH2, and CDRH3, wherein the CDRH1 consists of the amino acid sequence of SEQ ID NO: 72, the CDRH2 consists of the amino acid sequence of SEQ ID NO: 73, and the CDRH3 consists of the amino acid sequence of SEQ ID NO: 74, and
the light chain sequence comprises a variable region having CDRL1, CDRL2, and CDRL3, wherein the CDRL1 consists of the amino acid sequence of SEQ ID NO: 75, the CDRL2 consists of the amino acid sequence of SEQ ID NO: 76, and the CDRL3 consists of the amino acid sequence of SEQ ID NO: 77.

(16) The antibody or the antigen-binding fragment thereof according to (15), wherein the antibody comprises a heavy chain variable region sequence consisting of the amino acid sequence of SEQ ID NO: 2 and a light chain variable region sequence consisting of the amino acid sequence of SEQ ID NO: 4.

(17) The antibody or the antigen-binding fragment thereof according to any one of (1) to (8), wherein
the heavy chain sequence comprises a variable region having CDRH1, CDRH2, and CDRH3, wherein the CDRH1 consists of an amino acid sequence of SEQ ID NO: 59, the CDRH2 consists of an amino acid sequence of SEQ ID NO: 60, and the CDRH3 consists of an amino acid sequence of SEQ ID NO: 61, and
the light chain sequence comprises a variable region having CDRL1, CDRL2, and CDRL3, wherein the CDRL1 consists of the amino acid sequence of SEQ ID NO: 62, the CDRL2 consists of the amino acid sequence of SEQ ID NO: 63 or SEQ ID NO: 71, and the CDRL3 consists of the amino acid sequence of SEQ ID NO: 64.

(18) The antibody or the antigen-binding fragment thereof according to (17), wherein the antibody comprises a heavy chain variable region sequence consisting of the amino acid sequence of SEQ ID NO: 6 and a light chain variable region sequence consisting of the amino acid sequence of SEQ ID NO: 8 or the amino acid numbers 21 to 133 of the amino acid sequence of SEQ ID NO: 36.

(19) The antibody or the antigen-binding fragment of the antibody according to any one of (1) to (10), (13) and (14), wherein
a heavy chain sequence comprises a variable region having CDRH1, CDRH2, and CDRH3, wherein the CDRH1 consists of the amino acid sequence of SEQ ID NO: 78, the CDRH2 consists of the amino acid sequence of SEQ ID NO: 79, and the CDRH3 consists of the amino acid sequence of SEQ ID NO: 80; and a light chain sequence comprises a variable region having CDRL1, CDRL2, and CDRL3, wherein the CDRL1 consists of the amino acid sequence of SEQ ID NO: 81, the CDRL2 consists of the amino acid sequence of SEQ ID NO: 82, and the CDRL3 consists of the amino acid sequence of SEQ ID NO: 83.

(20) The antibody or the antigen-binding fragment thereof according to (19), wherein the antibody comprises a heavy chain variable region sequence consisting of the amino acid sequence of SEQ ID NO: 10 and a light chain variable region sequence consisting of the amino acid sequence of SEQ ID NO: 12.

(21) The antibody or the antigen-binding fragment thereof according to any one of (1) to (8) and (11) to (14), wherein
a heavy chain sequence comprises a variable region having CDRH1, CDRH2, and CDRH3, wherein the CDRH1 consists of the amino acid sequence of SEQ ID NO: 65, the CDRH2 consists of the amino acid sequence of SEQ ID NO: 66, and the CDRH3 consists of the amino acid sequence of SEQ ID NO: 67; and
a light chain sequence comprises a variable region having CDRL1, CDRL2, and CDRL3, wherein the CDRL1 consists of the amino acid sequence of SEQ ID NO: 68, the CDRL2 consists of the amino acid sequence of SEQ ID NO: 69, and the CDRL3 consists of the amino acid sequence of SEQ ID NO: 70.

(22) The antibody or the antigen-binding fragment thereof according to (21), wherein the antibody comprises a heavy chain variable region sequence consisting of the amino acid sequence of SEQ ID NO: 14 and a light chain variable region sequence consisting of the amino acid sequence of SEQ ID NO: 16.

(23) The antigen-binding fragment thereof according to any one of (1) to (22), wherein the antigen-binding fragment is selected from the group consisting of Fab, F(ab')$_2$, Fab', and Fv.

(24) The antibody according to any one of (1) to (22), wherein the antibody is scFv.

(25) The antibody or the antigen-binding fragment thereof according to any one of (1) to (22), wherein the antibody is a chimeric antibody.

(26) The antibody or the antigen-binding fragment thereof according to any one of (1) to (22), wherein the antibody is humanized.

(27) The antibody according to any one of (1) to (24), wherein the heavy chain comprises a constant region of a human immunoglobulin G1 heavy chain, a human immunoglobulin G2 heavy chain, or a human immunoglobulin G4 heavy chain, and the light chain comprises a constant region of a human immunoglobulin κ light chain.

(28) The antibody according to (27), wherein the heavy chain comprises a constant region of a human immunoglobulin G1 heavy chain.

(29) The antibody according to (28), wherein in the human immunoglobulin G1 heavy chain, leucine (Leu) at position 234 is substituted by alanine (Ala), and leucine (Leu) at position 235 is substituted by alanine (Ala).

(30) The antibody according to (27), wherein the heavy chain comprises a constant region of a human immunoglobulin G2 heavy chain.

(31) The antibody according to (27), wherein the heavy chain comprises a constant region of a human immunoglobulin G4 heavy chain.

(32) The antibody according to (31), wherein in the human immunoglobulin G4 heavy chain, serine (Ser) at position 241 is substituted by proline (Pro).

(33) An antibody or an antigen-binding fragment thereof which specifically binds to an extracellular region of ALK2 protein and inhibits ALK2-mediated BMP signal transduction, wherein the antibody or the antigen-binding fragment comprises (a) a heavy chain variable region sequence selected from the group consisting of the following amino acid sequences:
a1) an amino acid sequence consisting of amino acid numbers 20 to 142 of the amino acid sequence of SEQ ID NO: 28;
a2) an amino acid sequence consisting of amino acid numbers 20 to 142 of the amino acid sequence of SEQ ID NO: 30;
a3) an amino acid sequence consisting of amino acid numbers 20 to 142 of the amino acid sequence of SEQ ID NO: 105;
a4) an amino acid sequence having at least 95% identity to any of the amino acid sequences a1) to a3);
a5) an amino acid sequence having at least 99% identity to any of the amino acid sequences a1) to a3); and
a6) an amino acid sequence comprising a substitution(s), a deletion(s), or an addition(s) of one to several amino acid residues in any of the amino acid sequences a1) to a3); and
(b) a light chain variable region sequence selected from the group consisting of the following amino acid sequences:
b1) an amino acid sequence consisting of amino acid numbers 21 to 133 of the amino acid sequence of SEQ ID NO: 32;
b2) an amino acid sequence consisting of amino acid numbers 21 to 133 of the amino acid sequence of SEQ ID NO: 34;
b3) an amino acid sequence consisting of amino acid numbers 21 to 133 of the amino acid sequence of SEQ ID NO: 36;
b4) an amino acid sequence consisting of amino acid numbers 21 to 133 of the amino acid sequence of SEQ ID NO: 38;
b5) an amino acid sequence having at least 95% identity to any one amino acid sequence selected from the amino acid sequences b1) to b4);
b6) an amino acid sequence having at least 99% identity to any one amino acid sequence selected from the amino acid sequences b1) to b4); and
b7) an amino acid sequence comprising a substitution(s), a deletion(s), or an addition(s) of one to several amino acid residues in any one amino acid sequence selected from the amino acid sequences b1) to b4).

(34) The antibody or the antigen-binding fragment thereof according to (33), wherein the antibody is an antibody consisting of a heavy chain comprising a heavy chain variable region sequence consisting of amino acid numbers 20 to 142 of the amino acid sequence of SEQ ID NO: 30 and a light chain comprising a light chain variable region sequence consisting of amino acid numbers 21 to 133 of the amino acid sequence of SEQ ID NO: 36, or an antibody consisting of a heavy chain comprising a heavy chain variable region sequence consisting of amino acid numbers 20 to 142 of the amino acid sequence of SEQ ID NO: 105 and a light chain comprising a light chain variable region sequence consisting of amino acid numbers 21 to 133 of the amino acid sequence of SEQ ID NO: 36.

(35) The antibody according to (33), wherein the antibody is an antibody consisting of a heavy chain comprising an amino acid sequence consisting of amino acid numbers 20 to 472 of the amino acid sequence of SEQ ID NO: 30 and a light chain comprising an amino acid sequence consisting of amino acid numbers 21 to 238 of the amino acid sequence of SEQ ID NO: 36, or an antibody consisting of a heavy chain comprising an amino acid sequence consisting of amino acid numbers 20 to 468 of the amino acid sequence of SEQ ID NO: 105 and a light chain comprising an amino acid sequence consisting of amino acid numbers 21 to 238 of the amino acid sequence of SEQ ID NO: 36.

(36) The antibody according to (33), wherein the antibody is an antibody consisting of a heavy chain comprising an amino acid sequence consisting of amino acid numbers 20 to 468 of the amino acid sequence of SEQ ID NO: 105 and a light chain comprising an amino acid sequence consisting of amino acid numbers 21 to 238 of the amino acid sequence of SEQ ID NO: 36.

(37) An antibody or an antigen-binding fragment thereof which specifically binds to an extracellular region of ALK2 protein and inhibits ALK2-mediated BMP signal transduction, wherein the antibody comprises
(a) a heavy chain variable region sequence selected from the group consisting of the following amino acid sequences:
a1) an amino acid sequence consisting of amino acid numbers 20 to 140 of the amino acid sequence of SEQ ID NO: 40;
a2) an amino acid sequence consisting of amino acid numbers 20 to 140 of the amino acid sequence of SEQ ID NO: 42;
a3) an amino acid sequence consisting of amino acid numbers 20 to 140 of the amino acid sequence of SEQ ID NO: 44;

a4) an amino acid sequence consisting of the amino acid numbers 20 to 140 of the amino acid sequence of SEQ ID NO: 46;
a5) an amino acid sequence consisting of amino acid numbers 20 to 140 of an amino acid sequence of SEQ ID NO: 48;
a6) an amino acid sequence consisting of amino acid numbers 20 to 140 of the amino acid sequence of SEQ ID NO: 107;
a7) an amino acid sequence consisting of amino acid numbers 20 to 140 of the amino acid sequence of SEQ ID NO: 109;
a8) an amino acid sequence having at least 95% identity to any one amino acid sequence selected from the amino acid sequences a1) to a7);
a9) an amino acid sequence having at least 99% identity to any one amino acid sequence selected from the amino acid sequences a1) to a7); and
a10) an amino acid sequence comprising a substitution(s), a deletion(s), or an addition(s) of one to several amino acid residues in any one amino acid sequence selected from the amino acid sequences a1) to a7); and
(b) a light chain variable region sequence selected from the group consisting of the following amino acid sequences:
b1) an amino acid sequence consisting of amino acid numbers 21 to 129 of the amino acid sequence of SEQ ID NO: 50;
b2) an amino acid sequence consisting of amino acid numbers 21 to 129 of an amino acid sequence of SEQ ID NO: 52;
b3) an amino acid sequence consisting of amino acid numbers 21 to 129 of the amino acid sequence of SEQ ID NO: 54;
b4) an amino acid sequence consisting of amino acid numbers 21 to 129 of an amino acid sequence of SEQ ID NO: 56;
b5) an amino acid sequence consisting of amino acid numbers 21 to 129 of the amino acid sequence of SEQ ID NO: 58;
b6) an amino acid sequence having at least 95% identity to any one amino acid sequence selected from the amino acid sequences b1) to b5);
b7) an amino acid sequence having at least 99% identity to any one amino acid sequence selected from the amino acid sequences b1) to b5); and
b8) an amino acid sequence comprising a substitution(s), a deletion(s), or an addition(s) of one to several amino acid residues in any one amino acid sequence selected from the amino acid sequences b1) to b5).

(38) The antibody or the antigen-binding fragment thereof according to (37), wherein the antibody is an antibody consisting of a heavy chain comprising a heavy chain variable region sequence consisting of amino acid numbers 20 to 140 of the amino acid sequence of SEQ ID NO: 42 and a light chain comprising a light chain variable region sequence consisting of amino acid numbers 21 to 129 of the amino acid sequence of SEQ ID NO: 52, an antibody consisting of a heavy chain comprising a heavy chain variable region sequence consisting of amino acid numbers 20 to 140 of the amino acid sequence of SEQ ID NO: 44 and a light chain comprising a light chain variable region sequence consisting of amino acid numbers 21 to 129 of the amino acid sequence of SEQ ID NO: 56, an antibody consisting of a heavy chain comprising a heavy chain variable region sequence consisting of amino acid numbers 20 to 140 of the amino acid sequence of SEQ ID NO: 107 and a light chain comprising a light chain variable region sequence consisting of amino acid numbers 21 to 129 of the amino acid sequence of SEQ ID NO: 52, or an antibody consisting of a heavy chain comprising a heavy chain variable region sequence consisting of amino acid numbers 20 to 140 of the amino acid sequence of SEQ ID NO: 109 and a light chain comprising a light chain variable region sequence consisting of amino acid numbers 21 to 129 of the amino acid sequence of SEQ ID NO: 56.

(39) The antibody according to (37), wherein the antibody is an antibody consisting of a heavy chain comprising an amino acid sequence consisting of amino acid numbers 20 to 470 of the amino acid sequence of SEQ ID NO: 42 and a light chain comprising an amino acid sequence consisting of amino acid numbers 21 to 234 of the amino acid sequence of SEQ ID NO: 52, an antibody consisting of a heavy chain comprising an amino acid sequence consisting of amino acid numbers 20 to 470 of the amino acid sequence of SEQ ID NO: 44 and a light chain comprising an amino acid sequence consisting of amino acid numbers 21 to 234 of the amino acid sequence of SEQ ID NO: 56, an antibody consisting of a heavy chain comprising an amino acid sequence consisting of amino acid numbers 20 to 470 of the amino acid sequence of SEQ ID NO: 107 and a light chain comprising an amino acid sequence consisting of amino acid numbers 21 to 234 of the amino acid sequence of SEQ ID NO: 52, or an antibody consisting of a heavy chain comprising an amino acid sequence consisting of amino acid numbers 20 to 470 of the amino acid sequence of SEQ ID NO: 109 and a light chain comprising an amino acid sequence consisting of amino acid numbers 21 to 234 of the amino acid sequence of SEQ ID NO: 56.

(40) The antibody according to (37), wherein the antibody is an antibody consisting of a heavy chain comprising an amino acid sequence consisting of amino acid numbers 20 to 470 of the amino acid sequence of SEQ ID NO: 107 and a light chain comprising an amino acid sequence consisting of amino acid numbers 21 to 234 of the amino acid sequence of SEQ ID NO: 52, or an antibody consisting of a heavy chain comprising an amino acid sequence consisting of amino acid numbers 20 to 470 of the amino acid sequence of SEQ ID NO: 109 and a light chain comprising an amino acid sequence consisting of amino acid numbers 21 to 234 of the amino acid sequence of SEQ ID NO: 56.

(41) An antibody or an antigen-binding fragment thereof which specifically binds to an extracellular region of ALK2 protein and inhibits ALK2-mediated BMP signal transduction, wherein the antibody comprises
(a) a heavy chain variable region sequence selected from the group consisting of the following amino acid sequences:
a1) an amino acid sequence consisting of amino acid numbers 20 to 137 of the amino acid sequence of SEQ ID NO: 111;
a2) an amino acid sequence consisting of amino acid numbers 20 to 137 of the amino acid sequence of SEQ ID NO: 113;
a3) an amino acid sequence having at least 95% identity to the amino acid sequence a1) or a2);
a4) an amino acid sequence having at least 99% identity to the amino acid sequence a1) or a2); and
a5) an amino acid sequence comprising a substitution(s), a deletion(s), or an addition(s) of one to several amino acid residues in the amino acid sequence a1) or a2); and
(b) a light chain variable region sequence selected from the group consisting of the following amino acid sequences:
b1) an amino acid sequence consisting of amino acid numbers 21 to 128 of the amino acid sequence of SEQ ID NO: 115;

b2) an amino acid sequence consisting of amino acid numbers 21 to 128 of the amino acid sequence of SEQ ID NO: 117;
b3) an amino acid sequence consisting of amino acid numbers 21 to 128 of the amino acid sequence of SEQ ID NO: 119;
b4) an amino acid sequence having at least 95% identity to any one amino acid sequence selected from the amino acid sequences b1) to b3);
b5) an amino acid sequence having at least 99% identity to any one amino acid sequence selected from the amino acid sequences b1) to b3); and
b6) an amino acid sequence comprising a substitution(s), a deletion(s), or an addition(s) of one to several amino acid residues in any one amino acid sequence selected from the amino acid sequences b1) to b3).

(42) An antibody or an antigen-binding fragment thereof which specifically binds to an extracellular region of ALK2 protein and inhibits ALK2-mediated BMP signal transduction, wherein the antibody comprises
(a) a heavy chain variable region sequence selected from the group consisting of the following amino acid sequences:
a1) an amino acid sequence consisting of amino acid numbers 20 to 137 of the amino acid sequence of SEQ ID NO: 121;
a2) an amino acid sequence consisting of amino acid numbers 20 to 137 of the amino acid sequence of SEQ ID NO: 123;
a3) an amino acid sequence having at least 95% identity to the amino acid sequence a1) or a2);
a4) an amino acid sequence having at least 99% identity to the amino acid sequence a1) or a2); and
a5) an amino acid sequence comprising a substitution(s), a deletion(s), or an addition(s) of one to several amino acid residues in the amino acid sequence a1) or a2); and
(b) a light chain variable region sequence selected from the group consisting of the following amino acid sequences:
b1) an amino acid sequence consisting of amino acid numbers 21 to 129 of the amino acid sequence of SEQ ID NO: 125;
b2) an amino acid sequence consisting of amino acid numbers 21 to 129 of the amino acid sequence of SEQ ID NO: 127;
b3) an amino acid sequence consisting of amino acid numbers 21 to 129 of the amino acid sequence of SEQ ID NO: 129;
b4) an amino acid sequence having at least 95% identity to any one amino acid sequence selected from the amino acid sequences b1) to b3);
b5) an amino acid sequence having at least 99% identity to any one amino acid sequence selected from the amino acid sequences b1) to b3); and
b6) an amino acid sequence comprising a substitution(s), a deletion(s), or an addition(s) of one to several amino acid residues in any one amino acid sequence selected from the amino acid sequences b1) to b3).

(43) The antibody according to any one of (1) to (42), wherein the antibody is an antibody comprising a heavy chain in which one to several carboxyl-terminal amino acids are deleted.

(44) The antibody or the antigen-binding fragment thereof according to any one of (1) to (43), wherein the antibody is an antibody having a pyroglutamylated amino-terminal amino acid residue in a heavy or light chain thereof.

(45) A pharmaceutical composition comprising at least one antibody or antigen-binding fragment according to any one of (1) to (44).

(46) The pharmaceutical composition according to (45), wherein the pharmaceutical composition is a therapeutic and/or prophylactic drug for ectopic ossification.

(47) A pharmaceutical composition for the treatment and/or prevention of ectopic ossification, comprising at least any one antibody or antigen-binding fragment thereof according to any one of (1) to (44) and at least any one drug selected from the group consisting of anti-inflammatory drugs, steroids, bisphosphonates, muscle relaxants, and retinoic acid receptor (RAR) γ agonists.

(48) The pharmaceutical composition according to (46) or (47), wherein the ectopic ossification is fibrodysplasia ossificans progressiva (FOP), progressive osseous heteroplasia (POH), traumatic ectopic ossification, or ectopic ossification after implant arthroplasty.

(49) The pharmaceutical composition according to (46) or (47), wherein the ectopic ossification is fibrodysplasia ossificans progressiva (FOP).

(50) The pharmaceutical composition according to (45), wherein the pharmaceutical composition is a therapeutic and/or prophylactic drug for anemia.

(51) The pharmaceutical composition according to (45), wherein the pharmaceutical composition is a therapeutic and/or prophylactic drug for diffuse intrinsic pontine glioma (DIPG).

(52) A method for treating and/or preventing ectopic ossification, comprising administering at least one antibody or antigen-binding fragment according to any one of (1) to (44), or at least one pharmaceutical composition according to any one of (45) to (49).

(53) A method for treating and/or preventing ectopic ossification, comprising administering at least one antibody or antigen-binding fragment thereof according to any one of (1) to (44), or at least one pharmaceutical composition according to any one of (45) to (49), and at least any one drug selected from the group consisting of anti-inflammatory drugs steroids, bisphosphonates, muscle relaxants, and retinoic acid receptor (RAR) γ agonists, concurrently (or, at the same time) or separately (or, one after another).

(54) The method according to (52) or (53), wherein the ectopic ossification is fibrodysplasia ossificans progressiva (FOP), progressive osseous heteroplasia (POH), traumatic ectopic ossification, or ectopic ossification after implant arthroplasty.

(55) The method according to (52) or (53), wherein the ectopic ossification is fibrodysplasia ossificans progressiva (FOP).

(56) A method for treating and/or preventing anemia, comprising administering at least one antibody or antigen-binding fragment according to any one of (1) to (44), or at least one pharmaceutical composition according to (45) or (50).

(57) A method for treating and/or preventing diffuse intrinsic pontine glioma (DIPG), comprising administering at least one antibody or antigen-binding fragment according to any one of (1) to (44), or at least one pharmaceutical composition according to (45) or (51).

(58) A polynucleotide encoding an antibody according to any one of (1) to (44).

(59) A polynucleotide comprising
(a) a polynucleotide selected from the group consisting of the following nucleotide sequences:
a1) a nucleotide sequence consisting of nucleotide numbers 58 to 426 of the nucleotide sequence of SEQ ID NO: 27;
a2) a nucleotide sequence consisting of nucleotide numbers 58 to 426 of the nucleotide sequence of SEQ ID NO: 29;

a3) a nucleotide sequence consisting of nucleotide numbers 58 to 426 of the nucleotide sequence of SEQ ID NO: 104;
a4) a nucleotide sequence having at least 95% identity to any of the nucleotide sequences a1) to a3);
a5) a nucleotide sequence having at least 99% identity to any of the nucleotide sequences a1) to a3);
a6) a nucleotide sequence carried by a polynucleotide hybridizing under stringent conditions to a polynucleotide consisting of a nucleotide sequence complementary to any of the nucleotide sequences a1) to a3); and
a7) a nucleotide sequence comprising a substitution(s), a deletion(s), or an addition(s) of one to several nucleotides in the nucleotide sequence a1) or a2); and/or
(b) a polynucleotide selected from the group consisting of the following nucleotide sequences:
b1) a nucleotide sequence consisting of nucleotide numbers 86 to 424 of the nucleotide sequence of SEQ ID NO: 31;
b2) a nucleotide sequence consisting of nucleotide numbers 86 to 424 of the nucleotide sequence of SEQ ID NO: 33;
b3) a nucleotide sequence consisting of nucleotide numbers 86 to 424 of the nucleotide sequence of SEQ ID NO: 35;
b4) a nucleotide sequence consisting of nucleotide numbers 86 to 424 of the nucleotide sequence of SEQ ID NO: 37;
b5) a nucleotide sequence having at least 95% identity to any one nucleotide sequence selected from the nucleotide sequences b1) to b4);
b6) a nucleotide sequence having at least 99% identity to any one nucleotide sequence selected from the nucleotide sequences b1) to b4);
b7) a nucleotide sequence carried by a polynucleotide hybridizing under stringent conditions to a polynucleotide consisting of a nucleotide sequence complementary to any one nucleotide sequence selected from the nucleotide sequences b1) to b4); and
b8) a nucleotide sequence comprising a substitution(s), a deletion(s), or an addition(s) of one to several nucleotides in any one nucleotide sequence selected from the nucleotide sequences b1) to b4).

(60) A polynucleotide comprising
(a) a polynucleotide selected from the group consisting of the following nucleotide sequences:
a1) a nucleotide sequence consisting of nucleotide numbers 58 to 420 of the nucleotide sequence of SEQ ID NO: 39;
a2) a nucleotide sequence consisting of nucleotide numbers 58 to 420 of the nucleotide sequence of SEQ ID NO: 41;
a3) a nucleotide sequence consisting of nucleotide numbers 58 to 420 of the nucleotide sequence of SEQ ID NO: 43;
a4) a nucleotide sequence consisting of nucleotide numbers 58 to 420 of the nucleotide sequence of SEQ ID NO: 45;
a5) a nucleotide sequence consisting of nucleotide numbers 58 to 420 of the nucleotide sequence of SEQ ID NO: 47;
a6) a nucleotide sequence consisting of nucleotide numbers 58 to 420 of the nucleotide sequence of SEQ ID NO: 106;
a7) a nucleotide sequence consisting of nucleotide numbers 58 to 420 of the nucleotide sequence of SEQ ID NO: 108;
a8) a nucleotide sequence having at least 95% identity to any one nucleotide sequence selected from the nucleotide sequences a1) to a7);
a9) a nucleotide sequence having at least 99% identity to any one nucleotide sequence selected from the nucleotide sequences a1) to a7);
a10) a nucleotide sequence carried by a polynucleotide hybridizing under stringent conditions to a polynucleotide consisting of a nucleotide sequence complementary to any one nucleotide sequence selected from the nucleotide sequences a1) to a7); and
a11) a nucleotide sequence comprising a substitution(s), a deletion(s), or an addition(s) of one to several nucleotides in any one nucleotide sequence selected from the nucleotide sequences a1) to a7); and/or
(b) a polynucleotide selected from the group consisting of the following nucleotide sequences:
b1) a nucleotide sequence consisting of nucleotide numbers 86 to 412 of the nucleotide sequence of SEQ ID NO: 49;
b2) a nucleotide sequence consisting of nucleotide numbers 86 to 412 of the nucleotide sequence of SEQ ID NO: 51;
b3) a nucleotide sequence consisting of nucleotide numbers 86 to 412 of the nucleotide sequence of SEQ ID NO: 53;
b4) a nucleotide sequence consisting of nucleotide numbers 86 to 412 of the nucleotide sequence of SEQ ID NO: 55;
b5) a nucleotide sequence consisting of nucleotide numbers 86 to 412 of the nucleotide sequence of SEQ ID NO: 57;
b6) a nucleotide sequence having at least 95% identity to any one nucleotide sequence selected from the nucleotide sequences b1) to b5);
b7) a nucleotide sequence having at least 99% identity to any one nucleotide sequence selected from the nucleotide sequences b1) to b5);
b8) a nucleotide sequence carried by a polynucleotide hybridizing under stringent conditions to a polynucleotide consisting of a nucleotide sequence complementary to any one nucleotide sequence selected from the nucleotide sequences b1) to b5); and
b9) a nucleotide sequence comprising a substitution(s), a deletion(s), or an addition(s) of one to several nucleotides in any one nucleotide sequence selected from the nucleotide sequences b1) to b5).

(61) A polynucleotide comprising
(a) a polynucleotide selected from the group consisting of the following nucleotide sequences:
a1) a nucleotide sequence consisting of nucleotide numbers 58 to 411 of the nucleotide sequence of SEQ ID NO: 110;
a2) a nucleotide sequence consisting of nucleotide numbers 58 to 411 of the nucleotide sequence of SEQ ID NO: 112;
a3) a nucleotide sequence having at least 95% identity to the nucleotide sequence a1) or a2);
a4) a nucleotide sequence having at least 99% identity to the nucleotide sequence a1) or a2);
a5) a nucleotide sequence carried by a polynucleotide hybridizing under stringent conditions to a polynucleotide consisting of a nucleotide sequence complementary to the nucleotide sequence a1) or a2); and
a6) a nucleotide sequence comprising a substitution(s), a deletion(s), or an addition(s) of one to several nucleotides in the nucleotide sequence a1) or a2); and/or
(b) a polynucleotide selected from the group consisting of the following nucleotide sequences:
b1) a nucleotide sequence consisting of nucleotide numbers 61 to 384 of the nucleotide sequence of SEQ ID NO: 114;
b2) a nucleotide sequence consisting of nucleotide numbers 61 to 384 of the nucleotide sequence of SEQ ID NO: 116;
b3) a nucleotide sequence consisting of nucleotide numbers 61 to 384 of the nucleotide sequence of SEQ ID NO: 118;
b4) a nucleotide sequence having at least 95% identity to any one nucleotide sequence selected from the nucleotide sequences b1) to b3);
b5) a nucleotide sequence having at least 99% identity to any one nucleotide sequence selected from the nucleotide sequences b1) to b3);
b6) a nucleotide sequence carried by a polynucleotide hybridizing under stringent conditions to a polynucleotide consisting of a nucleotide sequence complementary to any one nucleotide sequence selected from the nucleotide sequences b1) to b3); and b7) a nucleotide sequence comprising a substitution(s), a deletion(s), or an addition(s) of one to several nucleotides in any one nucleotide sequence selected from the nucleotide sequences b1) to b3).

(62) A polynucleotide comprising
(a) a polynucleotide selected from the group consisting of the following nucleotide sequences:
a1) a nucleotide sequence consisting of nucleotide numbers 58 to 411 of the nucleotide sequence of SEQ ID NO: 120;
a2) a nucleotide sequence consisting of nucleotide numbers 58 to 411 of the nucleotide sequence of SEQ ID NO: 122;
a3) a nucleotide sequence having at least 95% identity to the nucleotide sequence a1) or a2);
a4) a nucleotide sequence having at least 99% identity to the nucleotide sequence a1) or a2);
a5) a nucleotide sequence carried by a polynucleotide hybridizing under stringent conditions to a polynucleotide consisting of a nucleotide sequence complementary to the nucleotide sequence a1) or a2); and
a6) a nucleotide sequence comprising a substitution(s), a deletion(s), or an addition(s) of one to several nucleotides in the nucleotide sequence a1) or a2); and/or
(b) a polynucleotide selected from the group consisting of the following nucleotide sequences:
b1) a nucleotide sequence consisting of nucleotide numbers 61 to 387 of the nucleotide sequence of SEQ ID NO: 124;
b2) a nucleotide sequence consisting of nucleotide numbers 61 to 387 of the nucleotide sequence of SEQ ID NO: 126;
b3) a nucleotide sequence consisting of nucleotide numbers 61 to 387 of the nucleotide sequence of SEQ ID NO: 128;
b4) a nucleotide sequence having at least 95% identity to any one nucleotide sequence selected from the nucleotide sequences b1) to b3);
b5) a nucleotide sequence having at least 99% identity to any one nucleotide sequence selected from the nucleotide sequences b1) to b3);
b6) a nucleotide sequence carried by a polynucleotide hybridizing under stringent conditions to a polynucleotide consisting of a nucleotide sequence complementary to any one nucleotide sequence selected from the nucleotide sequences b1) to b3); and
b7) a nucleotide sequence comprising a substitution(s), a deletion(s), or an addition(s) of one to several nucleotides in any one nucleotide sequence selected from the nucleotide sequences b1) to b3).

(63) A vector comprising any one polynucleotide according to any one of (58) to (62).

(64) A transformed host cell comprising any one polynucleotide according to any one of (58) to (62).

(65) A transformed host cell comprising a vector according to (63).

(66) A method for producing an antibody according to any one of (1) to (44), comprising the step of culturing a host cell according to (64) or (65) and purifying the antibody from the culture product.

According to the present invention, a therapeutic and/or prophylactic drug for ectopic ossification and/or bone dysplasia can be obtained.

The present specification encompasses the contents disclosed in Japanese Patent Application No. 2015-017882 from which the present application claims the priority.

BRIEF DESCRIPTION OF DRAWINGS

FIG. 11 This figure shows the amino acid sequence of each CDR sequence of the A2-15A antibody.

FIG. 12 This figure shows the amino acid sequence of each CDR sequence of the A2-27D antibody.

FIG. 13 This figure shows the amino acid sequence of each CDR sequence of the A2-11E antibody.

FIG. 14 This figure shows the amino acid sequence of each CDR sequence of the A2-25C antibody.

FIG. 15 This figure shows the nucleotide sequence and amino acid sequence of humanized hA2-15A-H1.

FIG. 16 This figure shows the nucleotide sequence and amino acid sequence of humanized hA2-15A-H4.

FIG. 17 This figure shows the nucleotide sequence of a DNA fragment comprising sequences encoding humanized hA2-15A-L1, and the amino acid sequence thereof.

FIG. 18 This figure shows the nucleotide sequence of a DNA fragment comprising sequences encoding humanized hA2-15A-L4, and the amino acid sequence thereof.

FIG. 19 This figure shows the nucleotide sequence of a DNA fragment comprising sequences encoding humanized hA2-15A-L6, and the amino acid sequence thereof.

FIG. 20 This figure shows the nucleotide sequence of a DNA fragment comprising sequences encoding humanized hA2-15A-L7, and the amino acid sequence thereof.

FIG. 21 This figure shows the nucleotide sequence and amino acid sequence of humanized hA2-27D-H1.

FIG. 22 This figure shows the nucleotide sequence and amino acid sequence of humanized hA2-27D-H2.

FIG. 23 This figure shows the nucleotide sequence and amino acid sequence of humanized hA2-27D-H3.

FIG. 24 This figure shows the nucleotide sequence and amino acid sequence of humanized hA2-27D-H4.

FIG. 25 This figure shows the nucleotide sequence and amino acid sequence of humanized hA2-27D-H5.

FIG. 26 This figure shows the nucleotide sequence of a DNA fragment comprising sequences encoding humanized hA2-27D-L1, and the amino acid sequence thereof.

FIG. 27 This figure shows the nucleotide sequence of a DNA fragment comprising sequences encoding humanized hA2-27D-L2, and the amino acid sequence thereof.

FIG. 28 This figure shows the nucleotide sequence of a DNA fragment comprising sequences encoding humanized hA2-27D-L3, and the amino acid sequence thereof.

FIG. 29 This figure shows the nucleotide sequence of a DNA fragment comprising sequences encoding humanized hA2-27D-L4, and the amino acid sequence thereof.

FIG. 30 This figure shows the nucleotide sequence of a DNA fragment comprising sequences encoding humanized hA2-27D-L5, and the amino acid sequence thereof.

FIG. 32 This figure shows the nucleotide sequence and amino acid sequence of humanized hA2-15A-H4 IgG2 type.

FIG. 33 This figure shows the nucleotide sequence and amino acid sequence of humanized hA2-27D-H2-LALA.

FIG. 34 This figure shows the nucleotide sequence and amino acid sequence of humanized hA2-27D-H3-LALA.

FIG. 38 This figure shows the nucleotide sequence and amino acid sequence of humanized hA2-11E-H3.

FIG. 39 This figure shows the nucleotide sequence and amino acid sequence of humanized hA2-11E-H4.

FIG. 40 This figure shows the nucleotide sequence and amino acid sequence of humanized hA2-11E-L2.

FIG. 41 This figure shows the nucleotide sequence and amino acid sequence of humanized hA2-11E-L3.

FIG. 42 This figure shows the nucleotide sequence and amino acid sequence of humanized hA2-11E-L4.

FIG. 43 This figure shows the nucleotide sequence and amino acid sequence of humanized hA2-25C-H3.

FIG. 44 This figure shows the nucleotide sequence and amino acid sequence of humanized hA2-25C-H4.

FIG. 45 This figure shows the nucleotide sequence and amino acid sequence of humanized hA2-25C-L1.

FIG. 46 This figure shows the nucleotide sequence and amino acid sequence of humanized hA2-25C-L2.

FIG. 47 This figure shows the nucleotide sequence and amino acid sequence of humanized hA2-25C-L3.

FIG. 48 This figure is a graph showing that humanized A2-11E antibodies (IgG1) and humanized A2-25C antibodies (IgG1) inhibit, in a dose-dependent manner, the BMP-induced differentiation of C2C12 cells into osteoblast-like cells.

MODES FOR CARRYING OUT THE INVENTION

1. Definition

Figure 1:
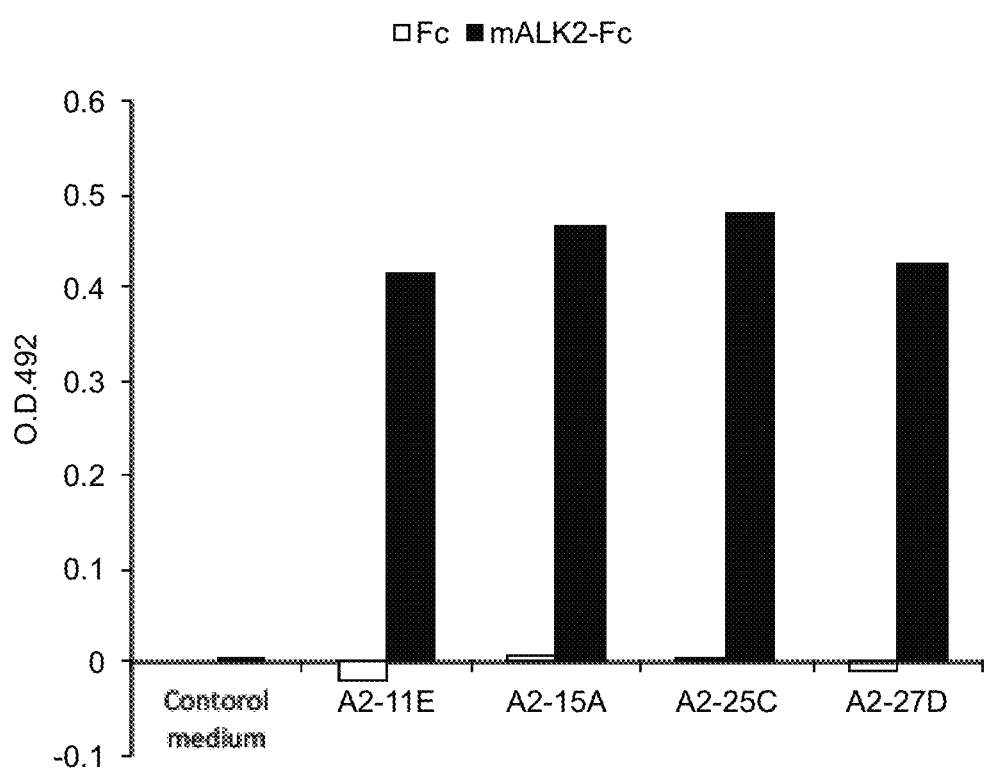
FIG. 1 This figure is a graph showing the recognition of mouse ALK2-His&Fc ("mALK2-Fc") by monoclonal antibodies produced by hybridomas A2-11E, A2-15A, A2-25C, and A2-27D, and the binding of these monoclonal antibodies to human Fc. A medium was used as a control ("Control medium").

As used herein, the term "gene" includes not only DNA but mRNA, cDNA, and cRNA.

As used herein, the term "polynucleotide" is used with the same meaning as a nucleic acid and also includes DNA, RNA, probes, oligonucleotides, and primers.

As used herein, the "polypeptide" and the "protein" are used interchangeably with each other.

As used herein, the "RNA fraction" refers to a fraction containing RNA.

As used herein, the "cell" also includes cells within animal individuals and cultured cells.

As used herein, "ALK2" is used with the same meaning as ALK2 protein and includes wild-type ALK2 and mutants (also referred to as mutant ALK2).

As used herein, the "antigen-binding fragment of an (the) antibody", also called "functional fragment of an (the) antibody", means a partial fragment of the antibody having an activity binding to the antigen and includes, for example, Fab, F(ab')$_2$, Fv, scFv, diabodies, linear antibodies, and multispecific antibodies formed from antibody fragments. The antigen-binding fragment of an antibody also includes Fab', which is a monovalent fragment of antibody variable regions obtained by treatment of F(ab')$_2$ under reducing conditions. However, the antigen-binding fragment of an antibody is not limited to these molecules as long as the antigen-binding fragment has the ability to bind to the antigen. Such an antigen-binding fragment includes not only a fragment obtained by treating a full-length molecule of the antibody protein with an appropriate enzyme but a protein produced in appropriate host cells using a genetically engineered antibody gene.

As used herein, the "epitope", also called "antigenic determinant", generally refers to an antibody-binding antigenic site consisting of at least 7 amino acids, at least 8 amino acids, at least 9 amino acids, or at least 10 amino acids, of an antigen. As used herein, the epitope means a partial peptide or a partial conformation of ALK2 to which a particular anti-ALK2 antibody binds. The epitope as a partial peptide of ALK2 can be determined by a method well known to those skilled in the art such as immunoassay and can be determined, for example, by the following method: various partial structures of ALK2 are prepared. For the preparation of the partial structures, an oligopeptide synthesis technique known in the art can be used. For example, a series of polypeptide fragments having an appropriate length are prepared in order from the C or N terminus of ALK2 by use of a gene recombination technique well known to those skilled in the art. Then, the reactivity of the antibody therewith is studied to roughly determine a recognition site. Then, shorter peptides are synthesized, and the reactivity of the antibody with these peptides can be studied to determine the epitope. Alternatively, the epitope as a partial conformation of ALK2 to which a particular ALK2 antibody binds can be determined by identifying amino acid residues of ALK2 adjacent to the antibody by X-ray crystal structure analysis. Provided that a second anti-ALK2 antibody binds to a partial peptide or a partial conformation that is bound by a first anti-ALK2 antibody, the first antibody and the second antibody can be determined to share an epitope. If the specific sequence or structure of an epitope is not determined, the first antibody and the second antibody can be determined to share the epitope by confirming that the second anti-ALK2 antibody (cross-)competes with the first anti-ALK2 antibody for binding to ALK2 (i.e., that the second antibody interferes with the binding of the first antibody to ALK2). When the first antibody and the second antibody bind to a common epitope and the first antibody has an activity such as inhibitory activity against ALK2-mediated BMP signals, the second antibody can also be expected to have similar activity.

The heavy and light chains of an antibody molecule are known to each have three complementarity determining regions (CDRs). The complementarity determining regions, also called hypervariable domains, are located in the variable regions of the antibody heavy and light chains. These sites have a particularly highly variable primary structure and are separated at three places on the respective primary structures of heavy and light chain polypeptide chains. As used herein, the complementarity determining regions of an antibody are referred to as CDRH1, CDRH2, and CDRH3 from the amino terminus of the heavy chain amino acid sequence for the complementarity determining regions of the heavy chain and as CDRL1, CDRL2, and CDRL3 from the amino terminus of the light chain amino acid sequence for the complementarity determining regions of the light chain. These sites are proximal to each other on the conformation and determine specificity for the antigen to be bound.

In the present invention, the wording "hybridizing under stringent conditions" means hybridization under conditions involving hybridization at approximately 50 to 70° C. (e.g., 68° C.) in a commercially available hybridization solution ExpressHyb Hybridization Solution (manufactured by Clontech Laboratories, Inc.), or hybridization at approximately 50 to 70° C. (e.g., 68° C.) in the presence of approximately 0.7 to 1.0 M NaCl using a DNA-immobilized filter, followed by washing at approximately 50 to 70° C. (e.g., 68° C.) using an SSC solution having an approximately 0.1 to 2× concentration (SSC having a 1× concentration consists of 150 mM NaCl and 15 mM sodium citrate; if necessary, the solution may contain approximately 0.1 to 0.5% SDS) which permits identification, or hybridization under conditions equivalent thereto.

As used herein, the term "several" in the phrase "one to several" and "one or several" refers to 2 to 10. The term "several" is preferably 10 or less, more preferably 5 or 6 or less, further preferably 2 or 3.

2. ALK2

The ALK2 gene is a responsible gene for FOP encoding a receptor of BMP that induces ectopic bone formation in soft tissues including skeletal muscle tissues. Mutant ALK2 having amino acid substitutions has been found from familial and sporadic FOP cases. For example, L196P (mutation that substitutes leucine at position 196 by proline), delP197_F198insL (mutation that deletes proline at position 197 and phenylalanine at position 198 and inserts leucine), R202I (mutation that substitutes arginine at position 202 by isoleucine), R206H (mutation that substitutes arginine at position 206 by histidine), Q207E (mutation that substitutes glutamine at position 207 by glutamic acid), R258S (mutation that substitutes arginine at position 258 by serine), R258G (mutation that substitutes arginine at position 258 by glycine), G325A (mutation that substitutes glycine at position 325 by alanine), G328E (mutation that substitutes glycine at position 328 by glutamic acid), G328R (mutation that substitutes glycine at position 328 by arginine), G328W (mutation that substitutes glycine at position 328 by tryptophan), G356D (mutation that substitutes glycine at position 356 by aspartic acid), and R375P (mutation that substitutes arginine at position 375 by proline) mutants are known as mutants of human ALK2.

ALK2 used in the present invention can be obtained by in vitro synthesis or by production from host cells through gene manipulation. Specifically, ALK2 cDNA is inserted into a vector that permits expression. Then, the ALK2 protein can be obtained by synthesis in a solution containing enzymes, substrates, and energy substances necessary for transcription and translation, or by expression from other prokaryotic or eukaryotic host cells transformed with the vector.

ALK2 used in the present invention is ALK2 derived from a mammal including a human or a mouse. For example, the amino acid sequence and nucleotide sequence of human ALK2 are available with reference to GenBank Accession No. NM-001105. Herein, the amino acid sequence is also disclosed as SEQ ID NO: 84, and the nucleotide sequence is disclosed as SEQ ID NO: 85. The amino acid sequence and nucleotide sequence of mouse ALK2 are available with reference to GenBank Accession No. NP-001103674. Herein the amino acid sequence is also disclosed as SEQ ID NO: 86, and the nucleotide sequence is disclosed as SEQ ID NO: 87. ALK2 is also called ACVR1 (activin A type I receptor 1) or ACTR1 (activin receptor type 1), and all of these terms represent the same molecules.

The ALK2 cDNA can be obtained by a so-called PCR method which involves carrying out polymerase chain reaction (hereinafter, referred to as "PCR") (Saiki, R. K., et al., Science, (1988) 239, 487-49), for example, with a cDNA library expressing the ALK2 cDNA as a template using primers specifically amplifying the ALK2 cDNA.

The ALK2 cDNA also includes a polynucleotide that hybridizes under stringent conditions to a polynucleotide consisting of a nucleotide sequence complementary to the nucleotide sequence encoding human or mouse ALK2 and encodes a protein having biological activity equivalent to ALK2. The ALK2 cDNA further includes a splicing variant that has been transcribed from the human or mouse ALK2 gene locus or a polynucleotide that hybridizes under stringent conditions thereto, and encodes a protein having biological activity equivalent to ALK2.

ALK2 also includes a protein that consists of an amino acid sequence derived from the amino acid sequence of human or mouse ALK2 or an amino acid sequence thereof free from the signal sequence by the substation, deletion, or addition of one or several amino acids, and has biological activity equivalent to ALK2. ALK2 further includes a protein that consists of an amino acid sequence encoded by a splicing variant transcribed from the human or mouse ALK2 gene locus, or an amino acid sequence derived from this amino acid sequence by the substation, deletion, or addition of one or several amino acids, and has biological activity equivalent to ALK2.

3. Detection of Ectopic Ossification and/or Bone Dysplasia

Ectopic ossification and/or bone dysplasia is induced by ALK2-mediated BMP signal transduction.

The "ectopic ossification" means bone formation at a site where the bone is originally absent. The "bone dysplasia" means the abnormal shape or quality of the existing bone. Examples of the "ectopic ossification" can include, but are not limited to, fibrodysplasia ossificans progressiva (FOP), progressive osseous heteroplasia (POH), traumatic ectopic ossification, and ectopic ossification after implant arthroplasty. Examples of the "bone dysplasia" can include, but are not limited to, spondyloarthritis (SpA) and ankylosing spondylitis (AS).

ALK2 is a transmembrane serine-threonine kinase receptor binding to BMP. ALK2 binds to BMP at the N-terminal extracellular region and activates a downstream intracellular signal transduction system through intracellular serine-threonine kinase. Bone morphogenetic protein (BMP) is a multifunctional growth factor belonging to the transforming growth factor $\beta$ (TGF-$\beta$) superfamily, and approximately 20 BMP family members have been identified. BMP has been confirmed to induce ectopic bone formation in soft tissues including skeletal muscle tissues and is therefore considered to participate in diseases promoting abnormal bone formation. BMP-2 and BMP-4 are considered to have higher affinity for ALK3 than that for ALK2. Since ALK3 is expressed ubiquitously as compared with ALK2, BMP-2 or BMP-4 seems to be often used in general in experiments of inducing ectopic ossification at various sites. On the other hand, BMP-7 has relatively high affinity for ALK2. BMP-9 is generally considered to have high affinity for ALK1 and has also been found to have relatively high affinity for ALK2. In FOP, ectopic ossification occurs via ALK2. Therefore, the presence or absence of therapeutic and/or prophylactic effects on FOP can probably be confirmed by testing efficacy for ectopic osteoinduction caused by the activation of ALK2-mediated signals by BMP-7 and BMP-9.

The culture of myoblasts (C2C12 cells) in the presence of BMP suppresses their differentiation into mature muscle cells through an intracellular signal transduction mechanism specific for BMP and instead induces the differentiation into osteoblasts. Thus, ALK2-mediated BMP signal transduction can be analyzed with models of induction of differentiation of C2C12 cells into osteoblasts by BMP.

4. Production of Anti-ALK2 Antibody

The antibody of the present invention against ALK2 can be obtained by a method described in, for example, WO2009/091048, WO2011/027808, or WO2012/133572.

Specifically, nonhuman animals are immunized with the antigen of interest. Lymphs, lymph tissues, blood samples, or bone marrow-derived cells are collected from the animals after establishment of immunity. Plasma cells and/or plasmablasts of the nonhuman animals specifically binding to the antigen of interest are selected. A gene of an antibody to the antigen of interest is collected from the obtained plasma cells and/or plasmablasts, and its nucleotide sequence is identified. The antibody or a fragment thereof can be obtained on the basis of the identified nucleotide sequence of the gene. Alternatively, the antibody or the antibody fragment can be obtained by obtaining plasma cells and/or plasmablasts in the same way as above from the blood of a human infected patient. The obtained antibody can be tested for its binding activity to ALK2 to select an antibody applicable to human diseases. Examples of the monoclonal antibody thus obtained can include A2-11E, A2-15A, A2-25C, and A2-27D.

Herein, amino acid numbers assigned to CDR/FR characteristic of an antibody are laid out according to the KABAT numbering (KABAT et al., Sequences of Proteins of Immunological Interest, 5th Ed. Public Health Service National Institutes of Health, Bethesda, Md. (1991)).

The monoclonal antibody can also be obtained according to a method known in the art (e.g., Kohler and Milstein, Nature (1975) 256, p. 495-497; and Kennet, R. ed., Monoclonal Antibodies, p. 365-367, Plenum Press, N.Y. (1980)) by fusing antibody-producing cells that produce the antibody against ALK2 with myeloma cells to establish hybridomas. Specific examples of such a method are described in WO2009/48072 (published on Apr. 16, 2009) and WO2010/117011 (published on Oct. 14, 2010). However, the method for obtaining monoclonal antibodies corresponds to an already established field and is not limited to the specific examples described above.

The antibody of the present invention includes monoclonal antibodies against ALK2 described above as well as, for example, polyclonal antibodies similarly having therapeutic and/or prophylactic effects, recombinant antibodies artificially engineered for the purpose of, for example, reducing heterogeneous antigenicity against humans, for example, chimeric antibodies, humanized antibodies, human antibodies, and the like. These antibodies can be produced by use of known methods.

Examples of the chimeric antibody can include chimeric antibodies comprising variable regions and constant regions (Fc) of antibodies derived from different species, for example, the variable regions of a mouse- or rat-derived antibody joined to human-derived constant regions (see Proc. Natl. Acad. Sci. U.S.A., 81, 6851-6855, (1984)). One example of the chimeric antibody derived from A2-15A can include an antibody consisting of a heavy chain having an amino acid sequence consisting of amino acid numbers 20 to 472 of SEQ ID NO: 20 of the Sequence Listing and a light chain having an amino acid sequence consisting of amino acids 21 to 237 of SEQ ID NO: 22. One example of the chimeric antibody derived from A2-27D can include an antibody consisting of a heavy chain having an amino acid sequence consisting of amino acids 20 to 470 of SEQ ID NO: 24 of the Sequence Listing and a light chain having an amino acid sequence consisting of amino acids 21 to 234 of SEQ ID NO: 26.

Examples of the humanized antibody can include an antibody comprising CDRs alone integrated into a human-derived antibody (see Nature (1986) 321, p. 522-525), and an antibody comprising the CDR sequences as well as amino acid residues of a portion of frameworks grafted into a human antibody by a CDR grafting method (International Publication No. WO90/07861).

The humanized antibody derived from the A2-15A antibody is included in the antibody of the present invention as long as the humanized antibody contains all of the 6 CDR sequences of A2-15A and has binding activity against ALK2. The heavy chain variable region of the A2-15A antibody comprises CDRH1 consisting of the amino acid sequence of SEQ ID NO: 59 (GFTFSHYYMA), CDRH2 consisting of the amino acid sequence of SEQ ID NO: 60 (SITNSGGSINYRDSVKG), and CDRH3 consisting of the amino acid sequence of SEQ ID NO: 61 (EGGENYGGYPPFAY). The light chain variable region of the A2-15A antibody comprises CDRL1 consisting of the amino acid sequence of SEQ ID NO: 62 (RANQGVSLSRYNLMH), CDRL2 consisting of the amino acid sequence of SEQ ID NO: 63 (RSSNLAS), and CDRL3 consisting of the amino acid sequence of SEQ ID NO: 64 (QQSRESPFT). The amino acid sequences of these CDRs are also described in FIG. 11.

The humanized antibody derived from the A2-27D antibody is included in the antibody of the present invention as long as the humanized antibody contains all of the 6 CDR sequences of A2-27D and has binding activity against ALK2. The heavy chain variable region of the A2-27D antibody comprises CDRH1 consisting of the amino acid sequence of SEQ ID NO: 65 (GSTFSNYGMK), CDRH2 consisting of the amino acid sequence of SEQ ID NO: 66 (SISRSSTYIYYADTVKG), and CDRH3 consisting of the amino acid sequence of SEQ ID NO: 67 (AISTPFYWYFDF). The light chain variable region of the A2-27D antibody comprises CDRL1 consisting of the amino acid sequence of SEQ ID NO: 68 (LASSSVSYMT), CDRL2 consisting of the amino acid sequence of SEQ ID NO: 69 (GTSNLAS), and CDRL3 consisting of the amino acid sequence of SEQ ID NO: 70 (LHLTSYPPYT). The amino acid sequences of these CDRs are also described in FIG. 12.

The humanized antibody derived from the A2-11E antibody is included in the antibody of the present invention as long as the humanized antibody contains all of the 6 CDR sequences of A2-11E and has binding activity against ALK2. The heavy chain variable region of the A2-11E antibody comprises CDRH1 consisting of the amino acid sequence of SEQ ID NO: 72 (GFTFSNYYMY), CDRH2 consisting of the amino acid sequence of SEQ ID NO: 73 (SINTDGGSTYYPDSVKG), and CDRH3 consisting of the amino acid sequence of SEQ ID NO: 74 (STPNIPLAY). The light chain variable region of the A2-11E antibody comprises CDRL1 consisting of the amino acid sequence of SEQ ID NO: 75 (KASQNIYKYLN), CDRL2 consisting of the amino acid sequence of SEQ ID NO: 76 (YSNSLQT), and CDRL3 consisting of the amino acid sequence of SEQ ID NO: 77 (FQYSSGPT). The amino acid sequences of these CDRs are also described in FIG. 13.

The humanized antibody derived from the A2-25C antibody is included in the antibody of the present invention as long as the humanized antibody contains all of the 6 CDR sequences of A2-25C and has binding activity against ALK2. The heavy chain variable region of the A2-25C antibody comprises CDRH1 consisting of the amino acid sequence of SEQ ID NO: 78 (GFTFSYYAMS), CDRH2 consisting of the amino acid sequence of SEQ ID NO: 79 (SISRGGDNTYYRDTVKG), and CDRH3 consisting of the amino acid sequence of SEQ ID NO: 80 (LNYNNYFDY). The light chain variable region of the A2-25C antibody comprises CDRL1 consisting of the amino acid sequence of SEQ ID NO: 81 (QASQDIGNWLS), CDRL2 consisting of the amino acid sequence of SEQ ID NO: 82 (GATSLAD), and CDRL3 consisting of the amino acid sequence of SEQ ID NO: 83 (LQAYSAPFT). The amino acid sequences of these CDRs are also described in FIG. 14.

A CDR-engineered humanized antibody prepared by substitution of 1 to 3 amino acid residues in each CDR by other amino acid residues is also included in the antibody of the present invention as long as the humanized antibody has binding activity against ALK2. Examples of the amino acid substitution in CDRL2 can include the substitution of one amino acid of CDRL2 in the amino acid sequence of SEQ ID NO: 34. CDRL2 consisting of the amino acid sequence of SEQ ID NO: 71 (RSSNLAQ) is preferred. The amino acid sequence of this CDR is also described in FIG. 11.

Actual examples of the humanized antibody derived from the A2-15A antibody can include an arbitrary combination of a heavy chain comprising a heavy chain variable region consisting of an amino acid sequence consisting of amino acid numbers 20 to 142 of the amino acid sequence of SEQ ID NO: 28 of the Sequence Listing, an amino acid sequence consisting of amino acid numbers 20 to 142 of the amino acid sequence of SEQ ID NO: 30, or an amino acid sequence consisting of amino acid numbers 20 to 142 of the amino acid sequence of SEQ ID NO: 105 of the Sequence Listing, and a light chain comprising a light chain variable region consisting of an amino acid sequence consisting of amino acid numbers 21 to 133 of the amino acid sequence of SEQ ID NO: 32, an amino acid sequence consisting of amino acid numbers 21 to 133 of the amino acid sequence of SEQ ID NO: 34, an amino acid sequence consisting of amino acid numbers 21 to 133 of the amino acid sequence of SEQ ID NO: 36, or an amino acid sequence consisting of amino acid numbers 21 to 133 of the amino acid sequence of SEQ ID NO: 38.

Preferred examples of the combination can include an antibody consisting of a heavy chain comprising a heavy chain variable region sequence consisting of amino acid numbers 20 to 142 of the amino acid sequence of SEQ ID NO: 28 and a light chain comprising a light chain variable region sequence consisting of amino acid numbers 21 to 133 of the amino acid sequence of SEQ ID NO: 32, an antibody consisting of a heavy chain comprising a heavy chain variable region sequence consisting of amino acid numbers 20 to 142 of the amino acid sequence of SEQ ID NO: 28 and a light chain comprising a light chain variable region sequence consisting of amino acid numbers 21 to 133 of the amino acid sequence of SEQ ID NO: 34, an antibody consisting of a heavy chain comprising a heavy chain variable region sequence consisting of amino acid numbers 20 to 142 of an amino acid sequence of SEQ ID NO: 30 and a light chain comprising a light chain variable region sequence consisting of amino acid numbers 21 to 133 of the amino acid sequence of SEQ ID NO: 32, an antibody consisting of a heavy chain comprising a heavy chain variable region sequence consisting of amino acid numbers 20 to 142 of the amino acid sequence of SEQ ID NO: 30 and a light chain comprising a light chain variable region sequence consisting of amino acid numbers 21 to 133 of the amino acid sequence of SEQ ID NO: 34, an antibody consisting of a heavy chain comprising a heavy chain variable region sequence consisting of amino acid numbers 20 to 142 of the amino acid sequence of SEQ ID NO: 30 and a light chain comprising a light chain variable region sequence consisting of amino acid numbers 21 to 133 of the amino acid sequence of SEQ ID NO: 36, an antibody consisting of a heavy chain comprising a heavy chain variable region sequence consisting of amino acid numbers 20 to 142 of the amino acid sequence of SEQ ID NO: 30 and a light chain comprising a light chain variable region sequence consisting of amino acid numbers 21 to 133 of the amino acid sequence of SEQ ID NO: 38, and an antibody consisting of a heavy chain comprising a heavy chain variable region sequence consisting of amino acid numbers 20 to 142 of the amino acid sequence of SEQ ID NO: 105 and a light chain comprising a light chain variable region sequence consisting of amino acid numbers 21 to 133 of the amino acid sequence of SEQ ID NO: 36.

More preferred examples of the combination can include an antibody consisting of a heavy chain having an amino acid sequence consisting of amino acid numbers 20 to 472 of the amino acid sequence of SEQ ID NO: 28 and a light chain comprising an amino acid sequence consisting of amino acid numbers 21 to 238 of the amino acid sequence of SEQ ID NO: 32, an antibody consisting of a heavy chain comprising an amino acid sequence consisting of amino acid numbers 20 to 472 of the amino acid sequence of SEQ ID NO: 28 and a light chain comprising an amino acid sequence consisting of amino acid numbers 21 to 238 of the amino acid sequence of SEQ ID NO: 34, an antibody consisting of a heavy chain comprising an amino acid sequence consisting of amino acid numbers 20 to 472 of the amino acid sequence of SEQ ID NO: 30 and a light chain comprising an amino acid sequence consisting of amino acid numbers 21 to 238 of the amino acid sequence of SEQ ID NO: 32, an antibody consisting of a heavy chain comprising an amino acid sequence consisting of amino acid numbers 20 to 472 of the amino acid sequence of SEQ ID NO: 30 and a light chain comprising an amino acid sequence consisting of amino acid numbers 21 to 238 of the amino acid sequence of SEQ ID NO: 34, an antibody consisting of a heavy chain comprising an amino acid sequence consisting of amino acid numbers 20 to 472 of the amino acid sequence of SEQ ID NO: 30 and a light chain comprising an amino acid sequence consisting of amino acid numbers 21 to 238 of the amino acid sequence of SEQ ID NO: 36, an antibody consisting of a heavy chain comprising an amino acid sequence consisting of amino acid numbers 20 to 472 of the amino acid sequence of SEQ ID NO: 30 and a light chain comprising an amino acid sequence consisting of amino acid numbers 21 to 238 of the amino acid sequence of SEQ ID NO: 38, and an antibody consisting of a heavy chain comprising a heavy chain variable region sequence consisting of amino acid numbers 20 to 468 of the amino acid sequence of SEQ ID NO: 105 and a light chain comprising a light chain variable region sequence consisting of amino acid numbers 21 to 238 of the amino acid sequence of SEQ ID NO: 36.

Further preferred examples of the combination can include an antibody consisting of a heavy chain comprising a heavy chain variable region sequence consisting of amino acid numbers 20 to 142 of the amino acid sequence of SEQ ID NO: 30 and a light chain comprising a light chain variable region sequence consisting of amino acid numbers 21 to 133 of the amino acid sequence of SEQ ID NO: 36, and an antibody consisting of a heavy chain comprising a heavy chain variable region sequence consisting of amino acid numbers 20 to 142 of the amino acid sequence of SEQ ID NO: 105 and a light chain comprising a light chain variable region sequence consisting of amino acid numbers 21 to 133 of the amino acid sequence of SEQ ID NO: 36.

Still further preferred examples of the combination can include an antibody consisting of a heavy chain comprising an amino acid sequence consisting of amino acid numbers 20 to 472 of the amino acid sequence of SEQ ID NO: 30 and a light chain comprising an amino acid sequence consisting of amino acid numbers 21 to 238 of the amino acid sequence of SEQ ID NO: 36, and an antibody consisting of a heavy chain comprising an amino acid sequence consisting of amino acid numbers 20 to 468 of the amino acid sequence of SEQ ID NO: 105 and a light chain comprising an amino acid sequence consisting of amino acid numbers 21 to 238 of the amino acid sequence of SEQ ID NO: 36.

Most preferred examples of the combination can include an antibody consisting of a heavy chain comprising an amino acid sequence consisting of amino acid numbers 20 to 468 of the amino acid sequence of SEQ ID NO: 105 and a light chain comprising an amino acid sequence consisting of amino acid numbers 21 to 238 of the amino acid sequence of SEQ ID NO: 36.

Actual examples of the humanized antibody derived from the A2-27D antibody can include an arbitrary combination of a heavy chain comprising a heavy chain variable region consisting of an amino acid sequence consisting of amino acid numbers 20 to 140 of the amino acid sequence of SEQ ID NO: 40 of the Sequence Listing, an amino acid sequence consisting of amino acid numbers 20 to 140 of the amino acid sequence of SEQ ID NO: 42 of the Sequence Listing, an amino acid sequence consisting of amino acid numbers 20 to 140 of the amino acid sequence of SEQ ID NO: 44 of the Sequence Listing, an amino acid sequence consisting of amino acid numbers 20 to 140 of the amino acid sequence of SEQ ID NO: 46 of the Sequence Listing, an amino acid sequence consisting of amino acid numbers 20 to 140 of the amino acid sequence of SEQ ID NO: 48, an amino acid sequence consisting of amino acid numbers 20 to 140 of the amino acid sequence of SEQ ID NO: 107, or an amino acid sequence consisting of amino acid numbers 20 to 140 of the amino acid sequence of SEQ ID NO: 109, and a light chain comprising a light chain variable region consisting of an amino acid sequence consisting of amino acid numbers 21 to 129 of the amino acid sequence of SEQ ID NO: 50, an amino acid sequence consisting of amino acid numbers 21 to 129 of the amino acid sequence of SEQ ID NO: 52, an amino acid sequence consisting of amino acid numbers 21 to 129 of the amino acid sequence of SEQ ID NO: 54, an amino acid sequence consisting of amino acid numbers 21 to 129 of the amino acid sequence of SEQ ID NO: 56, or an amino acid sequence consisting of amino acid numbers 21 to 129 of the amino acid sequence of SEQ ID NO: 58.

Preferred examples of the combination can include an antibody consisting of a heavy chain comprising a heavy chain variable region sequence consisting of amino acid numbers 20 to 140 of the amino acid sequence of SEQ ID NO: 40 and a light chain comprising a light chain variable region sequence consisting of amino acid numbers 21 to 129 of the amino acid sequence of SEQ ID NO: 50, an antibody consisting of a heavy chain comprising a heavy chain variable region sequence consisting of amino acid numbers 20 to 140 of the amino acid sequence of SEQ ID NO: 40 and a light chain comprising a light chain variable region sequence consisting of amino acid numbers 21 to 129 of the amino acid sequence of SEQ ID NO: 52, an antibody consisting of a heavy chain comprising a heavy chain variable region sequence consisting of amino acid numbers 20 to 140 of an amino acid sequence of SEQ ID NO: 40 and a light chain comprising a light chain variable region sequence consisting of amino acid numbers 21 to 129 of the amino acid sequence of SEQ ID NO: 54, an antibody consisting of a heavy chain comprising a heavy chain variable region sequence consisting of amino acid numbers 20 to 140 of the amino acid sequence of SEQ ID NO: 42 and a light chain comprising a light chain variable region sequence consisting of amino acid numbers 21 to 129 of the amino acid sequence of SEQ ID NO: 50, an antibody consisting of a heavy chain comprising a heavy chain variable region sequence consisting of amino acid numbers 20 to 140 of an amino acid sequence of SEQ ID NO: 42 and a light chain comprising a light chain variable region sequence consisting of amino acid numbers 21 to 129 of the amino acid sequence of SEQ ID NO: 52, an antibody consisting of a heavy chain comprising a heavy chain variable region sequence consisting of amino acid numbers 20 to 140 of an amino acid sequence of SEQ ID NO: 42 and a light chain comprising a light chain variable region sequence consisting of amino acid numbers 21 to 129 of the amino acid sequence of SEQ ID NO: 54, an antibody consisting of a heavy chain comprising a heavy chain variable region sequence consisting of amino acid numbers 20 to 140 of the amino acid sequence of SEQ ID NO: 44 and a light chain comprising a light chain variable region sequence consisting of amino acid numbers 21 to 129 of the amino acid sequence of SEQ ID NO: 50, an antibody consisting of a heavy chain comprising a heavy chain variable region sequence consisting of amino acid numbers 20 to 140 of the amino acid sequence of SEQ ID NO: 44 and a light chain comprising a light chain variable region sequence consisting of amino acid numbers 21 to 129 of the amino acid sequence of SEQ ID NO: 52, an antibody consisting of a heavy chain comprising a heavy chain variable region sequence consisting of amino acid numbers 20 to 140 of an amino acid sequence of SEQ ID NO: 44 and a light chain comprising a light chain variable region sequence consisting of amino acid numbers 21 to 129 of the amino acid sequence of SEQ ID NO: 54, an antibody consisting of a heavy chain comprising a heavy chain variable region sequence consisting of amino acid numbers 20 to 140 of the amino acid sequence of SEQ ID NO: 44 and a light chain comprising a light chain variable region sequence consisting of amino acid numbers 21 to 129 of the amino acid sequence of SEQ ID NO: 56, an antibody consisting of a heavy chain comprising a heavy chain variable region sequence consisting of amino acid numbers 20 to 140 of the amino acid sequence of SEQ ID NO: 46 and a light chain comprising a light chain variable region sequence consisting of amino acid numbers 21 to 129 of the amino acid sequence of SEQ ID NO: 54, an antibody consisting of a heavy chain comprising a heavy chain variable region sequence consisting of amino acid numbers 20 to 140 of the amino acid sequence of SEQ ID NO: 46 and a light chain comprising a light chain variable region sequence consisting of amino acid numbers 21 to 129 of the amino acid sequence of SEQ ID NO: 56, an antibody consisting of a heavy chain comprising a heavy chain variable region sequence consisting of amino acid numbers 20 to 140 of the amino acid sequence of SEQ ID NO: 46 and a light chain comprising a light chain variable region sequence consisting of amino acid numbers 21 to 129 of the amino acid sequence of SEQ ID NO: 58, an antibody consisting of a heavy chain comprising a heavy chain variable region sequence consisting of amino acid numbers 20 to 140 of the amino acid sequence of SEQ ID NO: 48 and a light chain comprising a light chain variable region sequence consisting of amino acid numbers 21 to 129 of the amino acid sequence of SEQ ID NO: 56, an antibody consisting of a heavy chain comprising a heavy chain variable region sequence consisting of amino acid numbers 20 to 140 of the amino acid sequence of SEQ ID NO: 107 and a light chain comprising a light chain variable region sequence consisting of amino acid numbers 21 to 129 of the amino acid sequence of SEQ ID NO: 52, and an antibody consisting of a heavy chain comprising a heavy chain variable region sequence consisting of amino acid numbers 20 to 140 of the amino acid sequence of SEQ ID NO: 109 and a light chain comprising a light chain variable region sequence consisting of amino acid numbers 21 to 129 of the amino acid sequence of SEQ ID NO: 56.

More preferred examples of the combination can include an antibody consisting of a heavy chain comprising an amino acid sequence consisting of amino acid numbers 20 to 470 of the amino acid sequence of SEQ ID NO: 40 and a light chain comprising an amino acid sequence consisting of amino acid numbers 21 to 234 of the amino acid sequence of SEQ ID NO: 50, an antibody consisting of a heavy chain comprising an amino acid sequence consisting of amino acid numbers 20 to 470 of the amino acid sequence of SEQ ID NO: 40 and a light chain comprising an amino acid sequence consisting of amino acid numbers 21 to 234 of the amino acid sequence of SEQ ID NO: 52, an antibody consisting of a heavy chain comprising an amino acid sequence consisting of amino acid numbers 20 to 470 of the amino acid sequence of SEQ ID NO: 40 and a light chain comprising an amino acid sequence consisting of amino acid numbers 21 to 234 of the amino acid sequence of SEQ ID NO: 54, an antibody consisting of a heavy chain comprising an amino acid sequence consisting of amino acid numbers 20 to 470 of the amino acid sequence of SEQ ID NO: 42 and a light chain comprising an amino acid sequence consisting of amino acid numbers 21 to 234 of the amino acid sequence of SEQ ID NO: 50, an antibody consisting of a heavy chain comprising an amino acid sequence consisting of amino acid numbers 20 to 470 of the amino acid sequence of SEQ ID NO: 42 and a light chain comprising an amino acid sequence consisting of amino acid numbers 21 to 234 of the amino acid sequence of SEQ ID NO: 52, an antibody consisting of a heavy chain comprising an amino acid sequence consisting of amino acid numbers 20 to 470 of the amino acid sequence of SEQ ID NO: 42 and a light chain comprising an amino acid sequence consisting of amino acid numbers 21 to 234 of the amino acid sequence of SEQ ID NO: 54, an antibody consisting of a heavy chain comprising an amino acid sequence consisting of amino acid numbers 20 to 470 of the amino acid sequence of SEQ ID NO: 44 and a light chain comprising an amino acid sequence consisting of amino acid numbers 21 to 234 of the amino acid sequence of SEQ ID NO: 50, an antibody consisting of a heavy chain comprising an amino acid sequence consisting of amino acid numbers 20 to 470 of an amino acid sequence of SEQ ID NO: 44 and a light chain comprising an amino acid sequence consisting of amino acid numbers 21 to 234 of the amino acid sequence of SEQ ID NO: 52, an antibody consisting of a heavy chain comprising an amino acid sequence consisting of amino acid numbers 20 to 470 of the amino acid sequence of SEQ ID NO: 44 and a light chain comprising an amino acid sequence consisting of amino acid numbers 21 to 234 of the amino acid sequence of SEQ ID NO: 54, an antibody consisting of a heavy chain comprising an amino acid sequence consisting of amino acid numbers 20 to 470 of the amino acid sequence of SEQ ID NO: 44 and a light chain comprising an amino acid sequence consisting of amino acid numbers 21 to 234 of the amino acid sequence of SEQ ID NO: 56, an antibody consisting of a heavy chain comprising an amino acid sequence consisting of amino acid numbers 20 to 470 of the amino acid sequence of SEQ ID NO: 46 and a light chain comprising an amino acid sequence consisting of amino acid numbers 21 to 234 of the amino acid sequence of SEQ ID NO: 54, an antibody consisting of a heavy chain comprising an amino acid sequence consisting of amino acid numbers 20 to 470 of the amino acid sequence of SEQ ID NO: 46 and a light chain comprising an amino acid sequence consisting of amino acid numbers 21 to 234 of the amino acid sequence of SEQ ID NO: 56, an antibody consisting of a heavy chain comprising an amino acid sequence consisting of amino acid numbers 20 to 470 of the amino acid sequence of SEQ ID NO: 46 and a light chain comprising an amino acid sequence consisting of amino acid numbers 21 to 234 of the amino acid sequence of SEQ ID NO: 58, an antibody consisting of a heavy chain comprising an amino acid sequence consisting of amino acid numbers 20 to 470 of the amino acid sequence of SEQ ID NO: 48 and a light chain comprising an amino acid sequence consisting of amino acid numbers 21 to 234 of the amino acid sequence of SEQ ID NO: 56, an antibody consisting of a heavy chain comprising an amino acid sequence consisting of amino acid numbers 20 to 470 of the amino acid sequence of SEQ ID NO: 107 and a light chain comprising an amino acid sequence consisting of amino acid numbers 21 to 234 of the amino acid sequence of SEQ ID NO: 52, and an antibody consisting of a heavy chain comprising an amino acid sequence consisting of amino acid numbers 20 to 470 of the amino acid sequence of SEQ ID NO: 109 and a light chain comprising an amino acid sequence consisting of amino acid numbers 21 to 234 of the amino acid sequence of SEQ ID NO: 56.

Further preferred examples of the combination can include an antibody consisting of a heavy chain comprising a heavy chain variable region sequence consisting of amino acid numbers 20 to 140 of the amino acid sequence of SEQ ID NO: 42 and a light chain comprising a light chain variable region sequence consisting of amino acid numbers 21 to 129 of the amino acid sequence of SEQ ID NO: 52, an antibody consisting of a heavy chain comprising a heavy chain variable region sequence consisting of amino acid numbers 20 to 140 of the amino acid sequence of SEQ ID NO: 44 and a light chain comprising a light chain variable region sequence consisting of amino acid numbers 21 to 129 of the amino acid sequence of SEQ ID NO: 56, an antibody consisting of a heavy chain comprising a heavy chain variable region sequence consisting of amino acid numbers 20 to 140 of the amino acid sequence of SEQ ID NO: 107 and a light chain comprising a light chain variable region sequence consisting of amino acid numbers 21 to 129 of the amino acid sequence of SEQ ID NO: 52, and an antibody consisting of a heavy chain comprising a heavy chain variable region sequence consisting of amino acid numbers 20 to 140 of the amino acid sequence of SEQ ID NO: 109 and a light chain comprising a light chain variable region sequence consisting of amino acid numbers 21 to 129 of the amino acid sequence of SEQ ID NO: 56.

Still further preferred examples of the combination can include an antibody consisting of a heavy chain comprising an amino acid sequence consisting of amino acid numbers 20 to 470 of the amino acid sequence of SEQ ID NO: 42 and a light chain comprising an amino acid sequence consisting of amino acid numbers 21 to 234 of the amino acid sequence of SEQ ID NO: 52, an antibody consisting of a heavy chain comprising an amino acid sequence consisting of amino acid numbers 20 to 470 of the amino acid sequence of SEQ ID NO: 44 and a light chain comprising an amino acid sequence consisting of amino acid numbers 21 to 234 of the amino acid sequence of SEQ ID NO: 56, an antibody consisting of a heavy chain comprising an amino acid sequence consisting of amino acid numbers 20 to 470 of the amino acid sequence of SEQ ID NO: 107 and a light chain comprising an amino acid sequence consisting of amino acid numbers 21 to 234 of the amino acid sequence of SEQ ID NO: 52, and an antibody consisting of a heavy chain comprising an amino acid sequence consisting of amino acid numbers 20 to 470 of the amino acid sequence of SEQ ID NO: 109 and a light chain comprising an amino acid sequence consisting of amino acid numbers 21 to 234 of the amino acid sequence of SEQ ID NO: 56.

Most preferred examples of the combination can include an antibody consisting of a heavy chain comprising an amino acid sequence consisting of amino acid numbers 20 to 470 of the amino acid sequence of SEQ ID NO: 107 and a light chain comprising an amino acid sequence consisting of amino acid numbers 21 to 234 of the amino acid sequence of SEQ ID NO: 52, and an antibody consisting of a heavy chain comprising an amino acid sequence consisting of amino acid numbers 20 to 470 of the amino acid sequence of SEQ ID NO: 109 and a light chain comprising an amino acid sequence consisting of amino acid numbers 21 to 234 of the amino acid sequence of SEQ ID NO: 56.

Actual examples of the humanized antibody derived from the A2-11E antibody can include an arbitrary combination of a heavy chain comprising a heavy chain variable region consisting of an amino acid sequence consisting of amino acid numbers 20 to 137 of the amino acid sequence of SEQ ID NO: 111 of the Sequence Listing or an amino acid sequence consisting of amino acid numbers 20 to 137 of the amino acid sequence of SEQ ID NO: 113, and a light chain comprising a light chain variable region consisting of an amino acid sequence consisting of amino acid numbers 21 to 128 of the amino acid sequence of SEQ ID NO: 115, an amino acid sequence consisting of amino acid numbers 21 to 128 of the amino acid sequence of SEQ ID NO: 117, or an amino acid sequence consisting of amino acid numbers 21 to 128 of the amino acid sequence of SEQ ID NO: 119.

Preferred examples of the combination can include an antibody consisting of a heavy chain comprising a heavy chain variable region sequence consisting of amino acid numbers 20 to 137 of the amino acid sequence of SEQ ID NO: 111 and a light chain comprising a light chain variable region sequence consisting of amino acid numbers 21 to 128 of the amino acid sequence of SEQ ID NO: 115, an antibody consisting of a heavy chain comprising a heavy chain variable region sequence consisting of amino acid numbers 20 to 137 of the amino acid sequence of SEQ ID NO: 111 and a light chain comprising a light chain variable region sequence consisting of amino acid numbers 21 to 128 of the amino acid sequence of SEQ ID NO: 117, an antibody consisting of a heavy chain comprising a heavy chain variable region sequence consisting of amino acid numbers 20 to 137 of the amino acid sequence of SEQ ID NO: 111 and a light chain comprising a light chain variable region sequence consisting of amino acid numbers 21 to 128 of an amino acid sequence of SEQ ID NO: 119, an antibody consisting of a heavy chain comprising a heavy chain variable region sequence consisting of amino acid numbers 20 to 137 of the amino acid sequence of SEQ ID NO: 113 and a light chain comprising a light chain variable region sequence consisting of amino acid numbers 21 to 128 of the amino acid sequence of SEQ ID NO: 115, an antibody consisting of a heavy chain comprising a heavy chain variable region sequence consisting of amino acid numbers 20 to 137 of the amino acid sequence of SEQ ID NO: 113 and a light chain comprising a light chain variable region sequence consisting of amino acid numbers 21 to 128 of the amino acid sequence of SEQ ID NO: 117, and an antibody consisting of a heavy chain comprising a heavy chain variable region sequence consisting of amino acid numbers 20 to 137 of the amino acid sequence of SEQ ID NO: 113 and a light chain comprising a light chain variable region sequence consisting of amino acid numbers 21 to 128 of the amino acid sequence of SEQ ID NO: 119.

More preferred examples of the combination can include an antibody consisting of a heavy chain having an amino acid sequence consisting of amino acid numbers 20 to 467 of the amino acid sequence of SEQ ID NO: 111 and a light chain comprising an amino acid sequence consisting of amino acid numbers 21 to 233 of the amino acid sequence of SEQ ID NO: 115, an antibody consisting of a heavy chain comprising an amino acid sequence consisting of amino acid numbers 20 to 467 of the amino acid sequence of SEQ ID NO: 111 and a light chain comprising an amino acid sequence consisting of amino acid numbers 21 to 233 of the amino acid sequence of SEQ ID NO: 117, an antibody consisting of a heavy chain comprising an amino acid sequence consisting of amino acid numbers 20 to 467 of the amino acid sequence of SEQ ID NO: 111 and a light chain comprising an amino acid sequence consisting of amino acid numbers 21 to 233 of the amino acid sequence of SEQ ID NO: 119, an antibody consisting of a heavy chain comprising an amino acid sequence consisting of amino acid numbers 20 to 467 of an amino acid sequence of SEQ ID NO: 113 and a light chain comprising an amino acid sequence consisting of amino acid numbers 21 to 233 of the amino acid sequence of SEQ ID NO: 115, an antibody consisting of a heavy chain comprising an amino acid sequence consisting of amino acid numbers 20 to 467 of the amino acid sequence of SEQ ID NO: 113 and a light chain comprising an amino acid sequence consisting of amino acid numbers 21 to 233 of the amino acid sequence of SEQ ID NO: 117, and an antibody consisting of a heavy chain comprising an amino acid sequence consisting of amino acid numbers 20 to 467 of the amino acid sequence of SEQ ID NO: 113 and a light chain comprising an amino acid sequence consisting of amino acid numbers 21 to 233 of the amino acid sequence of SEQ ID NO: 119.

Actual examples of the humanized antibody derived from the A2-25C antibody can include an arbitrary combination of a heavy chain comprising a heavy chain variable region consisting of an amino acid sequence consisting of amino acid numbers 20 to 137 of the amino acid sequence of SEQ ID NO: 121 of the Sequence Listing or an amino acid sequence consisting of amino acid numbers 20 to 137 of the amino acid sequence of SEQ ID NO: 123, and a light chain comprising a light chain variable region consisting of an amino acid sequence consisting of amino acid numbers 21 to 129 of the amino acid sequence of SEQ ID NO: 125, an amino acid sequence consisting of amino acid numbers 21 to 129 of the amino acid sequence of SEQ ID NO: 127, or an amino acid sequence consisting of amino acid numbers 21 to 129 of the amino acid sequence of SEQ ID NO: 129.

Preferred examples of the combination can include an antibody consisting of a heavy chain comprising a heavy chain variable region sequence consisting of amino acid numbers 20 to 137 of the amino acid sequence of SEQ ID NO: 121 and a light chain comprising a light chain variable region sequence consisting of amino acid numbers 21 to 129 of the amino acid sequence of SEQ ID NO: 125, an antibody consisting of a heavy chain comprising a heavy chain variable region sequence consisting of amino acid numbers 20 to 137 of the amino acid sequence of SEQ ID NO: 121 and a light chain comprising a light chain variable region sequence consisting of amino acid numbers 21 to 129 of the amino acid sequence of SEQ ID NO: 127, an antibody consisting of a heavy chain comprising a heavy chain variable region sequence consisting of amino acid numbers 20 to 137 of the amino acid sequence of SEQ ID NO: 121 and a light chain comprising a light chain variable region sequence consisting of amino acid numbers 21 to 129 of the amino acid sequence of SEQ ID NO: 129, an antibody consisting of a heavy chain comprising a heavy chain variable region sequence consisting of amino acid numbers 20 to 137 of the amino acid sequence of SEQ ID NO: 123 and a light chain comprising a light chain variable region sequence consisting of amino acid numbers 21 to 129 of the amino acid sequence of SEQ ID NO: 125, an antibody consisting of a heavy chain comprising a heavy chain variable region sequence consisting of amino acid numbers 20 to 137 of the amino acid sequence of SEQ ID NO: 123 and a light chain comprising a light chain variable region sequence consisting of amino acid numbers 21 to 129 of the amino acid sequence of SEQ ID NO: 127, and an antibody consisting of a heavy chain comprising a heavy chain variable region sequence consisting of amino acid numbers 20 to 137 of the amino acid sequence of SEQ ID NO: 123 and a light chain comprising a light chain variable region sequence consisting of amino acid numbers 21 to 129 of the amino acid sequence of SEQ ID NO: 129.

More preferred examples of the combination can include an antibody consisting of a heavy chain having an amino acid sequence consisting of amino acid numbers 20 to 467 of the amino acid sequence of SEQ ID NO: 121 and a light chain comprising an amino acid sequence consisting of amino acid numbers 21 to 234 of the amino acid sequence of SEQ ID NO: 125, an antibody consisting of a heavy chain comprising an amino acid sequence consisting of amino acid numbers 20 to 467 of the amino acid sequence of SEQ ID NO: 121 and a light chain comprising an amino acid sequence consisting of amino acid numbers 21 to 234 of the amino acid sequence of SEQ ID NO: 127, an antibody consisting of a heavy chain comprising an amino acid sequence consisting of amino acid numbers 20 to 467 of the amino acid sequence of SEQ ID NO: 121 and a light chain comprising an amino acid sequence consisting of amino acid numbers 21 to 234 of the amino acid sequence of SEQ ID NO: 129, an antibody consisting of a heavy chain comprising an amino acid sequence consisting of amino acid numbers 20 to 467 of the amino acid sequence of SEQ ID NO: 123 and a light chain comprising an amino acid sequence consisting of amino acid numbers 21 to 234 of the amino acid sequence of SEQ ID NO: 125, an antibody consisting of a heavy chain comprising an amino acid sequence consisting of amino acid numbers 20 to 467 of the amino acid sequence of SEQ ID NO: 123 and a light chain comprising an amino acid sequence consisting of amino acid numbers 21 to 234 of the amino acid sequence of SEQ ID NO: 127, and an antibody consisting of a heavy chain comprising an amino acid sequence consisting of amino acid numbers 20 to 467 of the amino acid sequence of SEQ ID NO: 123 and a light chain comprising an amino acid sequence consisting of amino acid numbers 21 to 234 of the amino acid sequence of SEQ ID NO: 129.

Further examples of the antibody of the present invention can include a human antibody. The anti-ALK2 human antibody means a human antibody produced from only human chromosome-derived antibody gene sequences. The anti-ALK2 human antibody can be obtained by a method using human antibody-producing mice carrying human chromosome fragments that comprise human antibody heavy and light chain genes (see e.g., Tomizuka, K. et al., Nature Genetics (1997), 16, p. 133-143; Kuroiwa, Y. et al., Nuc. Acids Res. (1998), 26, p. 3447-3448; Yoshida, H. et al., Animal Cell Technology: Basic and Applied Aspects vol. 10, p. 69-73 (Kitagawa, Y., Matsuda, T. and Iijima, S. eds.), Kluwer Academic Publishers, 1999; and Tomizuka, K. et al., Proc. Natl. Acad. Sci. USA (2000), 97, p. 722-727).

Specifically, such a human antibody-producing mouse can be created as a recombinant animal in which the endogenous immunoglobulin heavy and light chain gene loci have been disrupted and instead human immunoglobulin heavy and light chain gene loci are integrated via a vector such as a human artificial chromosome (HAC) vector or a mouse artificial chromosome (MAC) vector, by preparing a knock-out animal or a transgenic animal or by crossing these animals.

Alternatively, eukaryotic cells may be transformed with cDNAs encoding the heavy and light chains, respectively, of such a human antibody, preferably with vectors comprising the cDNAs, by a gene recombination technique. The transformed cells producing a recombinant human monoclonal antibody are cultured. This antibody can be obtained from the culture supernatant. In this context, for example, eukaryotic cells, preferably mammalian cells such as CHO cells, lymphocytes, or myeloma cells, can be used as hosts.

Also, a method for obtaining a phage display-derived human antibody selected from a human antibody library (see e.g., Wormstone, I. M. et al., Investigative Ophthalmology & Visual Science (2002), 43 (7), p. 2301-2308; Carmen, S. et al., Briefings in Functional Genomics and Proteomics (2002), 1 (2), p. 189-203; and Siriwardena, D. et al., Ophthalmology (2002), 109 (3), p. 427-431) is known.

For example, a phage display method (Nature Biotechnology (2005), 23, (9), p. 1105-1116) can be used, which involves allowing the variable regions of a human antibody to be expressed as single-chain Fv (scFv) on phage surface and selecting a phage binding to the antigen. The phage selected on the basis of its ability to bind to the antigen can be subjected to gene analysis to determine DNA sequences encoding the variable regions of the human antibody binding to the antigen. If the DNA sequence of scFv binding to the antigen is determined, an expression vector having this sequence can be prepared and transferred to appropriate hosts, followed by expression to obtain the human antibody (WO92/01047, WO92/20791, WO93/06213, WO93/11236, WO93/19172, WO95/01438, WO95/15388, Annu. Rev. Immunol (1994), 12, p. 433-455; and Nature Biotechnology (2005), 23 (9), p. 1105-1116).

Antibodies binding to the same epitope as that for the antibody provided by the present invention are also included in the antibodies of the present invention. Examples thereof include antibodies binding to the same epitope as that for the A2-11E antibody, the A2-15A antibody, the A2-25C antibody, and/or the A2-27D antibody.

When an antibody binds to or recognizes a partial conformation of an antigen, the epitope for this antibody can be determined by identifying amino acid residues on the antigen adjacent to the antibody by use of X-ray structure analysis. For example, the antibody or a fragment thereof and the antigen or a fragment thereof can be bound to each other, crystallized, and structurally analyzed to identify amino acid residues on the antigen having an interaction distance between the amino acid residue and the antibody. The interaction distance is 8 angstroms or smaller, preferably 6 angstroms or smaller, more preferably 4 angstroms or smaller. One or more amino acid residues having such an interaction distance with the antibody can constitute the epitope (antigenic determinant) for the antibody. When the number of such amino acid residues is two or more, these amino acids may not be adjacent to each other on the primary sequence.

A Fab fragment of the chimeric A2-27D antibody and a peptide containing an ECD fragment (amino acid numbers 21 to 123 of SEQ ID NO: 84) of human ALK2 are bound to each other and crystallized under conditions involving 2% (v/v) Tacsimate (pH 7.0), 100 mM HEPES (pH 7.5), and 20% (w/v) polyethylene glycol 3,350 to obtain crystals having a body-centered monoclinic crystal system with a space group C121 and unit cells of a=c=119.39 angstroms, b=37.32 angstroms, and 3=92.54. The phase can be determined by a molecular replacement method using three-dimensional structure coordinates thereof (see Example 16).

The A2-27D antibody recognizes a partial conformation on human ALK2. In the amino acid sequence (SEQ ID NO: 84) of human ALK2, the amino acid residues having an interaction distance with the A2-27D antibody, i.e., the epitope, is constituted by each of the residues of glutamic acid (Glu) at position 18, glycine (Gly) at position 19, isoleucine (Ile) at position 39, asparagine (Asn) at position 40, aspartic acid (Asp) at position 41, glycine (Gly) at position 42, phenylalanine (Phe) at position 43, histidine (His) at position 44, valine (Val) at position 45, tyrosine (Tyr) at position 46, asparagine (Asn) at position 82, threonine (Thr) at position 84, glutamine (Gln) at position 86, and leucine (Leu) at position 87. The antibody, an antigen-binding fragment thereof, or a modified form of the antibody or the fragment which binds to this epitope or has an interaction distance between the antibody or the fragment and each of the amino acid residues are also encompassed by the antibody of the present invention, the antigen-binding fragment thereof, or a modified form of the antibody or the fragment.

A Fab fragment of the chimeric A2-25C antibody and a peptide containing an ECD fragment (amino acid numbers 21 to 123 of SEQ ID NO: 84) of human ALK2 are bound to each other and crystallized under conditions involving 0.15 M $Li_2SO_4$, 0.1 M Na citrate (pH 3.4), 18% (w/v) PEG6,000, and 20% (v/v) ethylene glycol to obtain crystals having an orthorhombic crystal system with a space group $P2_12_12_1$ and unit cells of a=74.49 angstroms, b=128.05 angstroms, and c=147.73 angstroms. The phase can be determined by a molecular replacement method using three-dimensional structure coordinates thereof (see Example 21).

The A2-25C antibody recognizes a partial conformation on human ALK2. In the amino acid sequence (SEQ ID NO: 84) of human ALK2, the amino acid residues having an interaction distance with the A2-25C antibody, i.e., the epitope, is constituted by each of the residues of glutamic acid (Glu) at position 18, glycine (Gly) at position 19, leucine (Leu) at position 20, isoleucine (Ile) at position 39, aspartic acid (Asp) at position 41, glycine (Gly) at position 42, phenylalanine (Phe) at position 43, histidine (His) at position 44, valine (Val) at position 45, tyrosine (Tyr) at position 46, and threonine (Thr) at position 84. The antibody, an antigen-binding fragment thereof, or a modified form of the antibody or the fragment which binds to this epitope or has an interaction distance with these amino acid residues are also encompassed by the antibody of the present invention, the antigen-binding fragment thereof, or a modified form of the antibody or the fragment.

The antibody described above can be evaluated for its binding activity to the antigen by, for example, a method described in Example 2, 6, 9, or 10 to select suitable antibodies. The dissociation constant of the antibody is, for example, $1 \times 10^{-6}$ to $1 \times 10^{-12}$ M, but is not limited to this range as long as the antibody of the present invention produces the therapeutic or prophylactic effects of interest. The dissociation constant of the antibody for the antigen (ALK2) can be measured using Biacore T200 (GE Healthcare Bio-Sciences Corp.) based on surface plasmon resonance (SPR) as detection principles. For example, the antibody set to an appropriate concentration is reacted as an analyte with the antigen immobilized as a ligand on a solid phase. The association and dissociation therebetween can be measured to obtain an association rate constant ka1, a dissociation rate constant kd1, and a dissociation constant (KD; KD=kd1/ka1). The evaluation of binding activity against ALK2 is not limited by use of Biacore T200 and may be conducted using, for example, an instrument based on surface plasmon resonance (SPR) as detection principles, KinExA (Sapidyne Instruments Inc.) based on kinetic exclusion assay as detection principles, BLItz system (Pall Corp.) based on bio-layer interferometry as detection principles, or ELISA (enzyme-linked immunosorbent assay).

One example of another index for comparing the properties of antibodies can include the stability of the antibodies. Differential scanning calorimetry (DSC) is a method that can rapidly and accurately measure a transition midpoint (Tm), which serves as a good index for the relative structural stability of proteins. Tm values can be measured using DSC and compared to determine difference in thermal stability. The preservation stability of an antibody is known to correlate with the thermal stability of the antibody to some extent (Lori Burton, et al., Pharmaceutical Development and Technology (2007) 12, p. 265-273). A suitable antibody can be selected with its thermal stability as the index. Examples of other indexes for selecting the antibody can include high yields in appropriate host cells and low aggregation in an aqueous solution. For example, an antibody having the highest yield does not always exhibit the highest thermal stability. Therefore, it is necessary to select an antibody most suitable for administration to humans by comprehensive judgment based on the indexes mentioned above.

A method for obtaining a single-chain immunoglobulin by linking the full-length sequences of antibody heavy and light chains using an appropriate linker is also known (Lee, H-S, et al., Molecular Immunology (1999) 36, p. 61-71; and Shirrmann, T. et al., mAbs (2010), 2, (1) p. 1-4). Such single-chain immunoglobulins can be dimerized to retain a structure and activity similar to those of antibodies which are originally tetramers. Alternatively, the antibody of the present invention may be an antibody that has a single heavy chain variable region and lacks a light chain sequence. Such an antibody, called single-domain antibody (sdAb) or nanobody, has actually been observed in camels or llamas and has been reported to maintain the ability to bind to an antigen (Muyldemans S. et al., Protein Eng. (1994) 7 (9), 1129-35; and Hamers-Casterman C. et al., Nature (1993) 363 (6428) 446-8). These antibodies may also be interpreted as an antigen-binding fragment of the antibody according to the present invention.

The antibody-dependent cellular cytotoxic activity of the antibody of the present invention can be enhanced by adjusting the modification of the sugar chain bound with the antibody. For example, methods described in WO99/54342, WO2000/61739, and WO2002/31140 are known as such a technique of adjusting the sugar chain modification of the antibody, though this technique is not limited thereto.

In the case of preparing an antibody by temporarily isolating the antibody gene and then transferring the gene to an appropriate host, the appropriate host can be used in combination with an expression vector.

Specific examples of the antibody gene can include a gene (or a polynucleotide) encoding a heavy chain sequence and a gene (or a polynucleotide) encoding a light chain sequence of the antibody described herein, and a combination of these genes (or polynucleotides).

Specific examples of the polynucleotide encoding the antibody or an antibody constituent (heavy or light chain) are as follows.

(1) A polynucleotide comprising the following polynucleotides (a) and/or (b):
(a) a polynucleotide selected from the group consisting of the following nucleotide sequences:
a1) a nucleotide sequence consisting of nucleotide numbers 58 to 426 of the nucleotide sequence of SEQ ID NO: 27;
a2) a nucleotide sequence consisting of nucleotide numbers 58 to 426 of the nucleotide sequence of SEQ ID NO: 29;
a3) a nucleotide sequence consisting of nucleotide numbers 58 to 426 of the nucleotide sequence of SEQ ID NO: 104;
a4) a nucleotide sequence having at least 95% identity to any of the nucleotide sequences a1) to a3);
a5) a nucleotide sequence having at least 99% identity to any of the nucleotide sequences a1) to a3);
a6) a nucleotide sequence carried by a polynucleotide hybridizing under stringent conditions to a polynucleotide consisting of a nucleotide sequence complementary to any of the nucleotide sequences a1) to a3); and
a7) a nucleotide sequence comprising a substitution(s), a deletion(s), or an addition(s) of one to several nucleotides in the nucleotide sequence a1) or a2); and/or
(b) a polynucleotide selected from the group consisting of the following nucleotide sequences:
b1) a nucleotide sequence consisting of nucleotide numbers 86 to 424 of the nucleotide sequence of SEQ ID NO: 31;
b2) a nucleotide sequence consisting of nucleotide numbers 86 to 424 of the nucleotide sequence of SEQ ID NO: 33;
b3) a nucleotide sequence consisting of nucleotide numbers 86 to 424 of the nucleotide sequence of SEQ ID NO: 35;
b4) a nucleotide sequence consisting of nucleotide numbers 86 to 424 of the nucleotide sequence of SEQ ID NO: 37;
b5) a nucleotide sequence having at least 95% identity to any one nucleotide sequence selected from the nucleotide sequences b1) to b4);
b6) a nucleotide sequence having at least 99% identity to any one nucleotide sequence selected from the nucleotide sequences b1) to b4);
b7) a nucleotide sequence carried by a polynucleotide hybridizing under stringent conditions to a polynucleotide consisting of a nucleotide sequence complementary to any one nucleotide sequence selected from the nucleotide sequences b1) to b4); and
b8) a nucleotide sequence comprising a substitution(s), a deletion(s), or an addition(s) of one to several nucleotides in any one nucleotide sequence selected from the nucleotide sequences b1) to b4).

(2) A polynucleotide comprising the following polynucleotides (a) and/or (b):
(a) a polynucleotide selected from the group consisting of the following nucleotide sequences:
a1) a nucleotide sequence consisting of nucleotide numbers 58 to 420 of the nucleotide sequence of SEQ ID NO: 39;
a2) a nucleotide sequence consisting of nucleotide numbers 58 to 420 of the nucleotide sequence of SEQ ID NO: 41;
a3) a nucleotide sequence consisting of nucleotide numbers 58 to 420 of the nucleotide sequence of SEQ ID NO: 43;
a4) a nucleotide sequence consisting of nucleotide numbers 58 to 420 of the nucleotide sequence of SEQ ID NO: 45;

a5) a nucleotide sequence consisting of nucleotide numbers 58 to 420 of the nucleotide sequence of SEQ ID NO: 47;
a6) a nucleotide sequence consisting of nucleotide numbers 58 to 420 of the nucleotide sequence of SEQ ID NO: 106;
a7) a nucleotide sequence consisting of nucleotide numbers 58 to 420 of the nucleotide sequence of SEQ ID NO: 108;
a8) a nucleotide sequence having at least 95% identity to any one nucleotide sequence selected from the nucleotide sequences a1) to a7);
a9) a nucleotide sequence having at least 99% identity to any one nucleotide sequence selected from the nucleotide sequences a1) to a7);
a10) a nucleotide sequence carried by a polynucleotide hybridizing under stringent conditions to a polynucleotide consisting of a nucleotide sequence complementary to any one nucleotide sequence selected from the nucleotide sequences a1) to a7); and
a11) a nucleotide sequence comprising a substitution(s), a deletion(s), or an addition(s) of one to several nucleotides in any one nucleotide sequence selected from the nucleotide sequences a1) to a7); and/or
(b) a polynucleotide selected from the group consisting of the following nucleotide sequences:
b1) a nucleotide sequence consisting of nucleotide numbers 86 to 412 of the nucleotide sequence of SEQ ID NO: 49;
b2) a nucleotide sequence consisting of nucleotide numbers 86 to 412 of the nucleotide sequence of SEQ ID NO: 51;
b3) a nucleotide sequence consisting of nucleotide numbers 86 to 412 of the nucleotide sequence of SEQ ID NO: 53;
b4) a nucleotide sequence consisting of nucleotide numbers 86 to 412 of the nucleotide sequence of SEQ ID NO: 55;
b5) a nucleotide sequence consisting of nucleotide numbers 86 to 412 of the nucleotide sequence of SEQ ID NO: 57;
b6) a nucleotide sequence having at least 95% identity to any one nucleotide sequence selected from the nucleotide sequences b1) to b5);
b7) a nucleotide sequence having at least 99% identity to any one nucleotide sequence selected from the nucleotide sequences b1) to b5);
b8) a nucleotide sequence carried by a polynucleotide hybridizing under stringent conditions to a polynucleotide consisting of a nucleotide sequence complementary to any one nucleotide sequence selected from the nucleotide sequences b1) to b5); and
b9) a nucleotide sequence comprising a substitution(s), a deletion(s), or an addition(s) of one to several nucleotides in any one nucleotide sequence selected from the nucleotide sequences b1) to b5).

(3) A polynucleotide comprising the following polynucleotides (a) and/or (b):
(a) a polynucleotide selected from the group consisting of the following nucleotide sequences:
a1) a nucleotide sequence consisting of nucleotide numbers 58 to 411 of the nucleotide sequence of SEQ ID NO: 110;
a2) a nucleotide sequence consisting of nucleotide numbers 58 to 411 of the nucleotide sequence of SEQ ID NO: 112;
a3) a nucleotide sequence having at least 95% identity to the nucleotide sequence a1) or a2);
a4) a nucleotide sequence having at least 99% identity to the nucleotide sequence a1) or a2);
a5) a nucleotide sequence carried by a polynucleotide hybridizing under stringent conditions to a polynucleotide consisting of a nucleotide sequence complementary to the nucleotide sequence a1) or a2); and
a6) a nucleotide sequence comprising a substitution(s), a deletion(s), or an addition(s) of one to several nucleotides in the nucleotide sequence a1) or a2); and/or
(b) a polynucleotide selected from the group consisting of the following nucleotide sequences:
b1) a nucleotide sequence consisting of nucleotide numbers 61 to 384 of the nucleotide sequence of SEQ ID NO: 114;
b2) a nucleotide sequence consisting of nucleotide numbers 61 to 384 of the nucleotide sequence of SEQ ID NO: 116;
b3) a nucleotide sequence consisting of nucleotide numbers 61 to 384 of the nucleotide sequence of SEQ ID NO: 118;
b4) a nucleotide sequence having at least 95% identity to any one nucleotide sequence selected from the nucleotide sequences b1) to b3);
b5) a nucleotide sequence having at least 99% identity to any one nucleotide sequence selected from the nucleotide sequences b1) to b3);
b6) a nucleotide sequence carried by a polynucleotide hybridizing under stringent conditions to a polynucleotide consisting of a nucleotide sequence complementary to any one nucleotide sequence selected from the nucleotide sequences b1) to b3); and
b7) a nucleotide sequence comprising a substitution(s), a deletion(s), or an addition(s) of one to several nucleotides in any one nucleotide sequence selected from the nucleotide sequences b1) to b3).

(4) A polynucleotide comprising the following polynucleotides (a) and/or (b):
(a) a polynucleotide selected from the group consisting of the following nucleotide sequences:
a1) a nucleotide sequence consisting of nucleotide numbers 58 to 411 of the nucleotide sequence of SEQ ID NO: 120;
a2) a nucleotide sequence consisting of nucleotide numbers 58 to 411 of the nucleotide sequence of SEQ ID NO: 122;
a3) a nucleotide sequence having at least 95% identity to the nucleotide sequence a1) or a2);
a4) a nucleotide sequence having at least 99% identity to the nucleotide sequence a1) or a2);
a5) a nucleotide sequence carried by a polynucleotide hybridizing under stringent conditions to a polynucleotide consisting of a nucleotide sequence complementary to the nucleotide sequence a1) or a2); and
a6) a nucleotide sequence comprising a substitution(s), a deletion(s), or an addition(s) of one to several nucleotides in the nucleotide sequence a1) or a2); and/or
(b) a polynucleotide selected from the group consisting of the following nucleotide sequences:
b1) a nucleotide sequence consisting of nucleotide numbers 61 to 387 of the nucleotide sequence of SEQ ID NO: 124;
b2) a nucleotide sequence consisting of nucleotide numbers 61 to 387 of the nucleotide sequence of SEQ ID NO: 126;
b3) a nucleotide sequence consisting of nucleotide numbers 61 to 387 of the nucleotide sequence of SEQ ID NO: 128;
b4) a nucleotide sequence having at least 95% identity to any one nucleotide sequence selected from the nucleotide sequences b1) to b3);
b5) a nucleotide sequence having at least 99% identity to any one nucleotide sequence selected from the nucleotide sequences b1) to b3);
b6) a nucleotide sequence carried by a polynucleotide hybridizing under stringent conditions to a polynucleotide consisting of a nucleotide sequence complementary to any one nucleotide sequence selected from the nucleotide sequences b1) to b3); and
b7) a nucleotide sequence comprising a substitution(s), a deletion(s), or an addition(s) of one to several nucleotides in any one nucleotide sequence selected from the nucleotide sequences b1) to b3).

For the transformation of host cells, a heavy chain sequence gene (or polynucleotide) and a light chain sequence gene (or polynucleotide) may be inserted in a same expression vector or may be inserted in separate expression vectors. In the case of using host eukaryotic cells, animal cells, plant cells, or eukaryotic microorganisms can be used. Examples of the animal cells can include mammalian cells, for example, monkey COS cells (Gluzman, Y., Cell (1981) 23, p. 175-182, ATCC CRL-1650), mouse fibroblast NIH3T3 (ATCC No. CRL-1658), and dihydrofolate reductase-deficient cell lines (Urlaub, G. and Chasin, L. A., Proc. Natl. Acad. Sci. U.S.A. (1980) 77, p. 4126-4220) of Chinese hamster ovary cells (CHO cells, ATCC CCL-61). In the case of using prokaryotic cells, examples thereof can include *E. coli* and *Bacillus subtilis*. The antibody gene of interest is transferred to these cells by transformation, and the transformed cells are cultured in vitro to obtain antibodies. Such culture methods may differ in yield depending on the sequences of the antibodies. An antibody that is easy to produce as a drug can be selected with its yield as an index from among antibodies having equivalent binding activity.

Examples of the isotype of the antibody of the present invention can include, but are not limited to, IgG (IgG1, IgG2, IgG3, and IgG4), IgM, IgA (IgA1 and IgA2), IgD, and IgE. Preferred examples of the isotype can include IgG and IgM, more preferably IgG1, IgG2, and IgG4.

In the case of using IgG1 as an isotype of the antibody of the present invention, the effector functions can be adjusted by substitution of a part of amino acid residues in constant regions (see WO88/07089, WO94/28027, and WO94/29351). Examples of such a variant of IgG1 include IgG1 LALA (IgG1-L234A,L235A) and IgG1 LAGA (IgG1-L235A,G237A). IgG1 LALA is preferred.

In the case of using IgG4 as an isotype of the antibody of the present invention, splitting unique to IgG4 can be suppressed with extended half-life by substitution of a part of amino acid residues in constant regions (see Molecular Immunology, 30, 1 105-108 (1993)). Examples of such a mutant of IgG4 include IgG4 pro (IgG4-S241P).

The antibody of the present invention may be an antigen-binding fragment of the antibody having the antigen-binding site of the antibody, or a modified form thereof. A fragment of the antibody can be obtained by treating the antibody with a proteolytic enzyme such as papain or pepsin or by expressing a genetically engineered antibody gene in appropriate cultured cells. Among such antibody fragments, a fragment that maintains the whole or a portion of the functions possessed by the full-length molecule of the antibody can be referred to as an antigen-binding fragment of the antibody. Examples of the functions of the antibody can generally include antigen binding activity, activity of inhibiting the activity of the antigen, activity of enhancing the activity of the antigen, antibody-dependent cellular cytotoxic activity, complement-dependent cytotoxic activity, and complement-dependent cellular cytotoxic activity. The function possessed by the antigen-binding fragment of the antibody according to the present invention is an activity of binding to ALK2 and is preferably an activity of inhibiting the activity of ALK2, more preferably an activity of inhibiting ALK2-mediated BMP signal transduction, most preferably an activity of suppressing ectopic ossification and/or bone dysplasia.

Examples of the fragment of the antibody can include Fab, F(ab')$_2$, Fv, single-chain Fv (scFv) comprising heavy and light chain Fvs linked via an appropriate linker, diabody or diabodies, linear antibodies, and multispecific antibodies formed from antibody fragments. The fragment of the antibody also includes Fab', which is a monovalent fragment of antibody variable regions obtained by the treatment of F(ab')$_2$ under reducing conditions.

The antibody of the present invention may be a multi-specific antibody having specificity for at least two different types of antigens. Such a molecule usually binds to two types of antigens (i.e., a bispecific antibody). The "multispecific antibody" according to the present invention encompasses an antibody having specificity for more types (e.g., 3 types) of antigens.

The multispecific antibody of the present invention may be an antibody consisting of a full length, or may be a fragment of such an antibody (e.g., a bispecific antibody). The bispecific antibody may be prepared by linking the heavy and light chains (HL pairs) of two types of antibodies, or may be prepared by fusing hybridomas producing different monoclonal antibodies to prepare bispecific antibody-producing fusion cells (Millstein et al., Nature (1983) 305, p. 537-539).

The antibody of the present invention may be single-chain Fv (also referred to as scFv). The single-chain Fv is obtained by linking the heavy and light chain variable regions of the antibody via a polypeptide linker (Pluckthun, The Pharmacology of Monoclonal Antibodies, 113 (Rosenberg and Moore ed., Springer Verlag, New York, p. 269-315 (1994); and Nature Biotechnology (2005), 23, p. 1126-1136). Also, a biscFv fragment prepared by linking two scFvs via a polypeptide linker can also be used as a bispecific antibody.

The method for preparing the single-chain Fv is well-known in the art (see e.g., U.S. Pat. Nos. 4,946,778, 5,260,203, 5,091,513, and 5,455,030). In this scFv, the heavy chain variable region and the light chain variable region are linked via a linker that prevents these regions from forming a conjugate, preferably a polypeptide linker (Huston, J. S. et al., Proc. Natl. Acad. Sci. U.S.A. (1988), 85, p. 5879-5883). The heavy chain variable region and the light chain variable region in the scFv may be derived from the same antibody or may be derived from different antibodies. For example, an arbitrary single-chain peptide consisting of 12 to 19 residues is used as the polypeptide linker that links these variable regions.

In order to obtain DNA encoding the scFv, each DNA portion encoding the whole or desired amino acid sequence in the sequences of DNA encoding the heavy chain or heavy chain variable region of the antibody and DNA encoding the light chain or light chain variable region thereof, is used as a template and amplified by PCR using a primer pair flanking both ends of the template. Subsequently, DNA encoding the polypeptide linker moiety is further amplified in combination with a primer pair defined so that the polypeptide linker moiety can be linked at its ends to the heavy and light chain DNAs, respectively.

Once the DNA encoding the scFv is prepared, an expression vector comprising the DNA and a host transformed with the expression vector can be obtained by routine methods. In addition, the host can be used to obtain the scFv according to a routine method. These antibody fragments can be produced by a host in the same way as above by obtaining and expressing the gene.

The antibody of the present invention may have enhanced affinity for the antigen by multimerization. Antibodies of the same type may be multimerized, or a plurality of antibodies recognizing a plurality of epitopes, respectively, of the same antigen may be multimerized. Examples of a method for multimerizing these antibodies can include the binding of two scFvs to an IgG CH3 domain, the binding thereof to streptavidin, and the introduction of a helix-turn-helix motif.

The antibody of the present invention may be a polyclonal antibody which is a mixture of plural types of anti-ALK2 antibodies differing in amino acid sequence. One example of the polyclonal antibody can include a mixture of plural types of antibodies differing in CDRs. An antibody obtained by culturing a mixture of cells producing different antibodies, followed by purification from the cultures can be used as such a polyclonal antibody (see WO2004/061104).

The antibody of the present invention may be an antibody having 80% to 99% identity as compared with the heavy and/or light chains of the antibody. In this context, the term "identity" has general definition used in the art. The % identity refers to the percentage of the number of identical amino acids relative to the total number of amino acids (including gaps) when two amino acid sequences are aligned so as to give the largest consistency of amino acids. Antibodies that have an ability to bind to the antigen and an inhibitory effect on BMP signal transduction at analogous levels to the antibodies described above can be selected by combining sequences that exhibit high identity to the amino acid sequences of the heavy and light chains. Such identity is generally 80% or higher identity, preferably 90% or higher identity, more preferably 95% or higher identity, most preferably 99% or higher identity. Alternatively, antibodies that have various effects equivalent to the antibodies described above may be selected by combining amino acid sequences that comprise a substitution(s), a deletion(s), and/or an addition(s) of one to several amino acid residues in the amino acid sequences of the heavy and/or light chains. The number of amino acid residues to be substituted, deleted, and/or added is generally 10 or less amino acid residues, preferably 5 or 6 or less amino acid residues, more preferably 2 or 3 or less amino acid residues, most preferably 1 amino acid residue.

The heavy chain of an antibody produced by cultured mammalian cells is known to lack a carboxyl-terminal lysine residue (Journal of Chromatography A, 705: 129-134 (1995)). Also, the heavy chain of such an antibody is known to lack two carboxyl-terminal amino acid residues (glycine and lysine) and instead have an amidated proline residue at the carboxy terminus (Analytical Biochemistry, 360: 75-83 (2007)).

An amino-terminal glutamine or glutamic acid residue in the heavy or light chain of an antibody is known to be modified by pyroglutamylation during preparation of the antibody, and the antibody of the present invention may have such a modification (WO2013/147153).

Such deletion in the heavy chain sequence or modification in the heavy or light chain sequence does not influence the ability of the antibody to bind to the antigen and its effector functions (complement activation, antibody-dependent cytotoxic effects, etc.).

Thus, the present invention also encompasses an antibody that has received the deletion or the modification. Examples thereof can include a deletion variant derived from a heavy chain by the deletion of 1 or 2 amino acids at its carboxyl terminus, an amidated form of the deletion variant (e.g., a heavy chain having an amidated proline residue at the carboxyl-terminal site), and an antibody having a pyroglutamylated amino-terminal amino acid residue in a heavy or light chain thereof. However, the deletion variant at the carboxyl terminus of the antibody heavy chain according to the present invention is not limited to the types described above as long as the deletion variant maintains the ability to bind to the antigen and the effector functions. Two heavy chains constituting the antibody according to the present invention may be heavy chains of any one type selected from the group consisting of the full-length heavy chain and the deletion variants described above, or may be a combination of heavy chains of any two types selected therefrom. The quantitative ratio of each deletion variant may be influenced by the type of cultured mammalian cells producing the antibody according to the present invention, and culture conditions. Examples of such a case can include the deletion of one carboxyl-terminal amino acid residue each in both the two heavy chains as main components of the antibody according to the present invention.

The identity between two types of amino acid sequences can be determined using the default parameters of Blast algorithm version 2.2.2 (Altschul, Stephen F., Thomas L. Madden, Alejandro A. Schaffer, Jinghui Zhang, Zheng Zhang, Webb Miller, and David J. Lipman (1997), "Gapped BLAST and PSI-BLAST: a new generation of protein database search programs", Nucleic Acids Res. 25: 3389-3402). The Blast algorithm is also available by access to www.ncbi.nlm.nih.gov/blast on the Internet. Two types of percentage values, Identity (or Identities) and Positivity (or Positivities), are calculated according to the Blast algorithm. The former is a value that indicates identical amino acid residues between two types of amino acid sequences between which the identity should be determined. The latter is a numerical value determined by also taking into consideration similar amino acid residues in terms of their chemical structures. Herein, the value of identity is defined as the value of "Identity" when amino acid residues are identical between the amino acid sequences.

An antibody conjugated with any of various molecules such as polyethylene glycol (PEG) can also be used as a modified form of the antibody.

The antibody of the present invention may further be any of conjugates formed by these antibodies with other drugs (immunoconjugates). Examples of such an antibody can include the antibody conjugated with a radioactive material or a compound having a pharmacological effect (Nature Biotechnology (2005) 23, p. 1137-1146).

The obtained antibody can be purified until homogeneous. A protein separation and purification method usually used can be used for the separation and purification of the antibody. The antibody can be separated and purified by appropriately selected or combined approaches, for example, column chromatography, filtration through a filter, ultrafiltration, salting-out, dialysis, preparative polyacrylamide gel electrophoresis, and/or isoelectric focusing (Strategies for Protein Purification and Characterization: A Laboratory Course Manual, Daniel R. Marshak et al. eds., Cold Spring Harbor Laboratory Press (1996); and Antibodies: A Laboratory Manual. Ed Harlow and David Lane, Cold Spring Harbor Laboratory (1988)), though the separation and purification method is not limited thereto.

Examples of the chromatography can include affinity chromatography, ion-exchange chromatography, hydrophobic chromatography, gel filtration chromatography, reverse-phase chromatography, and adsorption chromatography.

These chromatography approaches can be carried out using liquid chromatography such as HPLC or FPLC.

Examples of the column for use in the affinity chromatography can include protein A columns and protein G columns.

Examples of the protein A columns can include Hyper D, POROS, and Sepharose F. F. (GE Healthcare Bio-Sciences Corp.).

Also, the antibody may be purified by exploiting its binding activity to the antigen using an antigen-immobilized carrier.

5. Drug Comprising Anti-ALK2 Antibody

An antibody inhibiting the biological activity of ALK2 can be obtained from among anti-ALK2 antibodies obtained by the methods described above in the preceding paragraph "4. Production of anti-ALK2 antibody". Such an antibody inhibiting the biological activity of ALK2 inhibits the biological activity of ALK2, i.e., ALK2-mediated BMP signal transduction, in vivo and as such, can be pharmaceutically used as a therapeutic and/or prophylactic drug for ectopic ossification and/or bone dysplasia or a therapeutic and/or prophylactic drug for anemia.

Examples of the disease that can be treated and/or prevented with the anti-ALK2 antibody can include fibrodysplasia ossificans progressiva (FOP), progressive osseous heteroplasia (POH), traumatic ectopic ossification, ectopic ossification after implant arthroplasty, spondyloarthritis (SpA), ankylosing spondylitis (AS), anemia, diffuse intrinsic pontine glioma (DIPG), and thinning hair. The disease is preferably fibrodysplasia ossificans progressiva (FOP), progressive osseous heteroplasia (POH), traumatic ectopic ossification, or ectopic ossification after implant arthroplasty, more preferably fibrodysplasia ossificans progressiva (FOP), though the disease is not limited thereto as long as the disease is caused by ALK2-mediated BMP signal transduction. In FOP patients, finger or toe fusion or deformity, cervical fusion or deformity, or the like is also found, and hearing loss is also manifested. These conditions are also included in the disease caused by ALK2-mediated BMP signal transduction.

Activating mutations in ALK2 have been confirmed in all FOP patients, and 10 or more types of mutations have been reported so far. All of these mutations have been found to be amino acid mutations (missense mutations) present in the intracellular region of the ALK2 protein and do not cause any change in the amino acid sequence of the extracellular region. The antibody of the present invention binds to the extracellular region of ALK2 and as such, can be used as a therapeutic and/or prophylactic drug for every FOP patient, irrespective of the types of mutations.

The treatment of FOP means cure of FOP symptoms, amelioration of the symptoms, mitigation of the symptoms, or suppression of progression of the symptoms.

The prevention of FOP means circumvention or suppression of onset of flare-up or ectopic ossification.

The antibody of the present invention also binds not only to mutated ALK2 but to wild-type ALK2 and inhibits downstream signals. Therefore, the antibody of the present invention can also be used as a therapeutic and/or prophylactic drug for non-hereditary ectopic ossification different from FOP. Examples of the non-hereditary ectopic ossification include ectopic ossification after brain contusion, ectopic ossification after spinal cord injury, ectopic ossification after burn injury, and ectopic ossification after implant arthroplasty. The involvement of neuropeptides, fat cells, and immune system cells such as macrophages has been reported as a cause for the non-hereditary ectopic ossification (see J. Cell. Biochem., 112, 10 (2011); J. Cell. Biochem., 112, 10 (2011); and J. Pathol., 236, 2 (2015)). It has been suggested that a similar mechanism is also involved in flare-up in FOP patients (see Hum. Pathol., 32, 8 (2001); and Histol. Histopathol., 29, 10 (2014)). Thus, the antibody of the present invention can be used as a therapeutic and/or prophylactic drug not only for ectopic ossification in FOP but for non-hereditary ectopic ossification.

Hepcidin gene is known as a target gene whose transcription is positively regulated by the BMP-ALK signal transduction pathway in anemia (see Blood, 118, 15 (2011)). Hepcidin is a peptide hormone mainly produced in the liver, and regulates the degradation of a transporter, called ferroportin, which is expressed in the gastrointestinal tract and involved in iron absorption (see Science, 306, 5704 (2004)). A potential therapeutic drug for anemia has been reported because the functional inhibition of hepcidin or the suppression of its expression level leads to the promotion of iron uptake from the gastrointestinal tract via increase in the expression level of ferroportin (see Pharmacol Ther, 146 (2015)). Thus, the antibody of the present invention can also be used as a therapeutic and/or prophylactic drug for iron-deficiency anemia by increasing iron absorption via the suppression of hepcidin expression in the liver.

Alternatively, the antibody of the present invention may be used as a therapeutic and/or prophylactic drug for diffuse intrinsic pontine glioma (DIPG). DIPG is diffuse (infiltrative) astrocytoma that is found mainly in the pons of the brain stem and reportedly accounts for approximately 75 to 80% of pediatric brain stem tumors. There is a report stating that fewer than about 10% of children with DIPG survive for more than 2 years, because the brain stem regulates essential functions such as respiration (Khuong-Quang D-A et al., Acta Neuropathol 124: 439-447, 2012). The antibody of the present invention can also be used as a therapeutic and/or prophylactic drug for DIPG.

Examples of the anti-ALK2 antibody as these drugs can include chimeric antibodies and humanized antibodies prepared by the methods described in "4. Production of anti-ALK2 antibody" from the A2-15A antibody, the A2-27D antibody, the A2-11E antibody, or the A2-25C antibody. A chimeric antibody, a humanized antibody and a human antibody binding to the same epitope as that for the A2-15A antibody, the A2-27D antibody, the A2-11E antibody, and/or the A2-25C antibody may also be used as the drugs.

The biological activity of ALK2 (BMP signal inhibitory activity) of the anti-ALK2 antibody can be confirmed in vitro, for example, by luciferase assay using reporter plasmids having an insert of a BMP-responsive sequence, SMAD1/5/8 phosphorylation, expression analysis of BMP target genes, or measurement of alkaline phosphatase activity in mouse myoblasts C2C12 induced to differentiate into osteoblasts by stimulation with a BMP ligand.

The therapeutic or prophylactic effects of the anti-ALK2 antibody on ectopic ossification or bone dysplasia can be confirmed in vivo using laboratory animals, for example, by subcutaneously or intravenously administering the anti-ALK2 antibody to ectopic ossification-induced models with BMP ligand-containing pellets transplanted to mouse muscle, or FOP mouse models harboring mutated ALK2, and analyzing ectopic bone formation.

The anti-AKL2 antibody thus obtained is useful as a drug, particularly, a pharmaceutical composition aimed at treating or preventing ectopic ossification such as fibrodysplasia ossificans progressiva (FOP).

As one example, the anti-ALK2 antibody can be administered alone or in combination with at least one additional therapeutic drug for ectopic ossification in the treatment or prevention of ectopic ossification. As another example, the anti-ALK2 antibody can be administered in combination with a therapeutically effective amount of a therapeutic drug. Examples of the additional therapeutic drug for ectopic ossification that can be administered in combination with the anti-ALK2 antibody can include, but are not limited to, anti-inflammatory drugs, steroids, bisphosphonates, muscle relaxants, and retinoic acid receptor (RAR) γ agonists.

Examples of the anti-inflammatory drug can include aspirin, diclofenac, indomethacin, ibuprofen, ketoprofen, naproxen, piroxicam, rofecoxib, celecoxib, azathioprine, penicillamine, methotrexate, sulfasalazine, leflunomide, infliximab, and etanercept. Indomethacin, ibuprofen, piroxicam, or celecoxib is preferred.

Examples of the steroid can include prednisolone, beclomethasone, betamethasone, fluticasone, dexamethasone, and hydrocortisone. Prednisolone is preferred.

Examples of the bisphosphonate can include alendronate, cimadronate, clodronate, etidronate, ibandronate, incadronate, minodronate, neridronate, olpadronate, pamidronate, piridronate, risedronate, tiludronate, and zoledronate. Pamidronate or zoledronate is preferred.

Examples of the muscle relaxant can include cyclobenzaprine, metaxalone, and baclofen. Baclofen is preferred.

Examples of the retinoic acid receptor γ agonist can include palovarotene.

Depending on the condition of ectopic ossification or the intended degree of treatment and/or prevention, two or three or more additional therapeutic drugs can be administered, and these additional therapeutic drugs can be included in the same preparation and thereby administered at the same time. The additional therapeutic drug and the anti-ALK2 antibody can also be included in the same preparation and thereby administered at the same time. Also, the anti-ALK2 antibody and the additional therapeutic drug can be included in separate preparations and administered at the same time. Alternatively, the additional agent and the anti-ALK2 antibody may be separately administered one after another. Specifically, a therapeutic drug comprising the anti-ALK2 antibody or the antigen-binding fragment of the antibody as an active ingredient may be administered after administration of the additional therapeutic drug, or the additional therapeutic drug may be administered after administration of the therapeutic drug containing the anti-ALK2 antibody or the antigen-binding fragment of the antibody as an active ingredient. For administration in gene therapy, a gene for a protein serving as a therapeutic drug for ectopic ossification and the gene for the anti-ALK2 antibody can be inserted at a site downstream of separate promoter regions or the same promoter region and can be introduced to separate vectors or the same vector.

The anti-ALK2 antibody or the fragment thereof can be conjugated with a therapeutic drug for ectopic ossification to produce a targeted drug conjugate described in M. C. Garnet "Targeted drug conjugates: principles and progress", Advanced Drug Delivery Reviews, (2001) 53, 171-216. For this purpose, an antibody molecule as well as any antibody fragment is applicable unless their ALK2-recognizing properties are completely deleted. Examples of the antibody fragment can include fragments such as Fab, $F(ab')_2$, and Fv. In the present invention as well, the antibody and the fragment can be used. The conjugation manner of the anti-ALK2 antibody or the fragment of the antibody with the therapeutic drug for FOP can take various forms described in, for example, M. C. Garnet "Targeted drug conjugates: principles and progress", Advanced Drug Delivery Reviews, (2001) 53, 171-216, G. T. Hermanson "Bioconjugate Techniques" Academic Press, California (1996), Putnam and J. Kopecek "Polymer Conjugates with Anticancer Activity" Advances in Polymer Science (1995) 122, 55-123. Specific examples thereof can include a manner in which the anti-ALK2 antibody is chemically conjugated with the therapeutic drug for ectopic ossification either directly or via a spacer such as an oligopeptide, and a manner in which the anti-ALK2 antibody is conjugated with the therapeutic drug for ectopic ossification via an appropriate drug carrier. Examples of the drug carrier can include liposomes and water-soluble polymers. Examples of such a manner via the drug carrier can more specifically include a manner in which the therapeutic drug for ectopic ossification is encapsulated in a liposome and the liposome is conjugated with the antibody, and a manner in which the therapeutic drug for ectopic ossification is chemically conjugated with a water-soluble polymer (compound having a molecular weight on the order of 1000 to 100,000) either directly or via a spacer such as an oligopeptide and the water-soluble polymer is conjugated with the antibody. The conjugation of the antibody (or the fragment) with the therapeutic drug for ectopic ossification or the drug carrier (e.g., a liposome or a water-soluble polymer) can be carried out by a method well known to those skilled in the art, such as a method described in G. T. Hermanson "Bioconjugate Techniques" Academic Press, California (1996), and Putnam and J. Kopecek "Polymer Conjugates with Anticancer Activity" Advances in Polymer Science (1995) 122, 55-123. The encapsulation of the therapeutic drug for ectopic ossification in the liposome can be carried out by a method well known to those skilled in the art, such as a method described in, for example, D. D. Lasic "Liposomes: From Physics to Applications", Elsevier Science Publishers B. V., Amsterdam (1993). The conjugation of the therapeutic drug for ectopic ossification with the water-soluble polymer can be carried out by a method well known to those skilled in the art, such as a method described in D. Putnam and J Kopecek "Polymer Conjugates with Anticancer Activity" Advances in Polymer Science (1995) 122, 55-123. The conjugate of the antibody (or the fragment) with the protein as a therapeutic drug for ectopic ossification (or a fragment thereof) can be prepared by any of the methods described above or a genetic engineering method well known to those skilled in the art.

The present invention also provides a pharmaceutical composition comprising a therapeutically and/or prophylactically effective amount of the anti-ALK2 antibody and a pharmaceutically acceptable diluent, carrier, solubilizer, emulsifier, preservative, and/or auxiliary agent.

The present invention also provides a pharmaceutical composition comprising a therapeutically and/or prophylactically effective amount of the anti-ALK2 antibody, a therapeutically and/or prophylactically effective amount of at least one therapeutic drug for ectopic ossification, and a pharmaceutically acceptable diluent, carrier, solubilizer, emulsifier, preservative, and/or auxiliary agent.

It is preferred that the pharmaceutically acceptable material used in the pharmaceutical composition of the present invention should be nontoxic to a recipient of the pharmaceutical composition, preferably in terms of a dose or an administered concentration.

The pharmaceutical composition of the present invention can comprise pharmaceutical materials for changing or maintaining pH, osmotic pressure, viscosity, transparency, color, tonicity, sterility, stability, solubility, sustained release, absorbability, or permeability. Examples of the pharmaceutical materials can include, but are not limited to, the following: amino acids such as glycine, alanine, glutamine, asparagine, arginine, and lysine; antimicrobial agents; antioxidants such as ascorbic acid, sodium sulfate, and sodium bisulfite; buffers such as phosphate, citrate, or borate buffers, sodium bicarbonate, and Tris-HCl solutions; fillers such as mannitol and glycine; chelating agents such as ethylenediaminetetraacetic acid (EDTA); complexing agents such as caffeine, polyvinylpyrrolidine, β-cyclodextrin, and hydroxypropyl-β-cyclodextrin; bulking agents such as glucose, mannose, and dextrin; other carbohydrates such as monosaccharides and disaccharides; coloring agents; corrigents; diluents; emulsifiers; hydrophilic polymers such as polyvinylpyrrolidine; low-molecular-weight polypeptides; salt-forming counterions; antiseptics such as benzalkonium chloride, benzoic acid, salicylic acid, thimerosal, phenethyl alcohol, methylparaben, propylparaben, chlorhexidine, sorbic acid, and hydrogen peroxide; solvents such as glycerin, propylene glycol, and polyethylene glycol; sugar alcohols such as mannitol and sorbitol; suspending agents; surfactants such as sorbitan ester, polysorbates such as polysorbate 20 and polysorbate 80, triton, tromethamine, lecithin, and cholesterol; stability enhancers such as sucrose and sorbitol; elasticity enhancers such as sodium chloride, potassium chloride, mannitol, and sorbitol; transport agents; excipients; and/or pharmaceutical auxiliary agents. The amount of these pharmaceutical materials added is preferably 0.01 to 100 times, particularly, 0.1 to 10 times relative to the weight of the anti-ALK2 antibody. The suitable components of the pharmaceutical composition in a preparation can be appropriately determined by those skilled in the art according to an applicable disease, an applicable administration route, etc.

The excipient or the carrier in the pharmaceutical composition may be liquid or solid. Appropriate excipients or carriers may be injectable water, physiological saline, artificial cerebrospinal fluids, or other materials usually used in parenteral administration. Neutral physiological saline or physiological saline containing serum albumin may be used as a carrier. The pharmaceutical composition can contain a Tris buffer of pH 7.0 to 8.5, an acetate buffer of pH 4.0 to 5.5, or a citrate buffer of pH 3.0 to 6.2. These buffers can also contain sorbitol or other compounds. Examples of the pharmaceutical composition of the present invention can include a pharmaceutical composition comprising the anti-ALK2 antibody, and a pharmaceutical composition comprising the anti-ALK2 antibody and at least one therapeutic drug for ectopic ossification. The pharmaceutical composition of the present invention is prepared in the form of a freeze-dried product or a liquid as a drug having a selected recipe and a necessary purity. The pharmaceutical composition comprising the anti-ALK2 antibody, or the pharmaceutical composition comprising the anti-ALK2 antibody and at least one therapeutic drug for ectopic ossification can also be formed as a freeze-dried product using an appropriate excipient such as sucrose.

The pharmaceutical composition of the present invention may be prepared for parenteral administration or may be prepared for absorption in the gastrointestinal tract through an oral route. The recipe and concentration of the preparation can be determined according to an administration method. As the anti-ALK2 antibody contained in the pharmaceutical composition of the present invention has higher affinity for ALK2, i.e., a lower dissociation constant (KD value) for ALK2, the anti-ALK2 antibody can exert efficacy even at a reduced dose to a human. Therefore, the dose of the pharmaceutical composition of the present invention to a human can also be determined on the basis of this result. The dose for the administration of the human type anti-ALK2 antibody to a human is, for example, approximately 0.1 to 100 mg/kg, which can be administered once or twice or more per 1 to 180 days. However, the dose and the number of doses should generally be determined in consideration of the sex, body weight, and age of a patient, symptoms, severity, adverse reactions, etc., and therefore, are not limited to the dose or usage described above.

Non-limiting examples of the form of the pharmaceutical composition of the present invention can include injections including intravenous drips, suppositories, transnasal formulations, sublingual formulations, and transdermal absorption formulations. The administration route is an oral administration route or a parenteral administration route. Non-limiting examples of the parenteral administration route include intravenous, intraarterial, intramuscular, intrarectal, transmucosal, and intradermal routes.

EXAMPLES

The present invention will be specifically described hereinafter with Examples; however, the invention is not limited thereto. In the following Examples, unless otherwise specified, operations concerning genetic manipulation were performed in accordance with methods described in "Molecular Cloning" (Sambrook, J., Fritsch, E. F., and Maniatis, T., Cold Spring Harbor Laboratory Press, 1989), or where commercial reagents or kits were used, they were used in accordance with the manuals for such commercial products.

Example 1

Preparation of rat anti-ALK2 antibodies (11E2, 15A6, 25C11, and 27D11: hereinafter abbreviated as A2-11E, A2-15A, A2-25C, and A2-27D)

1)-1 Preparation of an Antigen

Mouse ALK2-His&Fc (Cat. #50297-M03H) from Sino Biological Inc. was used as mALK2-Fc, which is the antigen.

1)-2 Immunization of Animals 1 mg/mL of mouse ALK2-His&Fc was mixed with an equal volume of TiterMaxGold (TiterMax, USA) to prepare an emulsion. To two 6-week-old Wister female rats, 100 µg per rat of the antigen was subcutaneously administered with the adjuvant in two divided doses. After 1 to 2 weeks, 40 µg of only the antigen solution was subcutaneously administered, and after 3 days, spleen cells and various lymph glands were aseptically removed as antibody-producing cells, and subjected to the following cell fusion.

1)-3 Cell Fusion with Myeloma Cells

The above-described antibody-producing cells were mixed with a myeloma cell line (P3U1 cells) derived from BALB/c mice at a ratio of 5:1 to 10:1, and fused for 3 minutes using 50% polyethylene glycol 1500, and then diluted over 6 minutes. The fused cells were seeded with feeder cells (thymocytes) into ten 96-well plates per rat. The cells were cultured in 15% FBS-containing RPMI1640 medium (containing glutamine, pyruvic acid, penicillin, and streptomycin) containing HAT supplement.

1)-4 Selection of Hybridomas

One week after the cell fusion, using each culture supernatant, clones recognizing mouse ALK2-His&Fc used as the antigen were selected by the enzyme-linked immunosorbent assay (ELISA), and clones recognizing only human Fc (Sino Biological Inc.) were excluded. ELISA was performed as follows.

First, the antigen diluted to 1 µg/ml with PBS was immobilized onto a 96-well ELISA plate (NUNC, Cat. #442404) for 2 hours at room temperature or overnight at 4° C. The immobilized solution was removed, and the plate was blocked with a 0.5% skim milk solution dissolved in PBS for 30 minutes at room temperature. Next, the above-described culture supernatant of hybridomas was added, and the plate was left for 1 hour at room temperature. After the plate was washed, an ALP-labeled anti-rat IgG antibody (SBA, Inc.)

diluted with 0.5% skim milk to 1:2500 was added, and the plate was further left for 1 hour at room temperature. After the plate was washed, a phenyl phosphate substrate was reacted for 20 minutes at room temperature, and then absorbance at a wavelength of 492 nm was measured.

Selected hybridomas were cloned twice or more by limiting dilution. Through the above-described operations, hybridoma cell lines producing monoclonal antibodies A2-11E, A2-15A, A2-25C, and A2-27D were isolated.

The results are shown in FIG. 1. The results showed that each of the monoclonal antibodies produced by hybridomas A2-11E, A2-15A, A2-25C, and A2-27D recognized mouse ALK2-His&Fc, and did not bind to human Fc.

Example 2

In vitro evaluation of rat anti-ALK2 antibodies (A2-11E, A2-15A, A2-25C, and A2-27D)

2)-1 Antibody Screening by Flow Cytometry

2)-1-1 Preparation of Mouse and Human ALK2-Expressing Cells

HEK293A cells were seeded into a 100-mm dish at $3 \times 10^4$ cells/cm$^2$, and cultured overnight in 15% FBS-containing DMEM medium under the conditions of 5% $CO_2$ at 37° C. On the following day, the HEK293A cells were transfected with each of pcDEF3/mouse ALK2(WT)-EGFP, pcDEF3/human ALK2(WT)-EGFP, pcDEF3/human ALK2 (R206H)-EGFP, and pcDEF3, using Lipofectamine 2000 (Invitrogen), and further cultured overnight. On the following day, 100 μL each of the cell suspensions adjusted to $1 \times 10^6$ cells/mL was dispensed into a 1.5-mL microfuge and centrifuged at 500 g for 5 minutes, and then the supernatant was removed. To the cells, 100 μL of purified IgG diluted to 1 μg/mL was added, and the cells were left for 30 minutes at 4° C. After the cells were washed with PBS three times, 100 μL of Alexa flour 647 Goat anti-Rat IgG (H+L) (Life Technologies) diluted to 1:200 was added, and the cells were further left for 30 minutes at 4° C. After the cells were washed with PBS three times, fluorescence was detected by a flow cytometer (FACS Aria II: BD Biosciences). The data was analyzed using BD Diva Software (BD Biosciences), and the intensity of EGFP expressed by the cells and the fluorescence intensity of stained Alexa flour 647 were plotted.

Figure 2A:
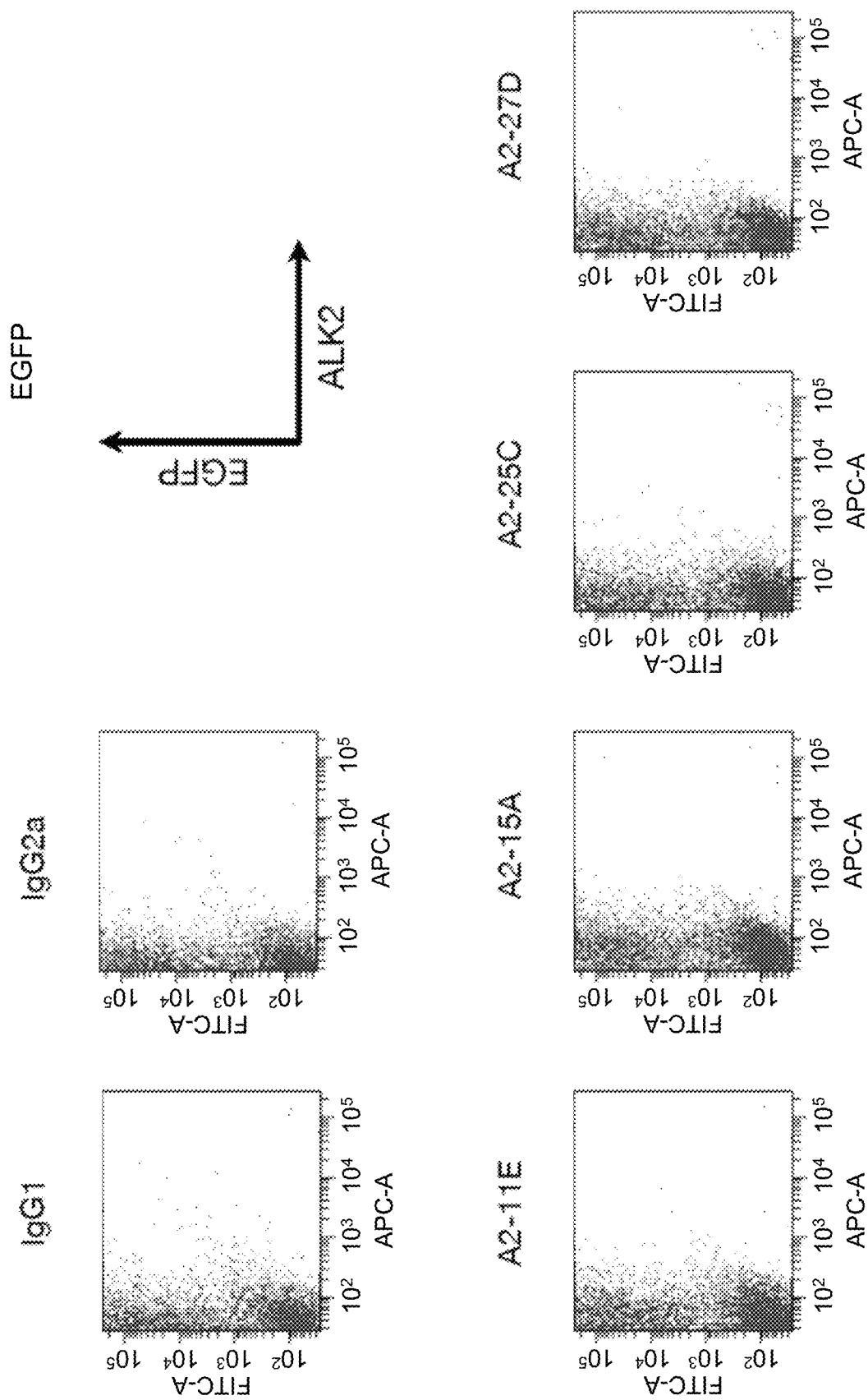
FIG. 2A This figure is a graph showing that the monoclonal antibodies produced by the hybridomas A2-11E, A2-15A, A2-25C, and A2-27D do not recognize cells expressing a fluorescent protein EGFP.
Figure 2B:
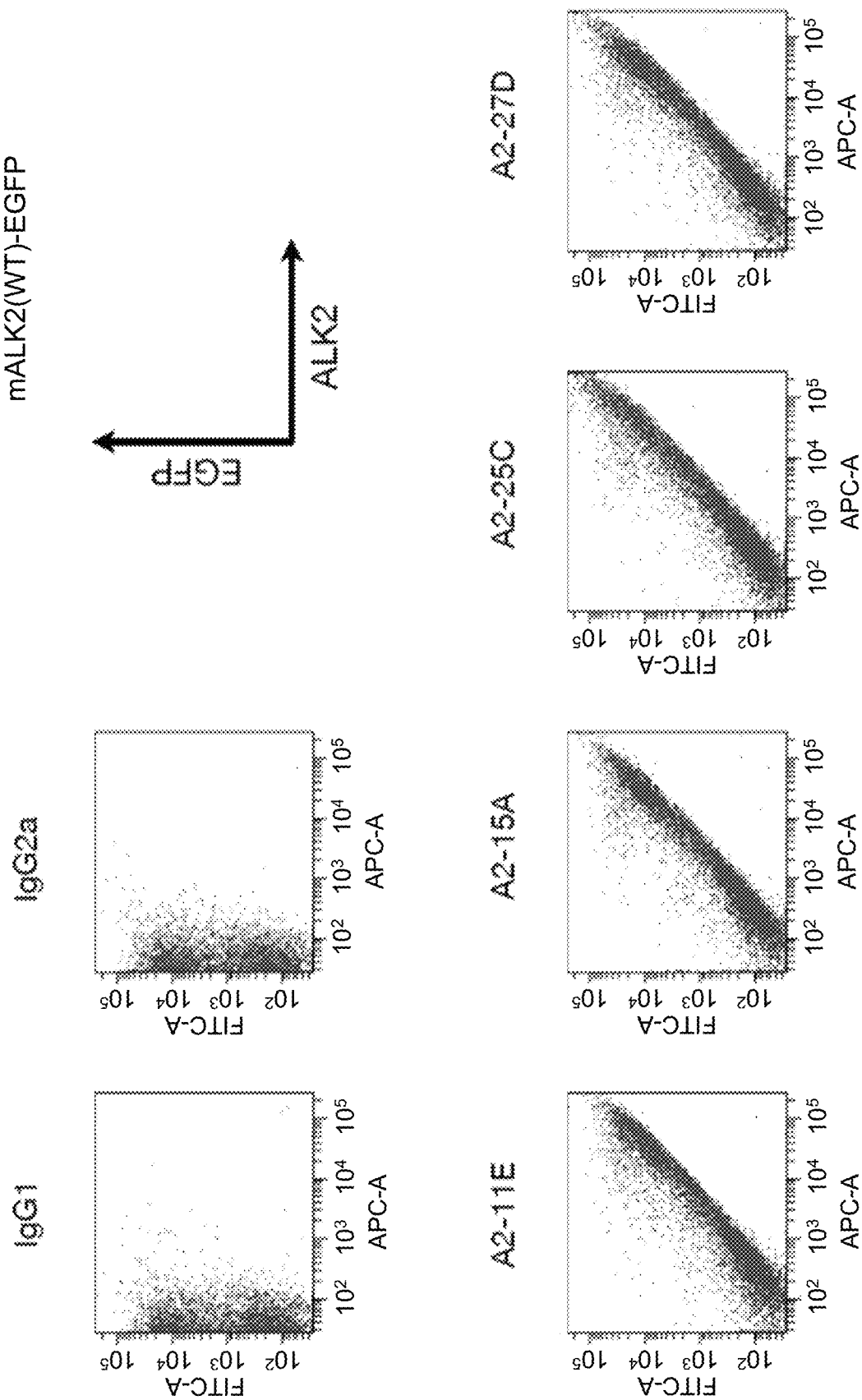
FIG. 2B This figure is a graph showing that the monoclonal antibodies produced by the hybridomas A2-11E, A2-15A, A2-25C, and A2-27D recognize cells expressing wild-type mouse ALK2 (mALK2(WT)-EGFP).
Figure 2C:
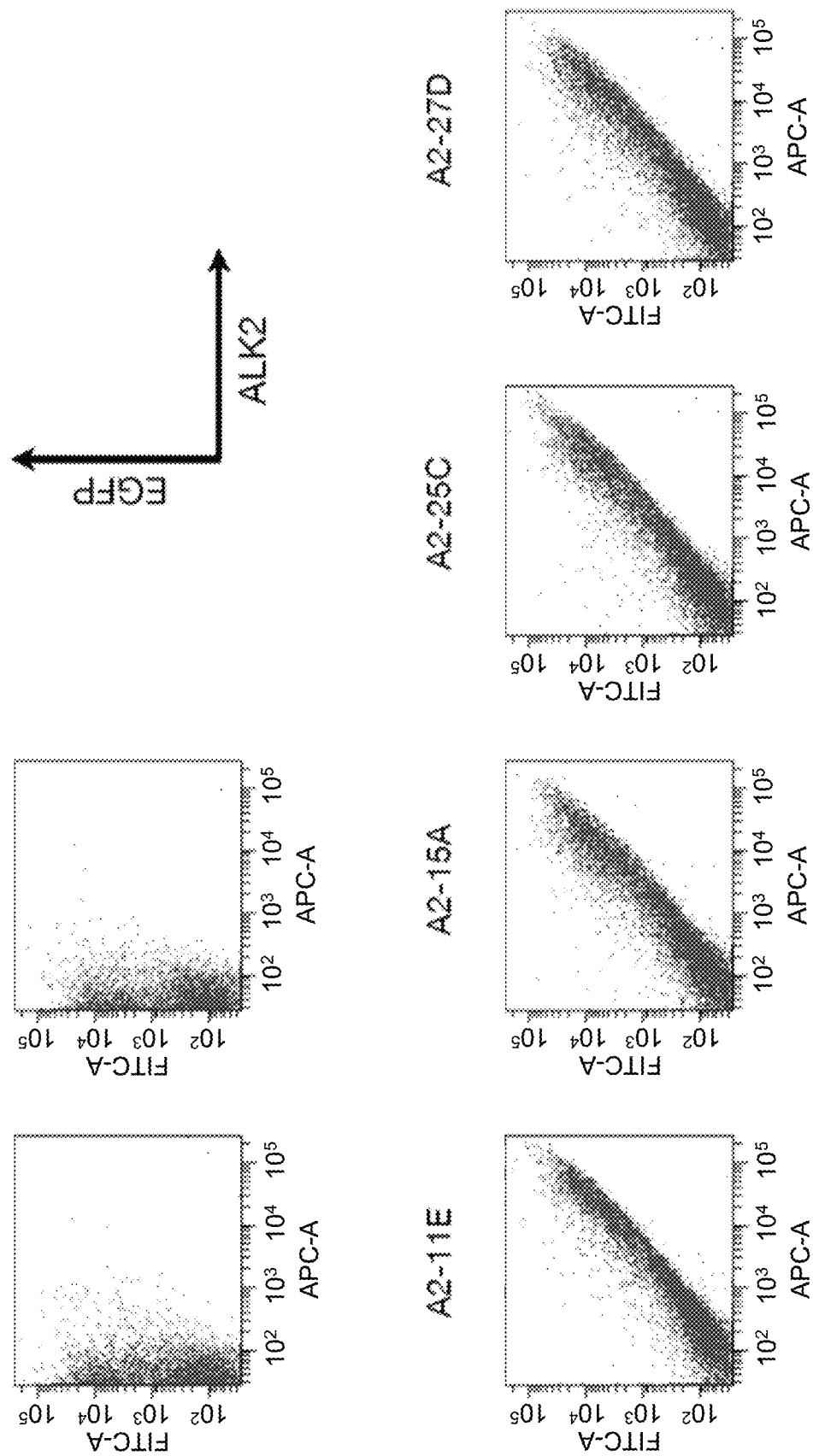
FIG. 2C This figure is a graph showing that the monoclonal antibodies produced by the hybridomas A2-11E, A2-15A, A2-25C, and A2-27D recognize cells expressing wild-type human ALK2 (hALK2(WT)-EGFP).
Figure 2D:
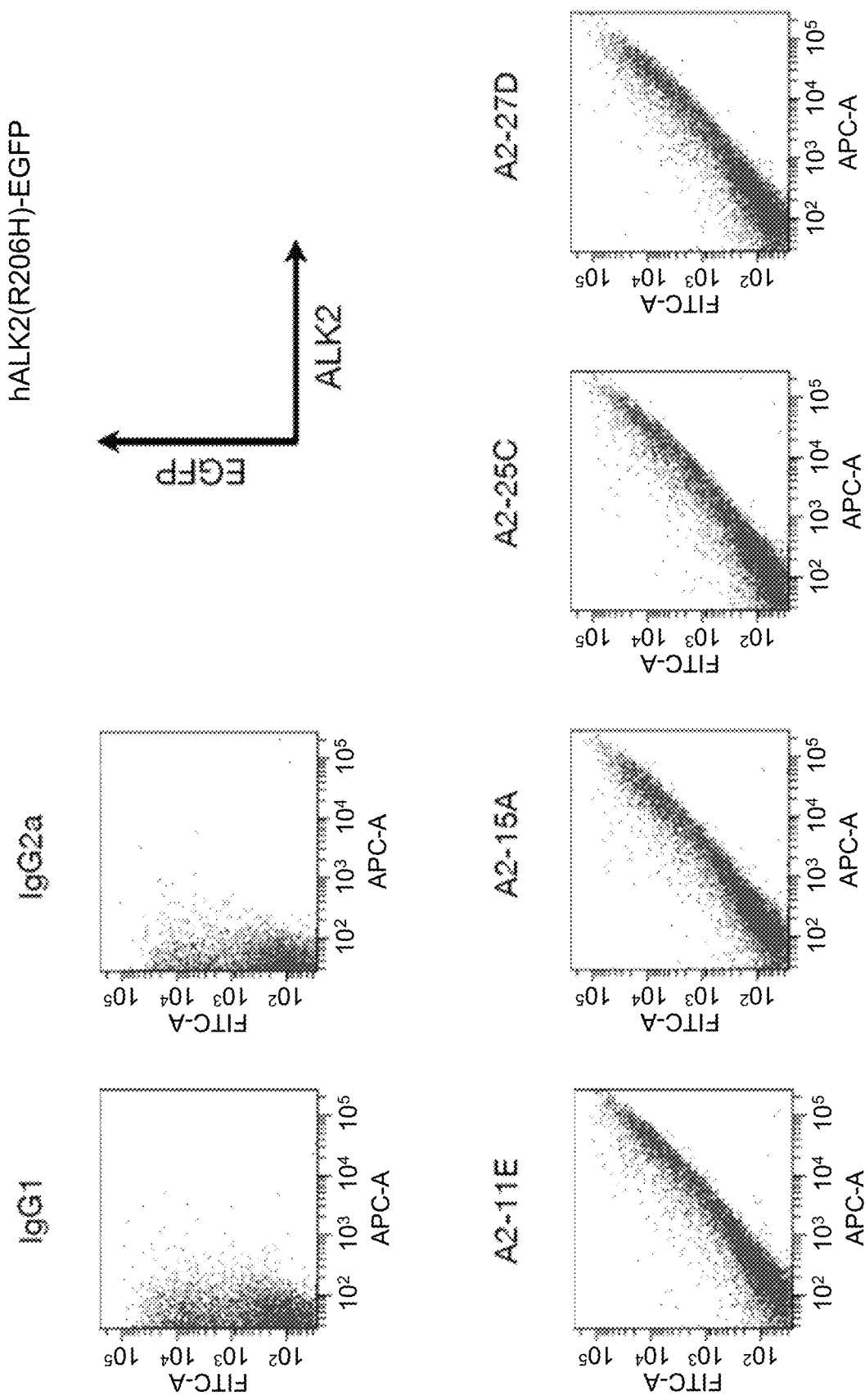
FIG. 2D This figure is a graph showing that the monoclonal antibodies produced by the hybridomas A2-11E, A2-15A, A2-25C, and A2-27D recognize cells expressing human ALK2 having a FOP mutation (R206H) (hALK2 (R206H)-EGFP).

The results are shown in FIGS. 2A to 2D. It was confirmed that each of the monoclonal antibodies produced by hybridomas A2-11E, A2-15A, A2-25C, and A2-27D did not recognize fluorescence protein EGFP-expressing cells (FIG. 2A), but specifically recognized mouse ALK2-expressing cells (FIG. 2B) as well as wild-type and FOP human ALK2-expressing cells (FIGS. 2C and 2D, respectively). These results show that the monoclonal antibodies produced by hybridomas A2-11E, A2-15A, A2-25C, and A2-27D are antibodies that bind to the extracellular region of ALK2.

2)-2 Antibody Screening by Immunostaining

2)-2-1 Preparation of Human ALK1-, ALK2-, ALK3-, and ALK6-Expressing Cells

Mouse C2C12 cells were seeded into a 96-well plate (Greiner Bio-One) at $5 \times 10^3$ cells/well, and cultured overnight in 15% FBS-containing DMEM medium under the conditions of 5% $CO_2$ at 37° C. On the following day, the C2C12 cells were transfected with each of pcDEF3/human ALK1-EGFP, pcDEF3/human ALK2-EGFP, pcDEF3/human ALK3-EGFP, pcDEF3/human ALK6-EGFP, and pcDEF3 as a control, using Lipofectamine 2000 (Invitrogen), and further cultured overnight.

2)-2-2 Immunofluorescence Staining of Human ALK1, ALK2, ALK3, and ALK6

The C2C12 cells were fixed with 10% neutral formalin (Nacalai Tesque, Japan) for 20 minutes at room temperature, and then blocked with 10% goat normal serum for 30 minutes. After the blocking agent was removed, purified IgG diluted to 10 μg/mL with the blocking agent was added, and the cells were left for 1 hour at room temperature. After the cells were washed with PBS three times, Goat Alexa 594-conjugated anti-rat IgG (Invitrogen) diluted to 1:1000 with the blocking agent was added, and the cells were left for 1 hour at room temperature. After the cells were washed with PBS three times, the cells were fixed with 10% neutral formalin for 15 minutes at room temperature, and nuclear-stained with DAPI (LifeTechnologies). Fluorescent signals were analyzed with a fluorescence microscope BZ-9000 (Keyence).

Figure 3:
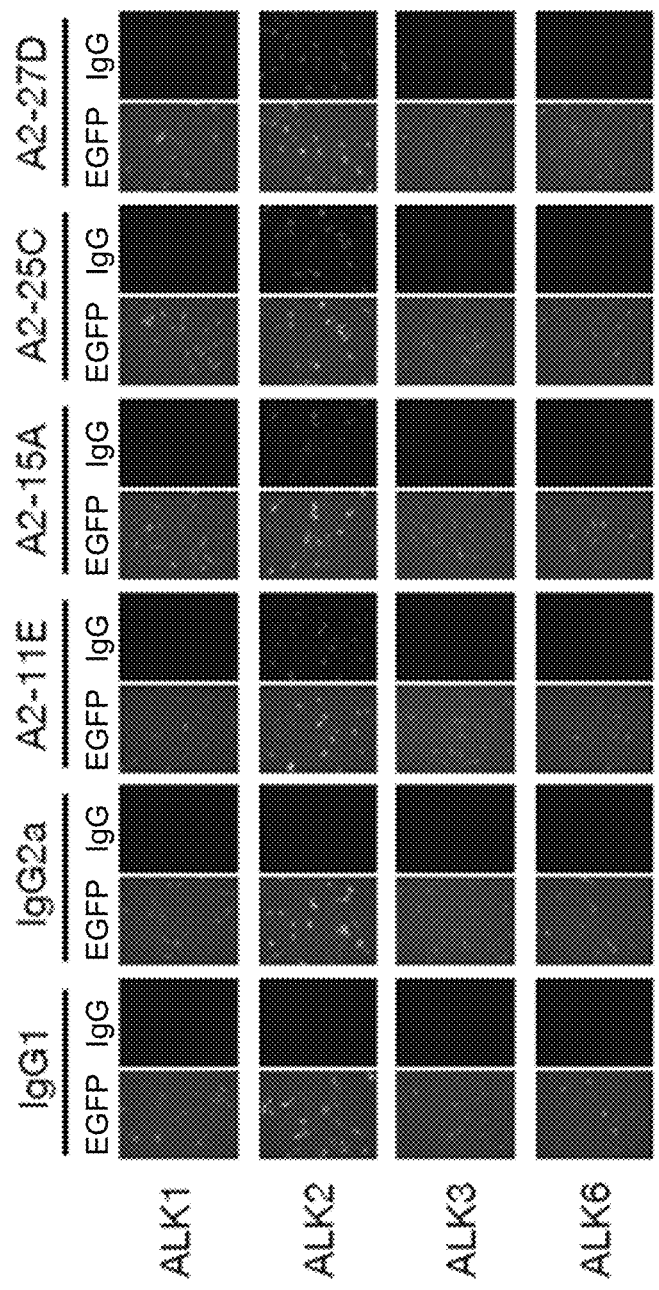
FIG. 3 This figure is a graph showing that the monoclonal antibodies produced by the hybridomas A2-11E, A2-15A, A2-25C, and A2-27D specifically recognize only ALK2-expressing cells and do not recognize cells expressing ALK1, ALK3, or ALK6.

The results are shown in FIG. 3. It was confirmed that the monoclonal antibodies produced by hybridomas A2-11E, A2-15A, A2-25C, and A2-27D specifically recognized only ALK2-expressing cells, and did not recognize ALK1-, ALK3-, and ALK6-expressing cells. These results show that the monoclonal antibodies produced by hybridomas A2-11E, A2-15A, A2-25C, and A2-27D are antibodies that specifically bind to ALK2.

2)-2-3 Preparation of Cells Expressing ALK2 Mutants Identified in FOP

Mouse C2C12 cells were seeded into a 96-well plate (Greiner Bio-One) at $0.5 \times 10^3$ cells/well, and cultured in 15% FBS-containing DMEM medium overnight under the conditions of 5% $CO_2$ at 37° C. On the following day, the C2C12 cells were transfected with each of a wild-type human ALK2 cDNA integrated into pcDEF3; pcDEF3/human ALK2-L196P, pcDEF3/human ALK2-P197_F198delinsL, pcDEF3/human ALK2-R202I, pcDEF3/human ALK2-R206H, pcDEF3/human ALK2-Q207E, pcDEF3/human ALK2-R258S, pcDEF3/human ALK2-G325A, pcDEF3/human ALK2-G328E, pcDEF3/human ALK2-G328R, pcDEF3/human ALK2-G328W, pcDEF3/human ALK2-G356D, and pcDEF3/human ALK2-R375P, which are variants identified in FOP; and pcDEF3 as a control, using Lipofectamine 2000 (Invitrogen), and further cultured overnight.

2)-2-4 Immunofluorescence Staining of ALK2 Mutants Identified in FOP

The C2C12 cells were fixed with 10% neutral formalin (Nacalai Tesque, Japan) for 20 minutes at room temperature, and then blocked with 10% goat normal serum for 30 minutes. After the blocking agent was removed, purified IgG diluted to 10 μg/mL with the blocking agent was added, and the cells were left for 1 hour at room temperature. After the cells were washed with PBS three times, Goat Alexa 594-conjugated anti-rat IgG (Invitrogen) diluted to 1:1000 with the blocking agent was added, and the cells were left for 1 hour at room temperature. After the cells were washed with PBS three times, the cells were fixed with 10% neutral formalin for 15 minutes at room temperature, and nuclear-stained with DAPI (LifeTechnologies). Fluorescent signals were analyzed with a fluorescence microscope BZ-9000 (Keyence).

Figure 4:
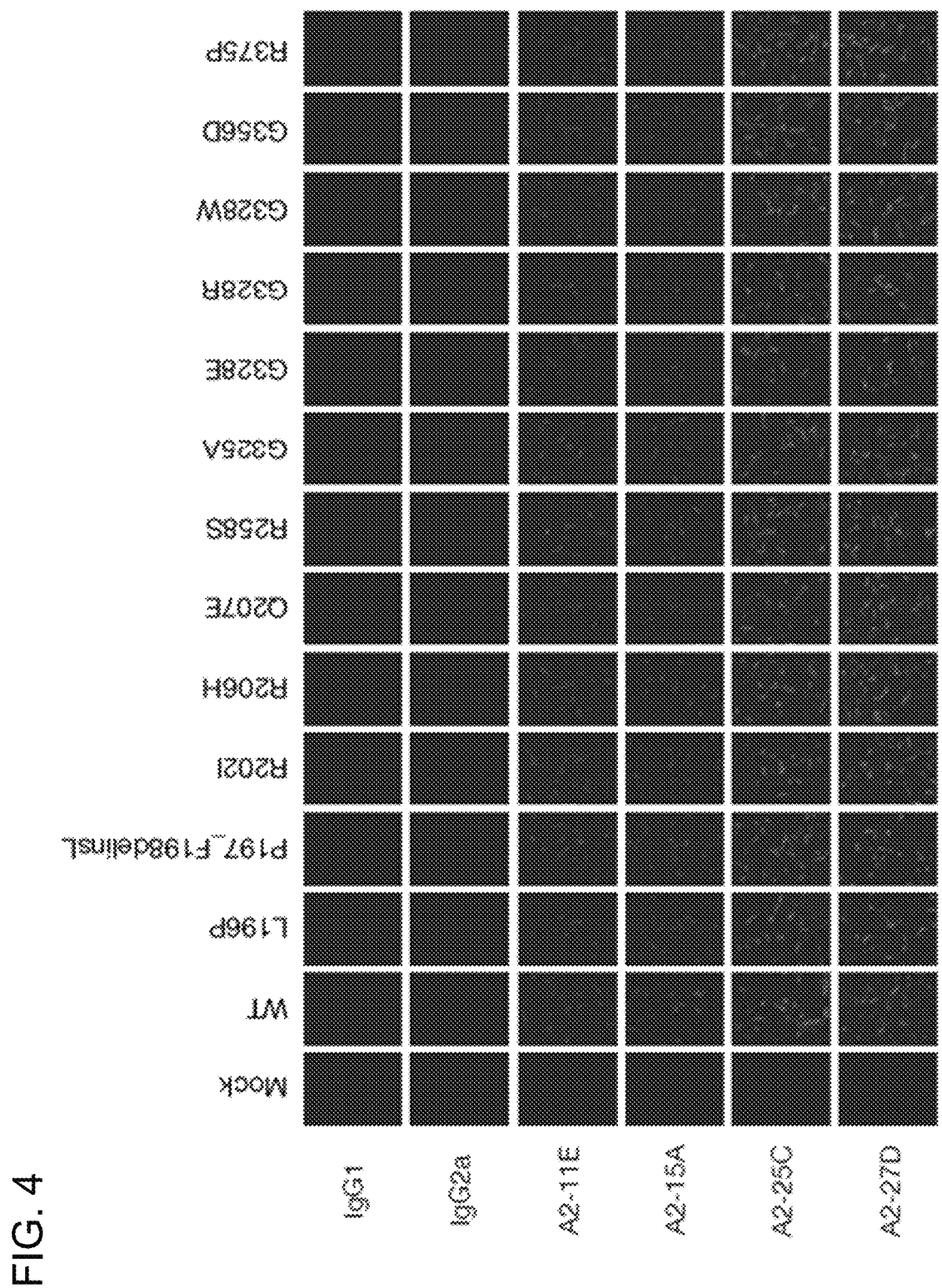
FIG. 4 This figure is a graph showing that the monoclonal antibodies produced by the hybridomas A2-11E, A2-15A, A2-25C, and A2-27D recognize cells expressing wild-type ALK2 and cells expressing the shown 12 types of ALK2 mutants identified in FOP.

The results are shown in FIG. 4. It was confirmed that the monoclonal antibodies produced by hybridomas A2-11E, A2-15A, A2-25C, and A2-27D recognized the cells expressing the 12 types of ALK2 mutants identified in FOP, in addition to the wild-type ALK2-expressing cells. These results show that the monoclonal antibodies produced by hybridomas A2-11E, A2-15A, A2-25C, and A2-27D are antibodies that bind to wild-type ALK2 and each of the ALK2 mutants in FOP.

2)-3 Antibody Screening by Luciferase Reporter Assay

The ALK2-mediated intracellular signaling inhibitory activity of each of the monoclonal antibodies was analyzed using a BMP-specific luciferase reporter. HEK293A cells were seeded into a 96-well white plate for luciferase assay (Greiner Bio-One) at 1×10$^4$ cells/well, and cultured overnight in 15% FBS-containing DMEM medium under the conditions of 5% $CO_2$ at 37° C. On the following day, the HEK293A cells were transfected with pcDEF3/human ALK2(WT)-V5-His or pcDEF3/human ALK2(R206H)-V5-His, pGL4.26/Id1WT4F-luc (Genes Cells, 7, 949 (2002)), and phRL SV40 (Promega), using Lipofectamine 2000 (Invitrogen). After 2.5 hours, the medium was replaced with fresh OPTI-MEM I (LifeTechnologies), and the cells were further cultured for 1 hour. Thereafter, the medium was replaced with OPTI-MEM I containing the serially diluted monoclonal antibody and 10 ng/mL of BMP7 (Milteney) or 0.5 ng/mL of BMP9 (Peprotech), and the cells were further cultured overnight. On the following day, the firefly and Renilla luciferase activities were measured with the plate reader GENios (TECAN), using Dual-Glo Luciferase Assay System (Promega).

Figure 5:
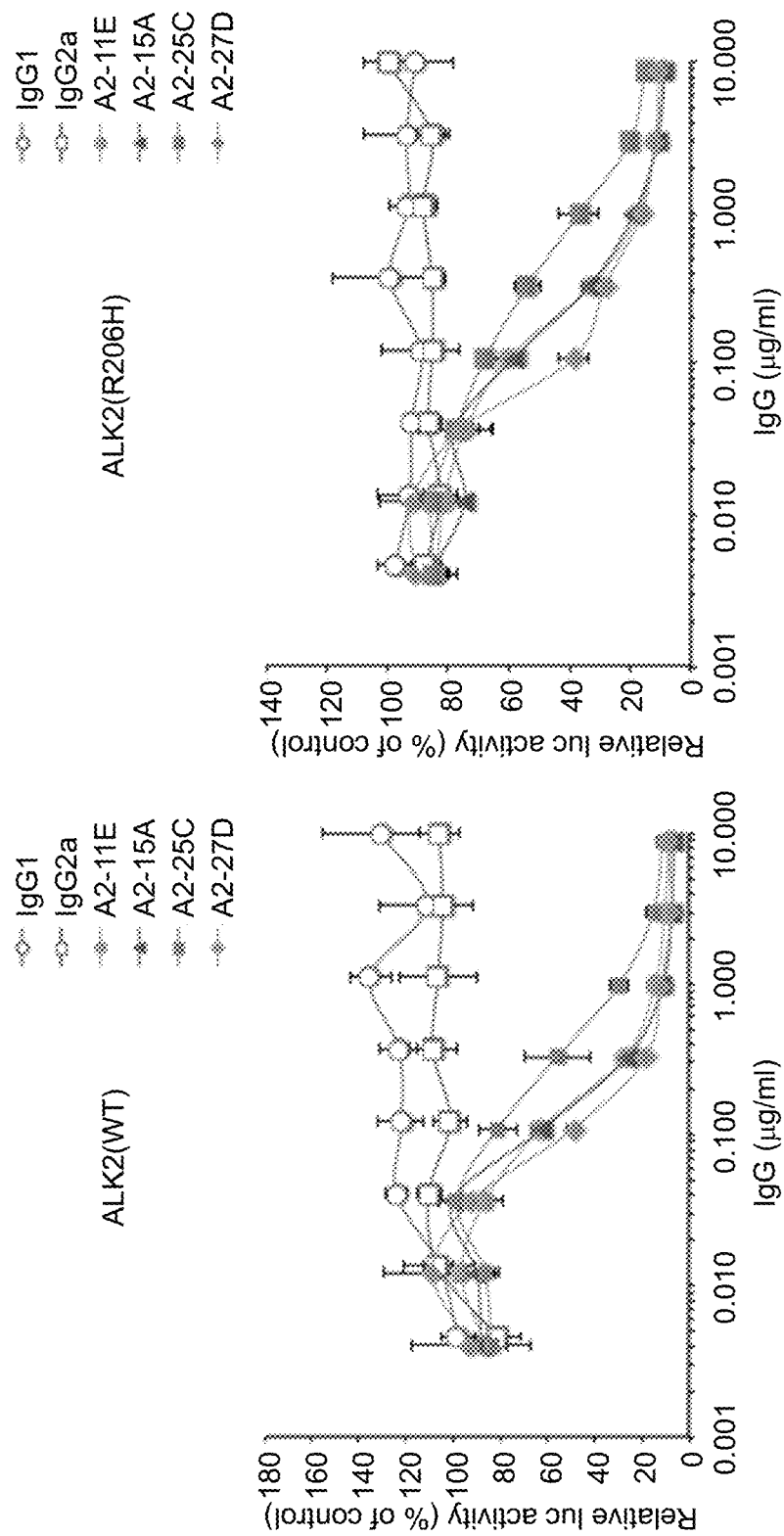
FIG. 5 This figure is a graph showing that the monoclonal antibodies produced by the hybridomas A2-11E, A2-15A, A2-25C, and A2-27D inhibit, in a dose-dependent manner, BMP-specific luciferase (luc) activity induced by BMP7 in HEK293A cells in which wild-type ALK2 or a R206H mutant has been overexpressed.

The results are shown in FIG. 5. It was confirmed that the monoclonal antibodies produced by hybridomas A2-11E, A2-15A, A2-25C, and A2-27D suppressed the BMP7-induced BMP-specific luciferase activity in a dose-dependent manner, in the HEK293A cells overexpressing wild-type ALK2 and mutant R206H.

2)-4 Antibody Screening by BMP-Induced Osteoblast Differentiation Induction Assay The endogenous ALK2-mediated intracellular signaling inhibitory activity of each of the monoclonal antibodies was analyzed based on the effect upon the BMP-induced activity of inducing the differentiation of C2C12 cells into osteoblasts. C2C12 cells were seeded into a 96-well plate (Greiner Bio-One) at 0.5×10$^3$ cells/well, and cultured in 15% FBS-containing DMEM medium overnight under the conditions of 5% $CO_2$ at 37° C. On the following day, the medium was replaced with OPTI-MEM I containing the serially diluted monoclonal antibody and 200 ng/mL of BMP2 (Corefront Corporation), 200 ng/mL of BMP7 (Miteney), or 20 ng/mL of GDF2/BMP9 (Peprotech), and the cells were further cultured for 3 days. After the medium was removed from the C2C12 cells and the cells were washed with PBS, the cells were treated with 50 μL/well of an ice-cold acetone:ethanol (1:1) solution for 1 minute, and further washed with PBS three times. ALP activity was measured as an index of the differentiation into cells for forming osteoblasts. To measure ALP activity, 100 μL/well of a substrate solution (0.1 M diethanolamine (Sigma-Aldrich)-HCl, pH 10.0, containing 1 mg/mL of 4-nitrophenyl phosphate (Sigma-Aldrich) and 1 mM of $MgCl_2$) was added, and reacted for 15 to 30 minutes at room temperature on an agitation shaker. The reaction was stopped by the addition of 50 μL of 3M NaOH, and absorbance at a wavelength of 405 nm was measured using the microplate reader Infinite F50 (TECAN).

Figure 6:
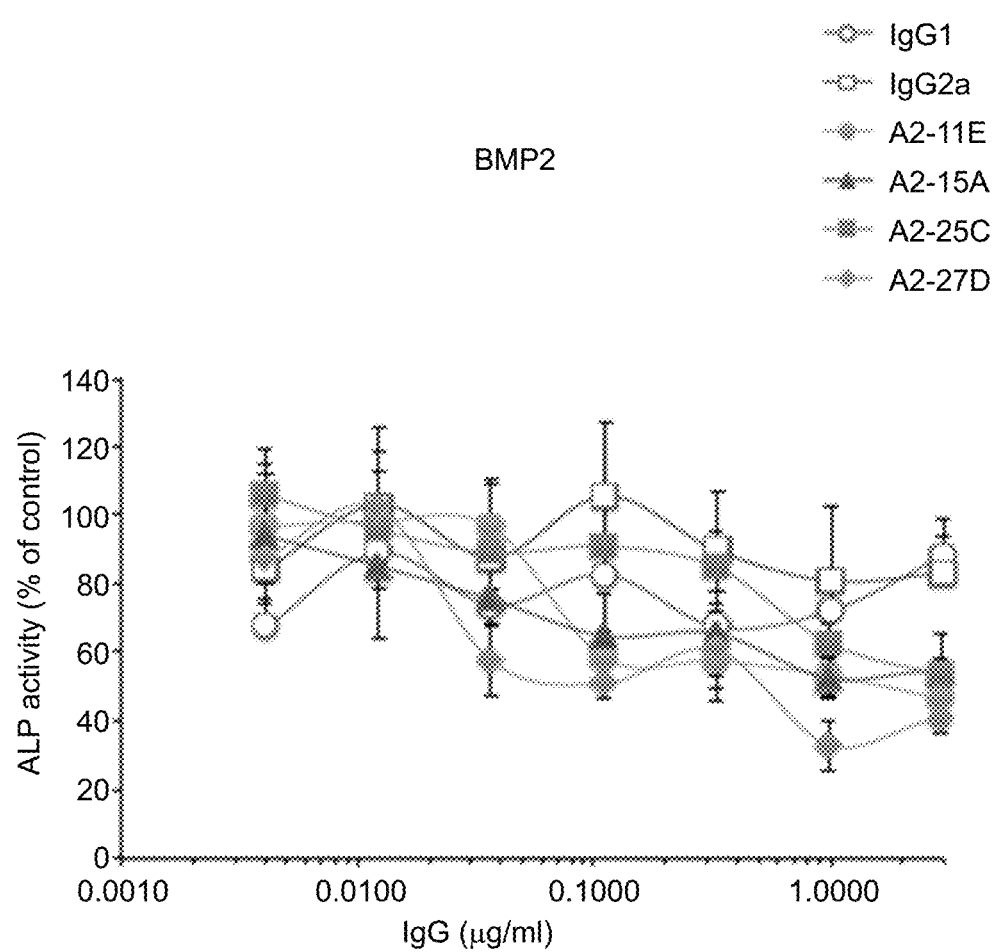
FIG. 6 This figure is a graph showing that the monoclonal antibodies produced by the hybridomas A2-11E, A2-15A, A2-25C, and A2-27D cannot completely inhibit the BMP2-induced differentiation of C2C12 cells into osteoblast-like cells.
Figure 7:
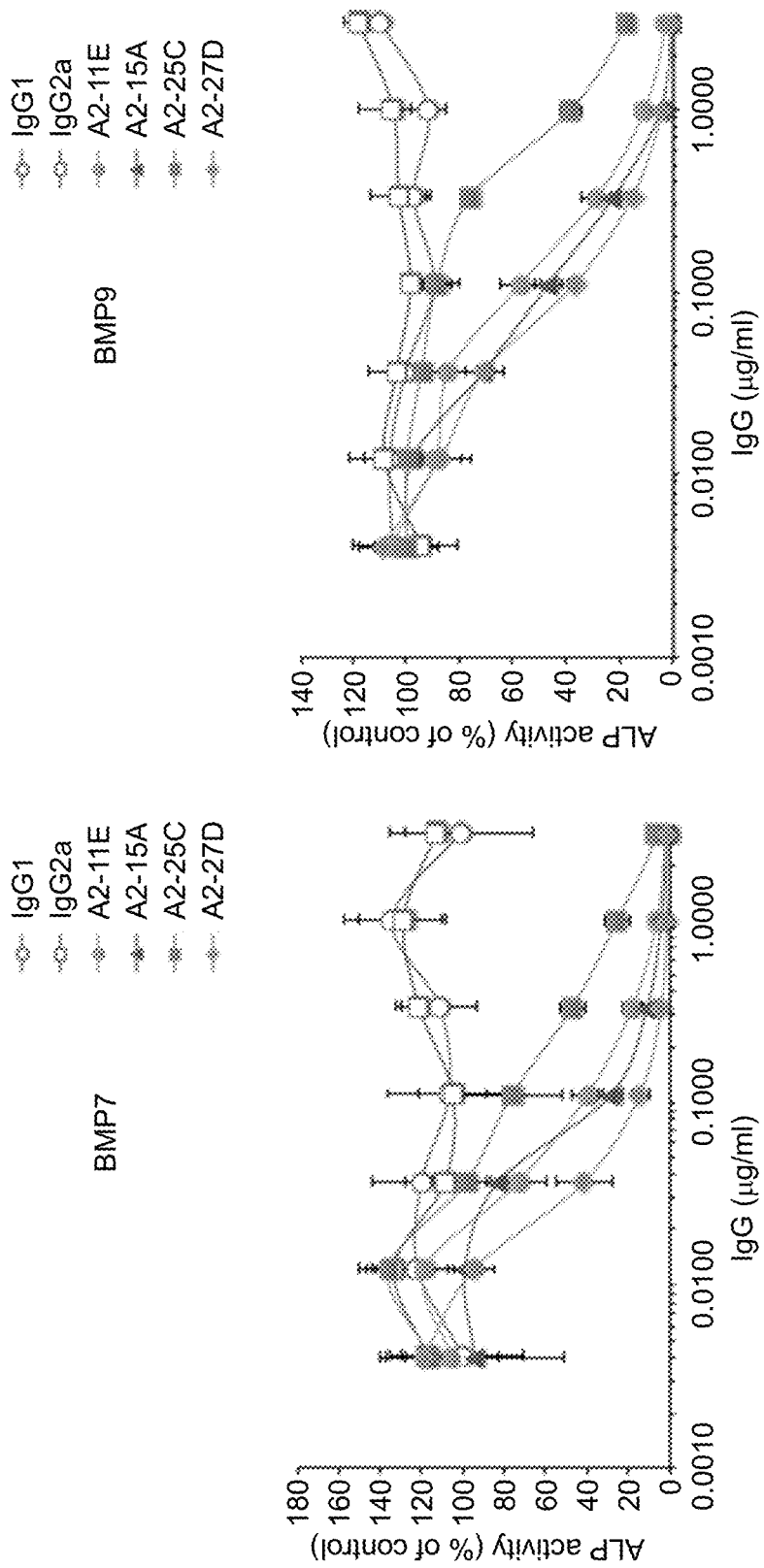
FIG. 7 This figure is a graph showing that the monoclonal antibodies produced by the hybridomas A2-11E, A2-15A, A2-25C, and A2-27D inhibit, in a dose-dependent manner, the BMP7- or GDF2/BMP9-induced differentiation of C2C12 cells into osteoblast-like cells.

The results are shown in FIGS. 6 and 7. It was confirmed that the monoclonal antibodies produced by hybridomas A2-11E, A2-15A, A2-25C, and A2-27D barely suppressed the BMP2-induced differentiation of the C2C12 cells into osteoblast-like cells (FIG. 6), but suppressed the BMP7- and GDF2/BMP9-induced differentiation of the C2C12 cells into osteoblast-like cells in a dose-dependent manner (FIG. 7). These results show that the monoclonal antibodies produced by hybridomas A2-11E, A2-15A, A2-25C, and A2-27D are antibodies that suppress endogenous ALK2 physiologically expressed by the C2C12 cells.

Example 3

Nucleotide sequencing of cDNAs encoding variable regions of rat anti-ALK2 antibodies (A2-11E, A2-15A, A2-25C, and A2-27D)

3)-1 Nucleotide Sequencing of cDNAs Encoding Variable Regions of A2-11E

3)-1-1 Preparation of Total RNA from A2-11E-Producing Hybridomas

To amplify cDNAs containing variable regions of A2-11E, total RNA was prepared from the A2-11E-producing hybridomas, using TRIzol Reagent (Ambion).

3)-1-2 Synthesis of a cDNA (5'-RACE-Ready cDNA)

A cDNA (5'-RACE-Ready cDNA) was synthesized from 1 μg of the total RNA prepared in Example 3)-1-1, using SMARTer RACE cDNA Amplification Kit (Clontech).

3)-1-3 Amplification by 5'-RACE PCR and Sequencing of a cDNA Containing a Heavy Chain Variable Region of A2-11E UPM (Universal Primer A Mix: included in SMARTer RACE cDNA Amplification Kit) and an oligonucleotide having the sequence: 5'-CTCCAGAGTTCCAGGT-CACGGTGACTGGC-3' (RG2AR3: SEQ ID NO: 88) were used as primers for PCR amplification of a cDNA containing the variable region of the heavy chain gene of A2-11E. UPM included in SMARTer RACE cDNA Amplification Kit (Clontech) was used, and RG2AR3 was designed from the sequence of a rat heavy chain constant region on a database.

A cDNA containing a heavy chain variable region of A2-1IE was amplified by 5'-RACE PCR using this combination of primers and the cDNA (5'-RACE-Ready cDNA) synthesized in Example 3)-1-2 as a template. PCR was performed using KOD-Plus-(TOYOBO, Japan) as polymerase, and using the touch-down PCR program in accordance with the manual of SMARTer RACE cDNA Amplification Kit (Clontech).

The cDNA containing the heavy chain variable region amplified by 5'-RACE PCR was purified using MinElute PCR Purification Kit (QIAGEN), and then cloned using Zero Blunt TOPO PCR Cloning Kit (Invitrogen), and the sequence analysis of the nucleotide sequence of the cloned cDNA containing the heavy chain variable region was performed.

As sequence primers, the oligonucleotide having the sequence: 5'-CTCCAGAGTTCCAGGT-CACGGTGACTGGC-3' (RG2AR3: SEQ ID NO: 88) designed from the sequence of a rat heavy chain constant region on a database and NUP (Nested Universal Primer A: included in SMARTer RACE cDNA Amplification Kit) were used.

The sequence analysis was performed using a gene sequence analyzer ("ABI PRISM 3700 DNA Analyzer; Applied Biosystems" or "Applied Biosystems 3730xl Analyzer; Applied Biosystems"), and the sequence reaction was performed using GeneAmp 9700 (Applied Biosystems).

The determined nucleotide sequence of the cDNA encoding the heavy chain variable region of A2-11E is shown in SEQ ID NO: 1 in the Sequence Listing, and the amino acid sequence is shown in SEQ ID NO: 2.

3)-1-4 Amplification by 5'-RACE PCR and Sequencing of a cDNA Containing a Light Chain Variable Region of A2-11E UPM (Universal Primer A Mix: included in SMARTer RACE cDNA Amplification Kit) and an oligonucleotide having the sequence: 5'-TCAGTAACACTGTCCAGGACACCATCTC-3' (RKR5; SEQ ID NO: 89) were used as primers for PCR amplification of a cDNA containing the variable region of the light chain gene of A2-11E. UPM included in SMARTer RACE cDNA Amplification Kit (Clontech) was used, and RKR5 was designed from the sequence of a rat light chain constant region on a database.

A cDNA containing a light chain variable region of A2-11E was amplified by 5'-RACE PCR using this combination of primers and the cDNA (5'-RACE-Ready cDNA) synthesized in Example 3)-1-2 as a template. PCR was performed using KOD-Plus-(TOYOBO, Japan) as polymerase, and using the touch-down PCR program in accordance with the manual of SMARTer RACE cDNA Amplification Kit (Clontech).

The cDNA containing the light chain variable region amplified by 5'-RACE PCR was purified using MinElute PCR Purification Kit (QIAGEN), and then cloned using Zero Blunt TOPO PCR Cloning Kit (Invitrogen), and the sequence analysis of the nucleotide sequence of the cloned cDNA containing the light chain variable region was performed.

As a sequence primer, the following sequence was designed from the sequence of a rat light chain constant region on a database. The oligonucleotide having the designed sequence: 5'-TCAGTAACACTGTCCAGGACACCATCTC-3' (RKR5; SEQ ID NO: 89) and NUP (Nested Universal Primer A: included in SMARTer RACE cDNA Amplification Kit) were used.

The sequence analysis was performed using a gene sequence analyzer ("ABI PRISM 3700 DNA Analyzer; Applied Biosystems" or "Applied Biosystems 3730xl Analyzer; Applied Biosystems"), and the sequence reaction was performed using GeneAmp 9700 (Applied Biosystems).

The determined nucleotide sequence of the cDNA encoding the light chain variable region of A2-11E is shown in SEQ ID NO: 3 in the Sequence Listing, and the amino acid sequence is shown in SEQ ID NO: 4.

3)-2 Nucleotide Sequencing of cDNAs Encoding Variable Regions of A2-15A

3)-2-1 Preparation of Total RNA from A2-15A-Producing Hybridomas

To amplify cDNAs containing variable regions of A2-15A, total RNA was prepared from the A2-15A-producing hybridomas, as in Example 3)-1-1.

3)-2-2 Synthesis of a cDNA (5'-RACE-Ready cDNA)

A cDNA (5'-RACE-Ready cDNA) was synthesized from 1 µg of the total RNA prepared in Example 3)-2-1, as in Example 3)-1-2.

3)-2-3 Amplification by 5'-RACE PCR and Sequencing of a cDNA Containing a Heavy Chain Variable Region of A2-15A A cDNA containing a heavy chain variable region of A2-15A was amplified as in Example 3)-1-3, using the cDNA (5'-RACE-Ready cDNA) synthesized in Example 3)-2-2 as a template, and the sequence was determined.

The determined nucleotide sequence of the cDNA encoding the heavy chain variable region of A2-15A is shown in SEQ ID NO: 5 in the Sequence Listing, and the amino acid sequence is shown in SEQ ID NO: 6.

3)-2-4 Amplification by 5'-RACE PCR and Sequencing of a cDNA Containing a Light Chain Variable Region of A2-15A A cDNA containing a light chain variable region of A2-15A was amplified as in Example 3)-1-4, using the cDNA (5'-RACE-Ready cDNA) synthesized in Example 3)-2-2 as a template, and the sequence was determined.

The determined nucleotide sequence of the cDNA encoding the light chain variable region of A2-15A is shown in SEQ ID NO: 7 in the Sequence Listing, and the amino acid sequence is shown in SEQ ID NO: 8.

3)-3 Nucleotide Sequencing of cDNAs Encoding Variable Regions of A2-25C

3)-3-1 Preparation of Total RNA from A2-25C-Producing Hybridomas

To amplify cDNAs containing variable regions of A2-25C, total RNA was prepared from the A2-25C-producing hybridomas, as in Example 3)-1-1.

3)-3-2 Synthesis of a cDNA (5'-RACE-Ready cDNA)

A cDNA (5'-RACE-Ready cDNA) was synthesized from 1 µg of the total RNA prepared in Example 3)-3-1, as in Example 3)-1-2.

3)-3-3 Amplification by 5'-RACE PCR and Sequencing of a cDNA Containing a Heavy Chain Variable Region of A2-25C A cDNA containing a heavy chain variable region of A2-25C was amplified as in Example 3)-1-3, using the cDNA (5'-RACE-Ready cDNA) synthesized in Example 3)-3-2 as a template, and the sequence was determined.

The determined nucleotide sequence of the cDNA encoding the heavy chain variable region of A2-25C is shown in SEQ ID NO: 9 in the Sequence Listing, and the amino acid sequence is shown in SEQ ID NO: 10.

3)-3-4 Amplification by 5'-RACE PCR and Sequencing of a cDNA Containing a Light Chain Variable Region of A2-25C A cDNA containing a light chain variable region of A2-25C was amplified as in Example 3)-1-4, using the cDNA (5'-RACE-Ready cDNA) synthesized in Example 3)-3-2 as a template, and the sequence was determined.

The determined nucleotide sequence of the cDNA encoding the light chain variable region of A2-25C is shown in SEQ ID NO: 11 in the Sequence Listing, and the amino acid sequence is shown in SEQ ID NO: 12.

3)-4 Nucleotide Sequencing of cDNAs Encoding Variable Regions of A2-27D

3)-4-1 Preparation of Total RNA from A2-27D-Producing Hybridomas

To amplify cDNAs containing variable regions of A2-27D, total RNA was prepared from the A2-27D-producing hybridomas, as in Example 3)-1-1.

3)-4-2 Synthesis of a cDNA (5'-RACE-Ready cDNA)

A cDNA (5'-RACE-Ready cDNA) was synthesized from 1 µg of the total RNA prepared in Example 3)-4-1, as in Example 3)-1-2.

3)-4-3 Amplification by 5'-RACE PCR and Sequencing of a cDNA Containing a Heavy Chain Variable Region of A2-27D A cDNA containing a heavy chain variable region of A2-27D was amplified as in Example 3)-1-3, using the cDNA (5'-RACE-Ready cDNA) synthesized in Example 3)-4-2 as a template, and the sequence was determined.

The determined nucleotide sequence of the cDNA encoding the heavy chain variable region of A2-27D is shown in SEQ ID NO: 13 in the Sequence Listing, and the amino acid sequence is shown in SEQ ID NO: 14.

3)-4-4 Amplification by 5'-RACE PCR and Sequencing of a cDNA Containing a Light Chain Variable Region of A2-27D A cDNA containing a light chain variable region of A2-27D was amplified as in Example 3)-1-4, using the cDNA (5'-RACE-Ready cDNA) synthesized in Example 3)-4-2 as a template, and the sequence was determined.

The determined nucleotide sequence of the cDNA encoding the light chain variable region of A2-27D is shown in SEQ ID NO: 15 in the Sequence Listing, and the amino acid sequence is shown in SEQ ID NO: 16.

Example 4

In vivo evaluation of rat anti-ALK2 antibodies (A2-15A and A2-27D)

4)-1 Preparation of Hybridoma Culture Supernatants $1.0 \times 10^6$ hybridomas obtained in Example 1)-4 were cultured in 10% FBS-containing TIL high-glucose medium (T75 flask), and then cultured at high density using INTEGRA CL1000 (10% FBS medium). Next, the medium was replaced with a serum-free medium, the cells were further cultured in INTEGRA CL1000, and then required volumes of hybridoma culture supernatants were obtained. The obtained hybridoma culture supernatants were stored at 2 to 8° C. until they were subjected to purification.

4)-2 Purification of the Antibodies from the Hybridoma Culture Supernatants

The antibodies were purified from the culture supernatants obtained in Example 4)-1 by protein G affinity chromatography (at 4 to 6° C.) in one step. The buffer replacement step after the purification by protein G affinity chromatography was performed at 4 to 6° C. Initially, each culture supernatant of hybridomas was applied to a PBS-equilibrated column packed with protein G (GE Healthcare Bioscience). After the entry of the whole culture supernatant in the column, the column was washed with at least twice the column volume of PBS. Next, fractions containing the antibody were collected by elution with a 0.1 M aqueous glycine/hydrochloric acid solution (pH 2.7). The collected fractions were adjusted to pH 7.0 to 7.5 by the addition of 1 M Tris-HCl (pH 9.0), and then subjected to buffer replacement with HBS or (25 mM histidine/5% sorbitol, pH 6.0) by dialysis (Thermo Scientific, Slide-A-Lyzer Dialysis Cassette). The fractions were concentrated using Centrifugal UF Filter Device VIVASPIN20 (molecular weight cutoff. UF10K, Sartorius, at 4° C.), and adjusted to an IgG concentration of 8 mg/ml or more. Finally, the fractions were filtered using the Minisart-Plus filter (Sartorius) to obtain a purified sample.

4)-3 BMP Transplantation-Induced Heterotopic Ossification Induction Models

The heterotopic ossification-suppressing activity of the monoclonal antibodies in skeletal muscle tissue was analyzed by BMP-induced heterotopic ossification induction experiments in mice. BMP-containing pellets were prepared by impregnating a type I collagen sponge (Collatape, Zimmer Dental) adjusted to a diameter of 4 mm with 1 µg of BMP7 (Milteney) or 1 µg of GDF2/BMP9 (Peprotech), and freeze-drying the sponge overnight in a freeze-drying machine (FDU-810, Tokyo Rikakikai Co., Ltd., Japan). 8- to 10-week-old C57BL/6 mice were placed under general anesthesia, using a simple inhalation anesthesia apparatus for small animal experiments (Natsume Seisakusho Co., Ltd., Japan) and 2% isoflurane (Wako Pure Chemical Industries, Ltd., Japan), and one of the BMP-containing pellets was transplanted into the thigh muscle tissue of each of the left and right lower extremities. The mice received subcutaneous administration of the monoclonal antibodies produced by hybridomas A2-15A and A2-27D at 10 mg/kg once a week, from 1 week before the transplantation until week 2 after the transplantation, as they were raised. An equal volume of a solvent (25 mM Histidine/5% Sorbitol, pH 6.0) was administered to a control group. Two weeks after the transplantation of the BMP-containing pellets, the thigh bone with the transplanted BMP-containing pellets were extracted, and heterotopic ossification was analyzed by micro-CT (µCT35, SCANCO).

Figure 8:
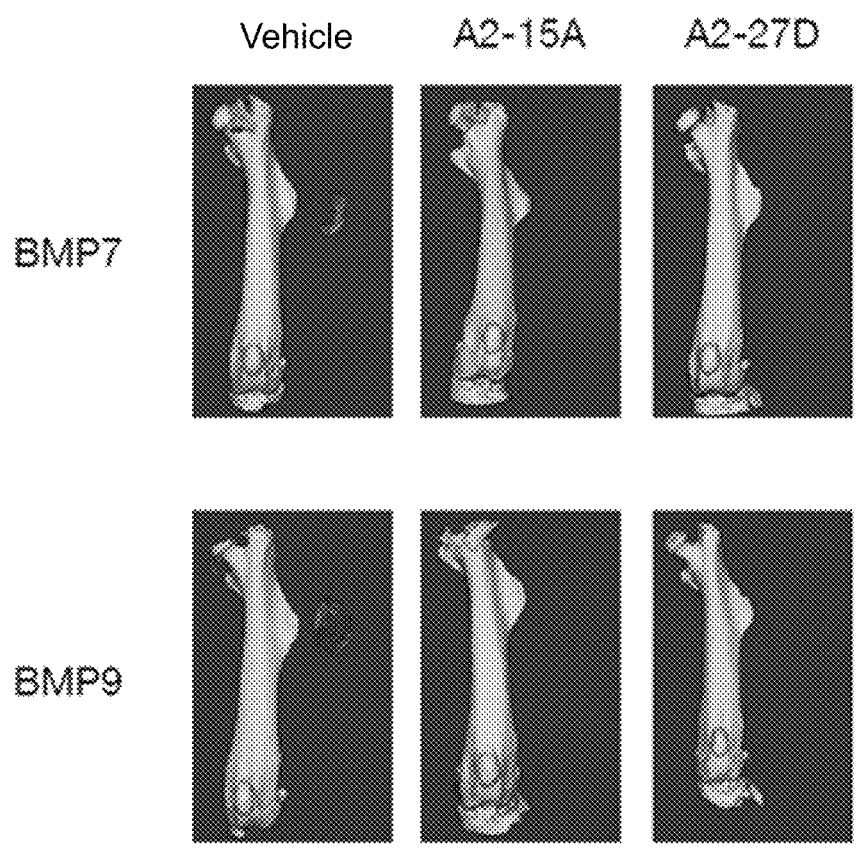
FIG. 8 This figure is a graph showing that the monoclonal antibodies produced by the hybridomas A2-15A and A2-27D inhibit BMP7- or GDF2/BMP9-induced ectopic osteoinduction in mouse skeletal muscle tissues.

The results are shown in FIG. 8. The micro-CT analysis showed that heterotopic ossification was induced on the right-hand side of the thigh bone in the mice transplanted with BMP7 and GDF2/BMP9 and treated with the vehicle. In contrast, heterotopic ossification was not detected in the mice that received the administration of the monoclonal antibodies produced by hybridomas A2-15A and A2-27D, although they were transplanted with BMP7 and GDF2/BMP9. It was thus confirmed that the monoclonal antibodies produced by hybridomas A2-15A and A2-27D suppressed the induction of heterotopic ossification in the skeletal muscle tissue induced by BMP7 and GDF2/BMP9.

Example 5

Preparation of human chimeric anti-ALK2 antibodies (cA2-15A and cA2-27D)

5)-1 Construction of a Chimeric and Humanized Antibody Light Chain Expression Vector pCMA-LK A fragment of about 5.4 kb obtained by digesting the plasmid pcDNA3.3-TOPO/LacZ (Invitrogen) with restriction enzymes XbaI and PmeI and a DNA fragment containing a DNA sequence encoding a human κ chain secretion signal and a human κ chain constant region shown in the SEQ ID NO: 17 were ligated using In-Fusion Advantage PCR Cloning Kit (Clontech) to prepare pcDNA3.3/LK.

pcDNA3.3/LK was used as a template in PCR using the following primer set. The obtained fragment of about 3.8 kb was phosphorylated and then self-ligated, thereby constructing a chimeric and humanized antibody light chain expression vector pCMA-LK having a signal sequence, a cloning site, and a human κ chain constant region downstream of the CMV promoter.

```
Primer set:
                                (3.3-F1; SEQ ID NO: 90)
5'-TATACCGTCGACCTCTAGCTAGAGCTTGGC-3'

(3.3-R1; SEQ ID NO: 91)
5'-GCTATGGCAGGGCCTGCCGCCCCGACGTTG-3'
```

5)-2 Construction of a Chimeric and Humanized Antibody IgG1 Type Heavy Chain Expression Vector pCMA-G1

A DNA fragment lacking the human κ chain secretion signal and the human κ chain constant region by digesting pCMA-LK with XbaI and PmeI and a DNA fragment containing a DNA sequence encoding amino acids of a human heavy chain signal sequence and a human IgG1 constant region of SEQ ID NO: 18 were ligated using In-Fusion Advantage PCR Cloning Kit (Clontech), thereby constructing a chimeric and humanized antibody IgG1 type heavy chain expression vector pCMA-G1 having a signal sequence, a cloning site, and a human IgG1 heavy chain constant region downstream of the CMV promoter.

5)-3 Construction of a cA2-15A Heavy Chain Expression Vector

Using the cDNA containing the heavy chain variable region of A2-15A obtained in Example 3)-2-3 as a template, a DNA fragment containing the cDNA encoding the heavy chain variable region was amplified, using KOD-Plus-(TOYOBO, Japan) and the following primer set, and inserted into a restriction enzyme BlpI-cleaved site of the chimeric and humanized IgG1 type heavy chain expression vector pCMA-G1, using In-Fusion HID PCR Cloning Kit (Clontech), thereby constructing a cA2-15A heavy chain expression vector. The obtained expression vector was designated as "pCMA-G1/cA2-15A". The nucleotide sequence of the cA2-15A heavy chain is shown in SEQ ID NO: 19, and the amino acid sequence is shown in SEQ ID NO: 20.

```
Primer set for the cA2-15A heavy chain:
                              (A2-15AH-F; SEQ ID NO: 92)
5'-CCAGATGGGTGCTGAGCGAGGTGCAGCTGGTGGAGTCTGGCGGA
G-3'

(A2-15AH-R; SEQ ID NO: 93)
5'-CTTGGTGGAGGCTGAGCTGACAGTGACCAGAGTGCCTTGGCCCC
AG-3'
```

5)-4 Construction of a cA2-15A Light Chain Expression Vector

Using the cDNA containing the light chain variable region of A2-15A obtained in Example 3)-2-4 as a template, a DNA fragment containing the cDNA encoding the light chain variable region was amplified, using KOD-Plus-(TOYOBO, Japan) and the following primer set, and inserted into a restriction enzyme BsiWI-cleaved site of the chimeric and humanized light chain expression general-purpose vector pCMA-LK, using In-Fusion HD PCR Cloning Kit (Clontech), thereby constructing a cA2-15A light chain expression vector. The obtained expression vector was designated as "pCMA-LK/cA2-15A". The nucleotide sequence of the cA2-15A light chain is shown in SEQ ID NO: 21 in the Sequence Listing, and the amino acid sequence is shown in SEQ ID NO: 22.

```
Primer set for the cA2-15A light chain:
                              (A2-15AL-F; SEQ ID NO: 94)
5'-ATCTCCGGCGCGTACGGCGACATTGTCTTGACCCAGTCTCCTGC-3'

(A2-15AL-R; SEQ ID NO: 95)
5'-GGAGGGGGCGGCCACAGCCCGTTTCAGTTCCAGCTTGGTCCCAG-3'
```

5)-5 Construction of a cA2-27D Heavy Chain Expression Vector

Using the cDNA containing the heavy chain variable region of A2-27D obtained in Example 3)-4-3 as a template, a DNA fragment containing the cDNA encoding the heavy chain variable region was amplified using KOD-Plus-(TOYOBO, Japan) and the following primer set, and inserted into a restriction enzyme BlpI-cleaved site of the chimeric and humanized IgG1 type heavy chain expression vector pCMA-G1, using In-Fusion HD PCR Cloning Kit (Clontech), thereby constructing a cA2-27D heavy chain expression vector. The obtained expression vector was designated as "pCMA-G1/cA2-27D". The nucleotide sequence of the cA2-27D heavy chain is shown in SEQ ID NO: 23 in the Sequence Listing, and the amino acid sequence is shown in SEQ ID NO: 24.

```
Primer set for the cA2-27D heavy chain:
                              (A2-27DH-F; SEQ ID NO: 96)
5'-CCAGATGGGTGCTGAGCGAGGTGCAGCTGGTGGAGTCTGGAGGAG-3'

(A2-27DH-R; SEQ ID NO: 97)
5'-CTTGGTGGAGGCTGAGCTCACGGTGACCACGGTTCCTGGGCCCAG-3'
```

5)-6 Construction of a cA2-27D Light Chain Expression Vector

Using the cDNA containing the light chain variable region of A2-27D obtained in Example 3)-4-4 as a template, a DNA fragment containing the cDNA encoding the light chain variable region was amplified using KOD-Plus-(TOYOBO, Japan) and the following primer set, and inserted into a restriction enzyme BsiWI-cleaved site of the chimeric and humanized antibody light chain expression general-purpose vector pCMA-LK, using In-Fusion HD PCR Cloning Kit (Clontech), thereby constructing a cA2-27D antibody light chain expression vector. The obtained expression vector was designated as "pCMA-LK/cA2-27D". The nucleotide sequence of the cA2-27D antibody light chain is shown in SEQ ID NO: 25, and the amino acid sequence is shown in SEQ ID NO: 26.

```
Primer set for the cA2-27D light chain:
                              (A2-27DL-F; SEQ ID NO: 98)
5'-ATCTCCGGCGCGTACGGCGAAATTGTTCTCACTCAGTCTCCAAC-3'

(A2-15AL-R; SEQ ID NO: 95)
5'-GGAGGGGGCGGCCACAGCCCGTTTCAGTTCCAGCTTGGTCCCAG-3'
```

5)-7 Production of cA2-15A and cA2-27D

FreeStyle 293F cells (Invitrogen) were subcultured and cultured in accordance with the manual. $1.2 \times 10^9$ FreeStyle 293F cells (Invitrogen) in the logarithmic growth phase were seeded into 3 L Fernbach Erlenmeyer Flask (Corning), and diluted with the FreeStyle293 expression medium (Invitrogen) to $2.0 \times 10^6$ cells/ml, and then the cells were cultured with shaking at 90 rpm for 1 hour in an 8% $CO_2$ incubator at 37° C. 1.8 mg of polyethyleneimine (Polyscience #24765) was dissolved in 20 ml of the Opti-Pro SFM medium (Invitrogen). Then, the H chain expression vector (0.24 mg) and the L chain expression vector (0.36 mg) prepared using NucleoBond Xtra (TaKaRa, Japan) were added into 20 ml of the Opti-Pro SFM medium (Invitrogen). 20 ml of the expression vector/Opti-Pro SFM mixed solution was added into 20 ml of the polyethyleneimine/Opti-Pro SFM mixed solution, and the mixture was gently stirred, further left for 5 minutes, and then added into the FreeStyle 293F cells. A culture supernatant obtained by shake culture at 90 rpm for 4 hours in an 8% $CO_2$ incubator at 37° C., followed by the addition of 600 ml of the EX-CELL VPRO medium (SAFC Biosciences), 18 ml of GlutaMAX I (GIBCO), and 30 ml of Yeastolate Ultrafiltrate (GIBCO), and by shake culture at 90 rmp for 7 days in an 8% $CO_2$ incubator at 37° C., was filtered through Disposable Capsule Filter (Advantec #CCS-045-E1H).

The chimeric antibody of the rat antibody A2-15A obtained by the combination of pCMA-G1/cA2-15A and pCMA-LK/cA2-15A was designated as "cA2-15A", and the chimeric antibody of the rat antibody A2-27D obtained by the combination of pCMA-G1/cA2-27D and pCMA-LK/cA2-27D was designated as "cA2-27D".

5)-8 Two-Step Purification of cA2-15A and cA2-27D

Each of the antibodies was purified from the culture supernatant obtained in Example 5)-7 by two steps using rProtein A affinity chromatography (at 4 to 6° C.) and ceramic hydroxyapatite (at room temperature). Buffer replacement steps after the rProtein A affinity chromatography purification and after the ceramic hydroxyapatite purification were performed at 4 to 6° C. The culture supernatant was applied to MabSelectSuRe (GE Healthcare Bioscience, HiTrap column) equilibrated with PBS. After the entry of the whole culture supernatant in the column, the column was washed with at least twice the column volume of PBS. Next, fractions containing the antibody were collected by elution with a 2 M arginine hydrochloride solution (pH 4.0). The fractions were subjected to buffer replacement with PBS by dialysis (Thermo Scientific, Slide-A-Lyzer Dialysis Cassette), and then diluted 5-fold with 5 mM sodium phosphate/ 50 mM MES/pH 7.0 buffer, and the resulting antibody solution was applied to a ceramic hydroxyapatite column (Bio-Rad Japan, Bio-Scale CHT Type-1 Hydroxyapatite Column) equilibrated with 5 mM NaPi/50 mM MES/30 mM NaCl/pH 7.0 buffer. The fractions containing the antibody were collected by performing linear concentration gradient elution with sodium chloride. The fractions were subjected to buffer replacement with HBS or (25 mM histidine/5% sorbitol, pH 6.0) by dialysis (Thermo Scientific, Slide-A-Lyzer Dialysis Cassette). The fractions were concentrated using Centrifugal UF Filter Device VIVASPIN20 (molecular weight cutoff. UF10K, Sartorius, at 4° C.), and adjusted to an IgG concentration of 2 mg/ml or more. Finally, the fractions were filtered using the Minisart-Plus filter (Sartorius) to obtain a purified sample.

Example 6

Evaluation of the in vitro activity of human chimeric anti-ALK2 antibodies (cA2-15A and cA2-27D)

6)-1 Evaluation of the Antibodies by Luciferase Reporter Assay

The ALK2-mediated intracellular signaling inhibitory activity of each of the human chimeric antibodies prepared was analyzed using a BMP-specific luciferase reporter. HEPG2 cells were seeded into a 96-well white plate for luciferase assay (Corning) at $1\times10^4$ cells/well, and cultured overnight in 10% FBS-containing DMEM medium under the conditions of 5% $CO_2$ at 37° C. On the following day, the HEPG2 cells were transfected with pGL4.26/Id1WT4F-luc (Genes Cells, 7, 949 (2002)), using Lipofectamine 2000 (Invitrogen). After 2.5 hours, the medium was replaced with fresh OPTI-MEM I (LifeTechnologies), and the cells were further cultured for 3 hours. Thereafter, the medium was replaced with OPTI-MEM I containing the serially diluted monoclonal antibody and 10 ng/mL of BMP7 (Milteney), and the cells were further cultured overnight. On the following day, the luciferase activity was measured with the plate reader SpectraMaxM4 (Molecular Devices), using Dual-Glo Luciferase Assay System (Promega).

Figure 9:
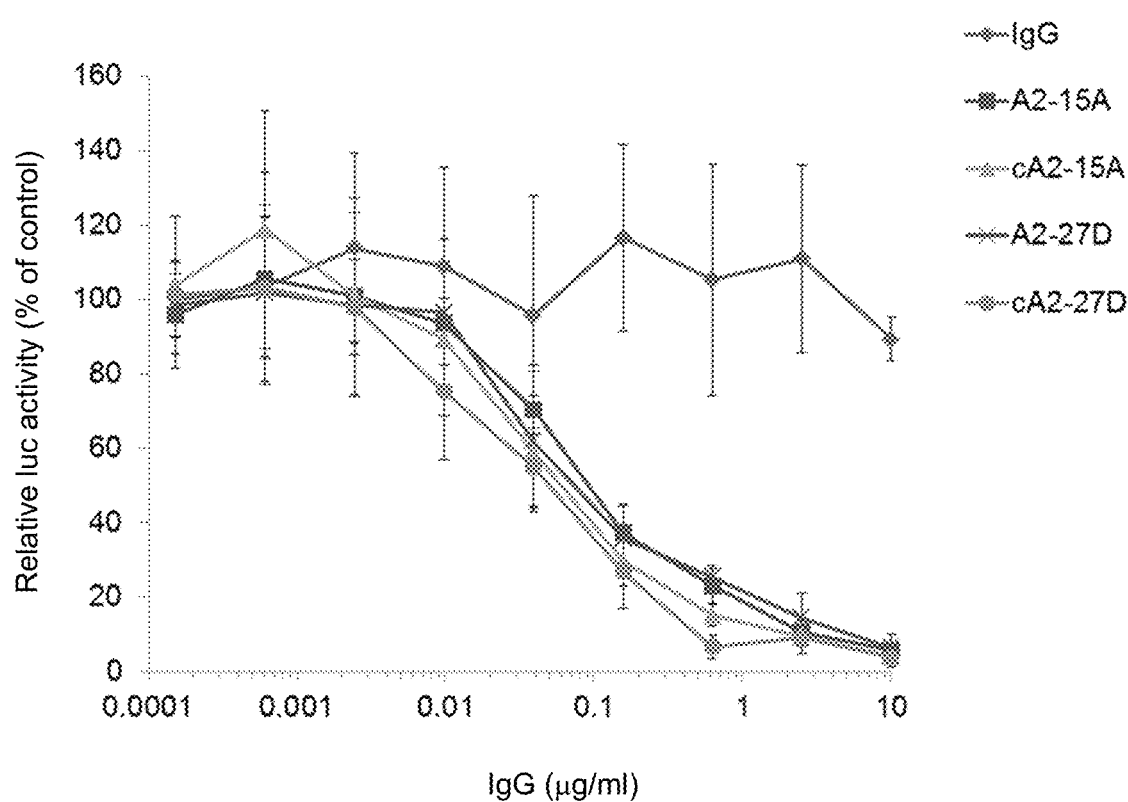
FIG. 9 This figure is a graph showing that chimeric antibodies cA2-15A and cA2-27D exhibit inhibitory activity equivalent to the rat monoclonal antibodies A2-15A and A2-27D, respectively, against BMP-specific luciferase (luc) activity induced by BMP7.

The results are shown in FIG. 9. Each of the chimeric antibodies cA2-15A and cA2-27D was confirmed to demonstrate an inhibitory activity comparable to that of the rat monoclonal antibody A2-15A or A2-27D, respectively, upon the BMP7-induced BMP-specific luciferase activity.

6)-2 Evaluation of the Antibodies by BMP-Induced Osteoblast Differentiation Assay The inhibitory activity of each of the human chimeric antibodies against endogenous ALK2-mediated intracellular signaling was analyzed based on the effect upon the BMP-induced osteoblast differentiation of C2C12 cells. C2C12 cells were seeded into a 96-well plate (Iwaki & Co., Ltd.) at $5\times10^3$ cells/well, and cultured in 15% FBS-containing DMEM medium overnight under the conditions of 5% $CO_2$ at 37° C. On the following day, the medium was replaced with fresh OPTI-MEM I (LifeTechnologies) containing the serially diluted monoclonal antibody and 2 ng/mL of GDF2/ BMP9 (Peprotech), and the cells were further cultured for 3 days. After the medium was removed from the C2C12 cells and the cells were washed with PBS, the cells were treated with 50 μL/well of an ice-cold acetone:ethanol (1:1) solution for 1 minute, and further washed with PBS three times. ALP activity was measured as an index of the differentiation into cells for forming osteoblasts. To measure ALP activity, 100 μL/well of a substrate solution (0.1 M diethanolamine (Sigma-Aldrich)-HCl, pH 10.0, containing 1 mg/mL of 4-nitrophenyl phosphate (Sigma-Aldrich) and 1 mM of $MgCl_2$) was added, and reacted for 15 to 30 minutes at room temperature on an agitation shaker. The reaction was stopped by the addition of 50 μL of 3M NaOH, and absorbance at a wavelength of 405 nm was measured using the microplate reader SpectraMax M4 (Molecular Devices).

Figure 10:
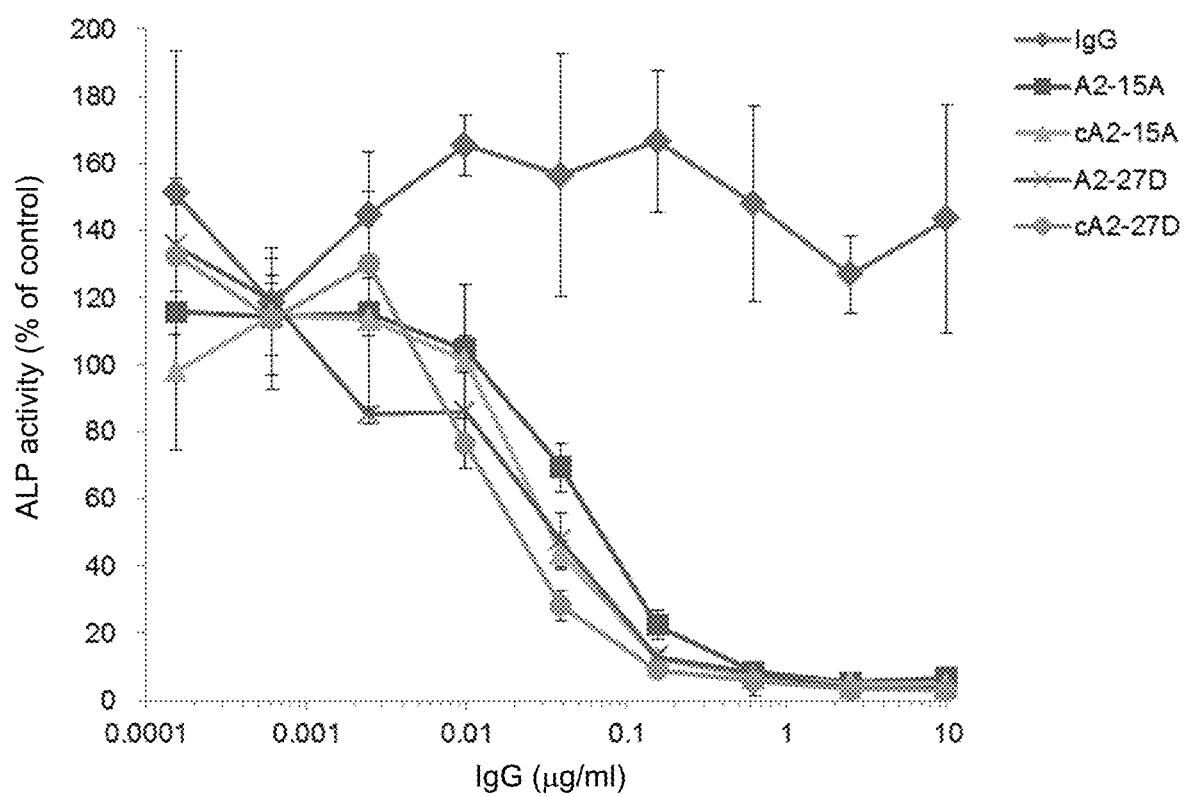
FIG. 10 This figure is a graph showing that the chimeric antibodies cA2-15A and cA2-27D inhibit, in a dose-dependent manner, the BMP-induced differentiation of C2C12 cells into osteoblast-like cells.

The results are shown in FIG. 10. It was confirmed that the chimeric antibodies cA2-15A and cA2-27D suppressed the BMP-induced differentiation of the C2C12 cells into osteoblast-like cells in a dose-dependent manner. These results show that the chimeric antibodies cA2-15A and cA2-27D are antibodies that suppress endogenous ALK2 physiologically expressed by the C2C12 cells. Moreover, the inhibitory activity of each of the chimeric antibodies cA2-15A and cA2-27D was confirmed to be comparable to that of the rat monoclonal antibody A2-15A or A2-27D, respectively.

Example 7

Design of humanized versions of anti-ALK2 antibodies 2-15A and A2-27D

7)-1 Design of Humanized hA2-15

7)-1-1 Molecular Modeling of the Variable Regions of A2-15A

The molecular modeling of the variable regions of A2-15A was performed using a method known as homology modeling (Methods in Enzymology, 203, 121-153, (1991)). The variable regions of A2-15A determined above were compared with the primary sequences of human immunoglobulin variable regions registered in Protein Data Bank (three-dimensional structures derived from X-ray crystal structures are available) (Nuc. Acid Res. 35, D301-D303 (2007)). As a result, 3KYM and 3S35 were selected as those having the highest sequence identity to the heavy chain variable region and the light chain variable region, respectively, of A2-15A. The three-dimensional structures of framework regions were prepared by obtaining a "framework model" by combining the coordinates of 3KYM and 3S35 corresponding to the heavy chain and the light chain of A2-15A. Then, a representative conformation of each CDR was incorporated into the framework model.

Finally, energy calculation for excluding disadvantageous interatomic contact was performed, in order to obtain possible molecular models of the variable regions of A2-15A in terms of energy. The above-described procedures were performed using a commercially available protein three-dimensional structure analysis program, Discovery Studio (Accelrys, Inc.).

7)-1-2 Design of an Amino Acid Sequence for Humanized hA2-15A

The humanized hA2-15 was constructed using a method commonly known as CDR grafting (Proc. Natl. Acad. Sci. USA 86, 10029-10033 (1989)). An acceptor antibody was selected based on the amino acid identity in framework regions.

The sequences of the framework regions of A2-15 were compared with the sequences of framework regions of human subgroup consensus sequences. As a result, the human γ chain subgroup 3 consensus sequence and the human κ chain subgroup 4 consensus sequence defined by KABAT et al. (Sequences of Proteins of Immunological Interest, 5th Ed. Public Health Service National Institutes of Health, Bethesda, Md. (1991)) were selected as acceptors due to their high sequence identity in framework regions. The amino acid residues of the framework regions in the human γ chain subgroup 3 consensus sequence and the human κ chain subgroup 4 consensus sequence were aligned with the amino acid residues of the framework regions of A2-15A to identify the numbers of amino acids differing therebetween. The numbers of these residues were analyzed using the three-dimensional model of A2-15A constructed above. Then, the donor residues to be grafted onto the acceptors were selected in accordance with the criteria provided by Queen et al. (Proc. Natl. Acad. Sci. USA 86, 10029-10033 (1989)). Some donor residues thus selected were transferred into the acceptor antibody to construct humanized hA2-15A sequences, as described in the following Examples.

7)-2 Humanization of A2-15A Heavy Chains

7)-2-1 Humanized hA2-15A-H1 Type Heavy Chain

A humanized hA2-15A heavy chain designed by substitution of amino acid number 35 (arginine) with glycine, amino acid number 38 (lysine) with arginine, amino acid number 61 (threonine) with glycine, amino acid number 94 (alanine) with serine, amino acid number 96 (serine) with asparagine, amino acid number 103 (aspartic acid) with asparagine, amino acid number 107 (serine) with alanine, amino acid number 112 (threonine) with valine, and amino acid number 116 (threonine) with alanine in the heavy chain of chimeric cA2-15A shown in SEQ ID NO: 20 was designated as "humanized hA2-15A-H1 type heavy chain" (sometimes also referred to as "hA2-15A-H1").

The amino acid sequence of the humanized hA2-15A-H1 type heavy chain is described in SEQ ID NO: 28 in the Sequence Listing. A sequence consisting of amino acid numbers 1 to 19, a sequence consisting of amino acid numbers 20 to 142, and a sequence consisting of amino acid numbers 143 to 472 in the amino acid sequence of SEQ ID NO: 28 correspond to the signal sequence, the heavy chain variable region, and the heavy chain constant region, respectively. The nucleotide sequence encoding the amino acid sequence of SEQ ID NO: 28 is described in SEQ ID NO: 27 in the Sequence Listing. A sequence consisting of nucleotide numbers 1 to 57, a sequence consisting of nucleotide numbers 58 to 426, and a sequence consisting of nucleotide numbers 427 to 1416 in the nucleotide sequence of SEQ ID NO: 27 encode the signal sequence, the heavy chain variable region sequence, and the heavy chain constant region sequence, respectively. The nucleotide sequence of SEQ ID NO: 27 and the amino acid sequence of SEQ ID NO: 28 are also described in FIG. 15.

7)-2-2 Humanized hA2-15A-H4 Type Heavy Chain

A humanized hA2-15A heavy chain designed by substitution of amino acid number 35 (arginine) with glycine, amino acid number 38 (lysine) with arginine, amino acid number 61 (threonine) with glycine, amino acid number 103 (aspartic acid) with asparagine, and amino acid number 107 (serine) with alanine in the heavy chain of chimeric cA2-15A shown in SEQ ID NO: 20 was designated as "humanized hA2-15A-H4 type heavy chain" (sometimes also referred to as "hA2-15A-H4").

The amino acid sequence of the humanized hA2-15A-H4 type heavy chain is described in SEQ ID NO: 30 in the Sequence Listing. A sequence consisting of amino acid numbers 1 to 19, a sequence consisting of amino acid numbers 20 to 142, and a sequence consisting of amino acid numbers 143 to 472 in the amino acid sequence of SEQ ID NO: 30 correspond to the signal sequence, the heavy chain variable region, and the heavy chain constant region, respectively. The nucleotide sequence encoding the amino acid sequence of SEQ ID NO: 30 is described in SEQ ID NO: 29 in the Sequence Listing. A sequence consisting of nucleotide numbers 1 to 57, a sequence consisting of nucleotide numbers 58 to 426, and a sequence consisting of nucleotide numbers 427 to 1416 in the nucleotide sequence of SEQ ID NO: 29 encode the signal sequence, the heavy chain variable region sequence, and the heavy chain constant region sequence, respectively. The nucleotide sequence of SEQ ID NO: 29 and the amino acid sequence of SEQ ID NO: 30 are also described in FIG. 16.

7)-3 Humanization of A2-15A Light Chain

7)-3-1 Humanized hA2-15A-L1 Type Light Chain

A humanized hA2-15A light chain designed by the substitution of amino acid number 24 (leucine) with methionine, amino acid number 29 (alanine) with aspartic acid, a position (missing residue) between amino acid numbers 29 and 30 with serine, amino acid number 36 (glutamine) with glutamic acid, amino acid number 41 (serine) with asparagine, amino acid number 66 (lysine) with proline, amino acid number 81 (isoleucine) with valine, amino acid number 83 (alanine) with aspartic acid, amino acid number 99 (asparagine) with serine, amino acid number 100 (proline) with serine, amino acid number 101 (valine) with leucine, amino acid number 104 (aspartic acid) with glutamic acid, amino acid number 106 (isoleucine) with valine, amino acid number 108 (threonine) with valine, amino acid number 123 (alanine) with glutamine, amino acid number 127 (leucine) with valine, and amino acid number 129 (leucine) with isoleucine in the light chain of chimeric cA2-15A shown in SEQ ID NO: 22 was designated as "humanized hA2-15A-L1 type light chain" (sometimes also referred to as "hA2-15A-L1").

The amino acid sequence of the humanized hA2-15A-L1 type light chain is described in SEQ ID NO: 32 in the Sequence Listing. A sequence consisting of amino acid numbers 1 to 20, a sequence consisting of amino acid numbers 21 to 133, and a sequence consisting of amino acid numbers 134 to 238 in the amino acid sequence of SEQ ID NO: 32 correspond to the signal sequence, the light chain variable region, and the light chain constant region, respectively. The nucleotide sequence encoding the amino acid sequence of SEQ ID NO: 32 is described in SEQ ID NO: 31 in the Sequence Listing. A sequence consisting of nucleotide numbers 26 to 85, a sequence consisting of nucleotide numbers 86 to 424, and a sequence consisting of nucleotide numbers 425 to 739 in the nucleotide sequence of SEQ ID NO: 31 encode the signal sequence, the light chain variable region sequence, and the light chain constant region sequence, respectively. The nucleotide sequence of SEQ ID NO: 31 and the amino acid sequence of SEQ ID NO: 32 are also described in FIG. 17.

7)-3-2 Humanized hA2-15A-L4 Type Light Chain

A humanized hA2-15A light chain designed by the substitution of amino acid number 29 (alanine) with aspartic acid, a position (missing residue) between amino acid numbers 29 and 30 with serine, amino acid number 36 (glutamine) with glutamic acid, amino acid number 41 (serine) with asparagine, amino acid number 99 (asparagine) with serine, amino acid number 100 (proline) with serine, amino acid number 108 (threonine) with valine, and amino acid number 123 (alanine) with glutamine in the light chain of chimeric cA2-15A shown in SEQ ID NO: 22 was designated as "humanized hA2-15A-L4 type light chain" (sometimes also referred to as "hA2-15A-L4").

The amino acid sequence of the humanized hA2-15A-L4 type light chain is described in SEQ ID NO: 34 in the Sequence Listing. A sequence consisting of amino acid numbers 1 to 20, a sequence consisting of amino acid numbers 21 to 133, and a sequence consisting of amino acid numbers 134 to 238 in the amino acid sequence of SEQ ID NO: 34 correspond to the signal sequence, the light chain variable region, and the light chain constant region, respectively. The nucleotide sequence encoding the amino acid sequence of SEQ ID NO: 34 is described in SEQ ID NO: 33 in the Sequence Listing. A sequence consisting of nucleotide numbers 26 to 85, a sequence consisting of nucleotide numbers 86 to 424, and a sequence consisting of nucleotide numbers 425 to 739 in the nucleotide sequence of SEQ ID NO: 33 encode the signal sequence, the light chain variable region sequence, and the light chain constant region sequence, respectively. The nucleotide sequence of SEQ ID NO: 33 and the amino acid sequence of SEQ ID NO: 34 are also described in FIG. 18.

7)-3-3 Humanized hA2-15A-L6 Type Light Chain

A humanized hA2-15A light chain designed by the substitution of amino acid number 29 (alanine) with aspartic acid, a position (missing residue) between amino acid numbers 29 and 30 with serine, amino acid number 36 (glutamine) with glutamic acid, amino acid number 41 (serine) with asparagine, amino acid number 79 (serine) with glutamine, amino acid number 99 (asparagine) with serine, amino acid number 100 (proline) with serine, amino acid number 108 (threonine) with valine, and amino acid number 123 (alanine) with glutamine in the light chain of chimeric cA2-15A shown in SEQ ID NO: 22 was designated as "humanized hA2-15A-L6 type light chain" (sometimes also referred to as "hA2-15A-L6").

The amino acid sequence of the humanized hA2-15A-L6 type light chain is described in SEQ ID NO: 36 in the Sequence Listing. A sequence consisting of amino acid numbers 1 to 20, a sequence consisting of amino acid numbers 21 to 133, and a sequence consisting of amino acid numbers 134 to 238 in the amino acid sequence of SEQ ID NO: 36 correspond to the signal sequence, the light chain variable region, and the light chain constant region, respectively. The nucleotide sequence encoding the amino acid sequence of SEQ ID NO: 36 is described in SEQ ID NO: 35 in the Sequence Listing. A sequence consisting of nucleotide numbers 26 to 85, a sequence consisting of nucleotide numbers 86 to 424, and a sequence consisting of nucleotide numbers 425 to 739 in the nucleotide sequence of SEQ ID NO: 35 encode the signal sequence, the light chain variable region sequence, and the light chain constant region sequence, respectively. The nucleotide sequence of SEQ ID NO: 35 and the amino acid sequence of SEQ ID NO: 36 are also described in FIG. 19.

7)-3-4 Humanized hA2-15A-L7 Type Light Chain

A humanized hA2-15A light chain designed by the substitution of amino acid number 29 (alanine) with aspartic acid, a position (missing residue) between amino acid numbers 29 and 30 with serine, amino acid number 36 (glutamine) with glutamic acid, amino acid number 41 (serine) with asparagine, amino acid number 70 (leucine) with alanine, amino acid number 99 (asparagine) with serine, amino acid number 100 (proline) with serine, amino acid number 108 (threonine) with valine, and amino acid number 123 (alanine) with glutamine in the light chain of chimeric cA2-15A shown in SEQ ID NO: 22 was designated as "humanized hA2-15A-L7 type light chain" (sometimes also referred to as "hA2-15A-L7").

The amino acid sequence of the humanized hA2-15A-L7 type light chain is described in SEQ ID NO: 38 in the Sequence Listing. A sequence consisting of amino acid numbers 1 to 20, a sequence consisting of amino acid numbers 21 to 133, and a sequence consisting of amino acid numbers 134 to 238 in the amino acid sequence of SEQ ID NO: 38 correspond to the signal sequence, the light chain variable region, and the light chain constant region, respectively. The nucleotide sequence encoding the amino acid sequence of SEQ ID NO: 38 is described in SEQ ID NO: 37 in the Sequence Listing. A sequence consisting of nucleotide numbers 26 to 85, a sequence consisting of nucleotide numbers 86 to 424, and a sequence consisting of nucleotide numbers 425 to 739 in the nucleotide sequence of SEQ ID NO: 37 encode the signal sequence, the light chain variable region sequence, and the light chain constant region sequence, respectively. The nucleotide sequence of SEQ ID NO: 37 and the amino acid sequence of SEQ ID NO: 38 are also described in FIG. 20.

7)-4 Design of Humanized hA2-15A by Combinations of Heavy Chains and Light Chains An antibody consisting of the humanized hA2-15A-H1 type heavy chain and the humanized hA2-15A-L1 type light chain was designed and designated as "humanized hA2-15A-H1/L1" (sometimes also referred to as "hA2-15A-H1/L1"). An antibody consisting of the humanized hA2-15A-H1 type heavy chain and the humanized hA2-15A-L4 type light chain was designed and designated as "humanized hA2-15A-H1/L4" (sometimes also referred to as "hA2-15A-H1/L4"). An antibody consisting of the humanized hA2-15A-H4 type heavy chain and the humanized hA2-15A-L1 type light chain was designed and designated as "humanized hA2-15A-H4/L1" (sometimes also referred to as "hA2-15A-H4/L1"). An antibody consisting of the humanized hA2-15A-H4 type heavy chain and the humanized hA2-15A-L4 type light chain was designed and designated as "humanized hA2-15A-H4/L4" (sometimes also referred to as "hA2-15A-H4/L4"). An antibody consisting of the humanized hA2-15A-H4 type heavy chain and the humanized hA2-15A-L6 type light chain was designed and designated as "humanized hA2-15A-H4/L6" (sometimes also referred to as "hA2-15A-H4/L6"). An antibody consisting of the humanized hA2-15A-H4 type heavy chain and the humanized hA2-15A-L7 type light chain was designed and designated as "humanized hA2-15A-H4/L7" (sometimes also referred to as "hA2-15A-H4/L7"). The antibodies designed above can be prepared in accordance with Example 8, and evaluated in accordance with Examples 2 and 4.

7)-5 Design of Humanized hA2-27D

7)-5-1 Molecular Modeling of the Variable Regions of A2-27D

The molecular modeling of the variable regions of A2-27D was performed using a method known as homology modeling (Methods in Enzymology, 203, 121-153, (1991)). The variable regions of A2-27D determined above were compared with the primary sequences of human immunoglobulin variable regions registered in Protein Data Bank (three-dimensional structures derived from X-ray crystal structures are available) (Nuc. Acid Res. 35, D301-D303 (2007)). As a result, 3EYQ and 4I9W were selected as those having the highest sequence identity to the heavy chain variable region and the light chain variable region, respectively, of A2-27D. The three-dimensional structures of framework regions were prepared by obtaining a "framework model" by combining the coordinates of 3EYQ and 4I9W corresponding to the heavy chain and the light chain of A2-27D. Then, a representative conformation of each CDR was incorporated into the framework model.

Finally, energy calculation for excluding disadvantageous interatomic contact was performed, in order to obtain possible molecular models of the variable regions of A2-27D in terms of energy. The above-described procedures were performed using a commercially available protein three-dimensional structure analysis program, Discovery Studio (Accelrys, Inc.).

7)-5-2 Design of an Amino Acid Sequence for Humanized hA2-27D

The humanized hA2-27D was constructed using a method commonly known as CDR grafting (Proc. Natl. Acad. Sci. USA 86, 10029-10033 (1989)). An acceptor antibody was selected based on the amino acid identity in framework regions.

The sequences of the framework regions of A2-27D were compared with the sequences of framework regions of human subgroup consensus sequences. As a result, the human γ chain subgroup 3 consensus sequence and the human κ chain subgroup 4 consensus sequence defined by KABAT et al. (Sequences of Proteins of Immunological Interest, 5th Ed. Public Health Service National Institutes of Health, Bethesda, Md. (1991)) were selected as acceptors due to their high sequence identity in framework regions. The amino acid residues of the framework regions in the human γ chain subgroup 3 consensus sequence and the human κ chain subgroup 3 consensus sequence were aligned with the amino acid residues of the framework regions of A2-27D to identify the numbers of amino acids differing therebetween. The numbers of these residues were analyzed using the three-dimensional model of A2-27D constructed above. Then, the donor residues to be grafted onto the acceptors were selected in accordance with the criteria provided by Queen et al. (Proc. Natl. Acad. Sci. USA 86, 10029-10033 (1989)). Some donor residues thus selected were transferred into the acceptor antibody to construct humanized hA2-27D sequences, as described in the following Examples.

7)-6 Humanization of A2-27D Heavy Chains

7)-6-1 Humanized hA2-27D-H1 Type Heavy Chain

A humanized hA2-15A heavy chain designed by the substitution of amino acid number 35 (arginine) with glycine, amino acid number 38 (lysine) with arginine, amino acid number 42 (leucine) with alanine, amino acid number 56 (isoleucine) with valine, amino acid number 68 (alanine) with serine, amino acid number 94 (alanine) with serine, amino acid number 95 (arginine) with lysine, amino acid number 103 (threonine) with asparagine, amino acid number 107 (serine) with alanine, amino acid number 112 (leucine) with valine, amino acid number 117 (alanine) with arginine, amino acid number 132 (proline) with glutamine, and amino acid number 135 (valine) with leucine in the heavy chain of chimeric cA2-27D shown in SEQ ID NO: 24 was designated as "humanized hA2-27D-H1 type heavy chain" (sometimes also referred to as "hA2-27D-H1").

The amino acid sequence of the humanized hA2-27D-H1 type heavy chain is described in SEQ ID NO: 40 in the Sequence Listing. A sequence consisting of amino acid numbers 1 to 19, a sequence consisting of amino acid numbers 20 to 140, and a sequence consisting of amino acid numbers 141 to 470 in the amino acid sequence of SEQ ID NO: 40 correspond to the signal sequence, the heavy chain variable region, and the heavy chain constant region, respectively. The nucleotide sequence encoding the amino acid sequence of SEQ ID NO: 40 is described in SEQ ID NO: 39 in the Sequence Listing. A sequence consisting of nucleotide numbers 1 to 57, a sequence consisting of nucleotide numbers 58 to 420, and a sequence consisting of nucleotide numbers 421 to 1410 in the nucleotide sequence of SEQ ID NO: 39 encode the signal sequence, the heavy chain variable region sequence, and the heavy chain constant region sequence, respectively. The nucleotide sequence of SEQ ID NO: 39 and the amino acid sequence of SEQ ID NO: 40 are also described in FIG. 21.

7)-6-2 Humanized hA2-27D-H2 Type Heavy Chain

A humanized hA2-27D heavy chain designed by the substitution of amino acid number 35 (arginine) with glycine, amino acid number 38 (lysine) with arginine, amino acid number 42 (leucine) with alanine, amino acid number 68 (alanine) with serine, amino acid number 94 (alanine) with serine, amino acid number 95 (arginine) with lysine, amino acid number 103 (threonine) with asparagine, amino acid number 107 (serine) with alanine, amino acid number 112 (leucine) with valine, amino acid number 132 (proline) with glutamine, and amino acid number 135 (valine) with leucine in the heavy chain of chimeric cA2-27D shown in SEQ ID NO: 24 was designated as "humanized hA2-27D-H2 type heavy chain" (sometimes also referred to as "hA2-27D-H2").

The amino acid sequence of the humanized hA2-27D-H2 type heavy chain is described in SEQ ID NO: 42 in the Sequence Listing. A sequence consisting of amino acid numbers 1 to 19, a sequence consisting of amino acid numbers 20 to 140, and a sequence consisting of amino acid residues 141 to 470 in the amino acid sequence of SEQ ID NO: 42 correspond to the signal sequence, the heavy chain variable region, and the heavy chain constant region, respectively. The nucleotide sequence encoding the amino acid sequence of SEQ ID NO: 42 is described in SEQ ID NO: 41 in the Sequence Listing. A sequence consisting of nucleotide numbers 1 to 57, a sequence consisting of nucleotide numbers 58 to 420, and a sequence consisting of nucleotide numbers 421 to 1410 in the nucleotide sequence of SEQ ID NO: 41 encode the signal sequence, the heavy chain variable region sequence, and the heavy chain constant region sequence, respectively. The nucleotide sequence of SEQ ID NO: 41 and the amino acid sequence of SEQ ID NO: 42 are also described in FIG. 22.

7)-6-3 Humanized hA2-27D-H3 Type Heavy Chain

A humanized hA2-27D heavy chain designed by the substitution of amino acid number 35 (arginine) with glycine, amino acid number 38 (lysine) with arginine, amino acid number 42 (leucine) with alanine, amino acid number 94 (alanine) with serine, amino acid number 95 (arginine) with lysine, amino acid number 103 (threonine) with asparagine, amino acid number 107 (serine) with alanine, amino acid number 112 (leucine) with valine, amino acid number 132 (proline) with glutamine, and amino acid number 135 (valine) with leucine in the heavy chain of chimeric cA2-27D shown in SEQ ID NO: 24 was designated as "humanized hA2-27D-H3 type heavy chain" (sometimes also referred to as "hA2-27D-H3").

The amino acid sequence of the humanized hA2-27D-H3 type heavy chain is described in SEQ ID NO: 44 in the Sequence Listing. A sequence consisting of amino acid numbers 1 to 19, a sequence consisting of amino acid numbers 20 to 140, and a sequence consisting of amino acid numbers 141 to 470 in the amino acid sequence of SEQ ID NO: 44 correspond to the signal sequence, the heavy chain variable region, and the heavy chain constant region, respectively. The nucleotide sequence encoding the amino acid sequence of SEQ ID NO: 44 is described in SEQ ID NO: 43 in the Sequence Listing. A sequence consisting of nucleotide numbers 1 to 57, a sequence consisting of nucleotides 58 to 420, and a sequence consisting of nucleotide numbers 421 to 1410 in the nucleotide sequence of SEQ ID NO: 43 encode the signal sequence, the heavy chain variable region sequence, and the heavy chain constant region sequence, respectively. The nucleotide sequence of SEQ ID NO: 43 and the amino acid sequence of SEQ ID NO: 44 are also described in FIG. 23.

7)-6-4 Humanized hA2-27D-H4 Type Heavy Chain

A humanized hA2-27D heavy chain designed by the substitution of amino acid number 35 (arginine) with glycine, amino acid number 38 (lysine) with arginine, amino acid number 42 (leucine) with alanine, amino acid number 94 (alanine) with serine, amino acid number 95 (arginine) with lysine, amino acid number 103 (threonine) with asparagine, amino acid number 107 (serine) with alanine, and amino acid number 135 (valine) with leucine in the heavy chain of chimeric cA2-27D shown in SEQ ID NO: 24 was designated as "humanized hA2-27D-H4 type heavy chain" (sometimes also referred to as "hA2-27D-H4").

The amino acid sequence of the humanized hA2-27D-H4 type heavy chain is described in SEQ ID NO: 46 in the Sequence Listing. A sequence consisting of amino acid numbers 1 to 19, a sequence consisting of amino acid numbers 20 to 140, and a sequence consisting of amino acid numbers 141 to 470 in the amino acid sequence of SEQ ID NO: 46 correspond to the signal sequence, the heavy chain variable region, and the heavy chain constant region, respectively. The nucleotide sequence encoding the amino acid sequence of SEQ ID NO: 46 is described in SEQ ID NO: 45 in the Sequence Listing. A sequence consisting of nucleotide numbers 1 to 57, a sequence consisting of nucleotide numbers 58 to 420, and a sequence consisting of nucleotide numbers 421 to 1410 in the nucleotide sequence of SEQ ID NO: 45 encode the signal sequence, the heavy chain variable region sequence, and the heavy chain constant region sequence, respectively. The nucleotide sequence of SEQ ID NO: 45 and the amino acid sequence of SEQ ID NO: 46 are also described in FIG. 24.

7)-6-5 Humanized hA2-27D-H5 Type Heavy Chain

A humanized hA2-27D heavy chain designed by the substitution of amino acid number 35 (arginine) with glycine, amino acid number 38 (lysine) with arginine, amino acid number 42 (leucine) with alanine, amino acid number 95 (arginine) with lysine, amino acid number 103 (threonine) with asparagine, and amino acid number 135 (valine) with leucine in the heavy chain of chimeric cA2-27D shown in SEQ ID NO: 24 was designated as "humanized hA2-27D-H5 type heavy chain" (sometimes also referred to as "hA2-27D-H5").

The amino acid sequence of the humanized hA2-27D-H5 type heavy chain is described in SEQ ID NO: 48 in the Sequence Listing. A sequence consisting of amino acid numbers 1 to 19, a sequence consisting of amino acid numbers 20 to 140, and a sequence consisting of amino acid numbers 141 to 470 in the amino acid sequence of SEQ ID NO: 48 correspond to the signal sequence, the heavy chain variable region, and the heavy chain constant region, respectively. The nucleotide sequence encoding the amino acid sequence of SEQ ID NO: 48 is described in SEQ ID NO: 47 in the Sequence Listing. A sequence consisting of nucleotide numbers 1 to 57, a sequence consisting of nucleotide numbers 58 to 420, and a sequence consisting of nucleotide numbers 421 to 1410 in the nucleotide sequence of SEQ ID NO: 47 encode the signal sequence, the heavy chain variable region sequence, and the heavy chain constant region sequence, respectively. The nucleotide sequence of SEQ ID NO: 47 and the amino acid sequence of SEQ ID NO: 48 are also described in FIG. 25.

7)-7 Humanization of A2-27D Light Chains

7)-7-1 Humanized hA2-27D-L1 Type Light Chain

A humanized hA2-27D light chain designed by the substitution of amino acid number 29 (threonine) with glycine, amino acid number 31 (methionine) with leucine, amino acid number 32 (alanine) with serine, amino acid number 33 (alanine) with leucine, amino acid number 38 (lysine) with arginine, amino acid number 39 (valine) with alanine, amino acid number 42 (asparagine) with serine, amino acid number 59 (serine) with proline, amino acid number 61 (alanine) with glutamine, amino acid number 62 (serine) with alanine, amino acid number 64 (lysine) with arginine, amino acid number 66 (tryptophan) with leucine, amino acid number 77 (valine) with isoleucine, amino acid number 79 (asparagine) with aspartic acid, amino acid number 89 (serine) with aspartic acid, amino acid number 90 (tyrosine) with phenylalanine, amino acid number 91 (serine) with threonine, amino acid number 93 (alanine) with threonine, amino acid number 96 (serine) with arginine, amino acid number 97 (methionine) with leucine, amino acid number 99 (alanine) with proline, amino acid number 102 (valine) with phenylalanine, amino acid number 104 (threonine) with valine, amino acid number 120 (alanine) with glutamine, amino acid number 124 (leucine) with valine, and amino acid number 126 (leucine) with isoleucine in the light chain of chimeric cA2-27D shown in SEQ ID NO: 26 was designated as "humanized hA2-27D-L1 type light chain" (sometimes also referred to as "hA2-27D-L1").

The amino acid sequence of the humanized hA2-27D-L1 type light chain is described in SEQ ID NO: 50 in the Sequence Listing. A sequence consisting of amino acid numbers 1 to 20, a sequence consisting of amino acid numbers 21 to 129, and a sequence consisting of amino acid numbers 130 to 234 in the amino acid sequence of SEQ ID NO: 50 correspond to the signal sequence, the light chain variable region, and the light chain constant region, respectively. The nucleotide sequence encoding the amino acid sequence of SEQ ID NO: 50 is described in SEQ ID NO: 49 in the Sequence Listing. A sequence consisting of nucleotide numbers 26 to 85, a sequence consisting of nucleotide numbers 86 to 412, and a sequence consisting of nucleotide numbers 413 to 727 in the nucleotide sequence of SEQ ID NO: 49 encode the signal sequence, the light chain variable region sequence, and the light chain constant region sequence, respectively. The nucleotide sequence of SEQ ID NO: 49 and the amino acid sequence of SEQ ID NO: 50 are also described in FIG. 26.

7)-7-2 Humanized hA2-27D-L2 Type Light Chain

A humanized hA2-27D light chain designed by the substitution of amino acid number 29 (threonine) with glycine, amino acid number 31 (methionine) with leucine, amino acid number 32 (alanine) with serine, amino acid number 33 (alanine) with leucine, amino acid number 38 (lysine) with arginine, amino acid number 39 (valine) with alanine, amino acid number 42 (asparagine) with serine, amino acid number 59 (serine) with proline, amino acid number 61 (alanine) with glutamine, amino acid number 64 (lysine) with arginine, amino acid number 79 (asparagine) with aspartic acid, amino acid number 89 (serine) with aspartic acid, amino acid number 90 (tyrosine) with phenylalanine, amino acid number 91 (serine) with threonine, amino acid number 93 (alanine) with threonine, amino acid number 96 (serine) with arginine, amino acid number 97 (methionine) with leucine, amino acid number 99 (alanine) with proline, amino acid number 102 (valine) with phenylalanine, amino acid number 104 (threonine) with valine, amino acid number 120 (alanine) with glutamine, amino acid number 124 (leucine) with valine, and amino acid number 126 (leucine) with isoleucine in the light chain of chimeric cA2-27D shown in SEQ ID NO: 26 was designated as "humanized hA2-27D-L2 type light chain" (sometimes also referred to as "hA2-27D-L2").

The amino acid sequence of the humanized hA2-27D-L2 type light chain is described in SEQ ID NO: 52 in the Sequence Listing. A sequence consisting of amino acid numbers 1 to 20, a sequence consisting of amino acid numbers 21 to 129, and a sequence consisting of amino acid numbers 130 to 234 in the amino acid sequence of SEQ ID NO: 52 correspond to the signal sequence, the light chain variable region, and the light chain constant region, respectively. The nucleotide sequence encoding the amino acid sequence of SEQ ID NO: 52 is described in SEQ ID NO: 51 in the Sequence Listing. A sequence consisting of nucleotide numbers 26 to 85, a sequence consisting of nucleotide numbers 86 to 412, and a sequence consisting of nucleotide numbers 413 to 727 in the nucleotide sequence of SEQ ID NO: 51 encode the signal sequence, the light chain variable region sequence, and the light chain constant region sequence, respectively. The nucleotide sequence of SEQ ID NO: 51 and the amino acid sequence of SEQ ID NO: 52 are also described in FIG. 27.

7)-7-3 Humanized hA2-27D-L3 Type Light Chain

A humanized hA2-27D light chain designed by the substitution of amino acid number 29 (threonine) with glycine, amino acid number 31 (methionine) with leucine, amino acid number 32 (alanine) with serine, amino acid number 33 (alanine) with leucine, amino acid number 38 (lysine) with arginine, amino acid number 39 (valine) with alanine, amino acid number 42 (asparagine) with serine, amino acid number 59 (serine) with proline, amino acid number 64 (lysine) with arginine, amino acid number 79 (asparagine) with aspartic acid, amino acid number 89 (serine) with aspartic acid, amino acid number 91 (serine) with threonine, amino acid number 93 (alanine) with threonine, amino acid number 96 (serine) with arginine, amino acid number 97 (methionine) with leucine, amino acid number 99 (alanine) with proline, amino acid number 102 (valine) with phenylalanine, amino acid number 124 (leucine) with valine, and amino acid number 126 (leucine) with isoleucine in the light chain of chimeric cA2-27D shown in SEQ ID NO: 26 was designated as "humanized hA2-27D-L3 type light chain" (sometimes also referred to as "hA2-27D-L3").

The amino acid sequence of the humanized hA2-27D-L3 type light chain is described in SEQ ID NO: 54 in the Sequence Listing. A sequence consisting of amino acid numbers 1 to 20, a sequence consisting of amino acid numbers 21 to 129, and a sequence consisting of amino acid numbers 130 to 234 in the amino acid sequence of SEQ ID NO: 54 correspond to the signal sequence, the light chain variable region, and the light chain constant region, respectively. The nucleotide sequence encoding the amino acid sequence of SEQ ID NO: 54 is described in SEQ ID NO: 53 in the Sequence Listing. A sequence consisting of nucleotide numbers 26 to 85, a sequence consisting of nucleotide numbers 86 to 412, and a sequence consisting of nucleotide numbers 413 to 727 in the nucleotide sequence of SEQ ID NO: 53 encode the signal sequence, the light chain variable region sequence, and the light chain constant region sequence, respectively. The nucleotide sequence of SEQ ID NO: 53 and the amino acid sequence of SEQ ID NO: 54 are also described in FIG. 28.

7)-7-4 Humanized hA2-27D-L4 Type Light Chain

A humanized hA2-27D light chain was designed by the substitution of amino acid number 29 (threonine) with glycine, amino acid number 32 (alanine) with serine, amino acid number 38 (lysine) with arginine, amino acid number 42 (asparagine) with serine, amino acid number 59 (serine) with proline, amino acid number 64 (lysine) with arginine, amino acid number 79 (asparagine) with aspartic acid, amino acid number 89 (serine) with aspartic acid, amino acid number 91 (serine) with threonine, amino acid number 93 (alanine) with threonine, amino acid number 96 (serine) with arginine, amino acid number 99 (alanine) with proline, and amino acid number 102 (valine) with phenylalanine in the light chain of chimeric cA2-27D shown in SEQ ID NO: 26 was designated as "humanized hA2-27D-L4 type light chain" (sometimes also referred to as "hA2-27D-L4").

The amino acid sequence of the humanized hA2-27D-L4 type light chain is described in SEQ ID NO: 56 in the Sequence Listing. A sequence consisting of amino acid numbers 1 to 20, a sequence consisting of amino acid numbers 21 to 129, and a sequence consisting of amino acid numbers 130 to 234 in the amino acid sequence of SEQ ID NO: 56 correspond to the signal sequence, the light chain variable region, and the light chain constant region, respectively. The nucleotide sequence encoding the amino acid sequence of SEQ ID NO: 56 is described in SEQ ID NO: 55 in the Sequence Listing. A sequence consisting of nucleotide numbers 26 to 85, a sequence consisting of nucleotide numbers 86 to 412, and a sequence consisting of nucleotide numbers 413 to 727 in the nucleotide sequence of SEQ ID NO: 55 encode the signal sequence, the light chain variable region sequence, and the light chain constant region sequence, respectively. The nucleotide sequence of SEQ ID NO: 55 and the amino acid sequence of SEQ ID NO: 56 are also described in FIG. 29.

7)-7-5 Humanized hA2-27D-L5 Type Light Chain

A humanized hA2-27D light chain designed by the substitution of amino acid number 29 (threonine) with glycine, amino acid number 32 (alanine) with serine, amino acid number 38 (lysine) with arginine, amino acid number 91 (serine) with threonine, amino acid number 93 (alanine) with threonine, amino acid number 96 (serine) with arginine, amino acid number 99 (alanine) with proline, and amino acid number 102 (valine) with phenylalanine in the light chain of chimeric cA2-27D shown in SEQ ID NO: 26 was designated as "humanized hA2-27D-L5 type light chain" (sometimes also referred to as "hA2-27D-L5").

The amino acid sequence of the humanized hA2-27D-L5 type light chain is described in SEQ ID NO: 58 in the Sequence Listing. A sequence consisting of amino acid numbers 1 to 20, a sequence consisting of amino acid numbers 21 to 129, and a sequence consisting of amino acid numbers 130 to 234 in the amino acid sequence of SEQ ID NO: 58 correspond to the signal sequence, the light chain variable region, and the light chain constant region, respectively. The nucleotide sequence encoding the amino acid sequence of SEQ ID NO: 58 is described in SEQ ID NO: 57 in the Sequence Listing. A sequence consisting of nucleotide numbers 26 to 85, a sequence consisting of nucleotide numbers 86 to 412, and a sequence consisting of nucleotide numbers 413 to 727 in the nucleotide sequence of SEQ ID NO: 57 encode the signal sequence, the light chain variable region sequence, and the light chain constant region sequence, respectively. The nucleotide sequence of SEQ ID NO: 57 and the amino acid sequence of SEQ ID NO: 58 are also described in FIG. 30.

7)-8 Design of Humanized hA2-27D by Combinations of Heavy Chains and Light Chains An antibody consisting of the humanized hA2-27D-H1 type heavy chain and the humanized hA2-27D-L1 type light chain was designed and designated as "humanized hA2-27D-H1/L1" (sometimes also referred to as "hA2-27D-H1/L1"). An antibody consisting of the humanized hA2-27D-H1 type heavy chain and the humanized hA2-27D-L2 type light chain was designed and designated as "humanized hA2-27D-H1/L2" (sometimes also referred to as "hA2-27D-H1/L2"). An antibody consisting of the humanized hA2-27D-H1 type heavy chain and the humanized hA2-27D-L3 type light chain was designed and designated as "humanized hA2-27D-H1/L3" (sometimes also referred to as "hA2-27D-H1/L3"). An antibody consisting of the humanized hA2-27D-H2 type heavy chain and the humanized hA2-27D-L1 type light chain was designed and designated as "humanized hA2-27D-H2/L1" (sometimes also referred to as "hA2-27D-H2/L1"). An antibody consisting of the humanized hA2-27D-H2 type heavy chain and the humanized hA2-27D-L2 type light chain was designed and designated as "humanized hA2-27D-H2/L2" (sometimes also referred to as "hA2-27D-H2/L2"). An antibody consisting of the humanized hA2-27D-H2 type heavy chain and the humanized hA2-27D-L3 type light chain was designed and designated as "humanized hA2-27D-H2/L3" (sometimes also referred to as "hA2-27D-H2/L3"). An antibody consisting of the humanized hA2-27D-H3 type heavy chain and the humanized hA2-27D-L1 type light chain was designed and designated as "humanized hA2-27D-H3/L1" (sometimes also referred to as "hA2-27D-H3/L1"). An antibody consisting of the humanized hA2-27D-H3 type heavy chain and the humanized hA2-27D-L2 type light chain was designed and designated as "humanized hA2-27D-H3/L2" (sometimes also referred to as "hA2-27D-H3/L2"). An antibody consisting of the humanized hA2-27D-H3 type heavy chain and the humanized hA2-27D-L3 type light chain was designed and designated as "humanized hA2-27D-H3/L3" (sometimes also referred to as "hA2-27D-H3/L3"). An antibody consisting of the humanized hA2-27D-H3 type heavy chain and the humanized hA2-27D-L4 type light chain was designed and designated as "humanized hA2-27D-H3/L4" (sometimes also referred to as "hA2-27D-H3/L4"). An antibody consisting of the humanized hA2-27D-H4 type heavy chain and the humanized hA2-27D-L3 type light chain was designed and designated as "humanized hA2-27D-H4/L3" (sometimes also referred to as "hA2-27D-H4/L3"). An antibody consisting of the humanized hA2-27D-H4 type heavy chain and the humanized hA2-27D-L4 type light chain was designed and designated as "humanized hA2-27D-H4/L4" (sometimes also referred to as "hA2-27D-H4/L4"). An antibody consisting of the humanized hA2-27D-H4 type heavy chain and the humanized hA2-27D-L5 type light chain was designed and designated as "humanized hA2-27D-H4/L5" (sometimes also referred to as "hA2-27D-H4/L5"). An antibody consisting of the humanized hA2-27D-H5 type heavy chain and the humanized hA2-27D-L4 type light chain was designed and designated as "humanized hA2-27D-H5/L4" (sometimes also referred to as "hA2-27D-H5/L4"). The antibodies designed as above can be prepared in accordance with Example 8, and evaluated in accordance with Examples 2 and 4.

Example 8

Construction of humanized A2-15A antibody and humanized A2-27D antibody expression vectors and preparation of the antibodies 8)-1 Construction of Humanized A2-15A Heavy Chain Expression Vector 8)-1-1 Construction of Humanized hA2-15A-H1 Type Heavy Chain Expression Vector A DNA fragment containing a humanized hA2-15A-H1 variable region-encoding DNA sequence represented by nucleotide numbers 36 to 443 of the nucleotide sequence of humanized hA2-15A-H1 shown in SEQ ID NO: 27 was synthesized (GeneArt Artificial Gene Synthesis Service). The DNA fragment containing a humanized hA2-15A-H1 variable region-encoding DNA sequence was amplified using the synthesized DNA fragment as a template, KOD-Plus-(Toyobo Co., Ltd., Japan), and a primer set given below, and inserted at the restriction enzyme BlpI-cleaved site of the chimeric and humanized antibody IgG1 type heavy chain expression vector pCMA-G1 using In-Fusion HD PCR cloning kit (Clontech Laboratories, Inc.) to construct a humanized hA2-15A-H1 expression vector. The obtained expression vector was designated as "pCMA-G1/hA2-15A-H1".

```
Primer set
                    (EG-Inf-F; SEQ ID NO: 99)
   5'-AGCTCCCAGATGGGTGCTGAGC-3'

(EG1-Inf-R; SEQ ID NO: 100)
   5'-GGGCCCTTGGTGGAGGCTGAGC-3'
```

8)-1-2 Construction of Humanized hA2-15A-H4 Type Heavy Chain Expression Vector

A DNA fragment containing a humanized hA2-15A-H4 variable region-encoding DNA sequence represented by nucleotide numbers 36 to 443 of the nucleotide sequence of humanized hA2-15A-H4 shown in SEQ ID NO: 29 was synthesized (GeneArt Artificial Gene Synthesis Service). A humanized hA2-15A-H4 expression vector was constructed in the same way as in Example 8)-1-1. The obtained expression vector was designated as "pCMA-G1/hA2-15A-H4".

8)-2 Construction of Humanized A2-15A Light Chain Expression Vector

8)-2-1 Construction of Humanized hA2-15A-L1 Type Light Chain Expression Vector

A DNA fragment containing a sequence encoding humanized hA2-15A-L1, of SEQ ID NO: 31, was synthesized (GeneArt Gene Synthesis Service). The DNA fragment containing a sequence encoding humanized hA2-15A-L1 was amplified using the synthesized DNA fragment as a template, KOD-Plus-(Toyobo Co., Ltd.), and a primer set given below, and inserted at the site from which the sequence encoding a K chain secretory signal and a human K chain constant region was removed by the digestion of the expression vector pCMA-LK with restriction enzymes XbaI and PmeI, using In-Fusion HD PCR cloning kit (Clontech Laboratories, Inc.) to construct a humanized hA2-15A-L1 expression vector. The obtained expression vector was designated as "pCMA/hA2-15A-L1".

```
Primer set
                    (CM-inf-F; SEQ ID NO: 101)
   5'-CCAGCCTCCGGACTCTAGAGCCACC-3'
```

```
                                  (CM-inf-R; SEQ ID NO: 102)
        5'-AGTTAGCCTCCCCCGTTTAAACTC-3'
```

8)-2-2 Construction of Humanized hA2-15A-L4 Type Light Chain Expression Vector

A DNA fragment containing a sequence encoding humanized hA2-15A-L4, of SEQ ID NO: 33, was synthesized (GeneArt Gene Synthesis Service). A humanized hA2-15A-L4 expression vector was constructed in the same way as in Example 8)-2-1. The obtained expression vector was designated as "pCMA/hA2-15A-L4".

8)-2-3 Construction of Humanized hA2-15A-L6 Type Light Chain Expression Vector

A DNA fragment containing a sequence encoding humanized hA2-15A-L6, as shown in SEQ ID NO: 35, was synthesized (GeneArt Gene Synthesis Service). A humanized hA2-15A-L6 expression vector was constructed in the same way as in Example 8)-2-1. The obtained expression vector was designated as "pCMA/hA2-15A-L6".

8)-2-4 Construction of Humanized hA2-15A-L7 Type Light Chain Expression Vector

A DNA fragment containing a sequence encoding humanized hA2-15A-L7, as shown in SEQ ID NO: 37, was synthesized (GeneArt Gene Synthesis Service). A humanized hA2-15A-L7 expression vector was constructed in the same way as in Example 8)-2-1. The obtained expression vector was designated as "pCMA/hA2-15A-L7".

8)-3 Construction of Humanized A2-27D Heavy Chain Expression Vector

8)-3-1 Construction of Humanized hA2-27D-H1 Type Heavy Chain Expression Vector

A DNA fragment containing a humanized hA2-27D-H1 variable region-encoding DNA sequence represented by nucleotide numbers 36 to 437 of the nucleotide sequence of humanized hA2-27D-H1 of SEQ ID NO: 39 was synthesized (GeneArt Artificial Gene Synthesis Service). A humanized hA2-27D-H1 expression vector was constructed in the same way as in Example 8)-1-1. The obtained expression vector was designated as "pCMA-G1/hA2-27D-H1".

8)-3-2 Construction of Humanized hA2-27D-H2 Type Heavy Chain Expression Vector

A DNA fragment containing a humanized hA2-27D-H2 variable region-encoding DNA sequence represented by nucleotide numbers 36 to 437 of the nucleotide sequence of humanized hA2-27D-H2 of SEQ ID NO: 41 was synthesized (GeneArt Artificial Gene Synthesis Service). A humanized hA2-27D-H2 expression vector was constructed in the same way as in Example 8)-1-1. The obtained expression vector was designated as "pCMA-G1/hA2-27D-H2".

8)-3-3 Construction of Humanized hA2-27D-H3 Type Heavy Chain Expression Vector

A DNA fragment containing a humanized hA2-27D-H3 variable region-encoding DNA sequence represented by nucleotide numbers 36 to 437 of the nucleotide sequence of humanized hA2-27D-H3 of SEQ ID NO: 43 was synthesized (GeneArt Artificial Gene Synthesis Service). A humanized hA2-27D-H3 expression vector was constructed in the same way as in Example 8)-1-1. The obtained expression vector was designated as "pCMA-G1/hA2-27D-H3".

8)-3-4 Construction of Humanized hA2-27D-H4 Type Heavy Chain Expression Vector

A DNA fragment containing a humanized hA2-27D-H4 variable region-encoding DNA sequence represented by nucleotide numbers 36 to 437 of the nucleotide sequence of humanized hA2-27D-H4 of SEQ ID NO: 45 was synthesized (GeneArt Artificial Gene Synthesis Service). A humanized hA2-27D-H4 expression vector was constructed in the same way as in Example 8)-1-1. The obtained expression vector was designated as "pCMA-G1/hA2-27D-H4".

8)-3-5 Construction of Humanized hA2-27D-H5 Type Heavy Chain Expression Vector

A DNA fragment containing a humanized hA2-27D-H5 variable region-encoding DNA sequence represented by nucleotide numbers 36 to 437 of the nucleotide sequence of humanized hA2-27D-H5 of SEQ ID NO: 47 was synthesized (GeneArt Artificial Gene Synthesis Service). A humanized hA2-27D-H5 expression vector was constructed in the same way as in Example 8)-1-1. The obtained expression vector was designated as "pCMA-G1/hA2-27D-H5".

8)-4 Construction of Humanized A2-27D Light Chain Expression Vector

8)-4-1 Construction of Humanized hA2-27D-L1 Type Light Chain Expression Vector

A DNA fragment containing a sequence encoding humanized hA2-27D-L1, as shown in SEQ ID NO: 49, was synthesized (GeneArt Gene Synthesis Service). A humanized hA2-27D-L1 expression vector was constructed in the same way as in Example 8)-2-1. The obtained expression vector was designated as "pCMA/hA2-27D-L1".

8)-4-2 Construction of Humanized hA2-27D-L2 Type Light Chain Expression Vector

A DNA fragment containing a sequence encoding humanized hA2-27D-L2, as shown in SEQ ID NO: 51, was synthesized (GeneArt Gene Synthesis Service). A humanized hA2-27D-L2 expression vector was constructed in the same way as in Example 8)-2-1. The obtained expression vector was designated as "pCMA/hA2-27D-L2".

8)-4-3 Construction of Humanized hA2-27D-L3 Type Light Chain Expression Vector

A DNA fragment containing a sequence encoding humanized hA2-27D-L3, as shown in SEQ ID NO: 53, was synthesized (GeneArt Gene Synthesis Service). A humanized hA2-27D-L3 expression vector was constructed in the same way as in Example 8)-2-1. The obtained expression vector was designated as "pCMA/hA2-27D-L3".

8)-4-4 Construction of Humanized hA2-27D-L4 Type Light Chain Expression Vector

A DNA fragment containing a sequence encoding humanized hA2-27D-L4, as shown in SEQ ID NO: 55, was synthesized (GeneArt Gene Synthesis Service). A humanized hA2-27D-L4 expression vector was constructed in the same way as in Example 8)-2-1. The obtained expression vector was designated as "pCMA/hA2-27D-L4".

8)-4-5 Construction of Humanized hA2-27D-L5 Type Light Chain Expression Vector

A DNA fragment containing a sequence encoding humanized hA2-27D-L5, as shown in SEQ ID NO: 57, was synthesized (GeneArt Gene Synthesis Service). A humanized hA2-27D-L5 expression vector was constructed in the same way as in Example 8)-2-1. The obtained expression vector was designated as "pCMA/hA2-27D-L5".

8)-5 Preparation of Humanized A2-15A Antibody (IgG1) and Humanized A2-27D Antibody (IgG1)

8)-5-1 Production of Humanized A2-15A Antibody (IgG1) and Humanized A2-27D Antibody (IgG1)

Each antibody was obtained in the same way as in Example 5)-7. Specifically, humanized hA2-15A-H4/L6 was obtained by the combination of pCMA-G1/hA2-15A-H4 constructed in Example 8)-1-2 and pCMA/hA2-15A-L6 constructed in Example 8)-2-3. Humanized hA2-27D-H2/L2 was obtained by the combination of pCMA-G1/hA2-27D-H2 constructed in Example 8)-3-2 and pCMA/hA2-

27D-L2 constructed in Example 8)-4-2. Humanized hA2-27D-H3/L4 was obtained by the combination of pCMA-G1/hA2-27D-H3 constructed in Example 8)-3-3 and pCMA/hA2-27D-L4 constructed in Example 8)-4-4.

8)-5-2 Two-Step Purification of Humanized A2-15A Antibody (IgG1) and Humanized A2-27D Antibody (IgG1)

Each culture supernatant obtained in Example 8)-5-1 was purified in the same way as in Example 5)-8.

Example 9

In vitro activity evaluation of humanized A2-15A antibody (IgG1) and humanized A2-27D antibody (IgG1)

9)-1 Antibody Evaluation by Luciferase Reporter Assay

Humanized hA2-15A-H4/L6, humanized hA2-27D-H2/L2, and humanized hA2-27D-H3/L4 prepared in Example 8)-5 were analyzed for their inhibitory activity against ALK2-mediated intracellular signals using a luciferase reporter specific for BMP. HEPG2 cells were transfected with pGL4.26/Id1WT4F-luc (Genes Cells, 7, 949 (2002)) in the same way as in Example 6)-1. After 3 hours, the medium was replaced with fresh FreeStyle 293 expression medium (Invitrogen Corp.). Then, each humanized antibody and 10 ng/mL BMP7 (manufactured by Miltenyi Biotec) were added thereto. On the next day, luciferase activity was measured.

Figure 31:
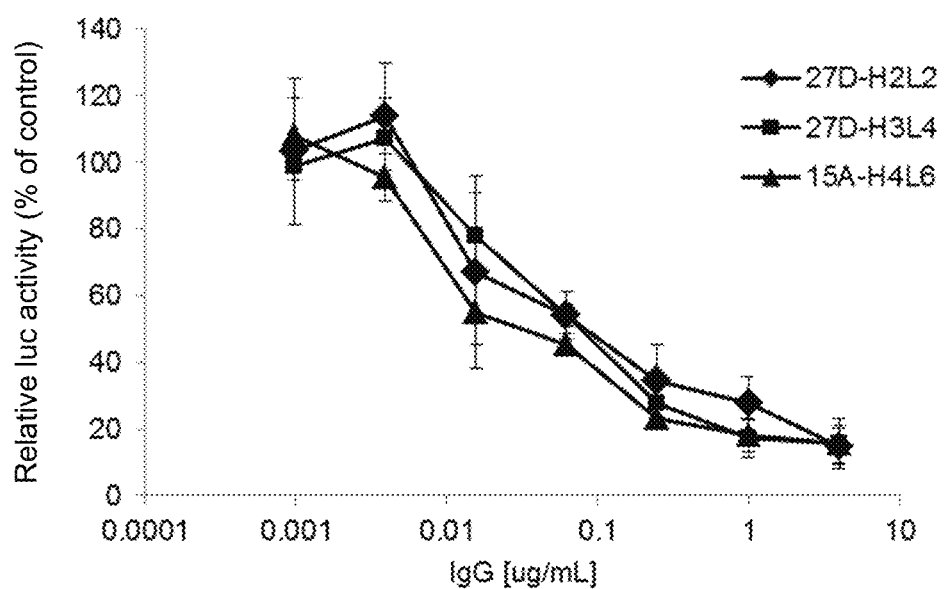
FIG. 31 This figure is a graph showing that a humanized A2-15A antibody (IgG1) and humanized A2-27D antibodies (IgG1) inhibit, in a dose-dependent manner, BMP-specific luciferase (luc) activity induced by BMP7.

The results are shown in FIG. 31. Humanized hA2-15A-H4/L6, humanized hA2-27D-H2/L2, and humanized hA2-27D-H3/L4 were confirmed to inhibit, in a dose-dependent manner, BMP-specific luciferase activity induced by BMP7.

Example 10

Evaluation of Binding Activity of Humanized A2-15A Antibody (IgG1) and Humanized A2-27D Antibody (IgG1) Against Human ALK2

The dissociation constants of humanized hA2-15A-H4/L6, humanized hA2-27D-H2/L2, and humanized hA2-27D-H3/L4 prepared in Example 8)-5 for the antigen (Recombinant Human ALK2 Fc Chimera, Sino Biological Inc.) were measured in Biacore T200 (GE Healthcare Bio-Sciences Corp.) by using the antigen immobilized as a ligand and each antibody as an analyte. The antigen was added at 1.25 µg/mL for 60 seconds and immobilized onto a sensor chip CM5 (GE Healthcare Bio-Sciences Corp.). The running buffer used was HBS-EP+(10 mM HEPES (pH 7.4), 0.15 M NaCl, 3 mM EDTA, and 0.05% Surfactant P20). Serially diluted solutions (0.2 to 50 nM) of the antibody were added onto the antigen-immobilized chip at a flow rate of 30 µl/min for 300 seconds. Subsequently, the dissociation phase was monitored for 1800 seconds. A 10 mM glycine/hydrochloric acid solution (pH 1.5) was added thereto as a regenerating solution at a flow rate of 10 µl/min for 30 seconds twice. The data was analyzed using bivalent binding models of analytical software (BIAevaluation software, version 1.0) to calculate an association rate constant ka, a dissociation rate constant kd, and a dissociation constant (KD; KD=kd/ka).

The results are shown in Table 1.

TABLE 1

Dissociation constants of humanized A2-15A antibody and humanized A2-27D antibody

| | Name | KD (nM) |
|---|---|---|
| 1 | hA2-27D-H2/L2 | 5.7 |
| 2 | hA2-27D-H3/L4 | 4.3 |
| 3 | hA2-15A-H4/L6 | 4.3 |

Example 11

Preparation of Humanized A2-15A Antibody (IgG2)

11)-1 Construction of Humanized IgG2 Type Heavy Chain Expression Vector pCMA-G2 pCMA-LK constructed in Example 5)-1 was digested with XbaI and PmeI. The obtained DNA fragment except for the DNA sequence encoding the K chain secretory signal and the human κ chain constant region was ligated with a DNA fragment (SEQ ID NO: 103) containing a nucleotide sequence encoding the amino acid sequence of a human heavy chain secretory signal sequence and a human IgG2 constant region using In-Fusion Advantage PCR cloning kit (Clontech Laboratories, Inc.) to construct a chimeric and humanized IgG2 type heavy chain expression vector pCMA-G2 having a signal sequence, a cloning site, and the nucleotide sequence encoding the human IgG2 heavy chain constant region, downstream of the CMV promoter.

11)-2 Construction of Humanized hA2-15A-H4 IgG2 Type Heavy Chain Expression Vector A DNA fragment containing heavy chain variable region-encoding cDNA was amplified using pCMA-G1/hA2-15A-H4 constructed in Example 8)-1-2 as a template, KOD-Plus-(Toyobo Co., Ltd.), and a primer set given below, and inserted at the restriction enzyme BlpI-cleaved site of the humanized IgG2 type heavy chain expression vector pCMA-G2 using In-Fusion HD PCR cloning kit (Clontech Laboratories, Inc.) to construct a humanized hA2-15A-H4 IgG2 type expression vector. The obtained expression vector was designated as "pCMA-G2/hA2-15A-H4".

The nucleotide sequence of the humanized hA2-15A-H4 IgG2 type heavy chain is shown in SEQ ID NO: 104, and the amino acid sequence thereof is shown in SEQ ID NO: 105. A sequence consisting of nucleotide numbers 1 to 57 of the nucleotide sequence of SEQ ID NO: 104, a sequence consisting of nucleotide numbers 58 to 426 thereof, and a sequence consisting of nucleotide numbers 427 to 1404 thereof encode the signal sequence, the heavy chain variable region sequence, and the heavy chain constant region sequence, respectively. A sequence consisting of amino acid numbers 1 to 19 of the amino acid sequence of SEQ ID NO: 105, a sequence consisting of amino acid numbers 20 to 142 thereof, and a sequence consisting of amino acid numbers 143 to 468 thereof correspond to the signal sequence, the heavy chain variable region, and the heavy chain constant region, respectively. The nucleotide sequence of SEQ ID NO: 104 and the amino acid sequence of SEQ ID NO: 105 are also described in FIG. 32.

```
Primer set for humanized hA2-15A-H4 IgG2 type
heavy chain
                        (15A-H4-F; SEQ ID NO: 130)
5'-CAGATGGGTGCTGAGCGAAGTGCAGCTGGTGGAATCTGGC-3'

(15A-H4-R; SEQ ID NO: 131)
5'-CTTGGTGCTGGCTGAGCTGACGGTCACGAGGGTGCC-3'
```

11)-3 Production of Humanized A2-15A Antibody (IgG2)

The antibody was produced in the same way as in Example 5)-7. A humanized A2-15A antibody obtained by the combination of pCMA-G2/hA2-15A-H4 constructed in Example 11)-2 and pCMA/hA2-15A-L6 constructed Example 8)-2-3 was designated as "humanized hA2-15A-H4/L6 (IgG2)".

11)-4 Two-Step Purification of Humanized hA2-15A-H4/L6 (IgG2)

The culture supernatant obtained in Example 11)-3 was purified in the same way as in Example 5)-8.

Example 12

Preparation of Humanized A2-27D Antibody (IgG1 LALA)

12)-1 Construction of Humanized hA2-27D-H2-LALA Type Heavy Chain Expression Vector Mutations were introduced using pCMA-G1/hA2-27D-H2 constructed in Example 8)-3-2 as a template, a primer set given below, and KOD-Plus-Mutagenesis Kit (Toyobo Co., Ltd.) to construct a hA2-27D-H2-LALA type heavy chain expression vector. The constructed expression vector was designated as "pCMA-G1/hA2-27D-H2-LALA".

The nucleotide sequence of the humanized hA2-27D-H2-LALA type heavy chain is shown in SEQ ID NO: 106, and the amino acid sequence thereof is shown in SEQ ID NO: 107. A sequence consisting of nucleotide numbers 1 to 57 of the nucleotide sequence of SEQ ID NO: 106, a sequence consisting of nucleotide numbers 58 to 420 thereof, and a sequence consisting of nucleotide numbers 421 to 1410 thereof encode the signal sequence, the heavy chain variable region sequence, and the heavy chain constant region sequence, respectively. A sequence consisting of amino acid numbers 1 to 19 of the amino acid sequence of SEQ ID NO: 107, a sequence consisting of amino acid numbers 20 to 140 thereof, and a sequence consisting of amino acid numbers 141 to 470 thereof correspond to the signal sequence, the heavy chain variable region, and the heavy chain constant region, respectively. The nucleotide sequence of SEQ ID NO: 106 and the amino acid sequence of SEQ ID NO: 107 are also described in FIG. 33.

```
Primer set:
                        (LALA-F; SEQ ID NO: 132)
5'-GCGGGGGGACCCTCAGTCTTCCTCTTCCCC-3'

(LALA-R; SEQ ID NO: 133)
5'-GGCTTCAGGTGCTGGGCAGGGTGGGCATGTG-3'
```

12)-2 Construction of Humanized hA2-27D-H3-LALA Type Heavy Chain Expression Vector A hA2-27D-H3-LALA type heavy chain expression vector was constructed in the same way as in Example 12)-1 using pCMA-G1/hA2-27D-H3 constructed in Example 8)-3-3 as a template. The constructed expression vector was designated as "pCMA-G1/hA2-27D-H3-LALA".

The nucleotide sequence of the humanized hA2-27D-H3-LALA type heavy chain is shown in SEQ ID NO: 108, and the amino acid sequence thereof is shown in SEQ ID NO: 109. A sequence consisting of nucleotide numbers 1 to 57 of the nucleotide sequence of SEQ ID NO: 108, a sequence consisting of nucleotide numbers 58 to 420 thereof, and a sequence consisting of nucleotide numbers 421 to 1410 thereof encode the signal sequence, the heavy chain variable region sequence, and the heavy chain constant region sequence, respectively. A sequence consisting of amino acid numbers 1 to 19 of the amino acid sequence of SEQ ID NO: 109, a sequence consisting of amino acid numbers 20 to 140 thereof, and a sequence consisting of amino acid numbers 141 to 470 thereof correspond to the signal sequence, the heavy chain variable region, and the heavy chain constant region, respectively. The nucleotide sequence of SEQ ID NO: 108 and the amino acid sequence of SEQ ID NO: 109 are also described in FIG. 34.

12)-3 Production of Humanized A2-27D Antibody (IgG1 LALA)

Each antibody was produced in the same way as in Example 5)-7. A humanized A2-27D antibody obtained by the combination of pCMA-G1/hA2-27D-H2-LALA constructed in Example 12)-1 and pCMA/hA2-27D-L2 constructed in Example 8)-4-2 was designated as "humanized hA2-27D-H2/L2 (IgG1 LALA)". A humanized A2-27D antibody obtained by the combination of pCMA-G1/hA2-27D-H3-LALA constructed in Example 12)-2 and pCMA/hA2-27D-L4 constructed in Example 8)-4-4 was designated as "humanized hA2-27D-H3/L4 (IgG1 LALA)".

12)-4 Two-Step Purification of Humanized A2-27D Antibody (IgG1 LALA)

Each culture supernatant obtained in Example 12)-3 was purified in the same way as in Example 5)-8.

Example 13

In vitro activity evaluation of humanized A2-15A antibody (IgG2) and humanized A2-27D antibody (IgG1 LALA)

13)-1 Antibody Evaluation by Luciferase Reporter Assay

Humanized A2-15A-H4/L6 (IgG2) prepared in Example 11)-4 and humanized A2-27D-H2/L2 (IgG1 LALA) obtained in Example 12)-4 were analyzed for their inhibitory activity against ALK2-mediated intracellular signals using a luciferase reporter specific for BMP. HEPG2 cells were transfected with pGL4.26/Id1WT4F-luc (Genes Cells, 7, 949 (2002)) in the same way as in Example 6)-1. After 3 hours, the medium was replaced with fresh FreeStyle 293 expression medium (Invitrogen Corp.). Then, each humanized antibody and 2.5 ng/mL BMP9 were added thereto. On the next day, luciferase activity was measured in the same way as in Example 6)-1.

Figure 35:
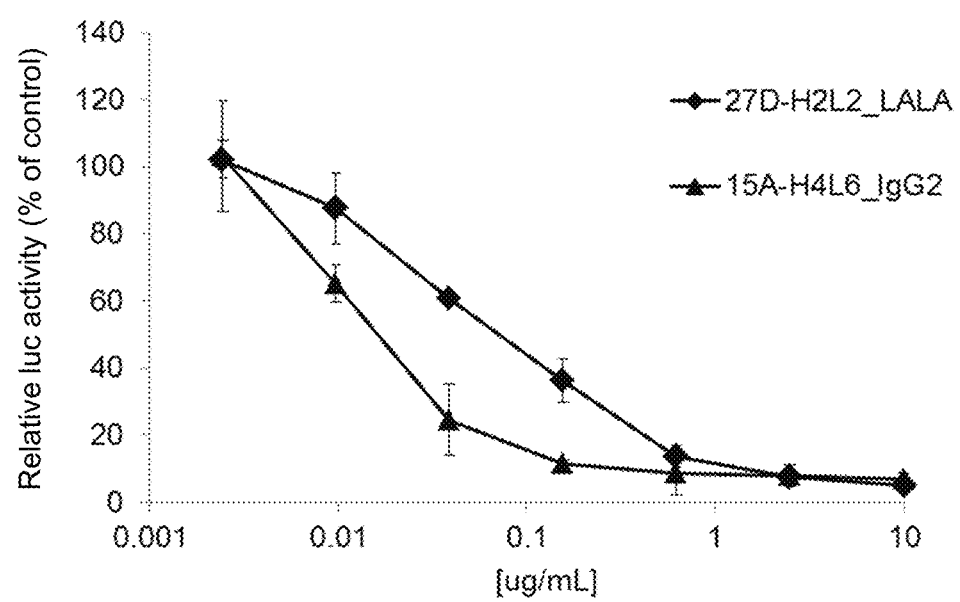
FIG. 35 This figure is a graph showing that a humanized A2-15A antibody (IgG2) and a humanized A2-27D antibody (LALA) inhibit, in a dose-dependent manner, BMP-specific luciferase (luc) activity induced by BMP7.

The results are shown in FIG. 35. Humanized A2-15A-H4/L6 (IgG2) and humanized A2-27D-H2/L2 (IgG1 LALA) were confirmed to inhibit, in a dose-dependent manner, BMP-specific luciferase activity induced by BMP9.

Example 14

Evaluation of Binding Activity of Humanized A2-15A Antibody (IgG2) and Humanized A2-27D Antibody (IgG1 LALA) Against Human ALK2

14)-1 Expression and Purification of Human ALK2 Extracellular Domain

DNA encoding a human ALK2 extracellular domain (polypeptide consisting of amino acid numbers 21 to 123 of the amino acid sequence of Accession No. NP_001096 of the NCBI protein database) was inserted into a vector pET-28b(+) (Novagen/Merck KGaA, Catalog No: 69865) to construct a plasmid for the expression of a protein C-terminally linked to a His tag sequence. E. coli SHuffle T7 (New England Biolabs Inc., Catalog No: C3029H) was transformed with this plasmid and cultured in TB medium (Sigma-Aldrich Co. LLC, Catalog No: T0918). The E. coli thus cultured was ultrasonicated, and the obtained bacterial cells were centrifuged. The supernatant was purified using HisTrap FF crude column (GE Healthcare Bio-Sciences Corp., Catalog No: 17-5286-01). Then, the human ALK2 extracellular domain was purified by electrophoresis using HiLoad 26/600 Superdex 200 column (GE Healthcare Bio-Sciences Corp., Catalog No: 28-9893-36) until a single band with a molecular weight of 12 kDa was obtained.

14)-2 Measurement of Ability of Humanized A2-15A Antibody (IgG2) and Humanized A2-27D Antibody (IgG1 LALA) to Bind to Antigen The dissociation constants of humanized hA2-15A-H4/L6 (IgG2) prepared in Example 11)-4, and humanized hA2-27D-H2/L2 (IgG1 LALA) and humanized hA2-27D-H3/L4 (IgG1 LALA) prepared in Example 12)-4 for the antigen (human ALK2 extracellular domain prepared in Example 14)-1) were measured using Biacore T200 (GE Healthcare Bio-Sciences Corp., Japan) by the capture method which involves capturing each antibody as a ligand onto an immobilized anti-human IgG (Fc) antibody and assaying the antigen as an analyte. Approximately 1000 RU of the anti-human IgG (Fc) antibody (Human Antibody Capture kit, GE Healthcare Bio-Sciences Corp.) was covalently bound to a sensor chip CM5 (GE Healthcare Bio-Sciences Corp.) by the amine coupling method. Similarly, this antibody was immobilized onto a reference cell. The running buffer used was HBS-EP+(10 mM HEPES (pH 7.4), 0.15 M NaCl, 3 mM EDTA, and 0.05% Surfactant P20). The antibody was added onto the anti-human IgG (Fc) antibody-immobilized chip for approximately 1 minute. Then, serially diluted solutions (0.78 to 200 nM) of the antigen were added thereto at a flow rate of 30 µl/min for 300 seconds. Subsequently, the dissociation phase was monitored for 600 seconds. A 3 M magnesium chloride solution was added thereto as a regenerating solution at a flow rate of 10 µl/min for 30 seconds. The data was analyzed using 1:1 binding models of analytical software (BIAevaluation software, version 1.0) to calculate an association rate constant ka, a dissociation rate constant kd, and a dissociation constant (KD; KD=kd/ka).

The results are shown in Table 2.

TABLE 2

Dissociation constants of humanized A2-15A antibody (IgG2) and humanized A2-27D antibody (IgG1 LALA)

| | Name | KD (nM) |
|---|---|---|
| 1 | hA2-15A-H4/L6, IgG2 | 17.4 |
| 2 | hA2-27D-H2/L2, IgG1 LALA | 13.6 |
| 3 | hA2-27D-H3/L4, IgG1 LALA | 13.3 |

Example 15

Evaluation of In Vivo Activity of Humanized A2-15A Antibody (IgG2) and Humanized A2-27D Antibody (IgG1 LALA)

Humanized hA2-15A-H4/L6 (IgG2) prepared in Example 11)-4 and humanized hA2-27D-H2/L2 (IgG1 LALA) prepared in Example 12)-4 were analyzed for their inhibitory activity against ectopic ossification using mouse models with ectopic ossification caused by the transplantation of BMP7. CollaTape (manufactured by Zimmer Biomet Dental K. K.) cut into a round shape of 4 mm in diameter was impregnated with 2.5 µg of BMP7 (manufactured by Miltenyi Biotec), frozen overnight −80° C., and then dried in vacuum. Skin hair near the thigh bone of each mouse (C57BL/6; 8-9 weeks old) was shaved, and an incision was made in this area under anesthesia by the aspiration of isoflurane. The freeze-dried filter paper was transplanted into skeletal muscle. Two weeks after the transplantation, calcified ectopic bone was analyzed as ectopic ossification by micro-CT (manufactured by Comscantecno Co., Ltd.). Then, the ectopic bone in the skeletal muscle was isolated, and the weight was measured. Each antibody was subcutaneously administered once a week (days −1 and 6 when the transplantation day was defined as day 0). The antibody was diluted with a solvent (HBSor) such that its concentration was 1, 3, or 10 mg/kg. Control human IgG (manufactured by Jackson ImmunoResearch Laboratories, Inc.) was adjusted to 10 mg/kg with a solvent and administered to mice in a control group.

Figure 36:
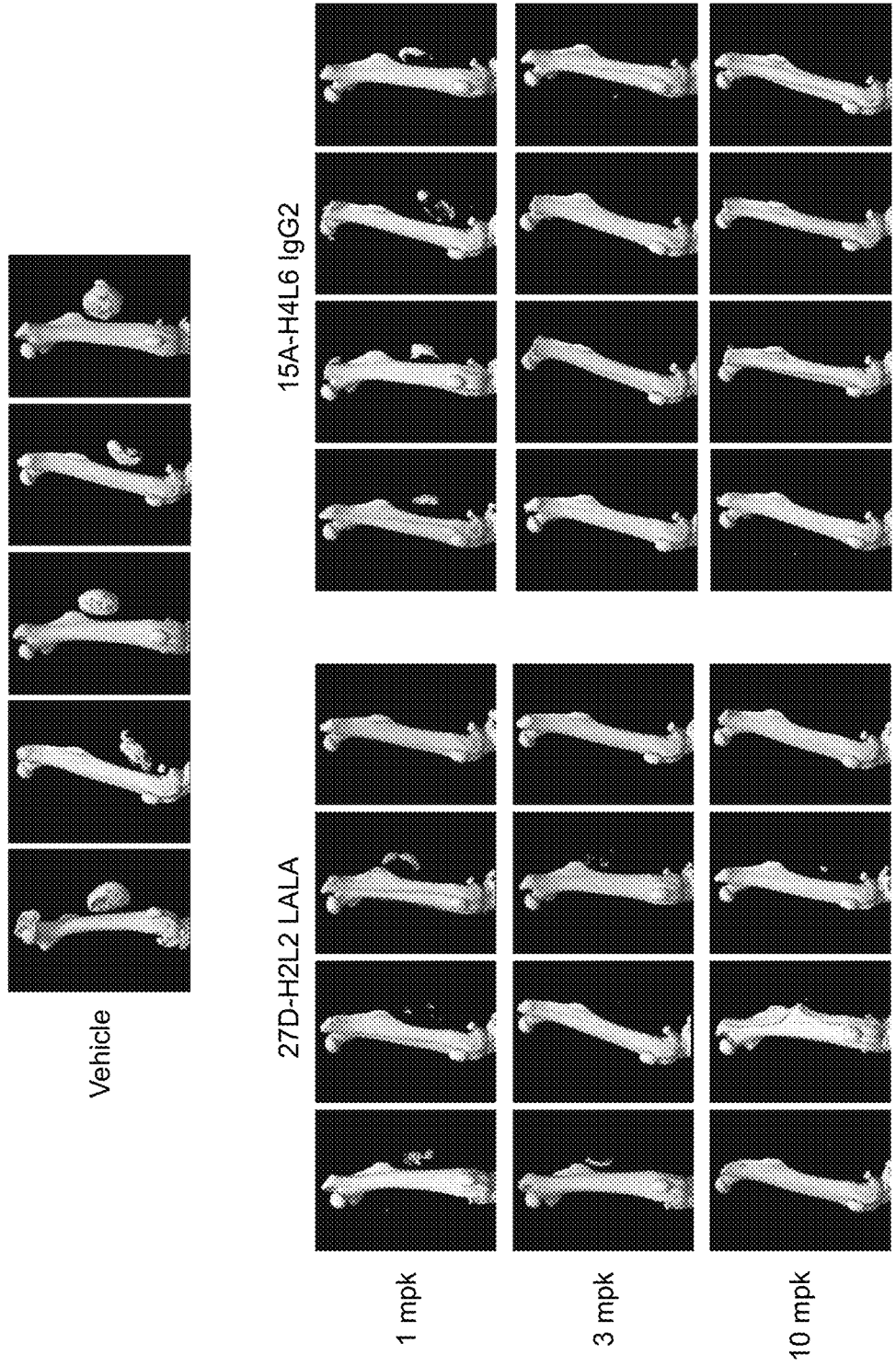
FIG. 36 This figure is a graph showing that the humanized A2-15A antibody (IgG2) and the humanized A2-27D antibody (LALA) inhibit BMP7-induced ectopic osteoinduction in mouse skeletal muscle tissues.

The results are shown in FIG. 36. Humanized hA2-15A-H4/L6 (IgG2) and humanized hA2-27D-H2/L2 (IgG1 LALA) were confirmed to suppress BMP7-induced ectopic osteoinduction in mouse skeletal muscle tissues.

Example 16

Epitope Analysis of A2-27D Antibody

16)-1 Preparation of Human Chimeric cA2-27D Fab Fragment

A Fab fragment was prepared from the human chimeric cA2-27D antibody obtained in Example 5)-8 using Pierce Fab Preparation Kit.

Figure 37:
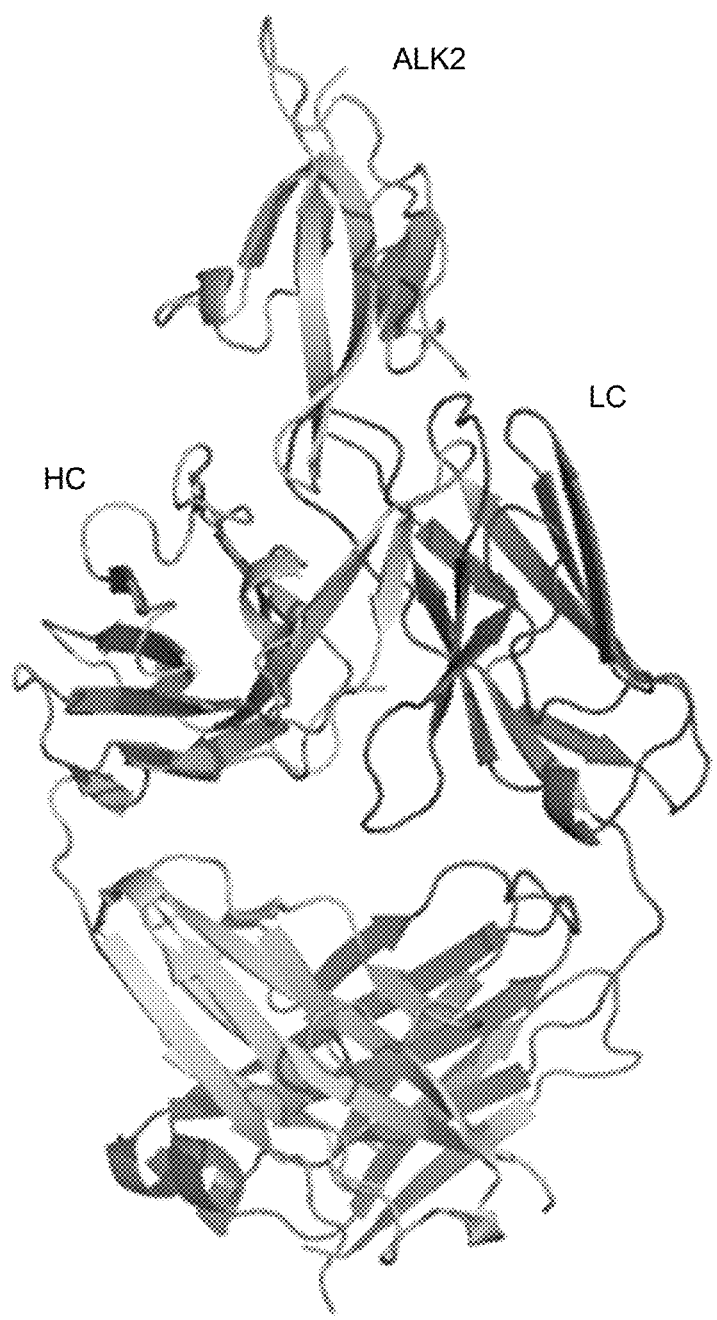
FIG. 37 This figure shows the X-ray crystal structure of a complex of human ALK2-ECD and human chimeric cA2-27D-Fab.

16)-2 Crystallization and Structural Analysis of Human Chimeric cA2-27D Fab Fragment and ALK2-ECD Complex The protein complex of the human chimeric cA2-27D Fab fragment obtained in Example 16)-1 and the ALK2-ECD prepared according to Example 14 were concentrated to 2.4 mg/mL and used in the crystallization trial employing vapor diffusion method. To 0.5 µL of the protein solution, an equal amount of a precipitant solution (2% (v/v) Tacsimate (pH 7.0), 100 mM HEPES (pH 7.5), and 20% (w/v) polyethylene glycol 3,350) was added, and the resulting solution was placed in a sealed container containing 50 µL of a precipitant solution such that these solutions had no contact with each other. The container was left standing at 20° C. Three days later, 0.1 mm×0.1 mm×0.1 mm single crystals were obtained. The obtained crystals were dipped in a precipitant solution supplemented with 20% (v/v) glycerol, and subsequently frozen in liquid nitrogen. X-ray diffraction data was collected under 95 K nitrogen stream using BL1A of KEK Photon Factory. Diffraction intensity was digitized from the obtained diffraction image using software XDS (Acta Cryst. (2010). D66, 125-132) to determine crystal structure factors. The crystals were in the body-centered monoclinic crystal system with a space group C121 and unit cells of a=c=119.39 angstroms, b=37.32 angstroms, and 3=92.54. The molecular replacement method was performed using the obtained structure factors and the three-dimensional structure coordinates of Fab (antibody structure determined by the past crystal structure analysis was used) to determine the phases. Software phaser (CCP4: Collaborative Computational Project No. 4) was used in calculation. The crystal contained one complex in the asymmetric unit. Structure refinement was performed using software Refmac5 (CCP4), and model correction was performed using software coot. This operation was repetitively performed to obtain a final R factor of 22.3% and a free R factor of 26.7% with a resolution of 2.6 angstroms. The model consists of one complex and contains amino acid numbers 1 to 211 of the A2-27D Fab L chain, amino acid numbers 1 to 134 and 141 to 223 of the A2-27D Fab H chain, amino acid numbers 11 to 89 of ALK2-ECD, and 61 water molecules. The determined amino acid residues of ALK2-ECD located within 4 angstroms from A2-27D Fab are as follows: Glu18, Gly19, Ile39, Asn40, Asp41, Gly42, Phe43, His44, Val45, Tyr46, Asn82, Thr84, Gln86, and Leu87. The ribbon model of the whole complex is shown in FIG. 37.

Example 17

Design of Humanized A2-11E Antibody and Humanized A2-25C Antibody

17)-1 Design of Humanized hA2-11E

17)-1-1 Molecular Modeling of A2-11E Variable Regions

The molecular modeling of the A2-11E variable regions was carried out by a method generally known as homology modeling (Methods in Enzymology, 203, 121-153, (1991)). The variable regions of A2-11E determined above were compared with the primary sequences (three-dimensional structures derived from X-ray crystal structures are available) of human immunoglobulin variable regions registered in Protein Data Bank (Nuc. Acid Res. 35, D301-D303 (2007)). As a result, 3BN9 was selected because of having the highest sequence identity to the heavy and light chain variable regions of A2-11E. The three-dimensional structures of framework regions were prepared as a "framework model" by combining the coordinates of 3BN9. Subsequently, the typical conformation of each CDR was incorporated into the framework model.

Finally, energy minimization calculation for excluding disadvantageous interatomic contact was conducted in order to obtain possible molecular models of the A2-11E variable regions in terms of energy. These procedures were performed using a commercially available protein three-dimensional structure analysis program Discovery Studio (manufactured by Accelrys).

17)-1-2 Design of Amino Acid Sequence of Humanized hA2-11E

Humanized hA2-11E was constructed by a method generally known as CDR grafting (Proc. Natl. Acad. Sci. USA 86, 10029-10033 (1989)). An acceptor antibody was selected on the basis of the identity of amino acids in framework regions.

The sequences of the framework regions of A2-11E were compared with the framework regions of human subgroup consensus sequences. As a result, a human γ chain subgroup 3 consensus sequence and a human κ chain subgroup 1 consensus sequence specified by KABAT et al. (Sequences of Proteins of Immunological Interest, 5th Ed. Public Health Service National Institutes of Health, Bethesda, Md. (1991)) were selected as acceptors due to their high sequence identity as to framework regions. The amino acid residues of the framework regions of the human γ chain subgroup 3 consensus sequence and the human κ chain subgroup 1 consensus sequence were aligned with the amino acid residues of the A2-11E framework regions to identify the numbers of amino acids that did not match therebetween. The numbers of these residues were analyzed using the three-dimensional model of A2-11E constructed above. Then, the donor residues to be grafted onto the acceptors were selected according to the criteria provided by Queen et al. (Proc. Natl. Acad. Sci. USA 86, 10029-10033 (1989)). Some donor residues thus selected were transferred to the acceptor antibody to construct the humanized hA2-11E sequence as described in Examples below.

17)-2 Humanization of A2-11E Heavy Chain

17)-2-1 Humanized hA2-11E-H3 Type Heavy Chain

A humanized hA2-11E heavy chain designed from the A2-11E heavy chain of SEQ ID NO: 2 of the Sequence Listing by the replacement of amino acid position 7 (threonine) with serine, amino acid position 16 (arginine) with glycine, amino acid position 19 (lysine) with arginine, amino acid position 23 (valine) with alanine, amino acid position 48 (isoleucine) with valine, amino acid position 61 (proline) with alanine, amino acid position 69 (alanine) with threonine, amino acid position 75 (alanine) with serine, amino acid position 76 (glutamic acid) with lysine, amino acid position 88 (serine) with alanine, and amino acid position 93 (threonine) with valine was designated as "hA2-11E-H3 type heavy chain".

The amino acid sequence of the humanized hA2-11E-H3 type heavy chain is described in SEQ ID NO: 111 of the Sequence Listing. A sequence consisting of amino acid numbers 1 to 19 of the amino acid sequence of SEQ ID NO: 111, a sequence consisting of amino acid numbers 20 to 137 thereof, and a sequence consisting of amino acid numbers 138 to 467 thereof correspond to the signal sequence, the heavy chain variable region, and the heavy chain constant region, respectively. The nucleotide sequence encoding the amino acid sequence of SEQ ID NO: 111 is described in SEQ ID NO: 110 of the Sequence Listing. A sequence consisting of nucleotide numbers 1 to 57 of the nucleotide sequence of SEQ ID NO: 110, a sequence consisting of nucleotide numbers 58 to 411 thereof, and a sequence consisting of nucleotide numbers 412 to 1401 thereof encode the signal sequence, the heavy chain variable region sequence, and the heavy chain constant region sequence, respectively. The nucleotide sequence of SEQ ID NO: 110 and the amino acid sequence of SEQ ID NO: 111 are also described in FIG. 38.

17)-2-2 Humanized hA2-11E-H4 Type Heavy Chain

A humanized hA2-11E heavy chain designed from the A2-11E heavy chain of SEQ ID NO: 2 of the Sequence Listing by the replacement of amino acid position 7 (threonine) with serine, amino acid position 16 (arginine) with glycine, amino acid position 19 (lysine) with arginine, amino acid position 23 (valine) with alanine, amino acid position 69 (alanine) with threonine, amino acid position 75 (alanine) with serine, amino acid position 76 (glutamic acid) with lysine, amino acid position 88 (serine) with alanine, and amino acid position 93 (threonine) with valine was designated as "hA2-11E-H4 type heavy chain".

The amino acid sequence of the humanized hA2-11E-H4 type heavy chain is described in SEQ ID NO: 113 of the Sequence Listing. A sequence consisting of amino acid numbers 1 to 19 of the amino acid sequence of SEQ ID NO: 113, a sequence consisting of amino acid numbers 20 to 137 thereof, and a sequence consisting of amino acid numbers 138 to 467 thereof correspond to the signal sequence, the heavy chain variable region, and the heavy chain constant region, respectively. The nucleotide sequence encoding the amino acid sequence of SEQ ID NO: 113 is described in SEQ ID NO: 112 of the Sequence Listing. A sequence consisting of nucleotide numbers 1 to 57 of the nucleotide sequence of SEQ ID NO: 112, a sequence consisting of nucleotide numbers 58 to 411 thereof, and a sequence consisting of nucleotide numbers 412 to 1401 thereof encode the signal sequence, the heavy chain variable region sequence, and the heavy chain constant region sequence, respectively. The nucleotide sequence of SEQ ID NO: 112 and the amino acid sequence of SEQ ID NO: 113 are also described in FIG. 39.

17)-3 Humanization of A2-11E Light Chain

17)-3-1 Humanized hA2-11E-L2 Type Light Chain

A humanized hA2-11E light chain designed from the A2-11E light chain of SEQ ID NO: 4 of the Sequence Listing by the replacement of amino acid number 10 (leucine) with serine, amino acid position 21 (leucine) with isoleucine, amino acid number 22 (serine) with threonine, amino acid number 40 (leucine) with proline, amino acid number 42 (glutamic acid) with lysine, amino acid number 58 (isoleucine) with valine, amino acid number 83 (valine) with phenylalanine, amino acid number 85 (isoleucine) with threonine, amino acid number 87 (phenylalanine) with tyrosine, amino acid number 99 (proline) with glutamine, amino acid number 103 (leucine) with valine, amino acid number 105 (leucine) with isoleucine, and amino acid number 108 (alanine) with threonine was designated as "hA2-11E-L2 type light chain".

The amino acid sequence of the humanized hA2-11E-L2 type light chain is described in SEQ ID NO: 115 of the Sequence Listing. A sequence consisting of amino acid numbers 1 to 20 of the amino acid sequence of SEQ ID NO: 115, a sequence consisting of amino acid numbers 21 to 128 thereof, and a sequence consisting of amino acid numbers 129 to 233 thereof correspond to the signal sequence, the light chain variable region, and the light chain constant region, respectively. The nucleotide sequence encoding the amino acid sequence of SEQ ID NO: 115 is described in SEQ ID NO: 114 of the Sequence Listing. A sequence consisting of nucleotide numbers 1 to 60 of the nucleotide sequence of SEQ ID NO: 114, a sequence consisting of nucleotide numbers 61 to 384 thereof, and a sequence consisting of nucleotide numbers 385 to 699 thereof encode the signal sequence, the light chain variable region sequence, and the light chain constant region sequence, respectively. The nucleotide sequence of SEQ ID NO: 114 and the amino acid sequence of SEQ ID NO: 115 are also described in FIG. 40.

17)-3-2 Humanized hA2-11E-L3 Type Light Chain

A humanized hA2-11E light chain designed from the A2-11E light chain of SEQ ID NO: 4 of the Sequence Listing by the replacement of amino acid number 10 (leucine) with serine, amino acid number 21 (leucine) with isoleucine, amino acid number 22 (serine) with threonine, amino acid number 40 (leucine) with proline, amino acid number 42 (glutamic acid) with lysine, amino acid number 83 (valine) with phenylalanine, amino acid number 85 (isoleucine) with threonine, amino acid number 87 (phenylalanine) with tyrosine, amino acid number 99 (proline) with glutamine, amino acid number 103 (leucine) with valine, amino acid number 105 (leucine) with isoleucine, and amino acid number 108 (alanine) with threonine was designated as "hA2-11E-L3 type light chain".

The amino acid sequence of the humanized hA2-11E-L3 type light chain is described in SEQ ID NO: 117 of the Sequence Listing. A sequence consisting of amino acid numbers 1 to 20 of the amino acid sequence of SEQ ID NO: 117, a sequence consisting of amino acid numbers 21 to 128 thereof, and a sequence consisting of amino acid numbers 129 to 233 thereof correspond to the signal sequence, the light chain variable region, and the light chain constant region, respectively. The nucleotide sequence encoding the amino acid sequence of SEQ ID NO: 117 is described in SEQ ID NO: 116 of the Sequence Listing. A sequence consisting of nucleotide numbers 1 to 60 of the nucleotide sequence of SEQ ID NO: 116, a sequence consisting of nucleotide numbers 61 to 384 thereof, and a sequence consisting of nucleotide numbers 385 to 699 thereof encode the signal sequence, the light chain variable region sequence, and the light chain constant region sequence, respectively. The nucleotide sequence of SEQ ID NO: 116 and the amino acid sequence of SEQ ID NO: 117 are also described in FIG. 41.

17)-3-3 Humanized hA2-11E-L4 Type Light Chain

A humanized hA2-11E light chain designed from the A2-11E light chain of SEQ ID NO: 4 of the Sequence Listing by the replacement of amino acid number 10 (leucine) with serine, amino acid number 21 (leucine) with isoleucine, amino acid number 40 (leucine) with proline, amino acid number 83 (valine) with phenylalanine, amino acid number 103 (leucine) with valine, amino acid number 105 (leucine) with isoleucine, and amino acid number 108 (alanine) with threonine was designated as "hA2-11E-L4 type light chain".

The amino acid sequence of the humanized hA2-11E-L4 type light chain is described in SEQ ID NO: 119 of the Sequence Listing. A sequence consisting of amino acid numbers 1 to 20 of the amino acid sequence of SEQ ID NO: 119, a sequence consisting of amino acid numbers 21 to 128 thereof, and a sequence consisting of amino acid numbers 129 to 233 thereof correspond to the signal sequence, the light chain variable region, and the light chain constant region, respectively. The nucleotide sequence encoding the amino acid sequence of SEQ ID NO: 119 is described in SEQ ID NO: 118 of the Sequence Listing. A sequence consisting of nucleotide numbers 1 to 60 of the nucleotide sequence of SEQ ID NO: 118, a sequence consisting of nucleotide numbers 61 to 384 thereof, and a sequence consisting of nucleotide numbers 385 to 699 thereof encode the signal sequence, the light chain variable region sequence, and the light chain constant region sequence, respectively. The nucleotide sequence of SEQ ID NO: 118 and the amino acid sequence of SEQ ID NO: 119 are also described in FIG. 42.

17)-4 Design of Humanized hA2-11E by Combination of Heavy Chain and Light Chain

An antibody consisting of the humanized hA2-11E-H3 type heavy chain and the humanized hA2-11E-L2 type light chain was designed and designated as "humanized hA2-11E-H3/L2" (also referred to as "hA2-11E-H3/L2"). An antibody consisting of the humanized hA2-11E-H3 type heavy chain and the humanized hA2-11E-L3 type light chain was designed and designated as "humanized hA2-11E-H3/L3" (also referred to as "hA2-11E-H3/L3"). An antibody consisting of the humanized hA2-11E-H3 type heavy chain and the humanized hA2-11E-L4 type light chain was designed and designated as "humanized hA2-11E-H3/L4" (also referred to as "hA2-11E-H3/L4"). An antibody consisting of the humanized hA2-11E-H4 type heavy chain and the humanized hA2-11E-L2 type light chain was designed and designated as "humanized hA2-11E-H4/L2" (also referred to as "hA2-11E-H4/L2"). An antibody consisting of the humanized hA2-11E-H4 type heavy chain and the humanized hA2-11E-L3 type light chain was designed and designated as "humanized hA2-11E-H4/L3" (also referred to as "hA2-11E-H4/L3"). An antibody consisting of the humanized hA2-11E-H4 type heavy chain and the humanized hA2-11E-L4 type light chain was designed and designated as "humanized hA2-11E-H4/L4" (also referred to as "hA2-11E-H4/L4"). These designed antibodies can be prepared according to Example 18 and evaluated according to Examples 2 and 4.

17)-5 Design of Humanized hA2-25C

17)-5-1 Molecular Modeling of A2-25C Variable Regions

The molecular modeling of the A2-25C variable regions was carried out by a method generally known as homology modeling (Methods in Enzymology, 203, 121-153, (1991)). The variable regions of AA2-25C determined above were compared with the primary sequences (three-dimensional structures derived from X-ray crystal structures are available) of human immunoglobulin variable regions registered in Protein Data Bank (Nuc. Acid Res. 35, D301-D303 (2007)). As a result, 3BN9 was selected because of having the highest sequence identity to the heavy and light chain variable regions of A2-25C. The three-dimensional structures of framework regions were prepared as a "framework model" by combining the coordinates of 3BN9. Subsequently, the typical conformation of each CDR was incorporated into the framework model.

Finally, energy minimization calculation for excluding disadvantageous interatomic contact was conducted in order to obtain possible molecular models of the A2-25C variable regions in terms of energy. These procedures were performed using a commercially available protein three-dimensional structure analysis program Discovery Studio (manufactured by Accelrys).

17)-5-2 Design of Amino Acid Sequence of Humanized hA2-25C

Humanized hA2-25C was constructed by a method generally known as CDR grafting (Proc. Natl. Acad. Sci. USA 86, 10029-10033 (1989)). An acceptor antibody was selected on the basis of the identity of amino acids in framework regions.

The sequences of the framework regions of A2-25C were compared with the framework regions of human subgroup consensus sequences. As a result, a human γ chain subgroup 3 consensus sequence and a human κ chain subgroup 1 consensus sequence specified by KABAT et al. (Sequences of Proteins of Immunological Interest, 5th Ed. Public Health Service National Institutes of Health, Bethesda, Md. (1991)) were selected as acceptors due to their high sequence identity as to framework regions. The amino acid residues of the framework regions of the human γ chain subgroup 3 consensus sequence and the human κ chain subgroup 1 consensus sequence were aligned with the amino acid residues of the A2-25C framework regions to identify the numbers of amino acids that did not match therebetween. The numbers of these residues were analyzed using the three-dimensional model of A2-25C constructed above. Then, the donor residues to be grafted onto the acceptors were selected according to the criteria provided by Queen et al. (Proc. Natl. Acad. Sci. USA 86, 10029-10033 (1989)). Some donor residues thus selected were transferred to the acceptor antibody to construct the humanized hA2-25C sequence as described in Examples below.

17)-6 Humanization of A2-25C Heavy Chain

17)-6-1 Humanized hA2-25C-H3 Type Heavy Chain

A humanized hA2-25C heavy chain designed from the A2-25C heavy chain of SEQ ID NO: 10 of the Sequence Listing by the replacement of amino acid number 19 (lysine) with arginine, amino acid number 38 (cysteine) with arginine, amino acid number 42 (threonine) with glycine, amino acid number 63 (threonine) with serine, amino acid number 75 (alanine) with serine, amino acid number 84 (aspartic acid) with asparagine, amino acid number 88 (serine) with alanine, amino acid number 93 (threonine) with valine, amino acid number 112 (valine) with threonine, and amino acid number 113 (methionine) with leucine was designated as "hA2-25C-H3 type heavy chain".

The amino acid sequence of the humanized hA2-25C-H3 type heavy chain is described in SEQ ID NO: 121 of the Sequence Listing. A sequence consisting of amino acid numbers 1 to 19 of the amino acid sequence of SEQ ID NO: 121, a sequence consisting of amino acid numbers 20 to 137 thereof, and a sequence consisting of amino acid numbers 138 to 467 thereof correspond to the signal sequence, the heavy chain variable region, and the heavy chain constant region, respectively. The nucleotide sequence encoding the amino acid sequence of SEQ ID NO: 121 is described in SEQ ID NO: 120 of the Sequence Listing. A sequence consisting of nucleotide numbers 1 to 57 of the nucleotide sequence of SEQ ID NO: 120, a sequence consisting of nucleotide numbers 58 to 411 thereof, and a sequence consisting of nucleotide numbers 412 to 1401 thereof encode the signal sequence, the heavy chain variable region sequence, and the heavy chain constant region sequence, respectively. The nucleotide sequence of SEQ ID NO: 120 and the amino acid sequence of SEQ ID NO: 121 are also described in FIG. 43.

17)-6-2 Humanized hA2-25C-H4 Type Heavy Chain

A humanized hA2-25C heavy chain designed from the A2-25C heavy chain of SEQ ID NO: 10 of the Sequence Listing by the replacement of amino acid number 19 (lysine) with arginine, amino acid number 38 (cysteine) with arginine, amino acid number 42 (threonine) with glycine, amino acid number 63 (threonine) with serine, amino acid number 75 (alanine) with serine, amino acid number 84 (aspartic acid) with asparagine, amino acid number 88 (serine) with alanine, and amino acid number 113 (methionine) with leucine was designated as "hA2-25C-H4 type heavy chain".

The amino acid sequence of the humanized hA2-25C-H4 type heavy chain is described in SEQ ID NO: 123 of the Sequence Listing. A sequence consisting of amino acid numbers 1 to 19 of the amino acid sequence of SEQ ID NO: 123, a sequence consisting of amino acid numbers 20 to 137 thereof, and a sequence consisting of amino acid numbers 138 to 467 thereof correspond to the signal sequence, the heavy chain variable region, and the heavy chain constant region, respectively. The nucleotide sequence encoding the amino acid sequence of SEQ ID NO: 123 is described in SEQ ID NO: 122 of the Sequence Listing. A sequence consisting of nucleotide numbers 1 to 57 of the nucleotide sequence of SEQ ID NO: 122, a sequence consisting of nucleotide numbers 58 to 411 thereof, and a sequence consisting of nucleotide numbers 412 to 1401 thereof encode the signal sequence, the heavy chain variable region sequence, and the heavy chain constant region sequence, respectively. The nucleotide sequence of SEQ ID NO: 122 and the amino acid sequence of SEQ ID NO: 123 are also described in FIG. 44.

17)-7 Humanization of A2-25C Light Chain

17)-7-1 Humanized hA2-25C-L1 Type Light Chain

A humanized hA2-25C light chain designed from the A2-25C light chain of SEQ ID NO: 12 of the Sequence Listing by the replacement of amino acid number 9 (alanine) with serine, amino acid number 15 (leucine) with valine, amino acid number 16 (glutamic acid) with glycine, amino acid number 17 (glutamic acid) with aspartic acid, amino acid number 18 (isoleucine) with arginine, amino acid number 43 (serine) with alanine, amino acid number 45 (glutamine) with lysine, amino acid number 66 (arginine) with glycine, amino acid number 70 (glutamine) with aspartic acid, amino acid number 71 (tyrosine) with phenylalanine, amino acid number 72 (serine) with threonine, amino acid number 74 (lysine) with threonine, amino acid number 77 (arginine) with serine, amino acid number 79 (arginine) with glutamine, amino acid number 80 (valine) with proline, amino acid number 83 (isoleucine) with phenylalanine, amino acid number 84 (glycine) with alanine, amino acid number 85 (isoleucine) with threonine, amino acid number 100 (serine) with glutamine, amino acid number 104 (leucine) with valine, and amino acid number 109 (alanine) with threonine was designated as "hA2-25C-L1 type light chain".

The amino acid sequence of the humanized hA2-25C-L1 type light chain is described in SEQ ID NO: 125 of the Sequence Listing. A sequence consisting of amino acid numbers 1 to 20 of the amino acid sequence of SEQ ID NO: 125, a sequence consisting of amino acid numbers 21 to 129 thereof, and a sequence consisting of amino acid numbers 130 to 234 thereof correspond to the signal sequence, the light chain variable region, and the light chain constant region, respectively. The nucleotide sequence encoding the amino acid sequence of SEQ ID NO: 125 is described in SEQ ID NO: 124 of the Sequence Listing. A sequence consisting of nucleotide numbers 1 to 60 of the nucleotide sequence of SEQ ID NO: 124, a sequence consisting of nucleotide numbers 61 to 387 thereof, and a sequence consisting of nucleotide numbers 388 to 702 thereof encode the signal sequence, the light chain variable region sequence, and the light chain constant region sequence, respectively. The nucleotide sequence of SEQ ID NO: 124 and the amino acid sequence of SEQ ID NO: 125 are also described in FIG. 45.

17)-7-2 Humanized hA2-25C-L2 Type Light Chain

A humanized hA2-25C light chain designed from the A2-25C light chain of SEQ ID NO: 12 of the Sequence Listing by the replacement of amino acid number 9 (alanine) with serine, amino acid number 15 (leucine) with valine, amino acid number 16 (glutamic acid) with glycine, amino acid number 17 (glutamic acid) with aspartic acid, amino acid number 18 (isoleucine) with arginine, amino acid number 43 (serine) with alanine, amino acid number 45 (glutamine) with lysine, amino acid number 70 (glutamine) with aspartic acid, amino acid number 72 (serine) with threonine, amino acid number 74 (lysine) with threonine, amino acid number 77 (arginine) with serine, amino acid number 79 (arginine) with glutamine, amino acid number 80 (valine) with proline, amino acid number 83 (isoleucine) with phenylalanine, amino acid number 84 (glycine) with alanine, amino acid number 85 (isoleucine) with threonine, amino acid number 100 (serine) with glutamine, amino acid number 104 (leucine) with valine, and amino acid number 109 (alanine) with threonine was designated as "hA2-25C-L2 type light chain".

The amino acid sequence of the humanized hA2-25C-L2 type light chain is described in SEQ ID NO: 127 of the Sequence Listing. A sequence consisting of amino acid numbers 1 to 20 of the amino acid sequence of SEQ ID NO: 127, a sequence consisting of amino acid numbers 21 to 129 thereof, and a sequence consisting of amino acid numbers 130 to 234 thereof correspond to the signal sequence, the light chain variable region, and the light chain constant region, respectively. The nucleotide sequence encoding the amino acid sequence of SEQ ID NO: 127 is described in SEQ ID NO: 126 of the Sequence Listing. A sequence consisting of nucleotide numbers 1 to 60 of the nucleotide sequence of SEQ ID NO: 126, a sequence consisting of nucleotide numbers 61 to 387 thereof, and a sequence consisting of nucleotide numbers 388 to 702 thereof encode the signal sequence, the light chain variable region sequence, and the light chain constant region sequence, respectively. The nucleotide sequence of SEQ ID NO: 126 and the amino acid sequence of SEQ ID NO: 127 are also described in FIG. 46.

17)-7-3 Humanized hA2-25C-L3 Type Light Chain

A humanized hA2-25C light chain designed from the A2-25C light chain of SEQ ID NO: 12 of the Sequence Listing by the replacement of amino acid number 9 (alanine) with serine, amino acid number 15 (leucine) with valine, amino acid number 16 (glutamic acid) with glycine, amino acid number 17 (glutamic acid) with aspartic acid, amino acid number 18 (isoleucine) with arginine, amino acid number 45 (glutamine) with lysine, amino acid number 72 (serine) with threonine, amino acid number 74 (lysine) with threonine, amino acid number 77 (arginine) with serine, amino acid number 79 (arginine) with glutamine, amino acid number 80 (valine) with proline, amino acid number 83 (isoleucine) with phenylalanine, amino acid number 84 (glycine) with alanine, amino acid number 85 (isoleucine) with threonine, amino acid number 104 (leucine) with valine, and amino acid number 109 (alanine) with threonine was designated as "hA2-25C-L3 type light chain".

The amino acid sequence of the humanized hA2-25C-L3 type light chain is described in SEQ ID NO: 129 of the Sequence Listing. A sequence consisting of amino acid numbers 1 to 20 of the amino acid sequence of SEQ ID NO: 129, a sequence consisting of amino acid numbers 21 to 129 thereof, and a sequence consisting of amino acid numbers 130 to 234 thereof correspond to the signal sequence, the light chain variable region, and the light chain constant region, respectively. The nucleotide sequence encoding the amino acid sequence of SEQ ID NO: 129 is described in SEQ ID NO: 128 of the Sequence Listing. A sequence consisting of nucleotide numbers 1 to 60 of the nucleotide sequence of SEQ ID NO: 128, a sequence consisting of nucleotide numbers 61 to 387 thereof, and a sequence consisting of nucleotide numbers 388 to 702 thereof encode the signal sequence, the light chain variable region sequence, and the light chain constant region sequence, respectively. The nucleotide sequence of SEQ ID NO: 128 and the amino acid sequence of SEQ ID NO: 129 are also described in FIG. 47.

17)-8 Design of Humanized hA2-25C by Combination of Heavy Chain and Light Chain

An antibody consisting of the humanized hA2-25C-H3 type heavy chain and the humanized hA2-25C-L1 type light chain was designed and designated as "humanized hA2-25C-H3/L1 (also referred to as "hA2-25C-H3/L1"). An antibody consisting of the humanized hA2-25C-H3 type heavy chain and the humanized hA2-25C-L2 type light chain was designed and designated as "humanized hA2-25C-H3/L2" (also referred to as "hA2-25C-H3/L2"). An antibody consisting of the humanized hA2-125C-H3 type heavy chain and the humanized hA2-25C-L3 type light chain was designed and designated as "humanized hA2-25C-H3/L3" (also referred to as "hA2-25C-H3/L3"). An antibody consisting of the humanized hA2-25C-H4 type heavy chain and the humanized hA2-25C-L1 type light chain was designed and designated as "humanized hA2-25C-H4/L1" (also referred to as "hA2-25C-H4/L1"). An antibody consisting of the humanized hA2-25C-H4 type heavy chain and the humanized hA2-25C-L2 type light chain was designed and designated as "humanized hA2-25C-H4/L2" (also referred to as "hA2-25C-H4/L2"). An antibody consisting of the humanized hA2-25C-H4 type heavy chain and the humanized hA2-25C-L3 type light chain was designed and designated as "humanized hA2-25C-H4/L3" (also referred to as "hA2-25C-H4/L3"). These designed antibodies can be prepared according to Example 18 and evaluated according to Examples 2 and 4.

Example 18

Construction and Preparation of Vectors for Humanized A2-11E Antibody (IgG1) and Humanized A2-25C Antibody (IgG1)

18)-1 Construction of Humanized A2-11E Heavy Chain Expression Vector

18)-1-1 Construction of Humanized hA2-11E-H3 Type Heavy Chain Expression Vector

A DNA fragment containing a humanized hA2-11E-H3 variable region-encoding DNA sequence represented by nucleotide numbers 36 to 428 of the nucleotide sequence of humanized hA2-11E-H3 of SEQ ID NO: 110 was synthesized (GeneArt Artificial Gene Synthesis Service). A humanized hA2-11E-H3 expression vector was constructed in the same way as in Example 8)-1-1. The obtained expression vector was designated as "pCMA-G1/hA2-11E-H3".

18)-1-2 Construction of Humanized hA2-11E-H4 Type Heavy Chain Expression Vector

A DNA fragment containing a humanized hA2-11E-H4 variable region-encoding DNA sequence represented by nucleotide numbers 36 to 428 of the nucleotide sequence of humanized hA2-11E-H4 of SEQ ID NO: 112 was synthesized (GeneArt Artificial Gene Synthesis Service). A humanized hA2-11E-H4 expression vector was constructed in the same way as in Example 8)-1-1. The obtained expression vector was designated as "pCMA-G1/hA2-11E-H4".

18)-2 Construction of Humanized A2-11E Light Chain Expression Vector

18)-2-1 Construction of Humanized hA2-11E-L2 Type Light Chain Expression Vector

A DNA fragment containing a humanized hA2-11E-L2 variable region-encoding DNA sequence represented by nucleotide numbers 37 to 399 of the nucleotide sequence of humanized hA2-11E-L2 of SEQ ID NO: 114 was synthesized (GeneArt Artificial Gene Synthesis Service). The DNA fragment containing a humanized hA2-11E-L2 variable region-encoding DNA sequence was amplified using the synthesized DNA fragment as a template, KOD-Plus- (Toyobo Co., Ltd.), and a primer set given below, and inserted at the restriction enzyme BsiWI-cleaved site of the chimeric and humanized antibody light chain expression vector pCMA-LK constructed in Example 5)-1 using In-Fusion HD PCR cloning kit (Clontech Laboratories, Inc.) to construct a humanized hA2-11E-L2 expression vector. The obtained expression vector was designated as "pCMA/hA2-11E-L2".

```
Primer set
                        (CM-LKF; SEQ ID NO: 134)
5'-CTGTGGATCTCCGGCGCGTACGGC-3'

(KCL-Inf-R; SEQ ID NO: 135)
5'-GGAGGGGGCGGCCACCGTACG-3'
```

18)-2-2 Construction of Humanized hA2-11E-L3 Type Light Chain Expression Vector

A DNA fragment containing a humanized hA2-11E-L3 variable region-encoding DNA sequence represented by nucleotide numbers 37 to 399 of the nucleotide sequence of humanized hA2-11E-L3 of SEQ ID NO: 116 was synthesized (GeneArt Artificial Gene Synthesis Service). A humanized hA2-11E-L3 expression vector was constructed in the same way as in Example 18)-2-1. The obtained expression vector was designated as "pCMA/hA2-11E-L3".

18)-2-3 Construction of Humanized hA2-11E-L4 Type Light Chain Expression Vector

A DNA fragment containing a humanized hA2-11E-L4 variable region-encoding DNA sequence represented by nucleotide numbers 37 to 339 of the nucleotide sequence of humanized hA2-11E-L4 of SEQ ID NO: 118 was synthesized (GeneArt Artificial Gene Synthesis Service). A humanized hA2-11E-L4 expression vector was constructed in the same way as in Example 18)-2-1. The obtained expression vector was designated as "pCMA/hA2-11E-L4".

18)-3 Construction of Humanized A2-25C Heavy Chain Expression Vector

18)-3-1 Construction of Humanized hA2-25C-H3 Type Heavy Chain Expression Vector

A DNA fragment containing a humanized hA2-25C-H3 variable region-encoding DNA sequence represented by nucleotide numbers 36 to 428 of the nucleotide sequence of humanized hA2-25C-H3 of SEQ ID NO: 120 was synthesized (GeneArt Artificial Gene Synthesis Service). A humanized hA2-25C-H3 expression vector was constructed in the same way as in Example 8)-1-1. The obtained expression vector was designated as "pCMA-G1/hA2-25C-H3".

18)-3-2 Construction of Humanized hA2-25C-H4 Type Heavy Chain Expression Vector

A DNA fragment containing a humanized hA2-25C-H4 variable region-encoding DNA sequence represented by nucleotide numbers 36 to 428 of the nucleotide sequence of humanized hA2-25C-H4 of SEQ ID NO: 122 was synthesized (GeneArt Artificial Gene Synthesis Service). A humanized hA2-25C-H4 expression vector was constructed in the same way as in Example 8)-1-1. The obtained expression vector was designated as "pCMA-G1/hA2-25C-H4".

18)-4 Construction of Humanized A2-25C Light Chain Expression Vector

18)-4-1 Construction of Humanized hA2-25C-L1 Type Light Chain Expression Vector

A DNA fragment containing a humanized hA2-25C-L1 variable region-encoding DNA sequence represented by nucleotide numbers 37 to 402 of the nucleotide sequence of humanized hA2-25C-L1 of SEQ ID NO: 124 was synthesized (GeneArt Artificial Gene Synthesis Service). A humanized hA2-25C-L1 expression vector was constructed in the same way as in Example 18)-2-1. The obtained expression vector was designated as "pCMA/hA2-25C-L1".

18)-4-2 Construction of Humanized hA2-25C-L2 Type Light Chain Expression Vector

A DNA fragment containing a humanized hA2-25C-L2 variable region-encoding DNA sequence represented by nucleotide numbers 37 to 402 of the nucleotide sequence of humanized hA2-25C-L2 of SEQ ID NO: 126 was synthesized (GeneArt Artificial Gene Synthesis Service). A humanized hA2-25C-L2 expression vector was constructed in the same way as in Example 18)-2-1. The obtained expression vector was designated as "pCMA/hA2-25C-L2".

18)-4-3 Construction of Humanized hA2-25C-L3 Type Light Chain Expression Vector

A DNA fragment containing a humanized hA2-25C-L3 variable region-encoding DNA sequence represented by nucleotide numbers 37 to 402 of the nucleotide sequence of humanized hA2-25C-L3 of SEQ ID NO: 128 was synthesized (GeneArt Artificial Gene Synthesis Service). A humanized hA2-25C-L3 expression vector was constructed in the same way as in Example 18)-2-1. The obtained expression vector was designated as "pCMA/hA2-25C-L3".

18)-5 Small-Scale Production of Humanized A2-11E Antibody (IgG1) and Humanized A2-25C Antibody (IgG1)

FreeStyle 293F cells (Invitrogen Corp.) were subcultured and cultured according to the manual.

$1 \times 10^7$ FreeStyle 293F cells (Invitrogen Corp.) in the logarithmic growth phase were diluted to 9.6 mL with FreeStyle 293 expression medium (Invitrogen Corp.), then inoculated to 30 mL Square Storage Bottle (Nalgene/Thermo Fisher Scientific Inc.), and shake-cultured at 90 rpm at 37° C. for 1 hour in an 8% $CO_2$ incubator. 30 μg of polyethyleneimine (Polysciences #24765) was dissolved in 200 μL of Opti-Pro SFM (Invitrogen Corp.). Next, each light chain expression vector (6 μg) and heavy chain expression vector (4 μg) prepared using NucleoBond Xtra (Takara Bio Inc.) were added to 200 μL of Opti-Pro SFM (Invitrogen Corp.). 200 μL of the expression vector/Opti-Pro SFM mixed solution was added to 200 μL of the polyethyleneimine/Opti-Pro SFM mixed solution, and the mixture was gently stirred, further left for 5 minutes, and then added to the FreeStyle 293F cells. The cells were shake-cultured at 90 rpm at 37° C. for 7 days in an 8% $CO_2$ incubator, and the obtained culture supernatant was filtered through Minisart-Plus filter (Sartorius Japan K.K.) and used as a sample for evaluation.

Humanized hA2-11E-H3/L2 was obtained by the combination of pCMA-G1/hA2-11E-H3 constructed in Example 18)-1-1 and pCMA/hA2-11E-L2 constructed in Example 18)-2-1. Humanized hA2-11E-H3/L3 was obtained by the combination of pCMA-G1/hA2-11E-H3 constructed in Example 18)-1-1 and pCMA/hA2-11E-L3 constructed in Example 18)-2-2. Humanized hA2-11E-H3/L4 was obtained by the combination of pCMA-G1/hA2-11E-H3 constructed in Example 18)-1-1 and pCMA/hA2-11E-L4 constructed in Example 18)-2-3. Humanized hA2-11E-H4/L2 was obtained by the combination of pCMA-G1/hA2-11E-H4 constructed in Example 18)-1-2 and pCMA/hA2-11E-L2 constructed in Example 18)-2-1. Humanized hA2-11E-H4/L3 was obtained by the combination of pCMA-G1/hA2-11E-H4 constructed in Example 18)-1-2 and pCMA/hA2-11E-L3 constructed in Example 18)-2-2. Humanized hA2-11E-H4/L4 was obtained by the combination of pCMA-G1/hA2-11E-H4 constructed in Example 18)-1-2 and pCMA/hA2-11E-L4 constructed in Example 18)-2-3.

Humanized hA2-25C-H3/L1 was obtained by the combination of pCMA-G1/hA2-25C-H3 constructed in Example 18)-3-1 and pCMA-/hA2-25C-L1 constructed in Example 18)-4-1. Humanized hA2-25C-H3/L2 was obtained by the combination of pCMA-G1/hA2-25C-H3 constructed in Example 18)-3-1 and pCMA-/hA2-25C-L2 constructed in Example 18)-4-2. Humanized hA2-25C-H3/L3 was obtained by the combination of pCMA-G1/hA2-25C-H3 constructed in Example 18)-3-1 and pCMA-/hA2-25C-L3 constructed in Example 18)-4-3. Humanized hA2-25C-H4/L1 was obtained by the combination of pCMA-G1/hA2-25C-H4 constructed in Example 18)-3-2 and pCMA-/hA2-25C-L1 constructed in Example 18)-4-1. Humanized hA2-25C-H4/L2 was obtained by the combination of pCMA-G1/hA2-25C-H4 constructed in Example 18)-3-2 and pCMA-/hA2-25C-L2 constructed in Example 18)-4-2. Humanized hA2-25C-H4/L3 was obtained by the combination of pCMA-G1/hA2-25C-H4 constructed in Example 18)-3-2 and pCMA-/hA2-25C-L3 constructed in Example 18)-4-3.

Example 19

Evaluation of In Vitro Activity of Humanized A2-11E Antibody (IgG1) and Humanized A2-25C Antibody (IgG1)

19)-1 Evaluation of the Antibodies in BMP-Induced Osteoblast Differentiation Assay The humanized A2-11E antibodies (IgG1) and the humanized A2-25C antibodies (IgG1) prepared in Example 18)-5 were analyzed for their inhibitory activity against intracellular signals through endogenous ALK2, on the basis of their effects on BMP-induced osteoblast differentiation assay using C2C12 cells in the same way as in Example 6)-2. 2.5 ng/mL GDF2/BMP9 (manufactured by R&D Systems, Inc.) was used in the differentiation induction.

The results are shown in FIG. 48. The humanized A2-11E antibodies (IgG1) and the humanized A2-25C antibodies (IgG1) were confirmed to inhibit, in a dose-dependent manner, the differentiation of C2C12 cells into osteoblast-like cells induced by BMP.

Example 20

Evaluation of Binding Activity of Humanized A2-11E Antibody (IgG1) and Humanized A2-25C Antibody (IgG1) Against Human ALK2

The dissociation constants of the humanized A2-11E antibodies (IgG1) and the humanized A2-25C antibodies (IgG1) prepared in Example 18)-5 for the antigen (human ALK2 extracellular domain prepared in Example 14)-1) were measured using Biacore T200 (GE Healthcare Bio-Sciences Corp.) by the capture method which involves capturing each antibody as a ligand onto an immobilized anti-human IgG (Fc) antibody and assaying the antigen as an analyte. Approximately 1000 RU of the anti-human IgG (Fc) antibody (Human Antibody Capture kit, GE Healthcare Bio-Sciences Corp.) was covalently bound to a sensor chip CM5 (GE Healthcare Bio-Sciences Corp.) by the amine coupling method. Similarly, this antibody was immobilized onto a reference cell. The running buffer used was HBS-EP+(10 mM HEPES (pH 7.4), 0.15 M NaCl, 3 mM EDTA, and 0.05% Surfactant P20). The culture supernatant containing the antibody was added onto the anti-human IgG (Fc) antibody-immobilized chip for approximately 1 minute. Then, serially diluted solutions (0.78 to 200 nM) of the antigen were added thereto at a flow rate of 30 µl/min for 300 seconds. Subsequently, the dissociation phase was monitored for 600 seconds. 3 M $MgCl_2$ was added thereto as a regenerating solution at a flow rate of 10 µl/min for 30 seconds. The data was analyzed using 1:1 binding models of analytical software (BIAevaluation software, version 1.0) to calculate an association rate constant ka, a dissociation rate constant kd, and a dissociation constant (KD; KD=kd/ka).

The results are shown in Table 3.

TABLE 3

Dissociation constants of humanized A2-11E antibody and humanized A2-25C antibody

| | Name | KD (nM) |
|---|---|---|
| 1 | hA2-11E-H3/L2 | 63.1 |
| 2 | hA2-11E-H3/L3 | 47.4 |
| 3 | hA2-11E-H3/L4 | 31.3 |
| 4 | hA2-11E-H4/L2 | 19.9 |
| 5 | hA2-11E-H4/L3 | 18.5 |
| 6 | hA2-11E-H4/L4 | 11.1 |
| 7 | hA2-25C-H3/L1 | 115.8 |
| 8 | hA2-25C-H3/L2 | 53.3 |
| 9 | hA2-25C-H3/L3 | 64.4 |
| 10 | hA2-25C-H4/L1 | 81.8 |
| 11 | hA2-25C-H4/L2 | 56.7 |
| 12 | hA2-25C-H4/L3 | 27.9 |

Example 21

Epitope Analysis of A2-25C Antibody

21)-1 Preparation of Human Chimeric cA2-25C Fab Fragment

Human chimeric cA2-25C prepared in the same way as in Example 5)-8 was cleaved into Fab and Fc fragments using papain (Sigma-Aldrich Co. LLC), and these fragments were added to HiTrap Protein A HP column (GE Healthcare Bio-Sciences Corp.). The Fab fragment recovered as a flow-through fraction was concentrated.

Figure 49:
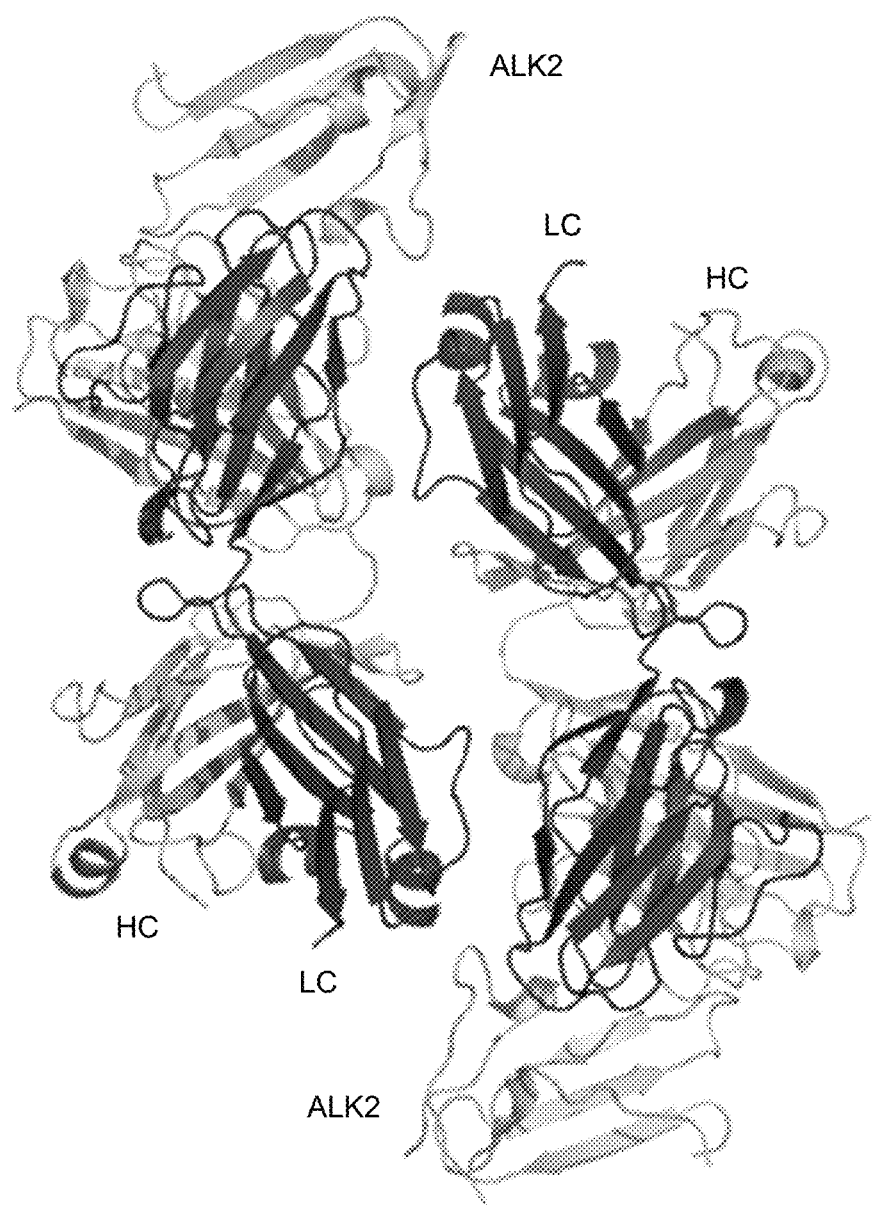
FIG. 49 This figure shows the X-ray crystal structure of a complex of human ALK2-ECD and human chimeric cA2-25C-Fab.

21)-2 Crystallization and Structural Analysis of Human Chimeric cA2-25C Fab Fragment and ALK2-ECD Complex The protein complex of the chimeric A2-25C Fab fragment obtained in Example 21)-1 and the ALK2-ECD prepared according to Example 14 were concentrated to 3.8 mg/mL and used in crystallization trial employing vapor diffusion method. To 0.5 µL of the protein solution, an equal amount of a precipitant solution (0.15 M $Li_2SO_4$, 0.1 M Na citrate (pH 3.4), 18% (w/v) PEG6,000, and 20% (v/v) ethylene glycol) was added, and the resulting solution was placed in a sealed container containing 50 μL of a precipitant solution such that these solutions had no contact with each other. The container was left standing at 20° C. Three days later, 0.1 mm×0.05 mm×0.02 mm single crystals were obtained. The obtained crystals were frozen in liquid nitrogen. X-ray diffraction data was collected under 95 K nitrogen stream using BL41XU of Spring8. Diffraction intensity was digitized from the obtained diffraction image using software mosfim (CCP4: Collaborative Computational Project No. 4) to determine crystal structure factors. The crystals were in the orthorhombic crystal system with a space group $P2_12_12_1$ and unit cells of a=74.49 angstroms, b=128.05 angstroms, and c=147.73 angstroms. The molecular replacement method was performed using the obtained structure factors and the three-dimensional structure coordinates of Fab (antibody structure determined by the past crystal structure analysis was used) to determine the phases. Software phaser (CCP4: Collaborative Computational Project No. 4) was used in calculation. The crystal contained two complexes in the asymmetric unit. Structure refinement was performed using software Refmac5 (CCP4), and model correction was performed using software coot. This operation was repetitively performed to obtain a final R factor of 22.4% and a free R factor of 25.3% with a resolution of 2.1 angstroms. The model consists of two complexes and contains amino acid residues 1 to 212 of the A2-25C Fab L chain, amino acid residues 1 to 219 of the A2-25C Fab H chain, amino acid residues 12 to 52 and 66 to 88 of ALK2-ECD, and 411 water molecules. The determined amino acid residues of ALK2-ECD commonly located within 4 angstroms from two A2-25C Fabs are as follows: Glu18, Gly19, Leu20, Ile39, Asp41, Gly42, Phe43, His44, Val45, Tyr46, and Thr84. The ribbon model of the whole complex is shown in FIG. 49.

Example 22

Evaluation of Inhibitory Activity of A2-27D Against Various ALK2 Mutants

The inhibitory activity of A2-27 against 13 types of mutants (L196P, delP197_F198insL, R202I, R206H, Q207E, R258S, R258G, G325A, G328E, G328R, G328W, G356D, and R375P) identified so far from FOP cases, and wild-type ALK2 was analyzed in the same way as in Example 2)-3 using HEK293A cells and BMP-specific Id1WT4F-luc luciferase reporter. 2.5 hours after transfection, the medium was replaced with fresh OPTI-MEM I (manufactured by Life Technologies Corp.) containing 10 ng/mL BMP7 (manufactured by Miltenyi Biotec) and 3 μg/mL rat IgG1 (manufactured by R&D Systems, Inc.) or A2-27D, and the cells were cultured overnight. On the next day, luciferase activity was measured using Dual-Glo Luciferase Assay System (manufactured by Promega Corp.).

Figure 50:
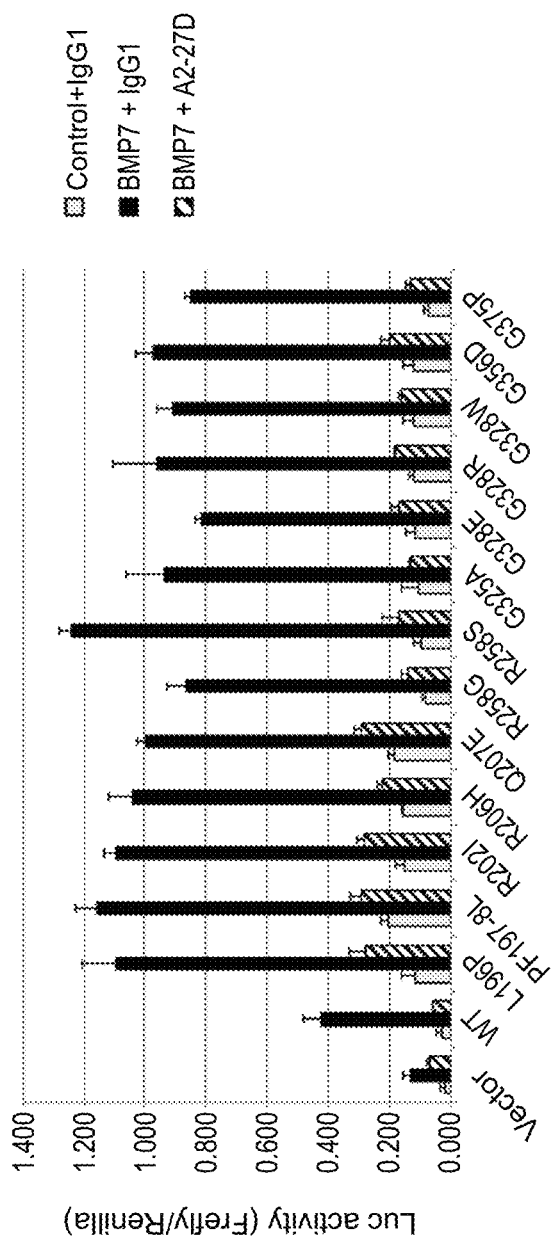
FIG. 50 This figure is a graph showing that the monoclonal antibody produced by the hybridoma A2-27D inhibits BMP7-induced luciferase (Luc) activity in wild-type ALK2 (WT) and all of the shown 13 types of mutants.

The results are shown in FIG. 50. The monoclonal antibody A2-27D was confirmed to inhibit luciferase activity induced by BMP7 in the wild-type ALK2 and all of the 13 types of mutants (FIG. 50).

INDUSTRIAL APPLICABILITY

The chimeric or humanized anti-ALK2 antibody of the present invention has an inhibitory effect on ALK2-mediated BMP signal transduction. The pharmaceutical composition comprising the anti-ALK2 antibody can serve as a therapeutic or prophylactic drug for ectopic ossification and/or bone dysplasia, anemia, or diffuse intrinsic pontine glioma (DIPG).

Free Text of Sequence Listing

SEQ ID NO: 1: Nucleotide sequence of cDNA encoding the heavy chain variable region of A2-11E
SEQ ID NO: 2: Amino acid sequence of the heavy chain variable region of A2-11E
SEQ ID NO: 3: Nucleotide sequence of cDNA encoding the light chain variable region of A2-11E
SEQ ID NO: 4: Amino acid sequence of the light chain variable region of A2-11E
SEQ ID NO: 5: Nucleotide sequence of cDNA encoding the heavy chain variable region of A2-15A
SEQ ID NO: 6: Amino acid sequence of the heavy chain variable region of A2-15A
SEQ ID NO: 7: Nucleotide sequence of cDNA encoding the light chain variable region of A2-15A
SEQ ID NO: 8: Amino acid sequence of the light chain variable region of A2-15A
SEQ ID NO: 9: Nucleotide sequence of cDNA encoding the heavy chain variable region of A2-25C
SEQ ID NO: 10: Amino acid sequence of the heavy chain variable region of A2-25C
SEQ ID NO: 11: Nucleotide sequence of cDNA encoding the light chain variable region of A2-25C
SEQ ID NO: 12: Amino acid sequence of the light chain variable region of A2-25C
SEQ ID NO: 13: Nucleotide sequence of cDNA encoding the heavy chain variable region of A2-27D
SEQ ID NO: 14: Amino acid sequence of the heavy chain variable region of A2-27D
SEQ ID NO: 15: Nucleotide sequence of cDNA encoding the light chain variable region of A2-27D
SEQ ID NO: 16: Amino acid sequence of the light chain variable region of A2-27D
SEQ ID NO: 17: Nucleotide sequence of a DNA fragment containing a sequence encoding the amino acids of a human κ chain secretory signal and a human κ chain constant region
SEQ ID NO: 18: Nucleotide sequence of a DNA fragment containing a sequence encoding the amino acids of a human heavy chain secretory signal and a human IgG1 constant region
SEQ ID NO: 19: Nucleotide sequence of the heavy chain of human chimeric cA2-15A
SEQ ID NO: 20: Amino acid sequence of the heavy chain of human chimeric cA2-15A
SEQ ID NO: 21: Nucleotide sequence of the light chain of human chimeric cA2-15A
SEQ ID NO: 22: Amino acid sequence of the light chain of human chimeric cA2-15A
SEQ ID NO: 23: Nucleotide sequence of the heavy chain of human chimeric cA2-27D
SEQ ID NO: 24: Amino acid sequence of the heavy chain of human chimeric cA2-27D
SEQ ID NO: 25: Nucleotide sequence of the light chain of human chimeric cA2-27D
SEQ ID NO: 26: Amino acid sequence of the light chain of human chimeric cA2-27D
SEQ ID NO: 27: Nucleotide sequence of humanized hA2-15A-H1
SEQ ID NO: 28: Amino acid sequence of humanized hA2-15A-H1
SEQ ID NO: 29: Nucleotide sequence of humanized hA2-15A-H4

SEQ ID NO: 30: Amino acid sequence of humanized hA2-15A-H4
SEQ ID NO: 31: Nucleotide sequence of a DNA fragment containing a sequence encoding humanized hA2-15A-L1
SEQ ID NO: 32: Amino acid sequence of humanized hA2-15A-L1
SEQ ID NO: 33: Nucleotide sequence of a DNA fragment containing a sequence encoding humanized hA2-15A-L4
SEQ ID NO: 34: Amino acid sequence of humanized hA2-15A-L4
SEQ ID NO: 35: Nucleotide sequence of a DNA fragment containing a sequence encoding humanized hA2-15A-L6
SEQ ID NO: 36: Amino acid sequence of humanized hA2-15A-L6
SEQ ID NO: 37: Nucleotide sequence of a DNA fragment containing a sequence encoding humanized hA2-15A-L7
SEQ ID NO: 38: Amino acid sequence of humanized hA2-15A-L7
SEQ ID NO: 39: Nucleotide sequence of humanized hA2-27D-H1
SEQ ID NO: 40: Amino acid sequence of humanized hA2-27D-H1
SEQ ID NO: 41: Nucleotide sequence of humanized hA2-27D-H2
SEQ ID NO: 42: Amino acid sequence of humanized hA2-27D-H2
SEQ ID NO: 43: Nucleotide sequence of humanized hA2-27D-H3
SEQ ID NO: 44: Amino acid sequence of humanized hA2-27D-H3
SEQ ID NO: 45: Nucleotide sequence of humanized hA2-27D-H4
SEQ ID NO: 46: Amino acid sequence of humanized hA2-27D-H4
SEQ ID NO: 47: Nucleotide sequence of humanized hA2-27D-H5
SEQ ID NO: 48: Amino acid sequence of humanized hA2-27D-H5
SEQ ID NO: 49: Nucleotide sequence of a DNA fragment containing a sequence encoding humanized hA2-27D-L1
SEQ ID NO: 50: Amino acid sequence of humanized hA2-27D-L1
SEQ ID NO: 51: Nucleotide sequence of a DNA fragment containing a sequence encoding humanized hA2-27D-L2
SEQ ID NO: 52: Amino acid sequence of humanized hA2-27D-L2
SEQ ID NO: 53: Nucleotide sequence of a DNA fragment containing a sequence encoding humanized hA2-27D-L3
SEQ ID NO: 54: Amino acid sequence of humanized hA2-27D-L3
SEQ ID NO: 55: Nucleotide sequence of a DNA fragment containing a sequence encoding humanized hA2-27D-L4
SEQ ID NO: 56: Amino acid sequence of humanized hA2-27D-L4
SEQ ID NO: 57: Nucleotide sequence of a DNA fragment containing a sequence encoding humanized hA2-27D-L5
SEQ ID NO: 58: Amino acid sequence of humanized hA2-27D-L5
SEQ ID NO: 59: Amino acid sequence of A2-15A CDRH1
SEQ ID NO: 60: Amino acid sequence of A2-15A CDRH2
SEQ ID NO: 61: Amino acid sequence of A2-15A CDRH3
SEQ ID NO: 62: Amino acid sequence of A2-15A CDRL1
SEQ ID NO: 63: Amino acid sequence of A2-15A CDRL2
SEQ ID NO: 64: Amino acid sequence of A2-15A CDRL3
SEQ ID NO: 65: Amino acid sequence of A2-27D CDRH1
SEQ ID NO: 66: Amino acid sequence of A2-27D CDRH2
SEQ ID NO: 67: Amino acid sequence of A2-27D CDRH3
SEQ ID NO: 68: Amino acid sequence of A2-27D CDRL1
SEQ ID NO: 69: Amino acid sequence of A2-27D CDRL2
SEQ ID NO: 70: Amino acid sequence of A2-27D CDRL3
SEQ ID NO: 71: Amino acid sequence of humanized hA2-15A-L6 CDRL2
SEQ ID NO: 72: Amino acid sequence of A2-11E CDRH1
SEQ ID NO: 73: Amino acid sequence of A2-11E CDRH2
SEQ ID NO: 74: Amino acid sequence of A2-11E CDRH3
SEQ ID NO: 75: Amino acid sequence of A2-11E CDRL1
SEQ ID NO: 76: Amino acid sequence of A2-11E CDRL2
SEQ ID NO: 77: Amino acid sequence of A2-11E CDRL3
SEQ ID NO: 78: Amino acid sequence of A2-25C CDRH1
SEQ ID NO: 79: Amino acid sequence of A2-25C CDRH2
SEQ ID NO: 80: Amino acid sequence of A2-25C CDRH3
SEQ ID NO: 81: Amino acid sequence of A2-25C CDRL1
SEQ ID NO: 82: Amino acid sequence of A2-25C CDRL2
SEQ ID NO: 83: Amino acid sequence of A2-25C CDRL3
SEQ ID NO: 84: Amino acid sequence of human ALK2
SEQ ID NO: 85: Nucleotide sequence of human ALK2
SEQ ID NO: 86: Amino acid sequence of mouse ALK2
SEQ ID NO: 87: Nucleotide sequence of mouse ALK2
SEQ ID NOs: 88 to 102: Primer
SEQ ID NO: 103: Nucleotide sequence of a DNA fragment containing a sequence encoding the amino acids of a human heavy chain signal sequence and a human IgG2 constant region
SEQ ID NO: 104: Nucleotide sequence of humanized hA2-15A-H4 IgG2 type
SEQ ID NO: 105: Amino acid sequence of humanized hA2-15A-H4 IgG2 type
SEQ ID NO: 106: Nucleotide sequence of humanized hA2-27D-H2-LALA
SEQ ID NO: 107: Amino sequence of humanized hA2-27D-H2-LALA
SEQ ID NO: 108: Nucleotide sequence of humanized hA2-27D-H3-LALA
SEQ ID NO: 109: Amino sequence of humanized hA2-27D-H3-LALA
SEQ ID NO: 110: Nucleotide sequence of humanized hA2-11E-H3
SEQ ID NO: 111: Amino acid sequence of humanized hA2-11E-H3
SEQ ID NO: 112: Nucleotide sequence of humanized hA2-11E-H4
SEQ ID NO: 113: Amino acid sequence of humanized hA2-11E-H4
SEQ ID NO: 114: Nucleotide sequence of humanized hA2-11E-L2
SEQ ID NO: 115: Amino acid sequence of humanized hA2-11E-L2
SEQ ID NO: 116: Nucleotide sequence of humanized hA2-11E-L3
SEQ ID NO: 117: Amino acid sequence of humanized hA2-11E-L3
SEQ ID NO: 118: Nucleotide sequence of humanized hA2-11E-L4
SEQ ID NO: 119: Amino acid sequence of humanized hA2-11E-L4
SEQ ID NO: 120: Nucleotide sequence of humanized hA2-25C-H3
SEQ ID NO: 121: Amino acid sequence of humanized hA2-25C-H3
SEQ ID NO: 122: Nucleotide sequence of humanized hA2-25C-H4
SEQ ID NO: 123: Amino acid sequence of humanized hA2-25C-H4

SEQ ID NO: 124: Nucleotide sequence of humanized hA2-25C-L1
SEQ ID NO: 125: Amino acid sequence of humanized hA2-25C-L1
SEQ ID NO: 126: Nucleotide sequence of humanized hA2-25C-L2
SEQ ID NO: 127: Amino acid sequence of humanized hA2-25C-L2
SEQ ID NO: 128: Nucleotide sequence of humanized hA2-25C-L3
SEQ ID NO: 129: Amino acid sequence of humanized hA2-25C-L3
SEQ ID NOs: 130 to 135: Primer All publications, patents, and patent applications cited herein are incorporated herein by reference in their entirety.

The invention claimed is:

1. An antibody or an antigen-binding fragment thereof, comprising:
   (i) heavy chain CDRs consisting of the amino acid sequences of SEQ ID NO: 65 for CDRH1, SEQ ID NO: 66 for CDRH2, and SEQ ID NO: 67 for CDRH3; and light chain CDRs consisting of the amino acid sequences of SEQ ID NO: 68 for CDRL1, SEQ ID NO: 69 for CDRL2, and SEQ ID NO: 70 for CDRL3;
   (ii) a heavy chain variable region sequence consisting of amino acid numbers 20 to 140 of the amino acid sequence of SEQ ID NO: 107; and a light chain comprising a light chain variable region sequence consisting of amino acid numbers 21 to 129 of the amino acid sequence of SEQ ID NO: 52;
   (iii) a heavy chain comprising the amino acid sequence consisting of amino acid numbers 20 to 470 of the amino acid sequence of SEQ ID NO: 107; and a light chain comprising the amino acid sequence consisting of amino acid numbers 21 to 234 of the amino acid sequence of SEQ ID NO: 52;
   (iv) heavy chain CDRs consisting of the amino acid sequences of SEQ ID NO: 72 for CDRH1, SEQ ID NO: 73 for CDRH2, and SEQ ID NO: 74 for CDRH3; and light chain CDRs consisting of the amino acid sequences of SEQ ID NO: 75 for CDRL1, SEQ ID NO: 76 for CDRL2, and SEQ ID NO: 77 for CDRL3;
   (v) a heavy chain variable region sequence consisting of amino acid numbers 20 to 137 of the amino acid sequence of SEQ ID NO: 113; and a light chain comprising a light chain variable region sequence consisting of amino acid numbers 21 to 128 of the amino acid sequence of SEQ ID NO: 119;
   (vi) a heavy chain comprising the amino acid sequence consisting of amino acid numbers 20 to 467 of the amino acid sequence of SEQ ID NO: 113; and a light chain comprising the amino acid sequence consisting of amino acid numbers 21 to 233 of the amino acid sequence of SEQ ID NO: 119;
   (vii) heavy chain CDRs consisting of the amino acid sequences of SEQ ID NO: 59 for CDRH1, SEQ ID NO: 60 for CDRH2, and SEQ ID NO: 61 for CDRH3; and light chain CDRs consisting of the amino acid sequences of SEQ ID NO: 62 for CDRL1, SEQ ID NO: 63 or 71 for CDRL2, and SEQ ID NO: 64 for CDRL3;
   (viii) a heavy chain variable region sequence consisting of amino acid numbers 20 to 142 of the amino acid sequence of SEQ ID NO: 105; and a light chain comprising a light chain variable region sequence consisting of amino acid numbers 21 to 133 of the amino acid sequence of SEQ ID NO: 36;
   (ix) a heavy chain comprising the amino acid sequence consisting of amino acid numbers 20 to 468 of the amino acid sequence of SEQ ID NO: 105; and a light chain comprising the amino acid sequence consisting of amino acid numbers 21 to 238 of the amino acid sequence of SEQ ID NO: 36;
   (x) heavy chain CDRs consisting of the amino acid sequences of SEQ ID NO: 78 for CDRH1, SEQ ID NO: 79 for CDRH2, and SEQ ID NO: 80 for CDRH3; and light chain CDRs consisting of the amino acid sequences of SEQ ID NO: 81 for CDRL1, SEQ ID NO: 82 for CDRL2, and SEQ ID NO: 83 for CDRL3;
   (xi) a heavy chain variable region sequence consisting of amino acid numbers 20 to 137 of the amino acid sequence of SEQ ID NO: 123; and a light chain comprising a light chain variable region sequence consisting of amino acid numbers 21 to 129 of the amino acid sequence of SEQ ID NO: 129; or
   (xii) a heavy chain comprising the amino acid sequence consisting of amino acid numbers 20 to 467 of the amino acid sequence of SEQ ID NO: 123; and a light chain comprising the amino acid sequence consisting of amino acid numbers 21 to 234 of the amino acid sequence of SEQ ID NO: 129.

2. The antibody or antigen-binding fragment thereof according to claim 1, comprising:
   (i) heavy chain CDRs consisting of the amino acid sequences of SEQ ID NO: 65 for CDRH1, SEQ ID NO: 66 for CDRH2, and SEQ ID NO: 67 for CDRH3; and light chain CDRs consisting of the amino acid sequences of SEQ ID NO: 68 for CDRL1, SEQ ID NO: 69 for CDRL2, and SEQ ID NO: 70 for CDRL3;
   (ii) a heavy chain variable region sequence consisting of amino acid numbers 20 to 140 of the amino acid sequence of SEQ ID NO: 107; and a light chain comprising a light chain variable region sequence consisting of amino acid numbers 21 to 129 of the amino acid sequence of SEQ ID NO: 52; or
   (iii) a heavy chain comprising the amino acid sequence consisting of amino acid numbers 20 to 470 of the amino acid sequence of SEQ ID NO: 107; and a light chain comprising the amino acid sequence consisting of amino acid numbers 21 to 234 of the amino acid sequence of SEQ ID NO: 52.

3. The antibody or antigen-binding fragment thereof according to claim 2, comprising heavy chain CDRs consisting of the amino acid sequences of SEQ ID NO: 65 for CDRH1, SEQ ID NO: 66 for CDRH2, and SEQ ID NO: 67 for CDRH3; and light chain CDRs consisting of the amino acid sequences of SEQ ID NO: 68 for CDRL1, SEQ ID NO: 69 for CDRL2, and SEQ ID NO: 70 for CDRL3.

4. The antibody or antigen-binding fragment thereof according to claim 2, comprising a heavy chain variable region sequence consisting of amino acid numbers 20 to 140 of the amino acid sequence of SEQ ID NO: 107; and a light chain comprising a light chain variable region sequence consisting of amino acid numbers 21 to 129 of the amino acid sequence of SEQ ID NO: 52.

5. The antibody or antigen-binding fragment thereof according to claim 2, comprising a heavy chain comprising the amino acid sequence consisting of amino acid numbers 20 to 470 of the amino acid sequence of SEQ ID NO: 107; and a light chain comprising the amino acid sequence consisting of amino acid numbers 21 to 234 of the amino acid sequence of SEQ ID NO: 52.

6. The antibody or antigen-binding fragment thereof according to claim 1, comprising:
   (i) heavy chain CDRs consisting of the amino acid sequences of SEQ ID NO: 72 for CDRH1, SEQ ID NO: 73 for CDRH2, and SEQ ID NO: 74 for CDRH3; and light chain CDRs consisting of the amino acid sequences of SEQ ID NO: 75 for CDRL1, SEQ ID NO: 76 for CDRL2, and SEQ ID NO: 77 for CDRL3;
   (ii) a heavy chain variable region sequence consisting of amino acid numbers 20 to 137 of the amino acid sequence of SEQ ID NO: 113; and a light chain comprising a light chain variable region sequence consisting of amino acid numbers 21 to 128 of the amino acid sequence of SEQ ID NO: 119; or
   (iii) a heavy chain comprising the amino acid sequence consisting of amino acid numbers 20 to 467 of the amino acid sequence of SEQ ID NO: 113; and a light chain comprising the amino acid sequence consisting of amino acid numbers 21 to 233 of the amino acid sequence of SEQ ID NO: 119.

7. The antibody or antigen-binding fragment thereof according to claim 6, comprising heavy chain CDRs consisting of the amino acid sequences of SEQ ID NO: 72 for CDRH1, SEQ ID NO: 73 for CDRH2, and SEQ ID NO: 74 for CDRH3; and light chain CDRs consisting of the amino acid sequences of SEQ ID NO: 75 for CDRL1, SEQ ID NO: 76 for CDRL2, and SEQ ID NO: 77 for CDRL3.

8. The antibody or antigen-binding fragment thereof according to claim 6, comprising a heavy chain variable region sequence consisting of amino acid numbers 20 to 137 of the amino acid sequence of SEQ ID NO: 113; and a light chain comprising a light chain variable region sequence consisting of amino acid numbers 21 to 128 of the amino acid sequence of SEQ ID NO: 119.

9. The antibody or antigen-binding fragment thereof according to claim 6, comprising a heavy chain comprising the amino acid sequence consisting of amino acid numbers 20 to 467 of the amino acid sequence of SEQ ID NO: 113; and a light chain comprising the amino acid sequence consisting of amino acid numbers 21 to 233 of the amino acid sequence of SEQ ID NO: 119.

10. The antibody or an antigen-binding fragment thereof according to claim 1, comprising:
    (i) heavy chain CDRs consisting of the amino acid sequences of SEQ ID NO: 59 for CDRH1, SEQ ID NO: 60 for CDRH2, and SEQ ID NO: 61 for CDRH3; and light chain CDRs consisting of the amino acid sequences of SEQ ID NO: 62 for CDRL1, SEQ ID NO: 63 or 71 for CDRL2, and SEQ ID NO: 64 for CDRL3;
    (ii) a heavy chain variable region sequence consisting of amino acid numbers 20 to 142 of the amino acid sequence of SEQ ID NO: 105; and a light chain comprising a light chain variable region sequence consisting of amino acid numbers 21 to 133 of the amino acid sequence of SEQ ID NO: 36; or
    (iii) a heavy chain comprising the amino acid sequence consisting of amino acid numbers 20 to 468 of the amino acid sequence of SEQ ID NO: 105; and a light chain comprising the amino acid sequence consisting of amino acid numbers 21 to 238 of the amino acid sequence of SEQ ID NO: 36.

11. The antibody or antigen-binding fragment thereof according to claim 10, comprising a heavy chain CDRs consisting of the amino acid sequences of SEQ ID NO: 59 for CDRH1, SEQ ID NO: 60 for CDRH2, and SEQ ID NO: 61 for CDRH3; and light chain CDRs consisting of the amino acid sequences of SEQ ID NO: 62 for CDRL1, SEQ ID NO: 63 or 71 for CDRL2, and SEQ ID NO: 64 for CDRL3.

12. The antibody or antigen-binding fragment thereof according to claim 10, comprising a heavy chain variable region sequence consisting of amino acid numbers 20 to 142 of the amino acid sequence of SEQ ID NO: 105; and a light chain comprising a light chain variable region sequence consisting of amino acid numbers 21 to 133 of the amino acid sequence of SEQ ID NO: 36.

13. The antibody or antigen-binding fragment thereof according to claim 10, comprising: a heavy chain comprising the amino acid sequence consisting of amino acid numbers 20 to 468 of the amino acid sequence of SEQ ID NO: 105; and a light chain comprising the amino acid sequence consisting of amino acid numbers 21 to 238 of the amino acid sequence of SEQ ID NO: 36.

14. An antibody or an antigen-binding fragment thereof according to claim 1, comprising:
    (i) heavy chain CDRs consisting of the amino acid sequences of SEQ ID NO: 78 for CDRH1, SEQ ID NO: 79 for CDRH2, and SEQ ID NO: 80 for CDRH3; and light chain CDRs consisting of the amino acid sequences of SEQ ID NO: 81 for CDRL1, SEQ ID NO: 82 for CDRL2, and SEQ ID NO: 83 for CDRL3;
    (ii) a heavy chain variable region sequence consisting of amino acid numbers 20 to 137 of the amino acid sequence of SEQ ID NO: 123; and a light chain comprising a light chain variable region sequence consisting of amino acid numbers 21 to 129 of the amino acid sequence of SEQ ID NO: 129; or
    (iii) a heavy chain comprising the amino acid sequence consisting of amino acid numbers 20 to 467 of the amino acid sequence of SEQ ID NO: 123; and a light chain comprising the amino acid sequence consisting of amino acid numbers 21 to 234 of the amino acid sequence of SEQ ID NO: 129.

15. The antibody or antigen-binding fragment thereof according to claim 14, comprising heavy chain CDRs consisting of the amino acid sequences of SEQ ID NO: 78 for CDRH1, SEQ ID NO: 79 for CDRH2, and SEQ ID NO: 80 for CDRH3; and light chain CDRs consisting of the amino acid sequences of SEQ ID NO: 81 for CDRL1, SEQ ID NO: 82 for CDRL2, and SEQ ID NO: 83 for CDRL3.

16. The antibody or antigen-binding fragment thereof according to claim 14, comprising a heavy chain variable region sequence consisting of amino acid numbers 20 to 137 of the amino acid sequence of SEQ ID NO: 123; and a light chain comprising a light chain variable region sequence consisting of amino acid numbers 21 to 129 of the amino acid sequence of SEQ ID NO: 129.

17. The antibody or antigen-binding fragment thereof according to claim 14, comprising a heavy chain comprising the amino acid sequence consisting of amino acid numbers 20 to 467 of the amino acid sequence of SEQ ID NO: 123; and a light chain comprising the amino acid sequence consisting of amino acid numbers 21 to 234 of the amino acid sequence of SEQ ID NO: 129.

18. The antibody or an antigen-binding fragment thereof according to claim 1, wherein the antibody or antigen binding fragment inhibits ALK2-mediated BMP signal transduction.

19. The antibody or an antigen-binding fragment thereof according to claim 1, wherein the antibody binds to a wild-type ALK2 protein and mutant ALK2 protein, and optionally binds to an ALK2 extracellular region.

20. The antibody or the antigen-binding fragment thereof according to claim 1, wherein the antibody or the antigen-binding fragment is a monoclonal antibody, a polyclonal antibody, a chimeric antibody, a humanized antibody, a human antibody, a single chain Fv, a bispecific antibody, or a multispecific antibody.

21. The antibody or the antigen-binding fragment thereof according to claim 1, wherein the antibody comprises a heavy chain in which one to several carboxyl-terminal amino acids are deleted and/or has a pyroglutamylated amino-terminal amino acid residue in a heavy or light chain thereof.

22. A pharmaceutical composition comprising the antibody or antigen-binding fragment thereof according to claim 1.

23. A pharmaceutical composition comprising the antibody or antigen-binding fragment thereof according to claim 2.

24. A pharmaceutical composition comprising the antibody or antigen-binding fragment thereof according to claim 6.

25. A pharmaceutical composition comprising the antibody or antigen-binding fragment thereof according to claim 10.

26. A pharmaceutical composition comprising the antibody or antigen-binding fragment thereof according to claim 14.

27. An antibody or an antigen binding fragment thereof, wherein the antibody comprises:
(a) a heavy chain comprising amino acids 20 to 142 of SEQ ID NO: 28 and a light chain comprising amino acids 21 to 133 of SEQ ID NO: 32;
(b) a heavy chain comprising amino acids 20 to 142 of SEQ ID NO: 28 and a light chain comprising amino acids 21 to 133 of SEQ ID NO: 34;
(c) a heavy chain comprising 20 to 142 of SEQ ID NO: 30 and a light chain comprising amino acids 21 to 133 of SEQ ID NO: 32;
(d) a heavy chain comprising 20 to 142 of SEQ ID NO: 30 and a light chain comprising amino acids 21 to 133 of SEQ ID NO: 34;
(e) a heavy chain comprising 20 to 142 of SEQ ID NO: 30 and a light chain comprising amino acids 21 to 133 of SEQ ID NO: 36;
(f) a heavy chain comprising 20 to 142 of SEQ ID NO: 30 and a light chain comprising amino acids 21 to 133 of SEQ ID NO: 38;
(g) a heavy chain comprising amino acids 20 to 142 of SEQ ID NO: 105 and a light chain comprising amino acids 21 to 133 of SEQ ID NO: 36;
(h) a heavy chain comprising amino acids 20 to 140 of SEQ ID NO: 40 and a light chain comprising amino acids 21 to 129 of SEQ ID NO: 50;
(i) a heavy chain comprising amino acids 20 to 140 of SEQ ID NO: 40 and a light chain comprising amino acids 21 to 129 of SEQ ID NO: 52;
(j) a heavy chain comprising amino acids 20 to 140 of SEQ ID NO: 40 and a light chain comprising amino acids 21 to 129 of SEQ ID NO: 54;
(k) a heavy chain comprising amino acids 20 to 140 of SEQ ID NO: 42 and a light chain comprising amino acids 21 to 129 of SEQ ID NO: 50;
(l) a heavy chain comprising amino acids 20 to 140 of SEQ ID NO: 42 and a light chain comprising amino acids 21 to 129 of SEQ ID NO: 52;
(m) a heavy chain comprising amino acids 20 to 140 of SEQ ID NO: 42 and a light chain comprising amino acids 21 to 129 of SEQ ID NO: 54;
(n) a heavy chain comprising amino acids 20 to 140 of SEQ ID NO: 44 and a light chain comprising amino acids 21 to 129 of SEQ ID NO: 50;
(o) a heavy chain comprising amino acids 20 to 140 of SEQ ID NO: 44 and a light chain comprising amino acids 21 to 129 of SEQ ID NO: 52;
(p) a heavy chain comprising amino acids 20 to 140 of SEQ ID NO: 44 and a light chain comprising amino acids 21 to 129 of SEQ ID NO: 54;
(q) a heavy chain comprising amino acids 20 to 140 of SEQ ID NO: 44 and a light chain comprising amino acids 21 to 129 of SEQ ID NO: 56;
(r) a heavy chain comprising amino acids 20 to 140 of SEQ ID NO: 46 and a light chain comprising amino acids 21 to 129 of SEQ ID NO: 54;
(s) a heavy chain comprising amino acids 20 to 140 of SEQ ID NO: 46 and a light chain comprising amino acids 21 to 129 of SEQ ID NO: 56;
(t) a heavy chain comprising amino acids 20 to 140 of SEQ ID NO: 46 and a light chain comprising amino acids 21 to 129 of SEQ ID NO: 58;
(u) a heavy chain comprising amino acids 20 to 140 of SEQ ID NO: 48 and a light chain comprising amino acids 21 to 129 of SEQ ID NO: 56;
(v) a heavy chain comprising amino acids 20 to 140 of SEQ ID NO: 107 and a light chain comprising amino acids 21 to 129 of SEQ ID NO: 52;
(w) a heavy chain comprising amino acids 20 to 140 of SEQ ID NO: 109 and a light chain comprising amino acids 21 to 129 of SEQ ID NO: 56;
(x) a heavy chain comprising amino acids 20 to 137 of SEQ ID NO: 111 and a light chain comprising amino acids 21 to 128 of SEQ ID NO: 115;
(y) a heavy chain comprising amino acids 20 to 137 of SEQ ID NO: 111 and a light chain comprising amino acids 21 to 128 of SEQ ID NO: 117;
(z) a heavy chain comprising amino acids 20 to 137 of SEQ ID NO: 111 and a light chain comprising amino acids 21 to 128 of SEQ ID NO: 119;
(aa) a heavy chain comprising amino acids 20 to 137 of SEQ ID NO: 113 and a light chain comprising amino acids 21 to 128 of SEQ ID NO: 115;
(bb) a heavy chain comprising amino acids 20 to 137 of SEQ ID NO: 113 and a light chain comprising amino acids 21 to 128 of SEQ ID NO: 117);
(cc) a heavy chain comprising amino acids 20 to 137 of SEQ ID NO: 113 and a light chain comprising amino acids 21 to 128 of SEQ ID NO: 119;
(dd) a heavy chain comprising amino acids 20 to 137 of SEQ ID NO: 121 and a light chain comprising amino acids 21 to 129 of SEQ ID NO: 125;
(ee) a heavy chain comprising amino acids 20 to 137 of SEQ ID NO: 121 and a light chain comprising amino acids 21 to 129 of SEQ ID NO: 127;
(ff) a heavy chain comprising amino acids 20 to 137 of SEQ ID NO: 121 and a light chain comprising amino acids 21 to 129 of SEQ ID NO: 129;
(gg) a heavy chain comprising amino acids 20 to 137 of SEQ ID NO: 123 and a light chain comprising amino acids 21 to 129 of SEQ ID NO: 125;

(hh) a heavy chain comprising amino acids 20 to 137 of SEQ ID NO: 123 and a light chain comprising amino acids 21 to 129 of SEQ ID NO: 127; or
(ii) a heavy chain comprising amino acids 20 to 137 of SEQ ID NO: 123 and a light chain comprising amino acids 21 to 129 of SEQ ID NO: 129.

* * * * *

UNITED STATES PATENT AND TRADEMARK OFFICE
CERTIFICATE OF CORRECTION

| | |
|---|---|
| PATENT NO. | : 11,447,554 B2 |
| APPLICATION NO. | : 17/511357 |
| DATED | : September 20, 2022 |
| INVENTOR(S) | : Takenobu Katagiri et al. |

It is certified that error appears in the above-identified patent and that said Letters Patent is hereby corrected as shown below:

On the Title Page

In Column 1, item (62), under Related U.S. Application Data, Line 2, delete "2019," and insert -- 2019, now Pat. No. 11,312,776, --.

In the Claims

In Column 250, Claim 2, Line 32, delete "antigen-binding" and insert -- the antigen-binding --.

In Column 250, Claim 3, Line 52, delete "antigen-binding" and insert -- the antigen-binding --.

In Column 250, Claim 4, Line 59, delete "antigen-binding" and insert -- the antigen-binding --.

In Column 250, Claim 5, Line 66, delete "antigen-binding" and insert -- the antigen-binding --.

In Column 251, Claim 6, Line 6, delete "antigen-binding" and insert -- the antigen-binding --.

In Column 251, Claim 7, Line 27, delete "antigen-binding" and insert -- the antigen-binding --.

In Column 251, Claim 8, Line 34, delete "antigen-binding" and insert -- the antigen-binding --.

In Column 251, Claim 9, Line 41, delete "antigen-binding" and insert -- the antigen-binding --.

In Column 251, Claim 10, Line 48, delete "an antigen-binding" and insert -- the antigen-binding --.

In Column 252, Claim 11, Line 1, delete "antigen-binding" and insert -- the antigen-binding --.

In Column 252, Claim 12, Line 9, delete "antigen-binding" and insert -- the antigen-binding --.

In Column 252, Claim 13, Line 16, delete "antigen-binding" and insert -- the antigen-binding --.

Signed and Sealed this
Third Day of January, 2023

Katherine Kelly Vidal
*Director of the United States Patent and Trademark Office*

CERTIFICATE OF CORRECTION (continued)
U.S. Pat. No. 11,447,554 B2

In Column 252, Claim 14, Line 23, delete "An antibody or an antigen-binding" and insert -- The antibody or the antigen-binding --.

In Column 252, Claim 15, Line 43, delete "antigen-binding" and insert -- the antigen-binding --.

In Column 252, Claim 16, Line 50, delete "antigen-binding" and insert -- the antigen-binding --.

In Column 252, Claim 17, Line 57, delete "antigen-binding" and insert -- the antigen-binding --.

In Column 252, Claim 18, Line 64, delete "an antigen-binding" and insert -- the antigen-binding --.

In Column 252, Claim 18, Lines 65-66, delete "antigen binding" and insert -- the antigen-binding --.

In Column 253, Claim 19, Line 1, delete "an antigen-binding" and insert -- the antigen-binding --.

In Column 253, Claim 22, Line 19, delete "antigen-binding" and insert -- the antigen-binding --.

In Column 253, Claim 23, Line 22, delete "antigen-binding" and insert -- the antigen-binding --.

In Column 253, Claim 24, Line 25, delete "antigen-binding" and insert -- the antigen-binding --.

In Column 253, Claim 25, Line 28, delete "antigen-binding" and insert -- the antigen-binding --.

In Column 253, Claim 26, Line 31, delete "antigen-binding" and insert -- the antigen-binding --.

In Column 253, Claim 27, Line 33, delete "antigen binding" and insert -- antigen-binding --.

In Column 253, Claim 27, Line 41, delete "comprising 20" and insert -- comprising amino acids 20 --.

In Column 253, Claim 27, Line 44, delete "comprising 20" and insert -- comprising amino acids 20 --.

In Column 253, Claim 27, Line 47, delete "comprising 20" and insert -- comprising amino acids 20 --.

In Column 253, Claim 27, Line 50, delete "comprising 20" and insert -- comprising amino acids 20 --.

In Column 254, Claim 27, Line 52, delete "117);" and insert -- 117; --.

SEQUENCE LISTING

```
<160> NUMBER OF SEQ ID NOS: 135

<210> SEQ ID NO 1
<211> LENGTH: 354
<212> TYPE: DNA
<213> ORGANISM: Rattus norvegicus
<220> FEATURE:
<221> NAME/KEY: V_region
<222> LOCATION: (1)..(354)

<400> SEQUENCE: 1
gaggtgcagc tagtggagac tgggggaggc ttagtgcagc ctggaaggtc tctgaaactc      60
tcctgtgtag cctctggatt cacattcagt aactactaca tgtactggat ccgccaggct     120
ccagggaagg gactggagtg gatttcatcc attaatactg atggtggtag cacttactat     180
ccagactccg tgaagggccg attcgctatc tccagagata atgcagaaaa caccgtatac     240
ctgcaaatga acagtctgag gtctgaggac acagcgactt attactgtgc aaaatccact     300
ccaaatatcc ctcttgctta ctggggccaa ggcactctgg tcactgtctc ttca           354

<210> SEQ ID NO 2
<211> LENGTH: 118
<212> TYPE: PRT
<213> ORGANISM: Rattus norvegicus
<220> FEATURE:
<221> NAME/KEY: V_region
<222> LOCATION: (1)..(118)

<400> SEQUENCE: 2

Glu Val Gln Leu Val Glu Thr Gly Gly Gly Leu Val Gln Pro Gly Arg
1               5                   10                  15

Ser Leu Lys Leu Ser Cys Val Ala Ser Gly Phe Thr Phe Ser Asn Tyr
            20                  25                  30

Tyr Met Tyr Trp Ile Arg Gln Ala Pro Gly Lys Gly Leu Glu Trp Ile
        35                  40                  45

Ser Ser Ile Asn Thr Asp Gly Gly Ser Thr Tyr Tyr Pro Asp Ser Val
    50                  55                  60

Lys Gly Arg Phe Ala Ile Ser Arg Asp Asn Ala Glu Asn Thr Val Tyr
65                  70                  75                  80

Leu Gln Met Asn Ser Leu Arg Ser Glu Asp Thr Ala Thr Tyr Tyr Cys
                85                  90                  95

Ala Lys Ser Thr Pro Asn Ile Pro Leu Ala Tyr Trp Gly Gln Gly Thr
            100                 105                 110

Leu Val Thr Val Ser Ser
        115

<210> SEQ ID NO 3
<211> LENGTH: 324
<212> TYPE: DNA
<213> ORGANISM: Rattus norvegicus
<220> FEATURE:
<221> NAME/KEY: V_region
<222> LOCATION: (1)..(324)
```

<400> SEQUENCE: 3

```
gacatccaga tgacccagtc tccttcactc ctgtcagcat ctgtgggaga cagagtcact    60
ctcagctgca aagcaagtca gaatatttac aagtacttaa actggttcca gcaaaagctt   120
ggagaagctc ccaaactcct gatatattat tcaaacagtt tgcaaacggg catcccatca   180
aggttcagtg gcagtggatc tggtactgat ttcacactta ccatcagcag cctgcagcct   240
gaagatgttg ccatatattt ctgctttcag tacagcagtg ggcccacgtt tggacctggg   300
accaagctgg aactgaaacg ggct                                          324
```

<210> SEQ ID NO 4
<211> LENGTH: 108
<212> TYPE: PRT
<213> ORGANISM: Rattus norvegicus
<220> FEATURE:
<221> NAME/KEY: V_region
<222> LOCATION: (1)..(108)

<400> SEQUENCE: 4

```
Asp Ile Gln Met Thr Gln Ser Pro Ser Leu Leu Ser Ala Ser Val Gly
1               5                  10                  15

Asp Arg Val Thr Leu Ser Cys Lys Ala Ser Gln Asn Ile Tyr Lys Tyr
            20                  25                  30

Leu Asn Trp Phe Gln Gln Lys Leu Gly Glu Ala Pro Lys Leu Leu Ile
        35                  40                  45

Tyr Tyr Ser Asn Ser Leu Gln Thr Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Ile Tyr Phe Cys Phe Gln Tyr Ser Ser Gly Pro Thr
                85                  90                  95

Phe Gly Pro Gly Thr Lys Leu Glu Leu Lys Arg Ala
            100                 105
```

<210> SEQ ID NO 5
<211> LENGTH: 369
<212> TYPE: DNA
<213> ORGANISM: Rattus norvegicus
<220> FEATURE:
<221> NAME/KEY: V_region
<222> LOCATION: (1)..(369)

<400> SEQUENCE: 5

```
gaggtgcagc tggtggagtc tggcggaggc ttagtacagc ctggaaggtc cctgaaactc    60
tcctgtgcag cctcaggatt cactttcagt cactattaca tggcctgggt ccgccaggct   120
ccaacgaagg gtctggagtg ggtcgcatcc attactaata gtggtggtag tattaactat   180
cgagactccg tcaagggccg attcactatc tccagagata tgcaaaaag caccctatac   240
ctgcaaatgg acagtctgag gtctgaggac acggccactt attactgtac aagagaaggt   300
ggagaaaact acggagggta tcccccgttt gcttactggg gccaaggcac tctggtcact   360
gtctcttca                                                          369
```

<210> SEQ ID NO 6
<211> LENGTH: 123
<212> TYPE: PRT
<213> ORGANISM: Rattus norvegicus
<220> FEATURE:
<221> NAME/KEY: V_region
<220> FEATURE:
<221> NAME/KEY: V_region
<222> LOCATION: (1)..(123)

<400> SEQUENCE: 6

Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser His Tyr
            20                  25                  30

Tyr Met Ala Trp Val Arg Gln Ala Pro Thr Lys Gly Leu Glu Trp Val
        35                  40                  45

Ala Ser Ile Thr Asn Ser Gly Ser Ile Asn Tyr Arg Asp Ser Val
    50                  55                  60

Lys Gly Arg Phe Thr Ile Ser Arg Asp Asn Ala Lys Ser Thr Leu Tyr
65                  70                  75                  80

Leu Gln Met Asp Ser Leu Arg Ser Glu Asp Thr Ala Thr Tyr Tyr Cys
                85                  90                  95

Thr Arg Glu Gly Gly Glu Asn Tyr Gly Gly Tyr Pro Pro Phe Ala Tyr
            100                 105                 110

Trp Gly Gln Gly Thr Leu Val Thr Val Ser Ser
        115                 120

<210> SEQ ID NO 7
<211> LENGTH: 336
<212> TYPE: DNA
<213> ORGANISM: Rattus norvegicus
<220> FEATURE:
<221> NAME/KEY: V_region
<222> LOCATION: (1)..(336)

<400> SEQUENCE: 7
gacattgtct tgacccagtc tcctgctttg gctgtgtctc tagggcagag ggccacaatc    60
tcctgtaggg ccaaccaagg tgtcagtcta tctagatata atcttatgca ctggtaccaa   120
cagaaaccag acagaaacc caaactcctc atctatcgtt catccaacct agcatctggg    180
atccctgcca ggttcagtgg cagtgggtct gggacagact tcaccctcac catcaatcct   240
gtgcaggctg atgatattgc aacctattac tgtcagcaga gtagggagtc tccgttcacg   300
tttggagctg gaccaagctg gaactgaaa cgggct                              336

<210> SEQ ID NO 8
<211> LENGTH: 112
<212> TYPE: PRT
<213> ORGANISM: Rattus norvegicus
<220> FEATURE:
<221> NAME/KEY: V_region
<222> LOCATION: (1)..(112)

<400> SEQUENCE: 8

Asp Ile Val Leu Thr Gln Ser Pro Ala Leu Ala Val Ser Leu Gly Gln
1               5                   10                  15

Arg Ala Thr Ile Ser Cys Arg Ala Asn Gln Gly Val Ser Leu Ser Arg
            20                  25                  30

Tyr Asn Leu Met His Trp Tyr Gln Gln Lys Pro Gly Gln Lys Pro Lys
        35                  40                  45

Leu Leu Ile Tyr Arg Ser Ser Asn Leu Ala Ser Gly Ile Pro Ala Arg
    50                  55                  60

Phe Ser Gly Ser Gly Ser Gly Thr Asp Phe Thr Leu Thr Ile Asn Pro
65                  70                  75                  80

Val Gln Ala Asp Asp Ile Ala Thr Tyr Tyr Cys Gln Gln Ser Arg Glu
                85                  90                  95

Ser Pro Phe Thr Phe Gly Ala Gly Thr Lys Leu Glu Leu Lys Arg Ala
            100                 105                 110

<210> SEQ ID NO 9
<211> LENGTH: 354
<212> TYPE: DNA
<213> ORGANISM: Rattus norvegicus
<220> FEATURE:
<221> NAME/KEY: V_region
<222> LOCATION: (1)..(354)

<400> SEQUENCE: 9
gaggtgcagc tggtggagtc tgggggaggc ttagtgcagc ctggaggatc cctgaaactc      60
tcctgtgcag cctcaggatt cactttcagt tactatgcca tgtcttgggt ctgccaggct     120
ccaacgaagg gtctggagtg gtcgcatcc attagtcgtg gtggtgataa cacttactat     180
cgagacaccg tgaagggccg attcactacc tccagagata atgcaaaaaa caccctatac     240
ctgcaaatgg acagtctgag gtctgaggac acggccactt attactgtgc aagactgaat     300
tataacaact actttgatta ctggggccaa ggagtcatgg tcacagtctc ctca           354

<210> SEQ ID NO 10
<211> LENGTH: 118
<212> TYPE: PRT
<213> ORGANISM: Rattus norvegicus
<220> FEATURE:
<221> NAME/KEY: V_region
<222> LOCATION: (1)..(118)

<400> SEQUENCE: 10

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Tyr Tyr
            20                  25                  30

Ala Met Ser Trp Val Cys Gln Ala Pro Thr Lys Gly Leu Glu Trp Val
        35                  40                  45

Ala Ser Ile Ser Arg Gly Gly Asp Asn Thr Tyr Tyr Arg Asp Thr Val
    50                  55                  60

Lys Gly Arg Phe Thr Thr Ser Arg Asp Asn Ala Lys Asn Thr Leu Tyr
65                  70                  75                  80

Leu Gln Met Asp Ser Leu Arg Ser Glu Asp Thr Ala Thr Tyr Tyr Cys
                85                  90                  95

Ala Arg Leu Asn Tyr Asn Asn Tyr Phe Asp Tyr Trp Gly Gln Gly Val
            100                 105                 110

Met Val Thr Val Ser Ser
        115

<210> SEQ ID NO 11
<211> LENGTH: 327
<212> TYPE: DNA
<213> ORGANISM: Rattus norvegicus
<220> FEATURE:
<221> NAME/KEY: V_region
<222> LOCATION: (1)..(327)

<400> SEQUENCE: 11
gacatccaga tgacacagtc tcctgcctcc ctgtctgcat ctctggaaga aattgtcacc      60
atcacatgcc aggcaagcca ggacattggt aattggttat catggtatca gcagaaacca     120
gggaaatctc ctcagctcct gatctatggt gcaaccagct ggcagatggg gtcccatca     180

-continued

```
aggttcagcg gcagtagatc tggcacacag tattctctta agatcagcag actacgggtt      240
gaagatattg gaatctatta ctgtctacag gcttatagtg ctccattcac gttcggctca      300
gggacgaagt tggaaataaa acgggct                                          327
```

<210> SEQ ID NO 12
<211> LENGTH: 109
<212> TYPE: PRT
<213> ORGANISM: Rattus norvegicus
<220> FEATURE:
<221> NAME/KEY: V_region
<222> LOCATION: (1)..(109)

<400> SEQUENCE: 12

```
Asp Ile Gln Met Thr Gln Ser Pro Ala Ser Leu Ser Ala Ser Leu Glu
1               5                   10                  15

Glu Ile Val Thr Ile Thr Cys Gln Ala Ser Gln Asp Ile Gly Asn Trp
            20                  25                  30

Leu Ser Trp Tyr Gln Gln Lys Pro Gly Lys Ser Pro Gln Leu Leu Ile
        35                  40                  45

Tyr Gly Ala Thr Ser Leu Ala Asp Gly Val Pro Ser Arg Phe Ser Gly
    50                  55                  60

Ser Arg Ser Gly Thr Gln Tyr Ser Leu Lys Ile Ser Arg Leu Arg Val
65                  70                  75                  80

Glu Asp Ile Gly Ile Tyr Tyr Cys Leu Gln Ala Tyr Ser Ala Pro Phe
                85                  90                  95

Thr Phe Gly Ser Gly Thr Lys Leu Glu Ile Lys Arg Ala
            100                 105
```

<210> SEQ ID NO 13
<211> LENGTH: 363
<212> TYPE: DNA
<213> ORGANISM: Rattus norvegicus
<220> FEATURE:
<221> NAME/KEY: V_region
<222> LOCATION: (1)..(363)

<400> SEQUENCE: 13

```
gaggtgcagc tggtggagtc tgaggaggc ttagtacagc ctggaaggtc cctgaaactc       60
tcctgtttag cctctggatc cactttcagt aactatggaa tgaaatggat tcgccaggct     120
ccagggaagg ggctggagtg ggttgcatct attagtagaa gtagcactta catctactat     180
gcagacacag tgaagggccg atttaccatc tccagagaca atgccaggaa cacccctgtac    240 ctgcaaatga ccagtctgag gtctgaagac acagccttgt attactgtgc ggcagctata     300
tctaccccct tctactggta ctttgacttc tggggccag gaaccgtggt caccgtgtcc     360
tca                                                                    363
```

<210> SEQ ID NO 14
<211> LENGTH: 121
<212> TYPE: PRT
<213> ORGANISM: Rattus norvegicus
<220> FEATURE:
<221> NAME/KEY: V_region
<222> LOCATION: (1)..(121)

<400> SEQUENCE: 14

```
Glu Val Gln Leu Val Glu Ser Gly Gly Gly Leu Val Gln Pro Gly Arg
1               5                   10                  15

Ser Leu Lys Leu Ser Cys Leu Ala Ser Gly Ser Thr Phe Ser Asn Tyr
            20                  25                  30
```

Gly Met Lys Trp Ile Arg Gln Ala Pro Gly Lys Gly Leu Glu Trp Val
        35                  40                  45

Ala Ser Ile Ser Arg Ser Ser Thr Tyr Ile Tyr Tyr Ala Asp Thr Val
 50                  55                  60

Lys Gly Arg Phe Thr Ile Ser Arg Asp Asn Ala Arg Asn Thr Leu Tyr
 65                  70                  75                  80

Leu Gln Met Thr Ser Leu Arg Ser Glu Asp Thr Ala Leu Tyr Tyr Cys
                 85                  90                  95

Ala Ala Ala Ile Ser Thr Pro Phe Tyr Trp Tyr Phe Asp Phe Trp Gly
            100                 105                 110

Pro Gly Thr Val Val Thr Val Ser Ser
            115                 120

<210> SEQ ID NO 15
<211> LENGTH: 327
<212> TYPE: DNA
<213> ORGANISM: Rattus norvegicus
<220> FEATURE:
<221> NAME/KEY: V_region
<222> LOCATION: (1)..(327)

<400> SEQUENCE: 15
gaaattgttc tcactcagtc tccaacaacc atggctgcat ctccggggga aaaggtcacc      60
ctcaactgcc ttgccagctc aagtgtaagt tacatgacct ggtaccagca gaagtcaggc     120
gcctccccca aactctggat ttatggcaca tccaacctag cttctggagt cccaaatcgc     180
ttcagtggca gtgggtctgg gacatcttat tcgctcgcaa tcagtccat ggaggctgaa      240 gatgttgcaa cttattactg cctgcacttg actagttacc caccgtacac gtttggagct     300
gggaccaagc tggaactgaa acgggct                                          327

<210> SEQ ID NO 16
<211> LENGTH: 109
<212> TYPE: PRT
<213> ORGANISM: Rattus norvegicus
<220> FEATURE:
<221> NAME/KEY: V_region
<222> LOCATION: (1)..(109)

<400> SEQUENCE: 16

Glu Ile Val Leu Thr Gln Ser Pro Thr Thr Met Ala Ala Ser Pro Gly
 1               5                  10                  15

Glu Lys Val Thr Leu Asn Cys Leu Ala Ser Ser Ser Val Ser Tyr Met
                20                  25                  30

Thr Trp Tyr Gln Gln Lys Ser Gly Ala Ser Pro Lys Leu Trp Ile Tyr
        35                  40                  45

Gly Thr Ser Asn Leu Ala Ser Gly Val Pro Asn Arg Phe Ser Gly Ser
 50                  55                  60

Gly Ser Gly Thr Ser Tyr Ser Leu Ala Ile Ser Ser Met Glu Ala Glu
 65                  70                  75                  80

Asp Val Ala Thr Tyr Tyr Cys Leu His Leu Thr Ser Tyr Pro Pro Tyr
                 85                  90                  95

Thr Phe Gly Ala Gly Thr Lys Leu Glu Leu Lys Arg Ala
            100                 105

<210> SEQ ID NO 17
<211> LENGTH: 449
<212> TYPE: DNA
<213> ORGANISM: Homo sapiens

<400> SEQUENCE: 17

```
gcctccggac tctagagcca ccatggtgct gcagacccag tgttcatct ccctgctgct    60
gtggatctcc ggcgcgtacg gcgatatcgt gatgattaaa cgtacggtgg ccgcccctc   120
cgtgttcatc ttcccccct ccgacgcaga gctgaagtcc ggcaccgcct ccgtggtgtg   180
cctgctgaat aacttctacc ccagagaggc caaggtgcag tggaaggtgg acaacgccct   240
gcagtccggg aactcccagg agagcgtgac cgagcaggac agcaaggaca gcacctacag   300
cctgagcagc accctgaccc tgagcaaagc cgactacgag aagcacaagg tgtacgcctg   360
cgaggtgacc caccagggcc tgagctcccc cgtcaccaag agcttcaaca gggggagtg   420
ttagggccc gtttaaacgg gggaggcta                                     449
```

<210> SEQ ID NO 18
<211> LENGTH: 1132
<212> TYPE: DNA
<213> ORGANISM: Homo sapiens

<400> SEQUENCE: 18

```
gcctccggac tctagagcca ccatgaaaca cctgtggttc ttcctcctgc tggtggcagc    60
tcccagatgg gtgctgagcc aggtgcaatt gtgcaggcgg ttagctcagc ctccaccaag   120
ggcccaagcg tcttcccct ggcaccctcc tccaagagca cctctggcgg cacagccgcc   180
ctgggctgcc tggtcaagga ctacttcccc gaacccgtga ccgtgagctg gaactcaggc   240
gccctgacca cggcgtgca ccttcccc gctgtcctgc agtcctcagg actctactcc   300
ctcagcagcg tggtgaccgt gccctccagc agcttgggca cccagaccta catctgcaac   360
gtgaatcaca gcccagcaa caccaaggtg gacaagagag ttgagcccaa atcttgtgac   420
aaaactcaca catgcccacc ctgcccagca cctgaactcc tggggggacc ctcagtcttc   480
ctcttcccc caaaacccaa ggacaccctc atgatctccc ggacccctga ggtcacatgc   540
gtggtggtgg acgtgagcca cgaagaccct gaggtcaagt tcaactggta cgtggacggc   600
gtggaggtgc ataatgccaa gacaaagccc cgggaggagc agtacaacag cacgtaccgg   660
gtggtcagcg tcctcaccgt cctgcaccag gactggctga atggcaagga gtacaagtgc   720
aaggtctcca acaaagccct cccagccccc atcgagaaaa ccatctccaa agccaaaggc   780
cagccccggg aaccacaggt gtacaccctg cccccatccc gggaggagat gaccaagaac   840
caggtcagcc tgacctgcct ggtcaaaggc ttctatccca gcgacatcgc cgtggagtgg   900
gagagcaatg ccagcccga gaacaactac aagaccaccc tcccgtgct ggactccgac   960
ggctccttct tcctctacag caagctcacc gtggacaaga gcaggtggca gcagggcaac  1020
gtcttctcat gctccgtgat gcatgaggct ctgcacaacc actacaccca gaagagcctc  1080
tccctgtctc ccggcaaatg agatatcggg cccgtttaaa cggggaggc ta          1132
```

<210> SEQ ID NO 19
<211> LENGTH: 1416
<212> TYPE: DNA
<213> ORGANISM: Artificial
<220> FEATURE:
<223> OTHER INFORMATION: Heavy chain nucleotide sequence of human chimeric cA2-15A
<220> FEATURE:
<221> NAME/KEY: sig_peptide
<222> LOCATION: (1)..(57)
<220> FEATURE:
<221> NAME/KEY: V_region
<222> LOCATION: (58)..(426)

```
<220> FEATURE:
<221> NAME/KEY: C_region
<222> LOCATION: (427)..(1416)

<400> SEQUENCE: 19
atgaaacacc tgtggttctt cctcctgctg gtggcagctc ccagatgggt gctgagcgag      60
gtgcagctgg tggagtctgg cggaggctta gtacagcctg gaaggtccct gaaactctcc     120
tgtgcagcct caggattcac tttcagtcac tattacatgg cctgggtccg ccaggctcca     180
acgaagggtc tggagtgggt cgcatccatt actaatagtg gtggtagtat taactatcga     240
gactccgtca agggccgatt cactatctcc agagataatg caaaaagcac cctatacctg     300
caaatggaca gtctgaggtc tgaggacacg gccacttatt actgtacaag agaaggtgga     360
gaaaactacg gagggtatcc cccgtttgct tactggggcc aaggcactct ggtcactgtc     420
agctcagcct ccaccaaggg cccaagcgtc ttccccctgg caccctcctc caagagcacc     480
tctggcggca cagccgccct gggctgcctg gtcaaggact acttccccga acccgtgacc     540
gtgagctgga actcaggcgc cctgaccagc ggcgtgcaca ccttccccgc tgtcctgcag     600
tcctcaggac tctactccct cagcagcgtg gtgaccgtgc cctccagcag cttgggcacc     660
cagacctaca tctgcaacgt gaatcacaag cccagcaaca ccaaggtgga caagagagtt     720
gagcccaaat cttgtgacaa aactcacaca tgcccaccct gcccagcacc tgaactcctg     780
gggggaccct cagtcttcct cttcccccca aaacccaagg acaccctcat gatctcccgg     840
acccctgagg tcacatgcgt ggtggtggac gtgagccacg aagaccctga ggtcaagttc     900
aactggtacg tggacggcgt ggaggtgcat aatgccaaga caaagccccg ggaggagcag     960
tacaacagca cgtaccgggt ggtcagcgtc ctcaccgtcc tgcaccagga ctggctgaat    1020
ggcaaggagt acaagtgcaa ggtctccaac aaagccctcc cagcccccat cgagaaaacc    1080
atctccaaag ccaaaggcca gccccgggaa ccacaggtgt acaccctgcc cccatcccgg    1140
gaggagatga ccaagaacca ggtcagcctg acctgcctgg tcaaaggctt ctatcccagc    1200
gacatcgccg tggagtggga gagcaatggc cagccggaga acaactacaa gaccacccct    1260
cccgtgctgg actccgacgg ctccttcttc ctctacagca agctcaccgt ggacaagagc    1320
aggtggcagc agggcaacgt cttctcatgc tccgtgatgc atgaggctct gcacaaccac    1380
tacacccaga gagcctctc cctgtctccc ggcaaa                                1416

<210> SEQ ID NO 20
<211> LENGTH: 472
<212> TYPE: PRT
<213> ORGANISM: Artificial
<220> FEATURE:
<223> OTHER INFORMATION: Heavy chain amino acid sequence of human
      chimeric cA2-15A
<220> FEATURE:
<221> NAME/KEY: SIGNAL
<222> LOCATION: (1)..(19)
<220> FEATURE:
<221> NAME/KEY: V_region
<222> LOCATION: (20)..(142)
<220> FEATURE:
<221> NAME/KEY: C_region
<222> LOCATION: (143)..(472)

<400> SEQUENCE: 20

Met Lys His Leu Trp Phe Phe Leu Leu Leu Val Ala Ala Pro Arg Trp
1               5                   10                  15

Val Leu Ser Glu Val Gln Leu Val Glu Ser Gly Gly Gly Leu Val Gln
            20                  25                  30
```

-continued

```
Pro Gly Arg Ser Leu Lys Leu Ser Cys Ala Ala Ser Gly Phe Thr Phe
            35                  40                  45
Ser His Tyr Tyr Met Ala Trp Val Arg Gln Ala Pro Thr Lys Gly Leu
    50                  55                  60
Glu Trp Val Ala Ser Ile Thr Asn Ser Gly Gly Ser Ile Asn Tyr Arg
65                  70                  75                  80
Asp Ser Val Lys Gly Arg Phe Thr Ile Ser Arg Asp Asn Ala Lys Ser
                85                  90                  95
Thr Leu Tyr Leu Gln Met Asp Ser Leu Arg Ser Glu Asp Thr Ala Thr
                100                 105                 110
Tyr Tyr Cys Thr Arg Glu Gly Glu Asn Tyr Gly Gly Tyr Pro Pro
            115                 120                 125
Phe Ala Tyr Trp Gly Gln Gly Thr Leu Val Thr Val Ser Ser Ala Ser
            130                 135                 140
Thr Lys Gly Pro Ser Val Phe Pro Leu Ala Pro Ser Ser Lys Ser Thr
145                 150                 155                 160
Ser Gly Gly Thr Ala Ala Leu Gly Cys Leu Val Lys Asp Tyr Phe Pro
                165                 170                 175
Glu Pro Val Thr Val Ser Trp Asn Ser Gly Ala Leu Thr Ser Gly Val
            180                 185                 190
His Thr Phe Pro Ala Val Leu Gln Ser Ser Gly Leu Tyr Ser Leu Ser
            195                 200                 205
Ser Val Val Thr Val Pro Ser Ser Ser Leu Gly Thr Gln Thr Tyr Ile
            210                 215                 220
Cys Asn Val Asn His Lys Pro Ser Asn Thr Lys Val Asp Lys Arg Val
225                 230                 235                 240
Glu Pro Lys Ser Cys Asp Lys Thr His Thr Cys Pro Pro Cys Pro Ala
                245                 250                 255
Pro Glu Leu Leu Gly Gly Pro Ser Val Phe Leu Phe Pro Pro Lys Pro
            260                 265                 270
Lys Asp Thr Leu Met Ile Ser Arg Thr Pro Glu Val Thr Cys Val Val
            275                 280                 285
Val Asp Val Ser His Glu Asp Pro Glu Val Lys Phe Asn Trp Tyr Val
            290                 295                 300
Asp Gly Val Glu Val His Asn Ala Lys Thr Lys Pro Arg Glu Glu Gln
305                 310                 315                 320
Tyr Asn Ser Thr Tyr Arg Val Val Ser Val Leu Thr Val Leu His Gln
                325                 330                 335
Asp Trp Leu Asn Gly Lys Glu Tyr Lys Cys Lys Val Ser Asn Lys Ala
            340                 345                 350
Leu Pro Ala Pro Ile Glu Lys Thr Ile Ser Lys Ala Lys Gly Gln Pro
            355                 360                 365
Arg Glu Pro Gln Val Tyr Thr Leu Pro Pro Ser Arg Glu Glu Met Thr
            370                 375                 380
Lys Asn Gln Val Ser Leu Thr Cys Leu Val Lys Gly Phe Tyr Pro Ser
385                 390                 395                 400
Asp Ile Ala Val Glu Trp Glu Ser Asn Gly Gln Pro Glu Asn Asn Tyr
                405                 410                 415
Lys Thr Thr Pro Pro Val Leu Asp Ser Asp Gly Ser Phe Phe Leu Tyr
            420                 425                 430
Ser Lys Leu Thr Val Asp Lys Ser Arg Trp Gln Gln Gly Asn Val Phe
            435                 440                 445
```

Ser Cys Ser Val Met His Glu Ala Leu His Asn His Tyr Thr Gln Lys
    450                 455                 460
Ser Leu Ser Leu Ser Pro Gly Lys
465                 470

<210> SEQ ID NO 21
<211> LENGTH: 711
<212> TYPE: DNA
<213> ORGANISM: Artificial
<220> FEATURE:
<223> OTHER INFORMATION: Light chain nucleotide sequence of human
      chimeric cA2-15A
<220> FEATURE:
<221> NAME/KEY: sig_peptide
<222> LOCATION: (1)..(60)
<220> FEATURE:
<221> NAME/KEY: V_region
<222> LOCATION: (61)..(396)
<220> FEATURE:
<221> NAME/KEY: C_region
<222> LOCATION: (397)..(711)

<400> SEQUENCE: 21
atggtgctgc agacccaggt gttcatctcc ctgctgctgt ggatctccgg cgcgtacggc      60
gacattgtct tgacccagtc tcctgctttg gctgtgtctc tagggcagag ggccacaatc     120
tcctgtaggg ccaaccaagg tgtcagtcta tctagatata tcttatgca ctggtaccaa      180 cagaaaccag gacagaaacc caaactcctc atctatcgtt catccaacct agcatctggg     240
atccctgcca ggttcagtgg cagtgggtct gggacagact tcaccctcac catcaatcct     300
gtgcaggctg atgatattgc aacctattac tgtcagcaga gtaggagtc tccgttcacg     360 tttggagctg ggaccaagct ggaactgaaa cgggctgtgg ccgcccccc cgtgttcatc     420 ttccccccct ccgacgagca gctgaagtcc ggcaccgcct ccgtggtgtg cctgctgaat     480
aacttctacc ccagagaggc caaggtgcag tggaaggtgg acaacgccct gcagtccggg     540
aactcccagg agagcgtgac cgagcaggac agcaaggaca gcacctacag cctgagcagc     600
accctgaccc tgagcaaagc cgactacgag aagcacaagg tgtacgcctg cgaggtgacc     660
caccagggcc tgagctcccc cgtcaccaag agcttcaaca ggggggagtg t              711

<210> SEQ ID NO 22
<211> LENGTH: 237
<212> TYPE: PRT
<213> ORGANISM: Artificial
<220> FEATURE:
<223> OTHER INFORMATION: Light chain amino acid sequence of human
      chimeric cA2-15A
<220> FEATURE:
<221> NAME/KEY: SIGNAL
<222> LOCATION: (1)..(20)
<220> FEATURE:
<221> NAME/KEY: V_region
<222> LOCATION: (21)..(132)
<220> FEATURE:
<221> NAME/KEY: C_region
<222> LOCATION: (133)..(237)

<400> SEQUENCE: 22

Met Val Leu Gln Thr Gln Val Phe Ile Ser Leu Leu Leu Trp Ile Ser
1               5                   10                  15

Gly Ala Tyr Gly Asp Ile Val Leu Thr Gln Ser Pro Ala Leu Ala Val
            20                  25                  30

Ser Leu Gly Gln Arg Ala Thr Ile Ser Cys Arg Ala Asn Gln Gly Val
        35                  40                  45

Ser Leu Ser Arg Tyr Asn Leu Met His Trp Tyr Gln Gln Lys Pro Gly
    50                  55                  60

Gln Lys Pro Lys Leu Leu Ile Tyr Arg Ser Ser Asn Leu Ala Ser Gly
65                  70                  75                  80

Ile Pro Ala Arg Phe Ser Gly Ser Gly Ser Gly Thr Asp Phe Thr Leu
                85                  90                  95

Thr Ile Asn Pro Val Gln Ala Asp Asp Ile Ala Thr Tyr Tyr Cys Gln
            100                 105                 110

Gln Ser Arg Glu Ser Pro Phe Thr Phe Gly Ala Gly Thr Lys Leu Glu
        115                 120                 125

Leu Lys Arg Ala Val Ala Ala Pro Ser Val Phe Ile Phe Pro Pro Ser
130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235

<210> SEQ ID NO 23
<211> LENGTH: 1410
<212> TYPE: DNA
<213> ORGANISM: Artificial
<220> FEATURE:
<223> OTHER INFORMATION: Heavy chain nucleotide sequence of human
      chimeric cA2-27D
<220> FEATURE:
<221> NAME/KEY: sig_peptide
<222> LOCATION: (1)..(57)
<220> FEATURE:
<221> NAME/KEY: V_region
<222> LOCATION: (58)..(420)
<220> FEATURE:
<221> NAME/KEY: C_region
<222> LOCATION: (421)..(1410)

<400> SEQUENCE: 23
atgaaacacc tgtggttctt cctcctgctg gtggcagctc ccagatgggt gctgagcgag      60
gtgcagctgg tggagtctgg aggaggctta gtacagcctg gaaggtccct gaaactctcc    120
tgtttagcct ctggatccac tttcagtaac tatggaatga atggattcg ccaggctcca    180 gggaaggggc tggagtgggt tgcatctatt agtagaagta gcacttacat ctactatgca    240
gacacagtga agggccgatt taccatctcc agagacaatg ccaggaacac cctgtacctg    300
caaatgacca gtctgaggtc tgaagacaca gccttgtatt actgtgcggc agctatatct    360
acccccttct actggtactt tgacttctgg ggcccaggaa ccgtggtcac cgtgagctca    420
gcctccacca agggcccaag cgtcttcccc ctggcaccct cctccaagag cacctctggc    480
ggcacagccg ccctgggctg cctggtcaag gactacttcc ccgaaccgt gaccgtgagc    540 tggaactcag cgccctgac cagcggcgtg cacaccttcc ccgctgtcct gcagtcctca    600
ggactctact ccctcagcag cgtggtgacc gtgccctcca gcagcttggg cacccagacc    660
tacatctgca acgtgaatca caagcccagc aacaccaagg tggacaagag agttgagccc    720

```
aaatcttgtg acaaaactca cacatgccca ccctgcccag cacctgaact cctgggggga    780
ccctcagtct tcctcttccc cccaaaaccc aaggacaccc tcatgatctc ccggacccct    840
gaggtcacat gcgtggtggt ggacgtgagc cacgaagacc ctgaggtcaa gttcaactgg    900
tacgtggacg gcgtggaggt gcataatgcc aagacaaagc cccgggagga gcagtacaac    960
agcacgtacc gggtggtcag cgtcctcacc gtcctgcacc aggactggct gaatggcaag   1020
gagtacaagt gcaaggtctc caacaaagcc ctcccagccc ccatcgagaa aaccatctcc   1080
aaagccaaag gccagccccg ggaaccacag gtgtacaccc tgcccccatc ccgggaggag   1140
atgaccaaga accaggtcag cctgacctgc ctggtcaaag gcttctatcc cagcgacatc   1200
gccgtggagt gggagagcaa tggccagccc gagaacaact acaagaccac ccctcccgtg   1260
ctggactccg acggctcctt cttcctctac agcaagctca ccgtggacaa gagcaggtgg   1320
cagcagggca acgtcttctc atgctccgtg atgcatgagg ctctgcacaa ccactacacc   1380
cagaagagcc tctccctgtc tccggcaaa                                      1410
```

<210> SEQ ID NO 24
<211> LENGTH: 470
<212> TYPE: PRT
<213> ORGANISM: Artificial
<220> FEATURE:
<223> OTHER INFORMATION: Heavy chain amino acid sequence of human chimeric cA2-27D
<220> FEATURE:
<221> NAME/KEY: SIGNAL
<222> LOCATION: (1)..(19)
<220> FEATURE:
<221> NAME/KEY: V_region
<222> LOCATION: (20)..(140)
<220> FEATURE:
<221> NAME/KEY: C_region
<222> LOCATION: (141)..(470)

<400> SEQUENCE: 24

```
Met Lys His Leu Trp Phe Phe Leu Leu Leu Val Ala Ala Pro Arg Trp
1               5                   10                  15

Val Leu Ser Glu Val Gln Leu Val Glu Ser Gly Gly Gly Leu Val Gln
            20                  25                  30

Pro Gly Arg Ser Leu Lys Leu Ser Cys Leu Ala Ser Gly Ser Thr Phe
        35                  40                  45

Ser Asn Tyr Gly Met Lys Trp Ile Arg Gln Ala Pro Gly Lys Gly Leu
    50                  55                  60

Glu Trp Val Ala Ser Ile Ser Arg Ser Ser Thr Tyr Ile Tyr Tyr Ala
65                  70                  75                  80

Asp Thr Val Lys Gly Arg Phe Thr Ile Ser Arg Asp Asn Ala Arg Asn
                85                  90                  95

Thr Leu Tyr Leu Gln Met Thr Ser Leu Arg Ser Glu Asp Thr Ala Leu
            100                 105                 110

Tyr Tyr Cys Ala Ala Ala Ile Ser Thr Pro Phe Tyr Trp Tyr Phe Asp
        115                 120                 125

Phe Trp Gly Pro Gly Thr Val Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
```

```
              180               185               190
Phe Pro Ala Val Leu Gln Ser Ser Gly Leu Tyr Ser Leu Ser Ser Val
            195               200               205

Val Thr Val Pro Ser Ser Ser Leu Gly Thr Gln Thr Tyr Ile Cys Asn
    210               215               220

Val Asn His Lys Pro Ser Asn Thr Lys Val Asp Lys Arg Val Glu Pro
225               230               235               240

Lys Ser Cys Asp Lys Thr His Thr Cys Pro Pro Cys Pro Ala Pro Glu
                245               250               255

Leu Leu Gly Gly Pro Ser Val Phe Leu Phe Pro Pro Lys Pro Lys Asp
            260               265               270

Thr Leu Met Ile Ser Arg Thr Pro Glu Val Thr Cys Val Val Val Asp
        275               280               285

Val Ser His Glu Asp Pro Glu Val Lys Phe Asn Trp Tyr Val Asp Gly
    290               295               300

Val Glu Val His Asn Ala Lys Thr Lys Pro Arg Glu Glu Gln Tyr Asn
305               310               315               320

Ser Thr Tyr Arg Val Val Ser Val Leu Thr Val Leu His Gln Asp Trp
                325               330               335

Leu Asn Gly Lys Glu Tyr Lys Cys Lys Val Ser Asn Lys Ala Leu Pro
            340               345               350

Ala Pro Ile Glu Lys Thr Ile Ser Lys Ala Lys Gly Gln Pro Arg Glu
        355               360               365

Pro Gln Val Tyr Thr Leu Pro Pro Ser Arg Glu Glu Met Thr Lys Asn
    370               375               380

Gln Val Ser Leu Thr Cys Leu Val Lys Gly Phe Tyr Pro Ser Asp Ile
385               390               395               400

Ala Val Glu Trp Glu Ser Asn Gly Gln Pro Glu Asn Asn Tyr Lys Thr
                405               410               415

Thr Pro Pro Val Leu Asp Ser Asp Gly Ser Phe Phe Leu Tyr Ser Lys
            420               425               430

Leu Thr Val Asp Lys Ser Arg Trp Gln Gln Gly Asn Val Phe Ser Cys
        435               440               445

Ser Val Met His Glu Ala Leu His Asn His Tyr Thr Gln Lys Ser Leu
    450               455               460

Ser Leu Ser Pro Gly Lys
465               470

<210> SEQ ID NO 25
<211> LENGTH: 702
<212> TYPE: DNA
<213> ORGANISM: Artificial
<220> FEATURE:
<223> OTHER INFORMATION: Light chain nucleotide sequence of human
      chimeric cA2-27D
<220> FEATURE:
<221> NAME/KEY: sig_peptide
<222> LOCATION: (1)..(60)
<220> FEATURE:
<221> NAME/KEY: V_region
<222> LOCATION: (61)..(387)
<220> FEATURE:
<221> NAME/KEY: C_region
<222> LOCATION: (388)..(702)

<400> SEQUENCE: 25
atggtgctgc agacccaggt gttcatctcc ctgctgctgt ggatctccgg cgcgtacggc    60
gaaattgttc tcactcagtc tccaacaacc atggctgcat ctccggggga aaaggtcacc   120
```

```
ctcaactgcc ttgccagctc aagtgtaagt tacatgacct ggtaccagca gaagtcaggc    180
gcctccccca aactctggat ttatggcaca tccaacctag cttctggagt cccaaatcgc    240
ttcagtggca gtgggtctgg gacatcttat tcgctcgcaa tcagctccat ggaggctgaa    300
gatgttgcaa cttattactg cctgcacttg actagttacc caccgtacac gtttggagct    360
gggaccaagc tggaactgaa acgggctgtg gccgccccct ccgtgttcat cttccccccc    420
tccgacgagc agctgaagtc cggcaccgcc tccgtggtgt gcctgctgaa taacttctac    480
cccagagagg ccaaggtgca gtggaaggtg gacaacgccc tgcagtccgg aactcccag    540 gagagcgtga ccgagcagga cagcaaggac agcacctaca gcctgagcag caccctgacc    600
ctgagcaaag ccgactacga aagcacaag gtgtacgcct gcgaggtgac ccaccagggc    660
ctgagctccc ccgtcaccaa gagcttcaac agggggagt gt                       702
```

<210> SEQ ID NO 26
<211> LENGTH: 234
<212> TYPE: PRT
<213> ORGANISM: Artificial
<220> FEATURE:
<223> OTHER INFORMATION: Light chain amino acid sequence of human
      chimeric cA2-27D
<220> FEATURE:
<221> NAME/KEY: SIGNAL
<222> LOCATION: (1)..(20)
<220> FEATURE:
<221> NAME/KEY: V_region
<222> LOCATION: (21)..(129)
<220> FEATURE:
<221> NAME/KEY: C_region
<222> LOCATION: (130)..(234)

<400> SEQUENCE: 26

Met Val Leu Gln Thr Gln Val Phe Ile Ser Leu Leu Trp Ile Ser
1               5                   10                  15

Gly Ala Tyr Gly Glu Ile Val Leu Thr Gln Ser Pro Thr Thr Met Ala
            20                  25                  30

Ala Ser Pro Gly Glu Lys Val Thr Leu Asn Cys Leu Ala Ser Ser Ser
        35                  40                  45

Val Ser Tyr Met Thr Trp Tyr Gln Gln Lys Ser Gly Ala Ser Pro Lys
    50                  55                  60

Leu Trp Ile Tyr Gly Thr Ser Asn Leu Ala Ser Gly Val Pro Asn Arg
65                  70                  75                  80

Phe Ser Gly Ser Gly Ser Gly Thr Ser Tyr Ser Leu Ala Ile Ser Ser
                85                  90                  95

Met Glu Ala Glu Asp Val Ala Thr Tyr Tyr Cys Leu His Leu Thr Ser
            100                 105                 110

Tyr Pro Pro Tyr Thr Phe Gly Ala Gly Thr Lys Leu Glu Leu Lys Arg
        115                 120                 125

Ala Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 27
<211> LENGTH: 1416
<212> TYPE: DNA
<213> ORGANISM: Artificial
<220> FEATURE:
<223> OTHER INFORMATION: Nucleotide sequence coding for humanized
      hA2-15A-H1
<220> FEATURE:
<221> NAME/KEY: sig_peptide
<222> LOCATION: (1)..(57)
<220> FEATURE:
<221> NAME/KEY: V_region
<222> LOCATION: (58)..(426)
<220> FEATURE:
<221> NAME/KEY: C_region
<222> LOCATION: (427)..(1416)

<400> SEQUENCE: 27

| | | | | | |
|---|---|---|---|---|---|
| atgaaacacc | tgtggttctt | cctcctgctg | gtggcagctc | ccagatgggt | gctgagcgaa | 60 |
| gtgcagctgg | tggaatctgg | cggcggactg | gtgcagcctg | gcggatctct | gagactgagc | 120 |
| tgtgccgcca | gcggcttcac | cttcagccac | tactacatgg | cctgggtgcg | ccaggcccct | 180 |
| ggcaaaggac | tggaatgggt | ggccagcatc | accaacagcg | gcggcagcat | caactaccgg | 240 |
| gacagcgtga | agggccggtt | caccatcagc | cgggacaaca | gcaagaacac | cctgtacctg | 300 |
| cagatgaaca | gcctgcgggc | cgaggacacc | gccgtgtact | attgtgccag | agagggcggc | 360 |
| gagaactacg | cggctatcc | cccttttgcc | tactggggcc | agggcaccct | cgtgaccgtc | 420 |
| agctcagcct | ccaccaaggg | cccaagcgtc | ttccccctgg | caccctcctc | caagagcacc | 480 |
| tctggcggca | cagccgccct | gggctgcctg | gtcaaggact | acttccccga | acccgtgacc | 540 |
| gtgagctgga | actcaggcgc | cctgaccagc | ggcgtgcaca | ccttcccgc | tgtcctgcag | 600 |
| tcctcaggac | tctactccct | cagcagcgtg | gtgaccgtgc | cctccagcag | cttgggcacc | 660 |
| cagacctaca | tctgcaacgt | gaatcacaag | cccagcaaca | ccaaggtgga | caagagagtt | 720 |
| gagcccaaat | cttgtgacaa | aactcacaca | tgcccaccct | gcccagcacc | tgaactcctg | 780 |
| gggggaccct | cagtcttcct | cttccccca | aaacccaagg | acaccctcat | gatctcccgg | 840 |
| acccctgagg | tcacatgcgt | ggtggtggac | gtgagccacg | aagaccctga | ggtcaagttc | 900 |
| aactggtacg | tggacggcgt | ggaggtgcat | aatgccaaga | caaagccccg | ggaggagcag | 960 |
| tacaacagca | cgtaccgggt | ggtcagcgtc | ctcaccgtcc | tgcaccagga | ctggctgaat | 1020 |
| ggcaaggagt | acaagtgcaa | ggtctccaac | aaagccctcc | cagcccccat | cgagaaaacc | 1080 |
| atctccaaag | ccaaaggcca | gccccgggaa | ccacaggtgt | acaccctgcc | cccatcccgg | 1140 |
| gaggagatga | ccaagaacca | ggtcagcctg | acctgcctgg | tcaaaggctt | ctatcccagc | 1200 |
| gacatcgccg | tggagtggga | gagcaatggc | cagcccgaga | acaactacaa | gaccaccct | 1260 |
| cccgtgctgg | actccgacgg | ctccttcttc | ctctacagca | agctcaccgt | ggacaagagc | 1320 |
| aggtggcagc | agggcaacgt | cttctcatgc | tccgtgatgc | atgaggctct | gcacaaccac | 1380 |
| tacacccaga | agagcctctc | cctgtctccc | ggcaaa | | | 1416 |

<210> SEQ ID NO 28
<211> LENGTH: 472
<212> TYPE: PRT

```
<213> ORGANISM: Artificial
<220> FEATURE:
<223> OTHER INFORMATION: Amino acid sequence of humanized hA2-15A-H1
<220> FEATURE:
<221> NAME/KEY: SIGNAL
<222> LOCATION: (1)..(19)
<220> FEATURE:
<221> NAME/KEY: V_region
<222> LOCATION: (20)..(142)
<220> FEATURE:
<221> NAME/KEY: C_region
<222> LOCATION: (143)..(472)

<400> SEQUENCE: 28
```

Met Lys His Leu Trp Phe Phe Leu Leu Val Ala Ala Pro Arg Trp
1               5                   10                  15

Val Leu Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser His Tyr Tyr Met Ala Trp Val Arg Gln Ala Pro Gly Lys Gly Leu
    50                  55                  60

Glu Trp Val Ala Ser Ile Thr Asn Ser Gly Gly Ser Ile Asn Tyr Arg
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Glu Gly Gly Glu Asn Tyr Gly Tyr Pro Pro
        115                 120                 125

Phe Ala Tyr Trp Gly Gln Gly Thr Leu Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Gln Thr Tyr Ile
    210                 215                 220

Cys Asn Val Asn His Lys Pro Ser Asn Thr Lys Val Asp Lys Arg Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala

```
                 340                 345                 350
Leu Pro Ala Pro Ile Glu Lys Thr Ile Ser Lys Ala Lys Gly Gln Pro
            355                 360                 365

Arg Glu Pro Gln Val Tyr Thr Leu Pro Pro Ser Arg Glu Glu Met Thr
        370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
    450                 455                 460

Ser Leu Ser Leu Ser Pro Gly Lys
465                 470

<210> SEQ ID NO 29
<211> LENGTH: 1416
<212> TYPE: DNA
<213> ORGANISM: Artificial
<220> FEATURE:
<223> OTHER INFORMATION: Nucleotide sequence coding for humanized
      hA2-15A-H4
<220> FEATURE:
<221> NAME/KEY: sig_peptide
<222> LOCATION: (1)..(57)
<220> FEATURE:
<221> NAME/KEY: V_region
<222> LOCATION: (58)..(426)
<220> FEATURE:
<221> NAME/KEY: C_region
<222> LOCATION: (427)..(1416)

<400> SEQUENCE: 29
atgaaacacc tgtggttctt cctcctgctg gtggcagctc ccagatgggt gctgagcgaa      60
gtgcagctgg tggaatctgg cggcggactg gtgcagcctg gcggatctct gagactgagc     120
tgtgccgcca gcggcttcac cttcagccac tactacatgg cctgggtgcg ccaggcccct     180
ggcaaaggac tggaatgggt ggccagcatc accaacagcg gcggcagcat caactaccgg     240
gacagcgtga agggccggtt caccatcagc cgggacaacg ccaagagcac cctgtacctg     300
cagatgaaca gcctgcgggc cgaggacacc gccacctact actgtacaag agagggcggc     360
gagaactacg gcggctaccc tccttttgcc tactggggcc agggcaccct cgtgaccgtc     420
agctcagcct ccaccaaggg cccaagcgtc ttccccctgg cacccctcct caagagcacc     480
tctgggggca cagccgccct gggctgcctg gtcaaggact acttccccga accggtgacc     540
gtgagctgga actcaggcgc cctgaccagc ggcgtgcaca ccttccccgc tgtcctgcag     600
tcctcaggac tctactccct cagcagcgtg gtgaccgtgc cctccagcag cttgggcacc     660
cagacctaca tctgcaacgt gaatcacaag cccagcaaca ccaaggtgga caagagagtt     720
gagcccaaat cttgtgacaa aactcacaca tgcccaccct gcccagcacc tgaactcctg     780
gggggaccct cagtcttcct cttccccccc aaacccaagg acaccctcat gatctcccgg     840
acccctgagg tcacatgcgt ggtggtggac gtgagccacg aagaccctga ggtcaagttc     900
aactggtacg tggacggcgt ggaggtgcat aatgccaaga caaagccccg ggaggagcag     960
tacaacagca cgtaccgggt ggtcagcgtc ctcaccgtcc tgcaccagga ctggctgaat    1020
```

```
ggcaaggagt acaagtgcaa ggtctccaac aaagccctcc cagcccccat cgagaaaacc    1080
atctccaaag ccaaaggcca gccccgggaa ccacaggtgt acaccctgcc cccatcccgg    1140
gaggagatga ccaagaacca ggtcagcctg acctgcctgg tcaaaggctt ctatcccagc    1200
gacatcgccg tggagtggga gagcaatggc cagcccgaga caactacaa gaccaccct     1260 cccgtgctgg actccgacgg ctccttcttc ctctacagca agctcaccgt ggacaagagc    1320
aggtggcagc agggcaacgt cttctcatgc tccgtgatgc atgaggctct gcacaaccac    1380
tacacccaga gagcctctc cctgtctccc ggcaaa                                1416
```

```
<210> SEQ ID NO 30
<211> LENGTH: 472
<212> TYPE: PRT
<213> ORGANISM: Artificial
<220> FEATURE:
<223> OTHER INFORMATION: Amino acid sequence of humanized hA2-15A-H4
<220> FEATURE:
<221> NAME/KEY: SIGNAL
<222> LOCATION: (1)..(19)
<220> FEATURE:
<221> NAME/KEY: V_region
<222> LOCATION: (20)..(142)
<220> FEATURE:
<221> NAME/KEY: C_region
<222> LOCATION: (143)..(472)

<400> SEQUENCE: 30

Met Lys His Leu Trp Phe Phe Leu Leu Leu Val Ala Ala Pro Arg Trp
1               5                   10                  15

Val Leu Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser His Tyr Tyr Met Ala Trp Val Arg Gln Ala Pro Gly Lys Gly Leu
    50                  55                  60

Glu Trp Val Ala Ser Ile Thr Asn Ser Gly Gly Ser Ile Asn Tyr Arg
65                  70                  75                  80

Asp Ser Val Lys Gly Arg Phe Thr Ile Ser Arg Asp Asn Ala Lys Ser
                85                  90                  95

Thr Leu Tyr Leu Gln Met Asn Ser Leu Arg Ala Glu Asp Thr Ala Thr
            100                 105                 110

Tyr Tyr Cys Thr Arg Glu Gly Gly Glu Asn Tyr Gly Gly Tyr Pro Pro
        115                 120                 125

Phe Ala Tyr Trp Gly Gln Gly Thr Leu Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Gln Thr Tyr Ile
    210                 215                 220

Cys Asn Val Asn His Lys Pro Ser Asn Thr Lys Val Asp Lys Arg Val
225                 230                 235                 240
```

-continued

Glu Pro Lys Ser Cys Asp Lys Thr His Thr Cys Pro Pro Cys Pro Ala
             245                 250                 255

Pro Glu Leu Leu Gly Gly Pro Ser Val Phe Leu Phe Pro Pro Lys Pro
         260                 265                 270

Lys Asp Thr Leu Met Ile Ser Arg Thr Pro Glu Val Thr Cys Val Val
     275                 280                 285

Val Asp Val Ser His Glu Asp Pro Glu Val Lys Phe Asn Trp Tyr Val
 290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
             325                 330                 335

Asp Trp Leu Asn Gly Lys Glu Tyr Lys Cys Lys Val Ser Asn Lys Ala
         340                 345                 350

Leu Pro Ala Pro Ile Glu Lys Thr Ile Ser Lys Ala Lys Gly Gln Pro
     355                 360                 365

Arg Glu Pro Gln Val Tyr Thr Leu Pro Pro Ser Arg Glu Glu Met Thr
 370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
             405                 410                 415

Lys Thr Thr Pro Pro Val Leu Asp Ser Asp Gly Ser Phe Phe Leu Tyr
         420                 425                 430

Ser Lys Leu Thr Val Asp Lys Ser Arg Trp Gln Gln Gly Asn Val Phe
     435                 440                 445

Ser Cys Ser Val Met His Glu Ala Leu His Asn His Tyr Thr Gln Lys
 450                 455                 460

Ser Leu Ser Leu Ser Pro Gly Lys
465                 470

<210> SEQ ID NO 31
<211> LENGTH: 764
<212> TYPE: DNA
<213> ORGANISM: Artificial
<220> FEATURE:
<223> OTHER INFORMATION: Nucleotide sequence of DNA fragment comprising
      the sequence coding for humanized hA2-15A-L1
<220> FEATURE:
<221> NAME/KEY: sig_peptide
<222> LOCATION: (26)..(85)
<220> FEATURE:
<221> NAME/KEY: V_region
<222> LOCATION: (86)..(424)
<220> FEATURE:
<221> NAME/KEY: C_region
<222> LOCATION: (425)..(739)

<400> SEQUENCE: 31
ccagcctccg gactctagag ccaccatggt gctgcagacc caggtgttca tcagcctgct      60
gctgtggatc agcggcgcct acggcgacat cgtgatgacc cagagccctg acagcctggc     120
cgtgtctctg ggagagaggg ccaccatcaa ctgcagagcc aaccagggcg tgtccctgag     180
ccggtacaac ctgatgcact ggtatcagca gaagcccggc cagccccccca agctgctgat     240 ctacagaagc tccaacctgg ccagcggcgt gcccgataga ttttctggca gcggctccgg     300
caccgacttc accctgacaa tcagctccct gcaggccgag gacgtggccg tgtactactg     360
ccagcagagc agagagagcc ccttcacctt tggccagggc accaaggtgg aaatcaagcg     420

```
ggctgtggcc gctccctccg tgttcatctt tccacccagc gacgagcagc tgaagtctgg      480
cacagccagc gtcgtgtgcc tgctgaacaa cttctacccc cgcgaggcca aggtgcagtg      540
gaaggtggac aatgccctgc agagcggcaa ctcccaggaa agcgtgaccg agcaggacag      600
caaggactcc acctacagcc tgagcagcac cctgaccctg agcaaggccg actacgagaa      660
gcacaaggtg tacgcctgcg aagtgaccca ccagggcctg tctagccccg tgaccaagag      720
cttcaaccgg ggcgagtgtt gagtttaaac gggggaggct aact                      764
```

```
<210> SEQ ID NO 32
<211> LENGTH: 238
<212> TYPE: PRT
<213> ORGANISM: Artificial
<220> FEATURE:
<223> OTHER INFORMATION: Amino acid sequence of humanized hA2-15A-L1
<220> FEATURE:
<221> NAME/KEY: SIGNAL
<222> LOCATION: (1)..(20)
<220> FEATURE:
<221> NAME/KEY: V_region
<222> LOCATION: (21)..(133)
<220> FEATURE:
<221> NAME/KEY: C_region
<222> LOCATION: (134)..(238)

<400> SEQUENCE: 32
```

```
Met Val Leu Gln Thr Gln Val Phe Ile Ser Leu Leu Trp Ile Ser
1               5                   10                  15

Gly Ala Tyr Gly Asp Ile Val Met Thr Gln Ser Pro Asp Ser Leu Ala
            20                  25                  30

Val Ser Leu Gly Glu Arg Ala Thr Ile Asn Cys Arg Ala Asn Gln Gly
        35                  40                  45

Val Ser Leu Ser Arg Tyr Asn Leu Met His Trp Tyr Gln Gln Lys Pro
    50                  55                  60

Gly Gln Pro Pro Lys Leu Leu Ile Tyr Arg Ser Ser Asn Leu Ala Ser
65                  70                  75                  80

Gly Val Pro Asp Arg Phe Ser Gly Ser Gly Ser Gly Thr Asp Phe Thr
                85                  90                  95

Leu Thr Ile Ser Ser Leu Gln Ala Glu Asp Val Ala Val Tyr Tyr Cys
            100                 105                 110

Gln Gln Ser Arg Glu Ser Pro Phe Thr Phe Gly Gln Gly Thr Lys Val
        115                 120                 125

Glu Ile Lys Arg Ala Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235
```

```
<210> SEQ ID NO 33
<211> LENGTH: 764
```

```
<212> TYPE: DNA
<213> ORGANISM: Artificial
<220> FEATURE:
<223> OTHER INFORMATION: Nucleotide sequence of DNA fragment comprising
      the sequence coding for humanized hA2-15A-L4
<220> FEATURE:
<221> NAME/KEY: sig_peptide
<222> LOCATION: (26)..(85)
<220> FEATURE:
<221> NAME/KEY: V_region
<222> LOCATION: (86)..(424)
<220> FEATURE:
<221> NAME/KEY: C_region
<222> LOCATION: (425)..(739)

<400> SEQUENCE: 33
ccagcctccg gactctagag ccaccatggt gctgcagacc caggtgttca tcagcctgct     60
gctgtggatc agcggcgcct acggcgatat cgtgctgacc cagagccctg acagcctggc    120
cgtgtctctg ggagagaggg ccaccatcaa ctgcagagcc aaccagggcg tgtccctgag    180
ccggtacaac ctgatgcact ggtatcagca gaagcccggc cagaagccca agctgctgat    240
ctaccggtcc agcaacctgg cctctggcat ccccgccaga ttttctggca gcggctccgg    300
caccgacttc accctgacaa tcagcagcgt gcaggccgac gacattgccg tgtactactg    360
ccagcagagc agagagagcc ccttcacctt tggccagggc accaagctgg aactgaagag    420
agccgtggcc gctccctccg tgttcatctt cccacctagc gacgagcagc tgaagtctgg    480
cacagccagc gtcgtgtgcc tgctgaacaa cttctacccc cgcgaggcca aggtgcagtg    540
gaaggtggac aatgccctgc agagcggcaa cagccaggaa agcgtgaccg agcaggacag    600
caaggactcc acctacagcc tgagcagcac cctgaccctg agcaaggccg actacgagaa    660
gcacaaggtg tacgcctgcg aagtgaccca ccagggcctg tctagccccg tgaccaagag    720
cttcaaccgg ggcgagtgtt gagtttaaac ggggagggct aact                     764

<210> SEQ ID NO 34
<211> LENGTH: 238
<212> TYPE: PRT
<213> ORGANISM: Artificial
<220> FEATURE:
<223> OTHER INFORMATION: Amino acid sequence of humanized hA2-15A-L4
<220> FEATURE:
<221> NAME/KEY: SIGNAL
<222> LOCATION: (1)..(20)
<220> FEATURE:
<221> NAME/KEY: V_region
<222> LOCATION: (21)..(133)
<220> FEATURE:
<221> NAME/KEY: C_region
<222> LOCATION: (134)..(238)

<400> SEQUENCE: 34

Met Val Leu Gln Thr Gln Val Phe Ile Ser Leu Leu Leu Trp Ile Ser
1               5                   10                  15

Gly Ala Tyr Gly Asp Ile Val Leu Thr Gln Ser Pro Asp Ser Leu Ala
            20                  25                  30

Val Ser Leu Gly Glu Arg Ala Thr Ile Asn Cys Arg Ala Asn Gln Gly
        35                  40                  45

Val Ser Leu Ser Arg Tyr Asn Leu Met His Trp Tyr Gln Gln Lys Pro
    50                  55                  60

Gly Gln Lys Pro Lys Leu Leu Ile Tyr Arg Ser Ser Asn Leu Ala Ser
65                  70                  75                  80

Gly Ile Pro Ala Arg Phe Ser Gly Ser Gly Ser Gly Thr Asp Phe Thr
                85                  90                  95
```

```
Leu Thr Ile Ser Ser Val Gln Ala Asp Asp Ile Ala Val Tyr Tyr Cys
            100                 105                 110

Gln Gln Ser Arg Glu Ser Pro Phe Thr Phe Gly Gln Gly Thr Lys Leu
        115                 120                 125

Glu Leu Lys Arg Ala Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235
```

```
<210> SEQ ID NO 35
<211> LENGTH: 764
<212> TYPE: DNA
<213> ORGANISM: Artificial
<220> FEATURE:
<223> OTHER INFORMATION: Nucleotide sequence of DNA fragment comprising
      the sequence coding for humanized hA2-15A-L6
<220> FEATURE:
<221> NAME/KEY: sig_peptide
<222> LOCATION: (26)..(85)
<220> FEATURE:
<221> NAME/KEY: V_region
<222> LOCATION: (86)..(424)
<220> FEATURE:
<221> NAME/KEY: C_region
<222> LOCATION: (425)..(739)

<400> SEQUENCE: 35
ccagcctccg gactctagag ccaccatggt gctgcagacc caggtgttca tcagcctgct      60
gctgtggatc agcggcgcct acggcgatat cgtgctgacc cagagccctg acagcctggc     120
cgtgtctctg ggagagaggg ccaccatcaa ctgcagagcc aaccagggcg tgtccctgag     180
ccggtacaac ctgatgcact ggtatcagca gaagcccggc cagaagccca gctgctgat      240 ctaccggtcc agcaacctgg cccagggcat ccctgccaga ttttctggca gcggctccgg     300
caccgacttc accctgacaa tcagcagcgt gcaggccgac gacattgccg tgtactactg     360
ccagcagagc agagagagcc ccttcacctt tggccagggc accaagctgg aactgaagag     420
agccgtggcc gctccctccg tgttcatctt cccacctagc gacgagcagc tgaagtctgg     480
cacagccagc gtcgtgtgcc tgctgaacaa cttctacccc cgcgaggcca aggtgcagtg     540
gaaggtggac aatgccctgc agagcggcaa cagccaggaa agcgtgaccg agcaggacag     600
caaggactcc acctacagcc tgagcagcac cctgaccctg agcaaggccg actacgagaa     660
gcacaaggtg tacgcctgcg aagtgaccca ccagggcctg tctagccccg tgaccaagag     720
cttcaaccgg ggcgagtgtt gagtttaaac gggggaggct aact                     764

<210> SEQ ID NO 36
<211> LENGTH: 238
<212> TYPE: PRT
<213> ORGANISM: Artificial
```

```
<220> FEATURE:
<223> OTHER INFORMATION: Amino acid sequence of humanized hA2-15A-L6
<220> FEATURE:
<221> NAME/KEY: SIGNAL
<222> LOCATION: (1)..(20)
<220> FEATURE:
<221> NAME/KEY: V_region
<222> LOCATION: (21)..(133)
<220> FEATURE:
<221> NAME/KEY: C_region
<222> LOCATION: (134)..(238)

<400> SEQUENCE: 36

Met Val Leu Gln Thr Gln Val Phe Ile Ser Leu Leu Leu Trp Ile Ser
1               5                   10                  15

Gly Ala Tyr Gly Asp Ile Val Leu Thr Gln Ser Pro Asp Ser Leu Ala
            20                  25                  30

Val Ser Leu Gly Glu Arg Ala Thr Ile Asn Cys Arg Ala Asn Gln Gly
        35                  40                  45

Val Ser Leu Ser Arg Tyr Asn Leu Met His Trp Tyr Gln Gln Lys Pro
    50                  55                  60

Gly Gln Lys Pro Lys Leu Leu Ile Tyr Arg Ser Ser Asn Leu Ala Gln
65                  70                  75                  80

Gly Ile Pro Ala Arg Phe Ser Gly Ser Gly Ser Gly Thr Asp Phe Thr
                85                  90                  95

Leu Thr Ile Ser Ser Val Gln Ala Asp Asp Ile Ala Val Tyr Tyr Cys
            100                 105                 110

Gln Gln Ser Arg Glu Ser Pro Phe Thr Phe Gly Gln Gly Thr Lys Leu
        115                 120                 125

Glu Leu Lys Arg Ala Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 37
<211> LENGTH: 764
<212> TYPE: DNA
<213> ORGANISM: Artificial
<220> FEATURE:
<223> OTHER INFORMATION: Nucleotide sequence of DNA fragment comprising
      the sequence coding for humanized hA2-15A-L7
<220> FEATURE:
<221> NAME/KEY: sig_peptide
<222> LOCATION: (26)..(85)
<220> FEATURE:
<221> NAME/KEY: V_region
<222> LOCATION: (86)..(424)
<220> FEATURE:
<221> NAME/KEY: C_region
<222> LOCATION: (425)..(739)

<400> SEQUENCE: 37
```

```
ccagcctccg gactctagag ccaccatggt gctgcagacc caggtgttca tcagcctgct    60
gctgtggatc agcggcgcct acggcgatat cgtgctgacc cagagccctg acagcctggc   120
cgtgtctctg ggagagaggg ccaccatcaa ctgcagagcc aaccagggcg tgtccctgag   180
ccggtacaac ctgatgcact ggtatcagca gaagcccggc cagaagccca agctggccat   240
ctacagaagc agcaacctgg ccagcggcat ccccgccaga tttctggca gcggctccgg   300
caccgacttc accctgacaa tcagcagcgt gcaggccgac gacattgccg tgtactactg   360
ccagcagagc agagagagcc ccttcacctt tggccagggc accaagctgg aactgaagag   420
agccgtggcc gctccctccg tgttcatctt cccacctagc gacgagcagc tgaagtctgg   480
cacagccagc gtcgtgtgcc tgctgaacaa cttctacccc cgcgaggcca aggtgcagtg   540
gaaggtggac aatgccctgc agagcggcaa cagccaggaa agcgtgaccg agcaggacag   600
caaggactcc acctacagcc tgagcagcac cctgaccctg agcaaggccg actacgagaa   660
gcacaaggtg tacgcctgcg aagtgaccca ccagggcctg tctagccccg tgaccaagag   720
cttcaaccgg ggcgagtgtt gagtttaaac gggggaggct aact                    764
```

<210> SEQ ID NO 38
<211> LENGTH: 238
<212> TYPE: PRT
<213> ORGANISM: Artificial
<220> FEATURE:
<223> OTHER INFORMATION: Amino acid sequence of humanized hA2-15A-L7
<220> FEATURE:
<221> NAME/KEY: SIGNAL
<222> LOCATION: (1)..(20)
<220> FEATURE:
<221> NAME/KEY: V_region
<222> LOCATION: (21)..(133)
<220> FEATURE:
<221> NAME/KEY: C_region
<222> LOCATION: (134)..(238)

<400> SEQUENCE: 38

Met Val Leu Gln Thr Gln Val Phe Ile Ser Leu Leu Leu Trp Ile
1               5                   10                  15

Ser Gly Ala Tyr Gly Asp Ile Val Leu Thr Gln Ser Pro Asp Ser Leu Ala
            20                  25                  30

Val Ser Leu Gly Glu Arg Ala Thr Ile Asn Cys Arg Ala Asn Gln Gly
        35                  40                  45

Val Ser Leu Ser Arg Tyr Asn Leu Met His Trp Tyr Gln Gln Lys Pro
    50                  55                  60

Gly Gln Lys Pro Lys Leu Ala Ile Tyr Arg Ser Ser Asn Leu Ala Ser
65                  70                  75                  80

Gly Ile Pro Ala Arg Phe Ser Gly Ser Gly Ser Gly Thr Asp Phe Thr
                85                  90                  95

Leu Thr Ile Ser Ser Val Gln Ala Asp Asp Ile Ala Val Tyr Tyr Cys
            100                 105                 110

Gln Gln Ser Arg Glu Ser Pro Phe Thr Phe Gly Gln Gly Thr Lys Leu
        115                 120                 125

Glu Leu Lys Arg Ala Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser

```
                    180                 185                 190
Lys Asp Ser Thr Tyr Ser Leu Ser Ser Thr Leu Thr Leu Ser Lys Ala
            195                 200                 205

Asp Tyr Glu Lys His Lys Val Tyr Ala Cys Glu Val Thr His Gln Gly
        210                 215                 220

Leu Ser Ser Pro Val Thr Lys Ser Phe Asn Arg Gly Glu Cys
225                 230                 235
```

<210> SEQ ID NO 39
<211> LENGTH: 1410
<212> TYPE: DNA
<213> ORGANISM: Artificial
<220> FEATURE:
<223> OTHER INFORMATION: Nucleotide sequence coding for humanized
      hA2-27D-H1
<220> FEATURE:
<221> NAME/KEY: sig_peptide
<222> LOCATION: (1)..(57)
<220> FEATURE:
<221> NAME/KEY: V_region
<222> LOCATION: (58)..(420)
<220> FEATURE:
<221> NAME/KEY: C_region
<222> LOCATION: (421)..(1410)

<400> SEQUENCE: 39

| | | |
|---|---|---|
| atgaaacacc tgtggttctt cctcctgctg gtggcagctc ccagatgggt gctgagcgaa | 60 |
| gtgcagctgg tggaatctgg cggcggactg gtgcagcctg gcggatctct gagactgagc | 120 |
| tgtgccgcca gcggcagcac cttcagcaac tacggcatga atgggtgcg ccaggcccct | 180 |
| ggcaagggac tggaatgggt gtccagcatc agcagaagca gcacctacat ctactacgcc | 240 |
| gacaccgtga aggccggtt caccatcagc cgggacaaca gcaagaacac cctgtacctg | 300 |
| cagatgaaca gcctgcgggc cgaggacacc gccgtgtact attgtgccag agccatcagc | 360 |
| accccttct actggtactt cgacttctgg ggccagggca ccctcgtgac cgtcagctca | 420 |
| gcctccacca agggcccaag cgtcttcccc ctggcaccct cctccaagag cacctctggc | 480 |
| ggcacagccg ccctgggctg cctggtcaag gactacttcc ccgaacccgt gaccgtgagc | 540 |
| tggaactcag gcgccctgac cagcggcgtg cacaccttcc ccgctgtcct gcagtcctca | 600 |
| ggactctact ccctcagcag cgtggtgacc gtgccctcca gcagcttggg cacccagacc | 660 |
| tacatctgca acgtgaatca caagcccagc aacaccaagg tggacaagag agttgagccc | 720 |
| aaatcttgtg acaaaactca cacatgccca ccctgcccag cacctgaact cctgggggga | 780 |
| ccctcagtct tcctcttccc cccaaaaccc aaggacaccc tcatgatctc ccggaccct | 840 |
| gaggtcacat gcgtggtggt ggacgtgagc cacgaagacc ctgaggtcaa gttcaactgg | 900 |
| tacgtggacg gcgtggaggt gcataatgcc aagacaaagc cccgggagga gcagtacaac | 960 |
| agcacgtacc gggtggtcag cgtcctcacc gtcctgcacc aggactggct gaatggcaag | 1020 |
| gagtacaagt gcaaggtctc caacaaagcc ctcccagccc ccatcgagaa aaccatctcc | 1080 |
| aaagccaaag gccagccccg ggaaccacag gtgtacaccc tgcccccatc ccgggaggag | 1140 |
| atgaccaaga accaggtcag cctgacctgc ctggtcaaag gcttctatcc cagcgacatc | 1200 |
| gccgtggagt gggagagcaa tggccagccc gagaacaact acaagaccac ccctcccgtg | 1260 |
| ctggactccg acggctcctt cttcctctac agcaagctca ccgtggacaa gagcaggtgg | 1320 |
| cagcagggca acgtcttctc atgctccgtg atgcatgagg ctctgcacaa ccactacacc | 1380 |
| cagaagagcc tctccctgtc tccgggcaaa | 1410 |

-continued

<210> SEQ ID NO 40
<211> LENGTH: 470
<212> TYPE: PRT
<213> ORGANISM: Artificial
<220> FEATURE:
<223> OTHER INFORMATION: Amino acid sequence of humanized hA2-27D-H1
<220> FEATURE:
<221> NAME/KEY: SIGNAL
<222> LOCATION: (1)..(19)
<220> FEATURE:
<221> NAME/KEY: V_region
<222> LOCATION: (20)..(140)
<220> FEATURE:
<221> NAME/KEY: C_region
<222> LOCATION: (141)..(470)

<400> SEQUENCE: 40

```
Met Lys His Leu Trp Phe Phe Leu Leu Leu Val Ala Ala Pro Arg Trp
1               5                   10                  15

Val Leu Ser Glu Val Gln Leu Val Glu Ser Gly Gly Gly Leu Val Gln
            20                  25                  30

Pro Gly Gly Ser Leu Arg Leu Ser Cys Ala Ala Ser Gly Ser Thr Phe
        35                  40                  45

Ser Asn Tyr Gly Met Lys Trp Val Arg Gln Ala Pro Gly Lys Gly Leu
    50                  55                  60

Glu Trp Val Ser Ser Ile Ser Arg Ser Ser Thr Tyr Ile Tyr Tyr Ala
65                  70                  75                  80

Asp Thr Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Ala Ile Ser Thr Pro Phe Tyr Trp Tyr Phe Asp
        115                 120                 125

Phe Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Arg Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320
```

```
Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 41
<211> LENGTH: 1410
<212> TYPE: DNA
<213> ORGANISM: Artificial
<220> FEATURE:
<223> OTHER INFORMATION: Nucleotide sequence coding for humanized
      hA2-27D-H2
<220> FEATURE:
<221> NAME/KEY: sig_peptide
<222> LOCATION: (1)..(57)
<220> FEATURE:
<221> NAME/KEY: V_region
<222> LOCATION: (58)..(420)
<220> FEATURE:
<221> NAME/KEY: C_region
<222> LOCATION: (421)..(1410)

<400> SEQUENCE: 41
atgaaacacc tgtggttctt cctcctgctg gtggcagctc ccagatgggt gctgagcgaa      60
gtgcagctgg tggaatctgg cggcggactg gtgcagcctg gcggatctct gagactgagc     120
tgtgccgcca gcggcagcac cttcagcaac tacggcatga gtggatccg gcaggcccct      180 ggcaagggcc tggaatgggt gtccagcatc agcagaagca gcacctacat ctactacgcc     240
gacaccgtga agggccggtt caccatcagc cgggacaaca gcaagaacac cctgtacctg     300
cagatgaaca gcctgcgggc cgaggacacc gccgtgtact attgtgccgc cgctatcagc     360 accccttct actggtactt cgacttctgg ggccagggca ccctcgtgac cgtcagctca      420
gcctccacca agggcccaag cgtcttcccc ctggcaccct cctccaagag cacctctggc     480
ggcacagccg ccctgggctg cctggtcaag gactacttcc ccgaacccgt gaccgtgagc     540
tggaactcag gcgccctgac cagcggcgtg cacaccttcc ccgctgtcct gcagtcctca     600
ggactctact ccctcagcag cgtggtgacc gtgccctcca gcagcttggg cacccagacc     660
tacatctgca acgtgaatca caagcccagc aacaccaagg tggacaagag agttgagccc     720
aaatcttgtg acaaaactca cacatgccca ccctgcccag cacctgaact cctgggggga     780
cctcagtctc tcctcttccc cccaaaaccc aaggacaccc tcatgatctc ccggaccctt     840
gaggtcacat gcgtggtggt ggacgtgagc cacgaagacc ctgaggtcaa gttcaactgg     900
```

-continued

```
tacgtggacg gcgtggaggt gcataatgcc aagacaaagc cccgggagga gcagtacaac    960
agcacgtacc gggtggtcag cgtcctcacc gtcctgcacc aggactggct gaatggcaag   1020
gagtacaagt gcaaggtctc caacaaagcc ctcccagccc ccatcgagaa aaccatctcc   1080
aaagccaaag gccagccccg ggaaccacag gtgtacaccc tgcccccatc ccgggaggag   1140
atgaccaaga accaggtcag cctgacctgc ctggtcaaag gcttctatcc cagcgacatc   1200
gccgtggagt gggagagcaa tggccagccc gagaacaact acaagaccac ccctcccgtg   1260
ctggactccg acggctcctt cttcctctac agcaagctca ccgtggacaa gagcaggtgg   1320
cagcagggca acgtcttctc atgctccgtg atgcatgagg ctctgcacaa ccactacacc   1380
cagaagagcc tctccctgtc tcccggcaaa                                    1410
```

<210> SEQ ID NO 42
<211> LENGTH: 470
<212> TYPE: PRT
<213> ORGANISM: Artificial
<220> FEATURE:
<223> OTHER INFORMATION: Amino acid sequence of humanized hA2-27D-H2
<220> FEATURE:
<221> NAME/KEY: SIGNAL
<222> LOCATION: (1)..(19)
<220> FEATURE:
<221> NAME/KEY: V_region
<222> LOCATION: (20)..(140)
<220> FEATURE:
<221> NAME/KEY: C_region
<222> LOCATION: (141)..(470)

<400> SEQUENCE: 42

```
Met Lys His Leu Trp Phe Phe Leu Leu Leu Val Ala Ala Pro Arg Trp
1               5                   10                  15

Val Leu Ser Glu Val Gln Leu Val Glu Ser Gly Gly Gly Leu Val Gln
            20                  25                  30

Pro Gly Gly Ser Leu Arg Leu Ser Cys Ala Ala Ser Gly Ser Thr Phe
        35                  40                  45

Ser Asn Tyr Gly Met Lys Trp Ile Arg Gln Ala Pro Gly Lys Gly Leu
    50                  55                  60

Glu Trp Val Ser Ser Ile Ser Arg Ser Ser Thr Tyr Ile Tyr Tyr Ala
65                  70                  75                  80

Asp Thr Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Ala Ala Ile Ser Thr Pro Phe Tyr Trp Tyr Phe Asp
        115                 120                 125

Phe Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220
```

```
Val Asn His Lys Pro Ser Asn Thr Lys Val Asp Lys Arg Val Glu Pro
225                 230                 235                 240

Lys Ser Cys Asp Lys Thr His Thr Cys Pro Pro Cys Pro Ala Pro Glu
            245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
            275                 280                 285

Val Ser His Glu Asp Pro Glu Val Lys Phe Asn Trp Tyr Val Asp Gly
290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
            355                 360                 365

Pro Gln Val Tyr Thr Leu Pro Pro Ser Arg Glu Glu Met Thr Lys Asn
370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 43
<211> LENGTH: 1410
<212> TYPE: DNA
<213> ORGANISM: Artificial
<220> FEATURE:
<223> OTHER INFORMATION: Nucleotide sequence coding for humanized
      hA2-27D-H3
<220> FEATURE:
<221> NAME/KEY: sig_peptide
<222> LOCATION: (1)..(57)
<220> FEATURE:
<221> NAME/KEY: V_region
<222> LOCATION: (58)..(420)
<220> FEATURE:
<221> NAME/KEY: C_region
<222> LOCATION: (421)..(1410)

<400> SEQUENCE: 43
atgaaacacc tgtggttctt cctcctgctg gtggcagctc ccagatgggt gctgagcgaa      60
gtgcagctgg tggaatctgg cggcggactg gtgcagcctg gcggatctct gagactgagc     120
tgtgccgcca gcggcagcac cttcagcaac tacggcatga gtggatccg gcaggcccct     180 ggcaagggcc tggaatgggt ggccagcatc agcagaagca gcacctacat ctactacgcc     240
gacaccgtga agggccggtt caccatcagc cgggacaaca gcaagaacac cctgtacctg     300
```

```
cagatgaaca gcctgcgggc cgaggacacc gccgtgtact attgtgccgc cgctatcagc      360 accccttct  actggtactt cgacttctgg ggccagggca ccctcgtgac cgtcagctca      420
gcctccacca agggcccaag cgtcttcccc ctggcaccct cctccaagag cacctctggc      480
ggcacagccg ccctgggctg cctggtcaag gactacttcc ccgaacccgt gaccgtgagc      540
tggaactcag gcgccctgac cagcggcgtg cacaccttcc ccgctgtcct gcagtcctca      600
ggactctact ccctcagcag cgtggtgacc gtgccctcca gcagcttggg cacccagacc      660
tacatctgca acgtgaatca caagcccagc aacaccaagg tggacaagag agttgagccc      720
aaatcttgtg acaaaactca cacatgccca ccctgcccag cacctgaact cctgggggga      780 cccctcagtct tcctcttccc cccaaaaccc aaggacaccc tcatgatctc ccggacccct      840
gaggtcacat gcgtggtggt ggacgtgagc cacgaagacc ctgaggtcaa gttcaactgg      900
tacgtggacg gcgtggaggt gcataatgcc aagacaaagc cccgggagga gcagtacaac      960
agcacgtacc gggtggtcag cgtcctcacc gtcctgcacc aggactggct gaatggcaag      1020
gagtacaagt gcaaggtctc caacaaagcc ctcccagccc ccatcgagaa aaccatctcc      1080
aaagccaaag gccagccccg ggaaccacag gtgtacaccc tgcccccatc ccgggaggag      1140
atgaccaaga accaggtcag cctgacctgc ctggtcaaag cttctatcc cagcgacatc      1200 gccgtggagt gggagagcaa tggccagccc gagaacaact acaagaccac ccctcccgtg      1260
ctggactccg acggctcctt cttcctctac agcaagctca ccgtggacaa gagcaggtgg      1320
cagcagggca acgtcttctc atgctccgtg atgcatgagg ctctgcacaa ccactacacc      1380
cagaagagcc tctccctgtc tccggcaaa                                        1410
```

<210> SEQ ID NO 44
<211> LENGTH: 470
<212> TYPE: PRT
<213> ORGANISM: Artificial
<220> FEATURE:
<223> OTHER INFORMATION: Amino acid sequence of humanized hA2-27D-H3
<220> FEATURE:
<221> NAME/KEY: SIGNAL
<222> LOCATION: (1)..(19)
<220> FEATURE:
<221> NAME/KEY: V_region
<222> LOCATION: (20)..(140)
<220> FEATURE:
<221> NAME/KEY: C_region
<222> LOCATION: (141)..(470)

<400> SEQUENCE: 44

```
Met Lys His Leu Trp Phe Phe Leu Leu Val Ala Ala Pro Arg Trp
1               5                   10                  15

Val Leu Ser Glu Val Gln Leu Val Glu Ser Gly Gly Gly Leu Val Gln
            20                  25                  30

Pro Gly Gly Ser Leu Arg Leu Ser Cys Ala Ala Ser Gly Ser Thr Phe
            35                  40                  45

Ser Asn Tyr Gly Met Lys Trp Ile Arg Gln Ala Pro Gly Lys Gly Leu
            50                  55                  60

Glu Trp Val Ala Ser Ile Ser Arg Ser Thr Tyr Ile Tyr Tyr Ala
65                  70                  75                  80

Asp Thr Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Ala Ala Ile Ser Thr Pro Phe Tyr Trp Tyr Phe Asp
```

```
            115                 120                 125
Phe Trp Gly Gln Gly Thr Leu Val Thr Val Ser Ser Ala Ser Thr Lys
        130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Leu Gly Thr Gln Thr Tyr Ile Cys Asn
210                 215                 220

Val Asn His Lys Pro Ser Asn Thr Lys Val Asp Lys Arg Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Glu Glu Met Thr Lys Asn
370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
        450                 455                 460

Ser Leu Ser Pro Gly Lys
465                 470

<210> SEQ ID NO 45
<211> LENGTH: 1410
<212> TYPE: DNA
<213> ORGANISM: Artificial
<220> FEATURE:
<223> OTHER INFORMATION: Nucleotide sequence coding for humanized
      hA2-27D-H4
<220> FEATURE:
<221> NAME/KEY: sig_peptide
<222> LOCATION: (1)..(57)
```

```
<220> FEATURE:
<221> NAME/KEY: V_region
<222> LOCATION: (58)..(420)
<220> FEATURE:
<221> NAME/KEY: C_region
<222> LOCATION: (421)..(1410)

<400> SEQUENCE: 45
atgaaacacc tgtggttctt cctcctgctg gtggcagctc ccagatgggt gctgagcgaa      60
gtgcagctgg tggaatctgg cggcggactg gtgcagcctg gcggatctct gagactgagc     120
tgtgccgcca gcggcagcac cttcagcaac tacggcatga agtggatccg gcaggcccct     180
ggcaagggcc tggaatgggt ggccagcatc agcagaagca gcacctacat ctactacgcc     240
gacaccgtga agggccggtt caccatcagc cggacaacag caagaacac cctgtacctg      300
cagatgaaca gcctgcgggc cgaggacacc gccctgtact attgtgccgc cgctatcagc     360
acccccttct actggtactt cgacttctgg ggccctggca ccctcgtgac cgtcagctca     420
gcctccacca agggcccaag cgtcttcccc ctggcaccct cctccaagag cacctctggc     480
ggcacagccg ccctgggctg cctggtcaag gactacttcc ccgaaccgt gaccgtgagc      540
tggaactcag cgccctgac cagcggcgtg cacaccttcc ccgctgtcct gcagtcctca      600
ggactctact ccctcagcag cgtggtgacc gtgccctcca gcagcttggg cacccagacc     660
tacatctgca acgtgaatca caagcccagc aacaccaagg tggacaagag agttgagccc     720
aaatcttgtg acaaaactca cacatgccca ccctgcccag cacctgaact cctgggggga     780
cccccagtct tcctcttccc cccaaaaccc aaggacaccc tcatgatctc ccggacccct     840
gaggtcacat gcgtggtggt ggacgtgagc cacgaagacc ctgaggtcaa gttcaactgg     900
tacgtggacg gcgtggaggt gcataatgcc aagacaaagc cccggaggga gcagtacaac     960
agcacgtacc gggtggtcag cgtcctcacc gtcctgcacc aggactggct gaatggcaag    1020
gagtacaagt gcaaggtctc caacaaagcc ctcccagccc ccatcgagaa aaccatctcc    1080
aaagccaaag gccagccccg ggaaccacag gtgtacaccc tgcccccatc ccgggaggag    1140
atgaccaaga accaggtcag cctgacctgc ctggtcaaag gcttctatcc cagcgacatc    1200
gccgtggagt gggagagcaa tggccagccc gagaacaact acaagaccac ccctcccgtg    1260
ctggactccg acggctcctt cttcctctac agcaagctca ccgtggacaa gagcaggtgg    1320
cagcagggca acgtcttctc atgctccgtg atgcatgagg ctctgcacaa ccactacacc    1380
cagaagagcc tctccctgtc tccgggcaaa                                     1410

<210> SEQ ID NO 46
<211> LENGTH: 470
<212> TYPE: PRT
<213> ORGANISM: Artificial
<220> FEATURE:
<223> OTHER INFORMATION: Amino acid sequence of humanized hA2-27D-H4
<220> FEATURE:
<221> NAME/KEY: SIGNAL
<222> LOCATION: (1)..(19)
<220> FEATURE:
<221> NAME/KEY: V_region
<222> LOCATION: (20)..(140)
<220> FEATURE:
<221> NAME/KEY: C_region
<222> LOCATION: (141)..(470)

<400> SEQUENCE: 46

Met Lys His Leu Trp Phe Phe Leu Leu Leu Val Ala Ala Pro Arg Trp
1               5                   10                  15
```

```
Val Leu Ser Glu Val Gln Leu Val Glu Ser Gly Gly Gly Leu Val Gln
            20                  25                  30

Pro Gly Gly Ser Leu Arg Leu Ser Cys Ala Ala Ser Gly Ser Thr Phe
        35                  40                  45

Ser Asn Tyr Gly Met Lys Trp Ile Arg Gln Ala Pro Gly Lys Gly Leu
    50                  55                  60

Glu Trp Val Ala Ser Ile Ser Arg Ser Ser Thr Tyr Ile Tyr Tyr Ala
65                  70                  75                  80

Asp Thr Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Leu
            100                 105                 110

Tyr Tyr Cys Ala Ala Ile Ser Thr Pro Phe Tyr Trp Tyr Phe Asp
        115                 120                 125

Phe Trp Gly Pro Gly Thr Leu Val Thr Val Ser Ser Ala Ser Thr Lys
130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
210                 215                 220

Val Asn His Lys Pro Ser Asn Thr Lys Val Asp Lys Arg Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Glu Glu Met Thr Lys Asn
370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
```

```
                435                 440                 445
Ser Val Met His Glu Ala Leu His Asn His Tyr Thr Gln Lys Ser Leu
    450                 455                 460
Ser Leu Ser Pro Gly Lys
465                 470

<210> SEQ ID NO 47
<211> LENGTH: 1410
<212> TYPE: DNA
<213> ORGANISM: Artificial
<220> FEATURE:
<223> OTHER INFORMATION: Nucleotide sequence coding for humanized
      hA2-27D-H5
<220> FEATURE:
<221> NAME/KEY: sig_peptide
<222> LOCATION: (1)..(57)
<220> FEATURE:
<221> NAME/KEY: V_region
<222> LOCATION: (58)..(420)
<220> FEATURE:
<221> NAME/KEY: C_region
<222> LOCATION: (421)..(1410)

<400> SEQUENCE: 47
atgaaacacc tgtggttctt cctcctgctg gtggcagctc ccagatgggt gctgagcgaa      60
gtgcagctgg tggaatctgg cggcggactg gtgcagcctg gcggatctct gagactgagc     120
tgtgccgcca gcggcagcac cttcagcaac tacggcatga gtggatccg gcaggccct      180 ggcaagggcc tggaatgggt ggccagcatc agcagaagca gcacctacat ctactacgcc     240
gacaccgtga agggccggtt caccatctcc cgggacaacg ccaagaacac cctgtacctg     300
cagatgaaca gcctgcggag cgaggacacc gccctgtact attgtgccgc cgctatcagc     360 accccttct actggtactt cgacttctgg ggccctggca cctcgtgac cgtcagctca      420 gcctccacca agggcccaag cgtcttcccc ctggcaccct cctccaagag cacctctggc     480
ggcacagccg ccctgggctg cctggtcaag gactacttcc ccgaaccgt gaccgtgagc     540 tggaactcag gcgccctgac cagcggcgtg cacaccttcc ccgctgtcct gcagtcctca     600
ggactctact ccctcagcag cgtggtgacc gtgccctcca gcagcttggg cacccagacc     660
tacatctgca acgtgaatca caagcccagc aacaccaagg tggacaagag agttgagccc     720
aaatcttgtg acaaaactca cacatgccca ccctgcccag cacctgaact cctgggggga     780
ccctcagtct tcctcttccc cccaaaaccc aaggacaccc tcatgatctc ccggacccct     840
gaggtcacat gcgtggtggt ggacgtgagc cacgaagacc ctgaggtcaa gttcaactgg     900
tacgtggacg gcgtggaggt gcataatgcc aagacaaagc cccgggagga gcagtacaac     960
agcacgtacc gggtggtcag cgtcctcacc gtcctgcacc aggactggct gaatggcaag    1020
gagtacaagt gcaaggtctc caacaaagcc ctcccagccc ccatcgagaa aaccatctcc    1080
aaagccaaag ccagccccg gaaccacag gtgtacaccc tgcccccatc ccgggaggag    1140
atgaccaaga accaggtcag cctgacctgc ctggtcaaag gcttctatcc cagcgacatc    1200
gccgtggagt gggagagcaa tggccagccc gagaacaact acaagaccac cctcccgtg    1260 ctggactccg acggctcctt cttcctctac agcaagctca ccgtggacaa gagcaggtgg    1320
cagcagggca acgtcttctc atgctccgtg atgcatgagg ctctgcacaa ccactacacc    1380
cagaagagcc tctccctgtc tccggcaaa                                     1410

<210> SEQ ID NO 48
<211> LENGTH: 470
```

```
<212> TYPE: PRT
<213> ORGANISM: Artificial
<220> FEATURE:
<223> OTHER INFORMATION: Amino acid sequence of humanized hA2-27D-H5
<220> FEATURE:
<221> NAME/KEY: SIGNAL
<222> LOCATION: (1)..(19)
<220> FEATURE:
<221> NAME/KEY: V_region
<222> LOCATION: (20)..(140)
<220> FEATURE:
<221> NAME/KEY: C_region
<222> LOCATION: (141)..(470)

<400> SEQUENCE: 48
```

Met Lys His Leu Trp Phe Phe Leu Leu Leu Val Ala Ala Pro Arg Trp
1               5                   10                  15

Val Leu Ser Glu Val Gln Leu Val Glu Ser Gly Gly Gly Leu Val Gln
            20                  25                  30

Pro Gly Gly Ser Leu Arg Leu Ser Cys Ala Ala Ser Gly Ser Thr Phe
        35                  40                  45

Ser Asn Tyr Gly Met Lys Trp Ile Arg Gln Ala Pro Gly Lys Gly Leu
    50                  55                  60

Glu Trp Val Ala Ser Ile Ser Arg Ser Ser Thr Tyr Ile Tyr Tyr Ala
65                  70                  75                  80

Asp Thr Val Lys Gly Arg Phe Thr Ile Ser Arg Asp Asn Ala Lys Asn
                85                  90                  95

Thr Leu Tyr Leu Gln Met Asn Ser Leu Arg Ser Glu Asp Thr Ala Leu
            100                 105                 110

Tyr Tyr Cys Ala Ala Ala Ile Ser Thr Pro Phe Tyr Trp Tyr Phe Asp
        115                 120                 125

Phe Trp Gly Pro Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Arg Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

-continued

```
Leu Asn Gly Lys Glu Tyr Lys Cys Lys Val Ser Asn Lys Ala Leu Pro
            340                 345                 350
Ala Pro Ile Glu Lys Thr Ile Ser Lys Ala Lys Gly Gln Pro Arg Glu
        355                 360                 365
Pro Gln Val Tyr Thr Leu Pro Pro Ser Arg Glu Glu Met Thr Lys Asn
370                 375                 380
Gln Val Ser Leu Thr Cys Leu Val Lys Gly Phe Tyr Pro Ser Asp Ile
385                 390                 395                 400
Ala Val Glu Trp Glu Ser Asn Gly Gln Pro Glu Asn Asn Tyr Lys Thr
                405                 410                 415
Thr Pro Pro Val Leu Asp Ser Asp Gly Ser Phe Phe Leu Tyr Ser Lys
            420                 425                 430
Leu Thr Val Asp Lys Ser Arg Trp Gln Gln Gly Asn Val Phe Ser Cys
        435                 440                 445
Ser Val Met His Glu Ala Leu His Asn His Tyr Thr Gln Lys Ser Leu
    450                 455                 460
Ser Leu Ser Pro Gly Lys
465                 470
```

<210> SEQ ID NO 49
<211> LENGTH: 752
<212> TYPE: DNA
<213> ORGANISM: Artificial
<220> FEATURE:
<223> OTHER INFORMATION: Nucleotide sequence of DNA fragment comprising
      the sequence coding for humanized hA2-27D-L1
<220> FEATURE:
<221> NAME/KEY: sig_peptide
<222> LOCATION: (26)..(85)
<220> FEATURE:
<221> NAME/KEY: V_region
<222> LOCATION: (86)..(412)
<220> FEATURE:
<221> NAME/KEY: C_region
<222> LOCATION: (413)..(727)

<400> SEQUENCE: 49

```
ccagcctccg gactctagag ccaccatggt gctgcagacc caggtgttca tcagcctgct    60
gctgtggatc agcggcgcct acggcgagat cgtgctgaca cagagccctg caccctgag   120
cctgtctcca ggcgaaagag ccaccctgtc ctgtctggcc agcagcagcg tgtcctacat   180
gacctggtat cagcagaagc ccggccaggc ccccagactg ctgatctacg acaagcaa    240
tctggcctcc ggcatccccg acagattttc cggctctggc agcggcaccg acttcaccct   300
gaccatcagc agactggaac ccgaggactt cgccgtgtac tactgcctgc acctgaccag   360
ctaccccccc tacacatttg gccagggcac caaggtggaa atcaagcggg ctgtggccgc   420
tccctccgtg ttcatctttc cacccagcga cgagcagctg aagtccggca cagctagcgt   480
cgtgtgcctg ctgaacaact tctaccccg cgaggccaag gtgcagtgga aggtggacaa   540
tgccctgcag agcggcaact cccaggaaag cgtgaccgag caggacagca aggactccac   600
ctacagcctg agcagcaccc tgacactgag caaggccgac tacgagaagc acaaggtgta   660
cgcctgcgaa gtgacccacc agggcctgtc tagccccgtg accaagagct caaccgggg   720
cgagtgttga gtttaaacgg gggaggctaa ct                                 752
```

<210> SEQ ID NO 50
<211> LENGTH: 234
<212> TYPE: PRT
<213> ORGANISM: Artificial
<220> FEATURE:

<223> OTHER INFORMATION: Amino acid sequence of humanized hA2-27D-L1
<220> FEATURE:
<221> NAME/KEY: SIGNAL
<222> LOCATION: (1)..(20)
<220> FEATURE:
<221> NAME/KEY: V_region
<222> LOCATION: (21)..(129)
<220> FEATURE:
<221> NAME/KEY: C_region
<222> LOCATION: (130)..(234)

<400> SEQUENCE: 50

```
Met Val Leu Gln Thr Gln Val Phe Ile Ser Leu Leu Trp Ile Ser
1               5                   10                  15

Gly Ala Tyr Gly Glu Ile Val Leu Thr Gln Ser Pro Gly Thr Leu Ser
            20                  25                  30

Leu Ser Pro Gly Glu Arg Ala Thr Leu Ser Cys Leu Ala Ser Ser Ser
        35                  40                  45

Val Ser Tyr Met Thr Trp Tyr Gln Gln Lys Pro Gly Gln Ala Pro Arg
    50                  55                  60

Leu Leu Ile Tyr Gly Thr Ser Asn Leu Ala Ser Gly Ile Pro Asp Arg
65                  70                  75                  80

Phe Ser Gly Ser Gly Ser Gly Thr Asp Phe Thr Leu Thr Ile Ser Arg
                85                  90                  95

Leu Glu Pro Glu Asp Phe Ala Val Tyr Tyr Cys Leu His Leu Thr Ser
            100                 105                 110

Tyr Pro Pro Tyr Thr Phe Gly Gln Gly Thr Lys Val Glu Ile Lys Arg
        115                 120                 125

Ala Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 51
<211> LENGTH: 752
<212> TYPE: DNA
<213> ORGANISM: Artificial
<220> FEATURE:
<223> OTHER INFORMATION: Nucleotide sequence of DNA fragment comprising the sequence coding for humanized hA2-27D-L2
<220> FEATURE:
<221> NAME/KEY: sig_peptide
<222> LOCATION: (26)..(85)
<220> FEATURE:
<221> NAME/KEY: V_region
<222> LOCATION: (86)..(412)
<220> FEATURE:
<221> NAME/KEY: C_region
<222> LOCATION: (413)..(727)

<400> SEQUENCE: 51
ccagcctccg gactctagag ccaccatggt gctgcagacc caggtgttca tcagcctgct    60

```
gctgtggatc agcggcgcct acggcgagat cgtgctgaca cagagccctg gcaccctgag    120
cctgtctcca ggcgaaagag ccaccctgtc ctgtctggcc agcagcagcg tgtcctacat    180
gacctggtat cagcagaagc ccggccagag ccccagactg tggatctacg gcaccagcaa    240
tctggcctcc ggcgtgcccg atagattttc cggctctggc agcggcaccg acttcaccct    300
gaccatcagc agactggaac ccgaggactt cgccgtgtac tactgcctgc acctgaccag    360
ctaccccccc tacacatttg gccagggcac caaggtggaa atcaagcggg ctgtggccgc    420
tccctccgtg ttcatctttc acccagcga cgagcagctg aagtccggca cagctagcgt    480
cgtgtgcctg ctgaacaact ctacccccg cgaggccaag gtgcagtgga aggtggacaa    540
tgccctgcag agcggcaact cccaggaaag cgtgaccgag caggacagca aggactccac    600
ctacagcctg agcagcaccc tgacactgag caaggccgac tacgagaagc acaaggtgta    660
cgcctgcgaa gtgacccacc agggcctgtc tagccccgtg accaagagct tcaaccgggg    720
cgagtgttga gtttaaacgg gggaggctaa ct                                  752
```

<210> SEQ ID NO 52
<211> LENGTH: 234
<212> TYPE: PRT
<213> ORGANISM: Artificial
<220> FEATURE:
<223> OTHER INFORMATION: Amino acid sequence of humanized hA2-27D-L2
<220> FEATURE:
<221> NAME/KEY: SIGNAL
<222> LOCATION: (1)..(20)
<220> FEATURE:
<221> NAME/KEY: V_region
<222> LOCATION: (21)..(129)
<220> FEATURE:
<221> NAME/KEY: C_region
<222> LOCATION: (130)..(234)

<400> SEQUENCE: 52

Met Val Leu Gln Thr Gln Val Phe Ile Ser Leu Leu Trp Ile Ser
1               5                   10                  15

Gly Ala Tyr Gly Glu Ile Val Leu Thr Gln Ser Pro Gly Thr Leu Ser
                20                  25                  30

Leu Ser Pro Gly Glu Arg Ala Thr Leu Ser Cys Leu Ala Ser Ser Ser
            35                  40                  45

Val Ser Tyr Met Thr Trp Tyr Gln Gln Lys Pro Gly Gln Ser Pro Arg
    50                  55                  60

Leu Trp Ile Tyr Gly Thr Ser Asn Leu Ala Ser Gly Val Pro Asp Arg
65                  70                  75                  80

Phe Ser Gly Ser Gly Ser Gly Thr Asp Phe Thr Leu Thr Ile Ser Arg
                85                  90                  95

Leu Glu Pro Glu Asp Phe Ala Val Tyr Tyr Cys Leu His Leu Thr Ser
            100                 105                 110

Tyr Pro Pro Tyr Thr Phe Gly Gln Gly Thr Lys Val Glu Ile Lys Arg
        115                 120                 125

Ala Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

```
Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 53
<211> LENGTH: 752
<212> TYPE: DNA
<213> ORGANISM: Artificial
<220> FEATURE:
<223> OTHER INFORMATION: Nucleotide sequence of DNA fragment comprising
      the sequence coding for humanized hA2-27D-L3
<220> FEATURE:
<221> NAME/KEY: sig_peptide
<222> LOCATION: (26)..(85)
<220> FEATURE:
<221> NAME/KEY: V_region
<222> LOCATION: (86)..(412)
<220> FEATURE:
<221> NAME/KEY: C_region
<222> LOCATION: (413)..(727)

<400> SEQUENCE: 53
ccagcctccg gactctagag ccaccatggt gctgcagacc caggtgttca tcagcctgct      60
gctgtggatc agcggcgcct acggcgagat cgtgctgaca cagagccctg gcaccctgag     120
cctgtctcca ggcgaaagag ccaccctgtc ctgtctggcc agcagcagcg tgtcctacat     180
gacctggtat cagcagaaag caggcgccag ccccagactg tggatctacg acacaagcaa     240
cctggccagc ggcgtgcccg atagattttc tggcagcggc tccggcaccg actacaccct     300
gacaatcagc agactggaac ccgaggactt cgccacctac tactgcctgc acctgaccag     360
ctaccccccc tacacatttg gagccggcac caaggtggaa atcaagcggg ctgtggccgc     420 tcccteegtt ttcatctttc cacccagcga cgagcagctg aagtctggca cagccagcgt     480
cgtgtgcctg ctgaacaact tctaccccg cgaggccaag gtgcagtgga aggtggacaa     540
tgccctgcag agcggcaact cccaggaaag cgtgaccgag caggacagca aggactccac     600
ctacagcctg agcagcacac tgaccctgag caaggccgac tacgagaagc acaaggtgta     660
cgcctgcgaa gtgacccacc agggcctgtc tagccccgtg accaagagct caaccgggg     720 cgagtgttga gtttaaacgg gggaggctaa ct                                   752

<210> SEQ ID NO 54
<211> LENGTH: 234
<212> TYPE: PRT
<213> ORGANISM: Artificial
<220> FEATURE:
<223> OTHER INFORMATION: Amino acid sequence of humanized hA2-27D-L3
<220> FEATURE:
<221> NAME/KEY: SIGNAL
<222> LOCATION: (1)..(20)
<220> FEATURE:
<221> NAME/KEY: V_region
<222> LOCATION: (21)..(129)
<220> FEATURE:
<221> NAME/KEY: C_region
<222> LOCATION: (130)..(234)

<400> SEQUENCE: 54

Met Val Leu Gln Thr Gln Val Phe Ile Ser Leu Leu Leu Trp Ile Ser
1               5                   10                  15

Gly Ala Tyr Gly Glu Ile Val Leu Thr Gln Ser Pro Gly Thr Leu Ser
```

```
                20                  25                  30
Leu Ser Pro Gly Glu Arg Ala Thr Leu Ser Cys Leu Ala Ser Ser
            35                  40                  45
Val Ser Tyr Met Thr Trp Tyr Gln Gln Lys Pro Gly Ala Ser Pro Arg
50                  55                  60
Leu Trp Ile Tyr Gly Thr Ser Asn Leu Ala Ser Gly Val Pro Asp Arg
65                  70                  75                  80
Phe Ser Gly Ser Gly Ser Gly Thr Asp Tyr Thr Leu Thr Ile Ser Arg
                85                  90                  95
Leu Glu Pro Glu Asp Phe Ala Thr Tyr Tyr Cys Leu His Leu Thr Ser
            100                 105                 110
Tyr Pro Pro Tyr Thr Phe Gly Ala Gly Thr Lys Val Glu Ile Lys Arg
            115                 120                 125
Ala Val Ala Ala Pro Ser Val Phe Ile Phe Pro Pro Ser Asp Glu Gln
            130                 135                 140
Leu Lys Ser Gly Thr Ala Ser Val Val Cys Leu Leu Asn Asn Phe Tyr
145                 150                 155                 160
Pro Arg Glu Ala Lys Val Gln Trp Lys Val Asp Asn Ala Leu Gln Ser
                165                 170                 175
Gly Asn Ser Gln Glu Ser Val Thr Glu Gln Asp Ser Lys Asp Ser Thr
            180                 185                 190
Tyr Ser Leu Ser Ser Thr Leu Thr Leu Ser Lys Ala Asp Tyr Glu Lys
            195                 200                 205
His Lys Val Tyr Ala Cys Glu Val Thr His Gln Gly Leu Ser Ser Pro
            210                 215                 220
Val Thr Lys Ser Phe Asn Arg Gly Glu Cys
225                 230

<210> SEQ ID NO 55
<211> LENGTH: 752
<212> TYPE: DNA
<213> ORGANISM: Artificial
<220> FEATURE:
<223> OTHER INFORMATION: Nucleotide sequence of DNA fragment comprising
      the sequence coding for humanized hA2-27D-L4
<220> FEATURE:
<221> NAME/KEY: sig_peptide
<222> LOCATION: (26)..(85)
<220> FEATURE:
<221> NAME/KEY: V_region
<222> LOCATION: (86)..(412)
<220> FEATURE:
<221> NAME/KEY: C_region
<222> LOCATION: (413)..(727)

<400> SEQUENCE: 55
ccagcctccg gactctagag ccaccatggt gctgcagacc caggtgttca tcagcctgct      60
gctgtggatc agcggcgcct acggcgagat cgtgctgaca cagagccctg caccatgtc     120 tgccagccct ggcgagagag tgaccctgag ctgtctggcc agctccagcg tgtcctacat     180
gacctggtat cagcagaagc caggcgccag ccccagactg tggatctacg gcacaagcaa     240
cctggccagc ggcgtgcccg atagattttc tggcagcggc tccggcaccg actacaccct     300
gaccatcagc cggatggaac ccgaggactt cgccacctac tactgcctgc acctgaccag     360
ctaccccccc tacacatttg gagccggcac caagctggaa ctgaagagag ccgtggctgc     420 ccctccgtg ttcatcttcc cacctagcga cgagcagctg aagtctggca cagccagcgt     480
cgtgtgcctg ctgaacaact ctaccccccg cgaggccaag gtgcagtgga aggtggacaa     540
```

```
tgccctgcag agcggcaaca gccaggaaag cgtgaccgag caggacagca aggactccac    600
ctacagcctg agcagcaccc tgacactgag caaggccgac tacgagaagc acaaggtgta    660
cgcctgcgaa gtgacccacc agggcctgtc tagccccgtg accaagagct caaccgggg     720 cgagtgttga gtttaaacgg gggaggctaa ct                                  752
```

<210> SEQ ID NO 56
<211> LENGTH: 234
<212> TYPE: PRT
<213> ORGANISM: Artificial
<220> FEATURE:
<223> OTHER INFORMATION: Amino acid sequence of humanized hA2-27D-L4
<220> FEATURE:
<221> NAME/KEY: SIGNAL
<222> LOCATION: (1)..(20)
<220> FEATURE:
<221> NAME/KEY: V_region
<222> LOCATION: (21)..(129)
<220> FEATURE:
<221> NAME/KEY: C_region
<222> LOCATION: (130)..(234)

<400> SEQUENCE: 56

```
Met Val Leu Gln Thr Gln Val Phe Ile Ser Leu Leu Trp Ile Ser
1               5                   10                  15

Gly Ala Tyr Gly Glu Ile Val Leu Thr Gln Ser Pro Gly Thr Met Ser
                20                  25                  30

Ala Ser Pro Gly Glu Arg Val Thr Leu Ser Cys Leu Ala Ser Ser Ser
            35                  40                  45

Val Ser Tyr Met Thr Trp Tyr Gln Gln Lys Pro Gly Ala Ser Pro Arg
50                  55                  60

Leu Trp Ile Tyr Gly Thr Ser Asn Leu Ala Ser Gly Val Pro Asp Arg
65                  70                  75                  80

Phe Ser Gly Ser Gly Ser Gly Thr Asp Tyr Thr Leu Thr Ile Ser Arg
                85                  90                  95

Met Glu Pro Glu Asp Phe Ala Thr Tyr Tyr Cys Leu His Leu Thr Ser
                100                 105                 110

Tyr Pro Pro Tyr Thr Phe Gly Ala Gly Thr Lys Leu Glu Leu Lys Arg
            115                 120                 125

Ala Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 57
<211> LENGTH: 752
<212> TYPE: DNA
<213> ORGANISM: Artificial
<220> FEATURE:
<223> OTHER INFORMATION: Nucleotide sequence of DNA fragment comprising the sequence coding for humanized hA2-27D-L5
<220> FEATURE:
<221> NAME/KEY: sig_peptide
<222> LOCATION: (26)..(85)
<220> FEATURE:
<221> NAME/KEY: V_region
<222> LOCATION: (86)..(412)
<220> FEATURE:
<221> NAME/KEY: C_region
<222> LOCATION: (413)..(727)

<400> SEQUENCE: 57

```
ccagcctccg gactctagag ccaccatggt gctgcagacc caggtgttca tcagcctgct      60
gctgtggatc agcggcgcct acggcgagat cgtgctgaca cagagccctg gcaccatgtc     120
tgccagccct ggcgagagag tgaccctgaa ttgtctggcc agcagcagcg tgtcctacat     180
gacctggtat cagcagaagt ccggcgccag ccccaaactg tggatctacg gcaccagcaa     240
cctggccagc ggcgtgccca atagattttc cggcagcggc tccggcacct cctacaccct     300
gaccatcagc cggatggaac ccgaggactt cgccacctac tactgcctgc acctgaccag     360
ctaccccccc tacacatttg gagccggcac caagctggaa ctgaagagag ccgtggccgc     420
tcccctccgt gttcatcttcc cacctagcga cgagcagctg aagtctggca cagccagcgt     480
cgtgtgcctg ctgaacaact ctacccccg cgaggccaag gtgcagtgga aggtggacaa     540
tgccctgcag agcggcaaca gccaggaaag cgtgaccgag caggacagca aggactccac     600
ctacagcctg agcagcaccc tgacactgag caaggccgac tacgagaagc acaaggtgta     660
cgcctgcgaa gtgacccacc agggcctgtc tagccccgtg accaagagct tcaaccgggg     720
cgagtgttga gtttaaacgg gggaggctaa ct                                   752
```

<210> SEQ ID NO 58
<211> LENGTH: 234
<212> TYPE: PRT
<213> ORGANISM: Artificial
<220> FEATURE:
<223> OTHER INFORMATION: Amino acid sequence of humanized hA2-27D-L5
<220> FEATURE:
<221> NAME/KEY: SIGNAL
<222> LOCATION: (1)..(20)
<220> FEATURE:
<221> NAME/KEY: V_region
<222> LOCATION: (21)..(129)
<220> FEATURE:
<221> NAME/KEY: C_region
<222> LOCATION: (130)..(234)

<400> SEQUENCE: 58

```
Met Val Leu Gln Thr Gln Val Phe Ile Ser Leu Leu Leu Trp Ile Ser
1               5                   10                  15

Gly Ala Tyr Gly Glu Ile Val Leu Thr Gln Ser Pro Gly Thr Met Ser
            20                  25                  30

Ala Ser Pro Gly Glu Arg Val Thr Leu Asn Cys Leu Ala Ser Ser Ser
        35                  40                  45

Val Ser Tyr Met Thr Trp Tyr Gln Gln Lys Ser Gly Ala Ser Pro Lys
    50                  55                  60

Leu Trp Ile Tyr Gly Thr Ser Asn Leu Ala Ser Gly Val Pro Asn Arg
65                  70                  75                  80

Phe Ser Gly Ser Gly Ser Gly Thr Ser Tyr Thr Leu Thr Ile Ser Arg
                85                  90                  95

Met Glu Pro Glu Asp Phe Ala Thr Tyr Tyr Cys Leu His Leu Thr Ser
            100                 105                 110
```

```
Tyr Pro Pro Tyr Thr Phe Gly Ala Gly Thr Lys Leu Glu Leu Lys Arg
            115                 120                 125

Ala Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
            165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
            195                 200                 205

His Lys Val Tyr Ala Cys Glu Val Thr His Gln Gly Leu Ser Ser Pro
            210                 215                 220

Val Thr Lys Ser Phe Asn Arg Gly Glu Cys
225                 230
```

<210> SEQ ID NO 59
<211> LENGTH: 10
<212> TYPE: PRT
<213> ORGANISM: Rattus norvegicus

<400> SEQUENCE: 59

```
Gly Phe Thr Phe Ser His Tyr Tyr Met Ala
1               5                   10
```

<210> SEQ ID NO 60
<211> LENGTH: 17
<212> TYPE: PRT
<213> ORGANISM: Rattus norvegicus

<400> SEQUENCE: 60

```
Ser Ile Thr Asn Ser Gly Gly Ser Ile Asn Tyr Arg Asp Ser Val Lys
1               5                   10                  15
Gly
```

<210> SEQ ID NO 61
<211> LENGTH: 14
<212> TYPE: PRT
<213> ORGANISM: Rattus norvegicus

<400> SEQUENCE: 61

```
Glu Gly Gly Glu Asn Tyr Gly Gly Tyr Pro Pro Phe Ala Tyr
1               5                   10
```

<210> SEQ ID NO 62
<211> LENGTH: 15
<212> TYPE: PRT
<213> ORGANISM: Rattus norvegicus

<400> SEQUENCE: 62

```
Arg Ala Asn Gln Gly Val Ser Leu Ser Arg Tyr Asn Leu Met His
1               5                   10                  15
```

<210> SEQ ID NO 63
<211> LENGTH: 7
<212> TYPE: PRT
<213> ORGANISM: Rattus norvegicus

<400> SEQUENCE: 63

Arg Ser Ser Asn Leu Ala Ser

<210> SEQ ID NO 64
<211> LENGTH: 9
<212> TYPE: PRT
<213> ORGANISM: Rattus norvegicus

<400> SEQUENCE: 64

Gln Gln Ser Arg Glu Ser Pro Phe Thr
1               5

<210> SEQ ID NO 65
<211> LENGTH: 10
<212> TYPE: PRT
<213> ORGANISM: Rattus norvegicus

<400> SEQUENCE: 65

Gly Ser Thr Phe Ser Asn Tyr Gly Met Lys
1               5                   10

<210> SEQ ID NO 66
<211> LENGTH: 17
<212> TYPE: PRT
<213> ORGANISM: Rattus norvegicus

<400> SEQUENCE: 66

Ser Ile Ser Arg Ser Ser Thr Tyr Ile Tyr Tyr Ala Asp Thr Val Lys
1               5                   10                  15

Gly

<210> SEQ ID NO 67
<211> LENGTH: 12
<212> TYPE: PRT
<213> ORGANISM: Rattus norvegicus

<400> SEQUENCE: 67

Ala Ile Ser Thr Pro Phe Tyr Trp Tyr Phe Asp Phe
1               5                   10

<210> SEQ ID NO 68
<211> LENGTH: 10
<212> TYPE: PRT
<213> ORGANISM: Rattus norvegicus

<400> SEQUENCE: 68

Leu Ala Ser Ser Ser Val Ser Tyr Met Thr
1               5                   10

<210> SEQ ID NO 69
<211> LENGTH: 7
<212> TYPE: PRT
<213> ORGANISM: Rattus norvegicus

<400> SEQUENCE: 69

Gly Thr Ser Asn Leu Ala Ser
1               5

<210> SEQ ID NO 70
<211> LENGTH: 10
<212> TYPE: PRT
<213> ORGANISM: Rattus norvegicus

<400> SEQUENCE: 70

Leu His Leu Thr Ser Tyr Pro Pro Tyr Thr

<210> SEQ ID NO 71
<211> LENGTH: 7
<212> TYPE: PRT
<213> ORGANISM: Rattus norvegicus

<400> SEQUENCE: 71

Arg Ser Ser Asn Leu Ala Gln
1               5

<210> SEQ ID NO 72
<211> LENGTH: 10
<212> TYPE: PRT
<213> ORGANISM: Rattus norvegicus

<400> SEQUENCE: 72

Gly Phe Thr Phe Ser Asn Tyr Tyr Met Tyr
1               5                   10

<210> SEQ ID NO 73
<211> LENGTH: 17
<212> TYPE: PRT
<213> ORGANISM: Rattus norvegicus

<400> SEQUENCE: 73

Ser Ile Asn Thr Asp Gly Gly Ser Thr Tyr Tyr Pro Asp Ser Val Lys
1               5                   10                  15

Gly

<210> SEQ ID NO 74
<211> LENGTH: 9
<212> TYPE: PRT
<213> ORGANISM: Rattus norvegicus

<400> SEQUENCE: 74

Ser Thr Pro Asn Ile Pro Leu Ala Tyr
1               5

<210> SEQ ID NO 75
<211> LENGTH: 11
<212> TYPE: PRT
<213> ORGANISM: Rattus norvegicus

<400> SEQUENCE: 75

Lys Ala Ser Gln Asn Ile Tyr Lys Tyr Leu Asn
1               5                   10

<210> SEQ ID NO 76
<211> LENGTH: 7
<212> TYPE: PRT
<213> ORGANISM: Rattus norvegicus

<400> SEQUENCE: 76

Tyr Ser Asn Ser Leu Gln Thr
1               5

<210> SEQ ID NO 77
<211> LENGTH: 8
<212> TYPE: PRT
<213> ORGANISM: Rattus norvegicus

<400> SEQUENCE: 77

Phe Gln Tyr Ser Ser Gly Pro Thr

```
<210> SEQ ID NO 78
<211> LENGTH: 10
<212> TYPE: PRT
<213> ORGANISM: Rattus norvegicus

<400> SEQUENCE: 78

Gly Phe Thr Phe Ser Tyr Tyr Ala Met Ser
1               5                   10

<210> SEQ ID NO 79
<211> LENGTH: 17
<212> TYPE: PRT
<213> ORGANISM: Rattus norvegicus

<400> SEQUENCE: 79

Ser Ile Ser Arg Gly Gly Asp Asn Thr Tyr Tyr Arg Asp Thr Val Lys
1               5                   10                  15

Gly

<210> SEQ ID NO 80
<211> LENGTH: 9
<212> TYPE: PRT
<213> ORGANISM: Rattus norvegicus

<400> SEQUENCE: 80

Leu Asn Tyr Asn Asn Tyr Phe Asp Tyr
1               5

<210> SEQ ID NO 81
<211> LENGTH: 11
<212> TYPE: PRT
<213> ORGANISM: Rattus norvegicus

<400> SEQUENCE: 81

Gln Ala Ser Gln Asp Ile Gly Asn Trp Leu Ser
1               5                   10

<210> SEQ ID NO 82
<211> LENGTH: 7
<212> TYPE: PRT
<213> ORGANISM: Rattus norvegicus

<400> SEQUENCE: 82

Gly Ala Thr Ser Leu Ala Asp
1               5

<210> SEQ ID NO 83
<211> LENGTH: 9
<212> TYPE: PRT
<213> ORGANISM: Rattus norvegicus

<400> SEQUENCE: 83

Leu Gln Ala Tyr Ser Ala Pro Phe Thr
1               5

<210> SEQ ID NO 84
<211> LENGTH: 509
<212> TYPE: PRT
<213> ORGANISM: Homo sapiens

<400> SEQUENCE: 84

Met Val Asp Gly Val Met Ile Leu Pro Val Leu Ile Met Ile Ala Leu
```

-continued

```
1               5                   10                  15
Pro Ser Pro Ser Met Glu Asp Glu Lys Pro Lys Val Asn Pro Lys Leu
                20                  25                  30

Tyr Met Cys Val Cys Glu Gly Leu Ser Cys Gly Asn Glu Asp His Cys
                35                  40                  45

Glu Gly Gln Gln Cys Phe Ser Ser Leu Ser Ile Asn Asp Gly Phe His
    50                  55                  60

Val Tyr Gln Lys Gly Cys Phe Gln Val Tyr Glu Gln Gly Lys Met Thr
65                  70                  75                  80

Cys Lys Thr Pro Pro Ser Pro Gly Gln Ala Val Glu Cys Cys Gln Gly
                85                  90                  95

Asp Trp Cys Asn Arg Asn Ile Thr Ala Gln Leu Pro Thr Lys Gly Lys
                100                 105                 110

Ser Phe Pro Gly Thr Gln Asn Phe His Leu Glu Val Gly Leu Ile Ile
                115                 120                 125

Leu Ser Val Val Phe Ala Val Cys Leu Leu Ala Cys Leu Leu Gly Val
                130                 135                 140

Ala Leu Arg Lys Phe Lys Arg Arg Asn Gln Glu Arg Leu Asn Pro Arg
145                 150                 155                 160

Asp Val Glu Tyr Gly Thr Ile Glu Gly Leu Ile Thr Thr Asn Val Gly
                165                 170                 175

Asp Ser Thr Leu Ala Asp Leu Leu Asp His Ser Cys Thr Ser Gly Ser
                180                 185                 190

Gly Ser Gly Leu Pro Phe Leu Val Gln Arg Thr Val Ala Arg Gln Ile
                195                 200                 205

Thr Leu Leu Glu Cys Val Gly Lys Gly Arg Tyr Gly Glu Val Trp Arg
    210                 215                 220

Gly Ser Trp Gln Gly Glu Asn Val Ala Val Lys Ile Phe Ser Ser Arg
225                 230                 235                 240

Asp Glu Lys Ser Trp Phe Arg Glu Thr Glu Leu Tyr Asn Thr Val Met
                245                 250                 255

Leu Arg His Glu Asn Ile Leu Gly Phe Ile Ala Ser Asp Met Thr Ser
                260                 265                 270

Arg His Ser Ser Thr Gln Leu Trp Leu Ile Thr His Tyr His Glu Met
                275                 280                 285

Gly Ser Leu Tyr Asp Tyr Leu Gln Leu Thr Thr Leu Asp Thr Val Ser
                290                 295                 300

Cys Leu Arg Ile Val Leu Ser Ile Ala Ser Gly Leu Ala His Leu His
305                 310                 315                 320

Ile Glu Ile Phe Gly Thr Gln Gly Lys Pro Ala Ile Ala His Arg Asp
                325                 330                 335

Leu Lys Ser Lys Asn Ile Leu Val Lys Lys Asn Gly Gln Cys Cys Ile
                340                 345                 350

Ala Asp Leu Gly Leu Ala Val Met His Ser Gln Ser Thr Asn Gln Leu
                355                 360                 365

Asp Val Gly Asn Asn Pro Arg Val Gly Thr Lys Arg Tyr Met Ala Pro
                370                 375                 380

Glu Val Leu Asp Glu Thr Ile Gln Val Asp Cys Phe Asp Ser Tyr Lys
385                 390                 395                 400

Arg Val Asp Ile Trp Ala Phe Gly Leu Val Leu Trp Glu Val Ala Arg
                405                 410                 415

Arg Met Val Ser Asn Gly Ile Val Glu Asp Tyr Lys Pro Pro Phe Tyr
                420                 425                 430
```

```
Asp Val Pro Asn Asp Pro Ser Phe Glu Asp Met Arg Lys Val Val
        435                 440                 445

Cys Val Asp Gln Gln Arg Pro Asn Ile Pro Asn Arg Trp Phe Ser Asp
    450                 455                 460

Pro Thr Leu Thr Ser Leu Ala Lys Leu Met Lys Glu Cys Trp Tyr Gln
465                 470                 475                 480

Asn Pro Ser Ala Arg Leu Thr Ala Leu Arg Ile Lys Lys Thr Leu Thr
                485                 490                 495

Lys Ile Asp Asn Ser Leu Asp Lys Leu Lys Thr Asp Cys
                500                 505
```

<210> SEQ ID NO 85
<211> LENGTH: 3062
<212> TYPE: DNA
<213> ORGANISM: Homo sapiens

<400> SEQUENCE: 85

```
gaagagatgt gggcctctgg ggccgctgga ttcagtaact tccgtcgggt tctagactgg      60
ctcggctctg tccagtttgt gccagatagt ctcccacccc ctcccaccc ctcctttccc     120
ctggagattt gaacgctgct tgcatgggag aaaagctact tagagaagaa aacgttccac     180
ttagtaacag aagaaaagtc ttggttaaaa agttgtcatg aatttggctt ttggagagag     240
gcagcaagcc tggagcattg gtaagcgtca cactgccaaa gtgagagctg ctggagaact     300
cataatccca ggaacgcctc ttctactctc cgagtacccc agtgaccaga gtgagagaag     360
ctctgaacga gggcacgcgg cttgaaggac tgtgggcaga tgtgaccaag agcctgcatt     420
aagttgtaca atggtagatg gagtgatgat tcttcctgtg cttatcatga ttgctctccc     480
ctcccctagt atgaagatg agaagcccaa ggtcaacccc aaactctaca tgtgtgtgtg     540
tgaaggtctc tcctgcggta atgaggacca ctgtgaaggc cagcagtgct tttcctcact     600
gagcatcaac gatggcttcc acgtctacca gaaaggctgc ttccaggttt atgagcaggg     660
aaagatgacc tgtaagaccc cgccgtcccc tggccaagcc gtggagtgct gccaagggga     720
ctggtgtaac aggaacatca cggcccagct gcccactaaa ggaaaatcct tccctggaac     780
acagaatttc cacttggagg ttggcctcat tattctctct gtagtgttcg cagtatgtct     840
tttagcctgc ctgctgggag ttgctctccg aaaatttaaa aggcgcaacc aagaacgcct     900
caatccccga cgtggagt atggcactat cgaagggctc atcaccacca atgttggaga     960
cagcacttta gcagatttat tggatcattc gtgtacatca ggaagtggct ctggtcttcc    1020
ttttctggta caaagaacag tggctcgcca gattacactg ttggagtgtg tcgggaaagg    1080
caggtatggt gaggtgtgga ggggcagctg gcaaggggag aatgttgccg tgaagatctt    1140
ctcctcccgt gatgagaagt catggttcag ggaaacggaa ttgtacaaca ctgtgatgct    1200
gaggcatgaa aatatcttag gtttcattgc ttcagacatg acatcaagac actccagtac    1260
ccagctgtgg ttaattacac attatcatga atgggatcg ttgtacgact atcttcagct    1320
tactactctg gatacagtta gctgccttcg aatagtgctg tccatagcta gtggtcttgc    1380
acatttgcac atagagatat ttgggaccca agggaaacca gccattgccc atcgagattt    1440
aaagagcaaa atattctggt taagaagaa tggacagtgt tgcatagcag atttgggcct    1500
ggcagtcatg cattcccaga gcaccaatca gcttgatgtg gggaacaatc ccgtgtggg    1560
caccaagcgc tacatggccc ccgaagttct agatgaaacc atccaggtgg attgtttcga    1620
ttcttataaa agggtcgata tttgggcctt tggacttgtt ttgtgggaag tggccaggcg    1680
```

```
gatggtgagc aatggtatag tggaggatta caagccaccg ttctacgatg tggttcccaa    1740
tgacccaagt tttgaagata tgaggaaggt agtctgtgtg gatcaacaaa ggccaaacat    1800
acccaacaga tggttctcag acccgacatt aacctctctg ccaagctaa tgaaagaatg     1860 ctggtatcaa aatccatccg caagactcac agcactgcgt atcaaaaaga ctttgaccaa    1920
aattgataat tccctcgaca aattgaaaac tgactgttga cattttcata gtgtcaagaa    1980
ggaagatttg acgttgttgt cattgtccag ctgggaccta atgctggcct gactggttgt    2040
cagaatggaa tccatctgtc tccctcccca atggctgct tgacaaggc agacgtcgta      2100 cccagccatg tgttggggag acatcaaaac caccctaacc tcgctcgatg actgtgaact    2160
gggcatttca cgaactgttc acactgcaga gactaatgtt ggacagacac tgttgcaaag    2220
gtagggactg gaggaacaca gagaaatcct aaaagagatc tgggcattaa gtcagtggct    2280
ttgcatagct ttcacaagtc tcctagacac tccccacggg aaactcaagg aggtggtgaa    2340
tttttaatca gcaatattgc ctgtgcttct cttctttatt gcactaggaa ttctttgcat    2400
tccttacttg cactgttact cttaatttta aagacccaac ttgccaaaat gttggctgcg    2460
tactccactg gtctgtcttt ggataatagg aattcaattt ggcaaaacaa atgtaatgt     2520 cagactttgc tgcattttac acatgtgctg atgtttacaa tgatgccgaa cattaggaat    2580 tgttataca caactttgca aattatttat tacttgtgca cttagtagtt tttacaaaac     2640
tgctttgtgc atatgttaaa gcttattttt atgtggtctt atgattttat tacagaaatg    2700
tttttaacac tatactctaa aatggacatt ttcttttatt atcagttaaa atcacatttt    2760
aagtgcttca catttgtatg tgtgtagact gtaacttttt ttcagttcat atgcagaacg    2820
tatttagcca ttacccacgt gacaccaccg aatatattac tgatttagaa gcaaagattt    2880
cagtagaatt ttagtcctga acgctacggg gaaaatgcat tttcttcaga attatccatt    2940
acgtgcattt aaactctgcc agaaaaaaat aactattttg ttttaatcta ctttttgtat    3000
ttagtagtta tttgtataaa ttaaataaac tgttttcaag tcaaaaaaaa aaaaaaaaa     3060 aa                                                                  3062
```

<210> SEQ ID NO 86
<211> LENGTH: 509
<212> TYPE: PRT
<213> ORGANISM: Mus musculus

<400> SEQUENCE: 86

```
Met Val Asp Gly Val Met Ile Leu Pro Val Leu Met Met Ala Phe
1               5                   10                  15

Pro Ser Pro Ser Val Glu Asp Glu Lys Pro Lys Val Asn Gln Lys Leu
            20                  25                  30

Tyr Met Cys Val Cys Glu Gly Leu Ser Cys Gly Asn Glu Asp His Cys
        35                  40                  45

Glu Gly Gln Gln Cys Phe Ser Ser Leu Ser Ile Asn Asp Gly Phe His
    50                  55                  60

Val Tyr Gln Lys Gly Cys Phe Gln Val Tyr Glu Gln Gly Lys Met Thr
65                  70                  75                  80

Cys Lys Thr Pro Pro Ser Pro Gly Gln Ala Val Glu Cys Cys Gln Gly
                85                  90                  95

Asp Trp Cys Asn Arg Asn Ile Thr Ala Gln Leu Pro Thr Lys Gly Lys
                100                 105                 110

Ser Phe Pro Gly Thr Gln Asn Phe His Leu Glu Val Gly Leu Ile Ile
```

```
            115                 120                 125
Leu Ser Val Val Phe Ala Val Cys Leu Leu Ala Cys Ile Leu Gly Val
130                 135                 140

Ala Leu Arg Lys Phe Lys Arg Arg Asn Gln Glu Arg Leu Asn Pro Arg
145                 150                 155                 160

Asp Val Glu Tyr Gly Thr Ile Glu Gly Leu Ile Thr Thr Asn Val Gly
                165                 170                 175

Asp Ser Thr Leu Ala Glu Leu Leu Asp His Ser Cys Thr Ser Gly Ser
            180                 185                 190

Gly Ser Gly Leu Pro Phe Leu Val Gln Arg Thr Val Ala Arg Gln Ile
        195                 200                 205

Thr Leu Leu Glu Cys Val Gly Lys Gly Arg Tyr Gly Glu Val Trp Arg
    210                 215                 220

Gly Ser Trp Gln Gly Glu Asn Val Ala Val Lys Ile Phe Ser Ser Arg
225                 230                 235                 240

Asp Glu Lys Ser Trp Phe Arg Glu Thr Glu Leu Tyr Asn Thr Val Met
                245                 250                 255

Leu Arg His Glu Asn Ile Leu Gly Phe Ile Ala Ser Asp Met Thr Ser
            260                 265                 270

Arg His Ser Ser Thr Gln Leu Trp Leu Ile Thr His Tyr His Glu Met
        275                 280                 285

Gly Ser Leu Tyr Asp Tyr Leu Gln Leu Thr Thr Leu Asp Thr Val Ser
    290                 295                 300

Cys Leu Arg Ile Val Leu Ser Ile Ala Ser Gly Leu Ala His Leu His
305                 310                 315                 320

Ile Glu Ile Phe Gly Thr Gln Gly Lys Ser Ala Ile Ala His Arg Asp
                325                 330                 335

Leu Lys Ser Lys Asn Ile Leu Val Lys Lys Asn Gly Gln Cys Cys Ile
            340                 345                 350

Ala Asp Leu Gly Leu Ala Val Met His Ser Gln Ser Thr Asn Gln Leu
        355                 360                 365

Asp Val Gly Asn Asn Pro Arg Val Gly Thr Lys Arg Tyr Met Ala Pro
    370                 375                 380

Glu Val Leu Asp Glu Thr Ile Gln Val Asp Cys Phe Asp Ser Tyr Lys
385                 390                 395                 400

Arg Val Asp Ile Trp Ala Phe Gly Leu Val Leu Trp Glu Val Ala Arg
                405                 410                 415

Arg Met Val Ser Asn Gly Ile Val Glu Asp Tyr Lys Pro Pro Phe Tyr
            420                 425                 430

Asp Val Val Pro Asn Asp Pro Ser Phe Glu Asp Met Arg Lys Val Val
        435                 440                 445

Cys Val Asp Gln Gln Arg Pro Asn Ile Pro Asn Arg Trp Phe Ser Asp
    450                 455                 460

Pro Thr Leu Thr Ser Leu Ala Lys Leu Met Lys Glu Cys Trp Tyr Gln
465                 470                 475                 480

Asn Pro Ser Ala Arg Leu Thr Ala Leu Arg Ile Lys Lys Thr Leu Thr
                485                 490                 495

Lys Ile Asp Asn Ser Leu Asp Lys Leu Lys Thr Asp Cys
            500                 505

<210> SEQ ID NO 87
<211> LENGTH: 3312
<212> TYPE: DNA
<213> ORGANISM: Mus musculus
```

<400> SEQUENCE: 87

```
ccgcctcccc gggttcagca cccgaccgcc gctggaccag aggaacaaag gagctgcccc      60
cgtgtcaccc agcccttcag tggaagtctg gaaaaggaac agaggtgata ttgcagtgga     120
tgagcagaga gaagccggcc tctggtgctc ttgagctggt ctgcccatag ggagcctgct     180
gggagaaggt acagcttccg gaagactcct cccggagcgc ctctcccatc ctcctctccc     240
ttggagcagt cagtacctct ctgctggagg atctgggctg ggtgtgccgg gagctggctt     300
taactgtagc cctgtcaggc tttccccgga cctcgcggaa gagcgtcacc agccccacg      360
gctttccaac acatcacctc ttttcatgcc gtttggcaca gatcgaatct acagggatga     420
atggatccag ggtctggttt taagttctat ggtagtcgtc caaggagcca ttggtattca     480
tctaacgcaa acgatcaagt acattctga aagtaacatc ccaccagaaa ccctccagca     540
gcagtcacgt ctgtgtaaag ccaagccctg gcatgcgcac tgccaggtca gagtgtggtg     600
gtacacgtgt taacaggtc atttgtcaac tgaaggaaag accccggctt gacttacctg     660
ttatacaatg gtcgatggag taatgatcct tcctgtgcta atgatgatgg ctttcccttc     720
cccgagtgtg aagatgaga agcccaaggt caaccagaaa ctttacatgt gtgtgtgtga     780
gggcctctcc tgcgggaacg aggaccactg tgaaggccag cagtgttttt cttctctgag     840
catcaacgat ggcttccacg tctaccagaa gggctgcttt caggtttatg agcaggggaa     900
gatgacgtgt aagaccccgc cgtcacctgg ccaggctgtg gagtgctgcc aagggggactg    960
gtgtaacagg aacatcacgg cccagctgcc cactaaaggg aagtccttcc ccggaacaca    1020
gaatttccac ctggaagttg gccttatcat cctctcggtg gtgtttgcag tatgtctttt    1080
agcttgcatc cttggagttg ctctcaggaa gtttaagaga cgcaatcaag agcgcctgaa    1140
ccccagagac gtggagtatg gtaccattga agggctcatc accaccaatg tgggagacag    1200
cactctagcg gaactactag atcactcgtg tacatcagga agtggctccg gtcttccttt    1260
cctggtacag agaacggtgg ctcgccagat aaccctgttg gagtgtgtcg ggaagggccg    1320
gtatggagaa gtatgggggg gcagctggca aggcgaaaat gtcgctgtga agatcttctc    1380
ctcccgagac gagaagtcat ggttcaggga acggaattg tacaacactg tgatgttgag    1440
gcatgaaaat atcttaggtt tcatcgcttc agacatgacc tccagacact ccagtaccca    1500
gctgtggctc atcacacatt accatgaaat gggatcgttg tatgactacc ttcagctcac    1560
tactctggat acggttagct gccttcggat tgtactgtcc atagccagcg gccttgccca    1620
tttgcacata gagatatttg ggacccaagg gaagtccgcc attgcccatc gagatctgaa    1680
gagcaaaaac atcctggtga agaagaatgg acagtgctgc atagcagatt gggcctggc     1740
agtcatgcat tccagagca caaaccagct tgatgtggga acaaccccc gtgtggggac    1800
caagcgctac atggctccgg aagtgctcga tgaaaccatc aagtggatt gctttgattc     1860
ttataagagg gtcgatattt gggccttttg ccttgttctg tgggaagtgg ccaggcgaat    1920
ggtgagcaat ggtatagtgg aagattacaa gccaccattc tatgatgtgg ttcccaatga    1980
cccaagtttt gaagatatga ggaaagttgt ctgtgtggat caacagaggc caaacatacc    2040
taacagatgg ttctcagacc cgacattaac ttctctggcg aagctgatga agagtgctg    2100
gtatcagaac ccatccgcaa gactcacagc tctacgtatc aaaaagactt tgaccaaaat    2160
cgataattcc ctagacaaat taaaaactga ctgttgacct tgtcaccggt gtcaagaagg    2220
agagtcaatg ctgtccttgt ccagctggga cctaatgctg gcctgactgg ttgtcagaac    2280
```

-continued

```
agaatccatc tgacccccctt cccgaagtgg ctgctttgac ggaagcagat gtctcttccc    2340
agccatgttc caggggggaga caccaaaacc accctaacct cgctcaaaaa ctgtgactcg    2400
agccctcgat gaactgttca caccacaaag acttaacggt gggcaggtct ggtggcaagg    2460
gggagggaag tggaggaacc cggaaagatc ctgcaggcga tctgggcatt aagacagtgg    2520
ctctctgcgt atctttcgcg ggtctcctag acactcccca cgggaagctc aaggaggcgg    2580
tgaattcgta atcagcaata tcggctgcat ctactcttcg ttgcactagg aattctgtgc    2640
attccttact tgcactgtgg cccttaatct taaagaccca acttgccaaa acattggctg    2700
cgtactccac tggcctgtct ctggataata ggaattcaat ctggcaacac aaaaatgtac    2760
cgttggactc tgctgcattt tacacacgtg ctgatgttta caaggatgcg aacattagga    2820
attgtttaga cacaactttg caaattattt attactggtg cacttagcgg tttgtttgaa    2880
accgcctcgt gcatatgtta aagcttattt ttatgtggtc ttatgatttt attaccgaaa    2940 tgttttttaac acccaactct gaaacggaca ttttctttta ttatcagtta aattcacatt   3000
taagtgcttc acattttttt ttttaaatgt gtgtagactg taactttctt ttcagttcgt    3060
atgcagaaca tatttagcca ttacccatgc aacaccaccc gatatattac tgatttagaa    3120
gcaaagattt cagtagaatt ttagtcccaa acgctgtggg gggaaatgca tcttcttcgg    3180
aattatccat tacgtgcatt taaactctgc cagaaaaaaa aataactatt ttgtttaat    3240 ctacttttg tatttagtag ttatttgtat aaattaaata aactgttttc aagtcaaaaa    3300
aaaaaaaaaa aa                                                       3312
```

<210> SEQ ID NO 88
<211> LENGTH: 29
<212> TYPE: DNA
<213> ORGANISM: Artificial
<220> FEATURE:
<223> OTHER INFORMATION: primer

<400> SEQUENCE: 88

```
ctccagagtt ccaggtcacg gtgactggc                                      29
```

<210> SEQ ID NO 89
<211> LENGTH: 28
<212> TYPE: DNA
<213> ORGANISM: Artificial
<220> FEATURE:
<223> OTHER INFORMATION: primer

<400> SEQUENCE: 89

```
tcagtaacac tgtccaggac accatctc                                       28
```

<210> SEQ ID NO 90
<211> LENGTH: 30
<212> TYPE: DNA
<213> ORGANISM: Artificial
<220> FEATURE:
<223> OTHER INFORMATION: primer

<400> SEQUENCE: 90

```
tataccgtcg acctctagct agagcttggc                                     30
```

<210> SEQ ID NO 91
<211> LENGTH: 30
<212> TYPE: DNA
<213> ORGANISM: Artificial
<220> FEATURE:
<223> OTHER INFORMATION: primer

```
<400> SEQUENCE: 91
gctatggcag ggcctgccgc cccgacgttg                                      30

<210> SEQ ID NO 92
<211> LENGTH: 45
<212> TYPE: DNA
<213> ORGANISM: Artificial
<220> FEATURE:
<223> OTHER INFORMATION: primer

<400> SEQUENCE: 92
ccagatgggt gctgagcgag gtgcagctgg tggagtctgg cggag                     45

<210> SEQ ID NO 93
<211> LENGTH: 46
<212> TYPE: DNA
<213> ORGANISM: Artificial
<220> FEATURE:
<223> OTHER INFORMATION: primer

<400> SEQUENCE: 93
cttggtggag gctgagctga cagtgaccag agtgccttgg ccccag                    46

<210> SEQ ID NO 94
<211> LENGTH: 44
<212> TYPE: DNA
<213> ORGANISM: Artificial
<220> FEATURE:
<223> OTHER INFORMATION: primer

<400> SEQUENCE: 94
atctccggcg cgtacggcga cattgtcttg acccagtctc ctgc                      44

<210> SEQ ID NO 95
<211> LENGTH: 44
<212> TYPE: DNA
<213> ORGANISM: Artificial
<220> FEATURE:
<223> OTHER INFORMATION: primer

<400> SEQUENCE: 95 ggaggggcg gccacagccc gtttcagttc cagcttggtc ccag                       44

<210> SEQ ID NO 96
<211> LENGTH: 45
<212> TYPE: DNA
<213> ORGANISM: Artificial
<220> FEATURE:
<223> OTHER INFORMATION: primer

<400> SEQUENCE: 96
ccagatgggt gctgagcgag gtgcagctgg tggagtctgg aggag                     45

<210> SEQ ID NO 97
<211> LENGTH: 46
<212> TYPE: DNA
<213> ORGANISM: Artificial
<220> FEATURE:
<223> OTHER INFORMATION: primer

<400> SEQUENCE: 97
cttggtggag gctgagctca cggtgaccac ggttcctggg ccccag                    46

<210> SEQ ID NO 98
```

-continued

```
<211> LENGTH: 44
<212> TYPE: DNA
<213> ORGANISM: Artificial
<220> FEATURE:
<223> OTHER INFORMATION: primer

<400> SEQUENCE: 98
atctccggcg cgtacggcga aattgttctc actcagtctc caac        44

<210> SEQ ID NO 99
<211> LENGTH: 22
<212> TYPE: DNA
<213> ORGANISM: Artificial
<220> FEATURE:
<223> OTHER INFORMATION: primer

<400> SEQUENCE: 99
agctcccaga tgggtgctga gc        22

<210> SEQ ID NO 100
<211> LENGTH: 22
<212> TYPE: DNA
<213> ORGANISM: Artificial
<220> FEATURE:
<223> OTHER INFORMATION: primer

<400> SEQUENCE: 100
gggcccttgg tggaggctga gc        22

<210> SEQ ID NO 101
<211> LENGTH: 25
<212> TYPE: DNA
<213> ORGANISM: Artificial
<220> FEATURE:
<223> OTHER INFORMATION: primer

<400> SEQUENCE: 101
ccagcctccg gactctagag ccacc        25

<210> SEQ ID NO 102
<211> LENGTH: 24
<212> TYPE: DNA
<213> ORGANISM: Artificial
<220> FEATURE:
<223> OTHER INFORMATION: primer

<400> SEQUENCE: 102
agttagcctc ccccgtttaa actc        24

<210> SEQ ID NO 103
<211> LENGTH: 1118
<212> TYPE: DNA
<213> ORGANISM: Artificial
<220> FEATURE:
<223> OTHER INFORMATION: nucleotide sequence of DNA fragment comprising
      the human heavy chain signal sequence and the sequence encoding
      human IgG2 constant region

<400> SEQUENCE: 103
gcctccggac tctagagcca ccatgaaaca cctgtggttc ttcctcctgc tggtggcagc        60
tcccagatgg gtgctgagcc aggtgcaatt gtgcaggcgg ttagctcagc cagcaccaag       120
ggcccttccg tgttccctct ggcccccttgt agccgttcca ccagcgagtc caccgccgcc       180
cttggctgtc tggtgaagga ctacttccct gagcctgtga ccgtgagctg gaactccgga       240
gcccttacca gcggcgtgca caccttccct gccgtgctgc agtccagcgg cctttactcc       300
```

```
ctgagctccg tggtgaccgt gcctagctcc aacttcggca cccaaaccta cacctgtaac      360
gtggaccaca agcctagcaa caccaaggtg acaagaccg tggagcgtaa gtgttgtgtg      420
gagtgtcctc cttgtcctgc ccctcctgtg gccggacctt ccgtgttcct tttccctcct      480
aagcctaagg acaccctgat gatcagccgt acccctgagg tgacctgtgt ggtggtggac      540
gtgtcccacg aggaccctga ggtgcagttc aactggtacg tggacggcgt ggaggtgcac      600
aacgccaaga ccaagcctcg tgaggagcaa ttcaacagca ccttccgtgt ggtgtccgtg      660
cttaccgtgg tgcaccaaga ctggctgaac ggcaaggagt acaagtgtaa ggtgagcaac      720
aagggacttc ctgcccctat cgagaagacc atctccaaga ccaagggcca acctcgtgag      780
cctcaagtgt acacccttcc tcctagccgt gaggagatga ccaagaacca agtgtccctt      840
acctgtctgg tgaagggctt ctaccctagc gacatcgccg tggagtggga gtccaacgga      900
caacctgaga caactacaa gaccacccct cctatgcttg acagcgacgg ctccttcttc      960
ctgtacagca agctgaccgt ggacaagtcc cgttggcaac aaggcaacgt gttcagctgt     1020
tccgtgatgc acgaggccct gcacaaccac tacacccaaa agagcctttc cctgagccct     1080
ggaaagtgat atcgggcccg tttaaacggg ggaggcta                              1118
```

<210> SEQ ID NO 104
<211> LENGTH: 1404
<212> TYPE: DNA
<213> ORGANISM: Artificial
<220> FEATURE:
<223> OTHER INFORMATION: nucleotide sequence of humanized hA2-15A-H4
     IgG2 type

<400> SEQUENCE: 104

```
atgaaacacc tgtggttctt cctcctgctg gtggcagctc ccagatgggt gctgagcgaa       60
gtgcagctgg tggaatctgg cggcggactg gtgcagcctg gcggatctct gagactgagc      120
tgtgccgcca gcggcttcac cttcagccac tactacatgg cctgggtgcg ccaggccccct     180 ggcaaaggac tggaatgggt ggccagcatc accaacagcg gcggcagcat caactaccgg      240
gacagcgtga agggccggtt caccatcagc cgggacaacg ccaagagcac cctgtacctg      300
cagatgaaca gcctgcgggc cgaggacacc gccacctact actgtacaag agagggcggc      360
gagaactacg gcggctaccc tccttttgcc tactgggggcc agggcaccct cgtgaccgtc      420
agctcagcca gcaccaaggg cccttccgtg ttccctctgg cccccttgtag ccgttccacc      480 agcgagtcca ccgccgccct ggctgtctg gtgaaggact acttccctga gcctgtgacc      540
gtgagctgga actccggagc ccttaccagc ggcgtgcaca ccttccctgc cgtgctgcag      600
tccagcggcc tttactccct gagctccgtg gtgaccgtgc ctagctccaa cttcggcacc      660
caaacctaca cctgtaacgt ggaccacaag cctagcaaca ccaaggtgga caagaccgtg      720
gagcgtaagt gttgtgtgga gtgtcctcct tgtcctgccc ctcctgtggc cggaccttcc      780
gtgttccttt tccctcctaa gcctaaggac accctgatga tcagccgtac ccctgaggtg      840
acctgtgtgg tggtggacgt gtcccacgag gaccctgagg tgcagttcaa ctggtacgtg      900 gacggcgtg aggtgcacaa cgccaagacc aagcctcgtg aggagcaatt caacagcacc      960
ttccgtgtgg tgtccgtgct taccgtggtg caccaagact ggctgaacgg caaggagtac     1020
aagtgtaagg tgagcaacaa gggacttcct gcccctatcg agaagaccat ctccaagacc     1080
aagggccaac tcgtgagcc tcaagtgtac acccttcctc ctagccgtga ggagatgacc     1140
aagaaccaag tgtcccttac ctgtctggtg aagggcttct accctagcga catcgccgtg     1200
```

-continued

```
gagtgggagt ccaacggaca acctgagaac aactacaaga ccaccoctcc tatgcttgac      1260 agcgacggct ccttcttcct gtacagcaag ctgaccgtgg acaagtcccg ttggcaacaa      1320
ggcaacgtgt tcagctgttc cgtgatgcac gaggccctgc acaaccacta cacccaaaag      1380
agcctttccc tgagccctgg aaag                                              1404
```

<210> SEQ ID NO 105
<211> LENGTH: 468
<212> TYPE: PRT
<213> ORGANISM: Artificial
<220> FEATURE:
<223> OTHER INFORMATION: amino acid sequence of humanized hA2-15A-H4
      IgG2 type

<400> SEQUENCE: 105

```
Met Lys His Leu Trp Phe Phe Leu Leu Val Ala Ala Pro Arg Trp
1               5                   10                  15

Val Leu Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser His Tyr Tyr Met Ala Trp Val Arg Gln Ala Pro Gly Lys Gly Leu
    50                  55                  60

Glu Trp Val Ala Ser Ile Thr Asn Ser Gly Gly Ser Ile Asn Tyr Arg
65                  70                  75                  80

Asp Ser Val Lys Gly Arg Phe Thr Ile Ser Arg Asp Asn Ala Lys Ser
                85                  90                  95

Thr Leu Tyr Leu Gln Met Asn Ser Leu Arg Ala Glu Asp Thr Ala Thr
            100                 105                 110

Tyr Tyr Cys Thr Arg Glu Gly Gly Glu Asn Tyr Gly Gly Tyr Pro Pro
        115                 120                 125

Phe Ala Tyr Trp Gly Gln Gly Thr Leu Val Thr Val Ser Ser Ala Ser
    130                 135                 140

Thr Lys Gly Pro Ser Val Phe Pro Leu Ala Pro Cys Ser Arg Ser Thr
145                 150                 155                 160

Ser Glu Ser Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Asn Phe Gly Thr Gln Thr Tyr Thr
    210                 215                 220

Cys Asn Val Asp His Lys Pro Ser Asn Thr Lys Val Asp Lys Thr Val
225                 230                 235                 240

Glu Arg Lys Cys Cys Val Glu Cys Pro Pro Cys Pro Ala Pro Pro Val
                245                 250                 255

Ala Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Gln Phe Asn Trp Tyr Val Asp Gly Val Glu
    290                 295                 300

Val His Asn Ala Lys Thr Lys Pro Arg Glu Glu Gln Phe Asn Ser Thr
305                 310                 315                 320
```

| Phe | Arg | Val | Val | Ser | Val | Leu | Thr | Val | His | Gln | Asp | Trp | Leu | Asn |
| | | | | 325 | | | | | 330 | | | | | 335 |

| Gly | Lys | Glu | Tyr | Lys | Cys | Lys | Val | Ser | Asn | Lys | Gly | Leu | Pro | Ala | Pro |
| | | | | 340 | | | | | 345 | | | | | 350 | |

| Ile | Glu | Lys | Thr | Ile | Ser | Lys | Thr | Lys | Gly | Gln | Pro | Arg | Glu | Pro | Gln |
| | | | 355 | | | | | 360 | | | | | 365 | | |

| Val | Tyr | Thr | Leu | Pro | Pro | Ser | Arg | Glu | Glu | Met | Thr | Lys | Asn | Gln | Val |
| | | 370 | | | | | 375 | | | | | 380 | | | |

| Ser | Leu | Thr | Cys | Leu | Val | Lys | Gly | Phe | Tyr | Pro | Ser | Asp | Ile | Ala | Val |
| 385 | | | | | 390 | | | | | 395 | | | | | 400 |

| Glu | Trp | Glu | Ser | Asn | Gly | Gln | Pro | Glu | Asn | Asn | Tyr | Lys | Thr | Thr | Pro |
| | | | | 405 | | | | | 410 | | | | | 415 | |

| Pro | Met | Leu | Asp | Ser | Asp | Gly | Ser | Phe | Phe | Leu | Tyr | Ser | Lys | Leu | Thr |
| | | | 420 | | | | | 425 | | | | | 430 | | |

| Val | Asp | Lys | Ser | Arg | Trp | Gln | Gln | Gly | Asn | Val | Phe | Ser | Cys | Ser | Val |
| | | 435 | | | | | 440 | | | | | 445 | | | |

| Met | His | Glu | Ala | Leu | His | Asn | His | Tyr | Thr | Gln | Lys | Ser | Leu | Ser | Leu |
| 450 | | | | | 455 | | | | | 460 | | | | | |

Ser Pro Gly Lys
465

<210> SEQ ID NO 106
<211> LENGTH: 1410
<212> TYPE: DNA
<213> ORGANISM: Artificial
<220> FEATURE:
<223> OTHER INFORMATION: nucleotide sequence of humanized hA2-27D-H2-
      LALA

<400> SEQUENCE: 106

| atgaaacacc | tgtggttctt | cctcctgctg | gtggcagctc | ccagatgggt | gctgagcgaa | 60 |
| gtgcagctgg | tggaatctgg | cggcggactg | gtgcagcctg | gcggatctct | gagactgagc | 120 |
| tgtgccgcca | gcggcagcac | cttcagcaac | tacggcatga | gtggatccg | gcaggcccct | 180 |
| ggcaagggcc | tggaatgggt | gtccagcatc | agcagaagca | gcacctacat | ctactacgcc | 240 |
| gacaccgtga | agggccggtt | caccatcagc | cgggacaaca | gcaagaacac | cctgtacctg | 300 |
| cagatgaaca | gcctgcgggc | cgaggacacc | gccgtgtact | attgtgccgc | cgctatcagc | 360 |
| accccttct | actggtactt | cgacttctgg | ggccagggca | ccctcgtgac | cgtcagctca | 420 |
| gcctccacca | agggcccaag | cgtcttcccc | ctggcaccct | cctccaagag | cacctctggc | 480 |
| ggcacagccg | ccctgggctg | cctggtcaag | gactacttcc | ccgaacccgt | gaccgtgagc | 540 |
| tggaactcag | gcgccctgac | cagcggcgtg | cacaccttcc | ccgctgtcct | gcagtcctca | 600 |
| ggactctact | ccctcagcag | cgtggtgacc | gtgccctcca | gcagcttggg | cacccagacc | 660 |
| tacatctgca | acgtgaatca | caagcccagc | aacaccaagg | tggacaagag | agttgagccc | 720 |
| aaatcttgtg | acaaaactca | cacatgccca | ccctgcccag | cacctgaagc | cgcggggga | 780 |
| ccctcagtct | tcctcttccc | cccaaaaccc | aaggacaccc | tcatgatctc | ccggacccct | 840 |
| gaggtcacat | gcgtggtggt | ggacgtgagc | cacgaagacc | ctgaggtcaa | gttcaactgg | 900 |
| tacgtggacg | gcgtggaggt | gcataatgcc | aagacaaagc | cccgggagga | gcagtacaac | 960 |
| agcacgtacc | gggtggtcag | cgtcctcacc | gtcctgcacc | aggactggct | gaatggcaag | 1020 |
| gagtacaagt | gcaaggtctc | caacaaagcc | ctcccagccc | ccatcgagaa | aaccatctcc | 1080 |
| aaagccaaag | gccagccccg | ggaaccacag | gtgtacaccc | tgcccccatc | ccgggaggag | 1140 |

```
atgaccaaga accaggtcag cctgacctgc ctggtcaaag gcttctatcc cagcgacatc    1200
gccgtggagt gggagagcaa tggccagccc gagaacaact acaagaccac ccctcccgtg    1260
ctggactccg acggctcctt cttcctctac agcaagctca ccgtggacaa gagcaggtgg    1320
cagcagggca acgtcttctc atgctccgtg atgcatgagg ctctgcacaa ccactacacc    1380
cagaagagcc tctccctgtc tcccggcaaa                                      1410
```

<210> SEQ ID NO 107
<211> LENGTH: 470
<212> TYPE: PRT
<213> ORGANISM: Artificial
<220> FEATURE:
<223> OTHER INFORMATION: amino acid sequence of humanized hA2-27D-H2-LALA

<400> SEQUENCE: 107

```
Met Lys His Leu Trp Phe Phe Leu Leu Leu Val Ala Ala Pro Arg Trp
1               5                   10                  15

Val Leu Ser Glu Val Gln Leu Val Glu Ser Gly Gly Gly Leu Val Gln
            20                  25                  30

Pro Gly Gly Ser Leu Arg Leu Ser Cys Ala Ala Ser Gly Ser Thr Phe
        35                  40                  45

Ser Asn Tyr Gly Met Lys Trp Ile Arg Gln Ala Pro Gly Lys Gly Leu
    50                  55                  60

Glu Trp Val Ser Ser Ile Ser Arg Ser Ser Thr Tyr Ile Tyr Tyr Ala
65                  70                  75                  80

Asp Thr Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Ala Ala Ile Ser Thr Pro Phe Tyr Trp Tyr Phe Asp
        115                 120                 125

Phe Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Arg Val Glu Pro
225                 230                 235                 240

Lys Ser Cys Asp Lys Thr His Thr Cys Pro Pro Cys Pro Ala Pro Glu
                245                 250                 255

Ala Ala Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300
```

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
            325                 330                 335

Leu Asn Gly Lys Glu Tyr Lys Cys Lys Val Ser Asn Lys Ala Leu Pro
        340                 345                 350

Ala Pro Ile Glu Lys Thr Ile Ser Lys Ala Lys Gly Gln Pro Arg Glu
            355                 360                 365

Pro Gln Val Tyr Thr Leu Pro Pro Ser Arg Glu Glu Met Thr Lys Asn
370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
            405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
450                 455                 460

Ser Leu Ser Pro Gly Lys
465             470

<210> SEQ ID NO 108
<211> LENGTH: 1410
<212> TYPE: DNA
<213> ORGANISM: Artificial
<220> FEATURE:
<223> OTHER INFORMATION: nucleotide sequence of humanized hA2-27D-H3-
      LALA

<400> SEQUENCE: 108
atgaaacacc tgtggttctt cctcctgctg gtggcagctc ccagatgggt gctgagcgaa       60
gtgcagctgg tggaatctgg cggcggactg gtgcagcctg gcggatctct gagactgagc      120
tgtgccgcca gcggcagcac cttcagcaac tacggcatga gtggatccg gcaggccct       180 ggcaagggcc tggaatgggt ggccagcatc agcagaagca gcacctacat ctactacgcc      240
gacaccgtga agggccggtt caccatcagc cgggacaaca gcaagaacac cctgtacctg      300
cagatgaaca gcctgcgggc cgaggacacc gccgtgtact attgtgccgc cgctatcagc      360
acccccttct actggtactt cgacttctgg ggccagggca ccctcgtgac cgtcagctca      420
gcctccacca agggcccaag cgtcttcccc ctggcaccct cctccaagag cacctctggc      480
ggcacagccg ccctgggctg cctggtcaag gactacttcc ccgaacccgt gaccgtgagc      540
tggaactcag gcgccctgac cagcggcgtg cacaccttcc cgctgtcct gcagtcctca      600 ggactctact ccctcagcag cgtggtgacc gtgccctca gcagcttggg cacccagacc      660
tacatctgca acgtgaatca caagcccagc aacaccaagg tggacaagag agttgagccc      720
aaatcttgtg acaaaactca cacatgccca cctgcccag cacctgaagc cgcgggggga      780
ccctcagtct tcctcttccc cccaaaaccc aaggacaccc tcatgatctc ccggaccct      840 gaggtcacat gcgtggtggt ggacgtgagc cacgaagacc ctgaggtcaa gttcaactgg      900
tacgtggacg gcgtggaggt gcataatgcc aagacaaagc cccggaggga gcagtacaac      960
agcacgtacc gggtggtcag cgtcctcacc gtcctgcacc aggactggct gaatggcaag     1020
gagtacaagt gcaaggtctc caacaaagcc ctcccagccc ccatcgagaa aaccatctcc     1080

```
aaagccaaag gccagccccg ggaaccacag gtgtacaccc tgccccatc ccgggaggag   1140 atgaccaaga accaggtcag cctgacctgc ctggtcaaag gcttctatcc cagcgacatc   1200
gccgtggagt gggagagcaa tggccagccc gagaacaact acaagaccac ccctcccgtg   1260
ctggactccg acggctcctt cttcctctac agcaagctca ccgtggacaa gagcaggtgg   1320
cagcagggca acgtcttctc atgctccgtg atgcatgagg ctctgcacaa ccactacacc   1380
cagaagagcc tctccctgtc tcccggcaaa                                    1410
```

<210> SEQ ID NO 109
<211> LENGTH: 470
<212> TYPE: PRT
<213> ORGANISM: Artificial
<220> FEATURE:
<223> OTHER INFORMATION: amino acid sequence of humanized hA2-27D-H3-LALA

<400> SEQUENCE: 109

```
Met Lys His Leu Trp Phe Phe Leu Leu Val Ala Ala Pro Arg Trp
1               5                   10                  15

Val Leu Ser Glu Val Gln Leu Val Glu Ser Gly Gly Gly Leu Val Gln
            20                  25                  30

Pro Gly Gly Ser Leu Arg Leu Ser Cys Ala Ala Ser Gly Ser Thr Phe
        35                  40                  45

Ser Asn Tyr Gly Met Lys Trp Ile Arg Gln Ala Pro Gly Lys Gly Leu
    50                  55                  60

Glu Trp Val Ala Ser Ile Ser Arg Ser Ser Thr Tyr Ile Tyr Tyr Ala
65                  70                  75                  80

Asp Thr Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Ala Ala Ile Ser Thr Pro Phe Tyr Trp Tyr Phe Asp
        115                 120                 125

Phe Trp Gly Gln Gly Thr Leu Val Thr Val Ser Ser Ala Ser Thr Lys
130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Arg Val Glu Pro
225                 230                 235                 240

Lys Ser Cys Asp Lys Thr His Thr Cys Pro Pro Cys Pro Ala Pro Glu
                245                 250                 255

Ala Ala Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
```

```
                    290                 295                 300
Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 110
<211> LENGTH: 1401
<212> TYPE: DNA
<213> ORGANISM: Artificial
<220> FEATURE:
<223> OTHER INFORMATION: nucleotide sequence of humanized hA2-11E-H3

<400> SEQUENCE: 110
atgaaacacc tgtggttctt cctcctgctg gtggcagctc ccagatgggt gctgagcgaa      60
gtgcagctgg tggaatctgg cggcggactg gtgcagcctg gcggatctct gagactgagc     120
tgtgccgcca gcggcttcac cttcagcaac tactacatgt actggatccg gcaggcccct     180
ggcaagggcc tggaatgggt gtccagcatc aacaccgatg gcggcagcac ctactacgcc     240
gacagcgtga agggccggtt caccatcagc cgggacaaca gcaagaacac cgtgtacctg     300
cagatgaaca gcctgcgggc cgaggacacc gccgtgtact actgtgccaa gagcaccccc     360
aacatccccc tggcctattg gggccaggga cccctcgtga ccgtcagctc agcctccacc     420
aagggcccaa gcgtcttccc cctggcaccc tcctccaaga gcacctctgg cggcacagcc     480
gccctgggct gcctggtcaa ggactacttc cccgaacccg tgaccgtgag ctggaactca     540
ggcgccctga ccagcggcgt gcacaccttc ccggctgtcc tgcagtcctc aggactctac     600
tccctcagca gcgtggtgac cgtgccctcc agcagcttgg gcacccagac ctacatctgc     660
aacgtgaatc acaagcccag caacaccaag gtggacaaga gagttgagcc caaatcttgt     720
gacaaaactc acacatgccc accctgccca gcacctgaac tcctgggggg accctcagtc     780
ttcctcttcc ccccaaaacc caaggacacc ctcatgatct cccggacccc tgaggtcaca     840
tgcgtggtgg tggacgtgag ccacgaagac cctgaggtca agttcaactg gtacgtggac     900
ggcgtggagg tgcataatgc caagacaaag ccccgggagg agcagtacaa cagcacgtac     960
cgggtggtca gcgtcctcac cgtcctgcac caggactggc tgaatggcaa ggagtacaag    1020
```

```
tgcaaggtct ccaacaaagc cctcccagcc cccatcgaga aaaccatctc caaagccaaa       1080
ggccagcccc gggaaccaca ggtgtacacc ctgcccccat cccgggagga gatgaccaag       1140
aaccaggtca gcctgacctg cctggtcaaa ggcttctatc ccagcgacat cgccgtggag       1200
tgggagagca atggccagcc cgagaacaac tacaagacca cccctcccgt gctggactcc       1260
gacggctcct tcttcctcta cagcaagctc accgtggaca gagcaggtg gcagcagggc       1320 aacgtcttct catgctccgt gatgcatgag gctctgcaca accactacac ccagaagagc       1380
ctctccctgt ctcccggcaa a                                                 1401

<210> SEQ ID NO 111
<211> LENGTH: 467
<212> TYPE: PRT
<213> ORGANISM: Artificial
<220> FEATURE:
<223> OTHER INFORMATION: amino acid sequence of humanized hA2-11E-H3

<400> SEQUENCE: 111
```

Met Lys His Leu Trp Phe Phe Leu Leu Leu Val Ala Ala Pro Arg Trp
1               5                   10                  15

Val Leu Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Asn Tyr Tyr Met Tyr Trp Ile Arg Gln Ala Pro Gly Lys Gly Leu
    50                  55                  60

Glu Trp Val Ser Ser Ile Asn Thr Asp Gly Gly Ser Thr Tyr Tyr Ala
65                  70                  75                  80

Asp Ser Val Lys Gly Arg Phe Thr Ile Ser Arg Asp Asn Ser Lys Asn
                85                  90                  95

Thr Val Tyr Leu Gln Met Asn Ser Leu Arg Ala Glu Asp Thr Ala Val
            100                 105                 110

Tyr Tyr Cys Ala Lys Ser Thr Pro Asn Ile Pro Leu Ala Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Arg Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val

```
            290                 295                 300
His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
                340                 345                 350

Glu Lys Thr Ile Ser Lys Ala Lys Gly Gln Pro Arg Glu Pro Gln Val
                355                 360                 365

Tyr Thr Leu Pro Pro Ser Arg Glu Glu Met Thr Lys Asn Gln Val Ser
                370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
                420                 425                 430

Asp Lys Ser Arg Trp Gln Gln Gly Asn Val Phe Ser Cys Ser Val Met
                435                 440                 445

His Glu Ala Leu His Asn His Tyr Thr Gln Lys Ser Leu Ser Leu Ser
                450                 455                 460

Pro Gly Lys
465

<210> SEQ ID NO 112
<211> LENGTH: 1401
<212> TYPE: DNA
<213> ORGANISM: Artificial
<220> FEATURE:
<223> OTHER INFORMATION: nucleotide sequence of humanized hA2-11E-H4

<400> SEQUENCE: 112
atgaaacacc tgtggttctt cctcctgctg gtggcagctc ccagatgggt gctgagcgaa     60
gtgcagctgg tggaatctgg cggcggactg gtgcagcctg gcggatctct gagactgagc    120
tgtgccgcca gcggcttcac cttcagcaac tactacatgt actggatccg gcaggcccct    180
ggcaagggcc tggaatggat cagcagcatc aacaccgacg gcggcagcac ctactacccc    240
gatagcgtga agggccggtt caccatcagc cgggacaaca gcaagaacac cgtgtacctg    300
cagatgaaca gcctgcgggc cgaggacacc gccgtgtact actgtgccaa gagcaccccc    360
aacatccccc tggcctattg gggccaggga accctcgtga ccgtcagctc agcctccacc    420
aagggcccaa gcgtcttccc cctggcaccc tcctccaaga gcacctctgg cggcacagcc    480
gccctgggct gcctggtcaa ggactacttc cccgaacccg tgaccgtgag ctggaactca    540
ggcgccctga ccagcggcgt gcacaccttc ccggctgtcc tgcagtcctc aggactctac    600
tccctcagca gcgtggtgac cgtgccctcc agcagcttgg gcacccagac ctacatctgc    660
aacgtgaatc acaagcccag caacaccaag gtggacaaga gagttgagcc caaatcttgt    720
gacaaaactc acacatgccc accctgccca gcacctgaac tcctgggggg accctcagtc    780
ttcctcttcc cccccaaaacc caaggacacc ctcatgatct cccggacccc tgaggtcaca    840
tgcgtggtgg tggacgtgag ccacgaagac cctgaggtca agttcaactg gtacgtggac    900
ggcgtggagg tgcataatgc caagacaaag ccccgggagg agcagtacaa cagcacgtac    960
cgggtggtca gcgtcctcac cgtcctgcac caggactggc tgaatggcaa ggagtacaag   1020
```

```
tgcaaggtct ccaacaaagc cctcccagcc cccatcgaga aaaccatctc caaagccaaa    1080
ggccagcccc gggaaccaca ggtgtacacc ctgccccat cccgggagga gatgaccaag      1140
aaccaggtca gcctgacctg cctggtcaaa ggcttctatc ccagcgacat cgccgtggag    1200
tgggagagca atggccagcc cgagaacaac tacaagacca cccctcccgt gctggactcc    1260
gacggctcct tcttcctcta cagcaagctc accgtggaca agagcaggtg gcagcagggc    1320
aacgtcttct catgctccgt gatgcatgag gctctgcaca accactacac ccagaagagc    1380
ctctccctgt ctcccggcaa a                                              1401
```

<210> SEQ ID NO 113
<211> LENGTH: 467
<212> TYPE: PRT
<213> ORGANISM: Artificial
<220> FEATURE:
<223> OTHER INFORMATION: amino acid sequence of humanized hA2-11E-H4

<400> SEQUENCE: 113

```
Met Lys His Leu Trp Phe Phe Leu Leu Val Ala Ala Pro Arg Trp
1               5                   10                  15

Val Leu Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Asn Tyr Tyr Met Tyr Trp Ile Arg Gln Ala Pro Gly Lys Gly Leu
    50                  55                  60

Glu Trp Ile Ser Ser Ile Asn Thr Asp Gly Gly Ser Thr Tyr Tyr Pro
65                  70                  75                  80

Asp Ser Val Lys Gly Arg Phe Thr Ile Ser Arg Asp Asn Ser Lys Asn
                85                  90                  95

Thr Val Tyr Leu Gln Met Asn Ser Leu Arg Ala Glu Asp Thr Ala Val
            100                 105                 110

Tyr Tyr Cys Ala Lys Ser Thr Pro Asn Ile Pro Leu Ala Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Arg Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
```

```
                290              295                 300
His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
            355                 360                 365

Tyr Thr Leu Pro Pro Ser Arg Glu Glu Met Thr Lys Asn Gln Val Ser
            370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
                420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
            450                 455                 460

Pro Gly Lys
465

<210> SEQ ID NO 114
<211> LENGTH: 699
<212> TYPE: DNA
<213> ORGANISM: Artificial
<220> FEATURE:
<223> OTHER INFORMATION: nucleotide sequence of humanized hA2-11E-L2

<400> SEQUENCE: 114
atggtgctgc agacccaggt gttcatctcc ctgctgctgt ggatctccgg cgcgtacggc      60
gacatccaga tgacccagag ccctagcagc ctgagcgcca gcgtgggcga cagagtgacc     120
atcacatgca aggccagcca gaacatctac aagtacctga ctggttccag cagaagccc      180 ggcaaggccc ccaagctgct gatctactac agcaacagcc tgcagaccgg cgtgcccagc     240
agattttctg gcagcggctc cggcaccgac ttcaccctga caatcagctc cctgcagccc     300
gaggacttcg ccacctacta ctgcttccag tacagcagcg cccccacctt tggccagggc     360
accaaggtgg aaatcaagcg tacggtggcc gccccctccg tgttcatctt cccccccttc     420
gacgagcagc tgaagtccgg caccgcctcc gtggtgtgcc tgctgaataa cttctacccc     480
agagaggcca aggtgcagtg gaaggtggac aacgccctgc agtccgggaa ctcccaggag     540
agcgtgaccg agcaggacag caaggacagc acctacagcc tgagcagcac cctgaccctg     600
agcaaagccg actacgagaa gcacaaggtg tacgcctgcg aggtgaccca ccagggcctg     660
agctcccccg tcaccaagag cttcaacagg ggggagtgt                           699

<210> SEQ ID NO 115
<211> LENGTH: 233
<212> TYPE: PRT
<213> ORGANISM: Artificial
<220> FEATURE:
<223> OTHER INFORMATION: amino acid sequence of humanized hA2-11E-L2

<400> SEQUENCE: 115
```

```
Met Val Leu Gln Thr Gln Val Phe Ile Ser Leu Leu Leu Trp Ile Ser
1               5                   10                  15
Gly Ala Tyr Gly Asp Ile Gln Met Thr Gln Ser Pro Ser Ser Leu Ser
            20                  25                  30
Ala Ser Val Gly Asp Arg Val Thr Ile Thr Cys Lys Ala Ser Gln Asn
        35                  40                  45
Ile Tyr Lys Tyr Leu Asn Trp Phe Gln Gln Lys Pro Gly Lys Ala Pro
    50                  55                  60
Lys Leu Leu Ile Tyr Tyr Ser Asn Ser Leu Gln Thr Gly Val Pro Ser
65                  70                  75                  80
Arg Phe Ser Gly Ser Gly Ser Gly Thr Asp Phe Thr Leu Thr Ile Ser
                85                  90                  95
Ser Leu Gln Pro Glu Asp Phe Ala Thr Tyr Tyr Cys Phe Gln Tyr Ser
            100                 105                 110
Ser Gly Pro Thr Phe Gly Gln Gly Thr Lys Val Glu Ile Lys Arg Thr
        115                 120                 125
Val Ala Ala Pro Ser Val Phe Ile Phe Pro Pro Ser Asp Glu Gln Leu
    130                 135                 140
Lys Ser Gly Thr Ala Ser Val Val Cys Leu Leu Asn Asn Phe Tyr Pro
145                 150                 155                 160
Arg Glu Ala Lys Val Gln Trp Lys Val Asp Asn Ala Leu Gln Ser Gly
                165                 170                 175
Asn Ser Gln Glu Ser Val Thr Glu Gln Asp Ser Lys Asp Ser Thr Tyr
            180                 185                 190
Ser Leu Ser Ser Thr Leu Thr Leu Ser Lys Ala Asp Tyr Glu Lys His
        195                 200                 205
Lys Val Tyr Ala Cys Glu Val Thr His Gln Gly Leu Ser Ser Pro Val
    210                 215                 220
Thr Lys Ser Phe Asn Arg Gly Glu Cys
225                 230
```

<210> SEQ ID NO 116
<211> LENGTH: 699
<212> TYPE: DNA
<213> ORGANISM: Artificial
<220> FEATURE:
<223> OTHER INFORMATION: nucleotide sequence of humanized hA2-11E-L3

<400> SEQUENCE: 116

```
atggtgctgc agacccaggt gttcatctcc ctgctgctgt ggatctccgg cgcgtacggc        60
gacatccaga tgacccagag ccctagcagc ctgagcgcca gcgtgggcga cagagtgacc       120
atcacatgca aggccagcca gaacatctac aagtacctga actggttcca gcagaagccc       180
ggcaaggccc ccaagctgct gatctactac agcaacagcc tgcagaccgg catccccagc       240
agatttctg gcagcggctc cggcaccgac ttcaccctga caatcagctc cctgcagccc       300
gaggacttcg ccacctacta ctgcttccag tacagcagcg gccccacctt tggccagggc       360
accaaggtgg aaatcaagcg tacggtggcc gcccctccg tgttcatctt ccccccctcc        420
gacgagcagc tgaagtccgg caccgcctcc gtggtgtgcc tgctgaataa cttctacccc       480
agagaggcca aggtgcagtg gaaggtggac aacgccctgc agtccgggaa ctcccaggag       540
agcgtgaccg agcaggacag caaggacagc acctacagcc tgagcagcac cctgaccctg       600
agcaaagccg actacgagaa gcacaaggtg tacgcctgcg aggtgaccca ccagggcctg       660
agctcccccg tcaccaagag cttcaacagg ggggagtgt                             699
```

<210> SEQ ID NO 117
<211> LENGTH: 233
<212> TYPE: PRT
<213> ORGANISM: Artificial
<220> FEATURE:
<223> OTHER INFORMATION: amino acide sequence of humanized hA2-11E-L3

<400> SEQUENCE: 117

```
Met Val Leu Gln Thr Gln Val Phe Ile Ser Leu Leu Trp Ile Ser
1               5                   10                  15

Gly Ala Tyr Gly Asp Ile Gln Met Thr Gln Ser Pro Ser Ser Leu Ser
            20                  25                  30

Ala Ser Val Gly Asp Arg Val Thr Ile Thr Cys Lys Ala Ser Gln Asn
        35                  40                  45

Ile Tyr Lys Tyr Leu Asn Trp Phe Gln Gln Lys Pro Gly Lys Ala Pro
    50                  55                  60

Lys Leu Leu Ile Tyr Tyr Ser Asn Ser Leu Gln Thr Gly Ile Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Phe Gln Tyr Ser
            100                 105                 110

Ser Gly Pro Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230
```

<210> SEQ ID NO 118
<211> LENGTH: 699
<212> TYPE: DNA
<213> ORGANISM: Artificial
<220> FEATURE:
<223> OTHER INFORMATION: nucleotide sequence of humanized hA2-11E-L4

<400> SEQUENCE: 118

```
atggtgctgc agacccaggt gttcatctcc ctgctgctgt ggatctccgg cgcgtacggc      60
gacatccaga tgacccagag ccctagcagc ctgagcgcca gcgtgggcga tagagtgacc     120
atcagctgca aggccagcca gaacatctac aagtacctga actggttcca gcagaagccc     180
ggcgaggccc ccaagctgct gatctactac agcaacagcc tgcagaccgg catccccagc     240 agatttctg gcagcggctc cggcaccgac ttcaccctga caatcagctc cctgcagccc     300
gaggacttcg ctatctactt ctgttttcaa tactccagcg gccccacctt cggcctggc      360 accaaggtgg aaatcaagcg tacggtggcc gccccctccg tgttcatctt ccccccctcc     420
```

```
gacgagcagc tgaagtccgg caccgcctcc gtggtgtgcc tgctgaataa cttctacccc    480
agagaggcca aggtgcagtg gaaggtggac aacgccctgc agtccgggaa ctcccaggag    540
agcgtgaccg agcaggacag caaggacagc acctacagcc tgagcagcac cctgaccctg    600
agcaaagccg actacgagaa gcacaaggtg tacgcctgcg aggtgaccca ccagggcctg    660 agctccccg tcaccaagag cttcaacagg ggggagtgt                           699
```

<210> SEQ ID NO 119
<211> LENGTH: 233
<212> TYPE: PRT
<213> ORGANISM: Artificial
<220> FEATURE:
<223> OTHER INFORMATION: amino acid sequence of humanized hA2-11E-L4

<400> SEQUENCE: 119

```
Met Val Leu Gln Thr Gln Val Phe Ile Ser Leu Leu Trp Ile Ser
1               5                   10                  15

Gly Ala Tyr Gly Asp Ile Gln Met Thr Gln Ser Pro Ser Ser Leu Ser
                20                  25                  30

Ala Ser Val Gly Asp Arg Val Thr Ile Ser Cys Lys Ala Ser Gln Asn
            35                  40                  45

Ile Tyr Lys Tyr Leu Asn Trp Phe Gln Gln Lys Pro Gly Glu Ala Pro
    50                  55                  60

Lys Leu Leu Ile Tyr Tyr Ser Asn Ser Leu Gln Thr Gly Ile Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Ile Tyr Phe Cys Phe Gln Tyr Ser
            100                 105                 110

Ser Gly Pro Thr Phe Gly Pro Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230
```

<210> SEQ ID NO 120
<211> LENGTH: 1401
<212> TYPE: DNA
<213> ORGANISM: Artificial
<220> FEATURE:
<223> OTHER INFORMATION: nucleotide sequence of humanized hA2-25C-H3

<400> SEQUENCE: 120

```
atgaaacacc tgtggttctt cctcctgctg gtggcagctc ccagatgggt gctgagcgaa    60
gtgcagctgg tggaatctgg cggcggactg gtgcagcctg gcggatctct gagactgagc    120
```

```
tgtgccgcca gcggcttcac cttcagctac tacgccatga gctgggtgcg ccaggcccct    180
ggaaaaggcc tggaatgggt ggccagcatc agcagaggcg gcgacaacac ctactaccgg    240
gacagcgtga agggccggtt caccaccagc cgggacaaca gcaagaacac cctgtacctg    300
cagatgaaca gcctgcgggc cgaggacacc gccgtgtact attgcgccag actgaactac    360
aacaactact cgactactg gggccagggc accctcgtga ccgtcagctc agcctccacc    420
aagggcccaa gcgtcttccc cctggcaccc tcctccaaga gcacctctgg cggcacagcc    480
gccctgggct gcctggtcaa ggactacttc cccgaacccg tgaccgtgag ctggaactca    540
ggcgccctga ccagcggcgt gcacaccttc ccgctgtcc tgcagtcctc aggactctac     600
tccctcagca gcgtggtgac cgtgccctcc agcagcttgg gcacccagac ctacatctgc    660
aacgtgaatc acaagcccag caacaccaag gtggacaaga gagttgagcc caaatcttgt    720
gacaaaactc acacatgccc accctgccca gcacctgaac tcctgggggg accctcagtc    780
ttcctcttcc ccccaaaacc caaggacacc ctcatgatct cccggacccc tgaggtcaca    840
tgcgtggtgg tggacgtgag ccacgaagac cctgaggtca agttcaactg gtacgtggac    900
ggcgtggagg tgcataatgc caagacaaag ccccgggagg agcagtacaa cagcacgtac    960
cgggtggtca gcgtcctcac cgtcctgcac caggactggc tgaatggcaa ggagtacaag   1020
tgcaaggtct ccaacaaagc cctcccagcc cccatcgaga aaaccatctc caaagccaaa   1080
ggccagcccc gggaaccaca ggtgtacacc ctgcccccat cccgggagga tgaccaag    1140 aaccaggtca gcctgacctg cctggtcaaa ggcttctatc ccagcgacat cgccgtggag   1200
tgggagagca atggccagcc cgagaacaac tacaagacca cccctcccgt gctggactcc   1260
gacggctcct tcttcctcta cagcaagctc accgtggaca gagcaggtg gcagcagggc    1320 aacgtcttct catgctccgt gatgcatgag gctctgcaca accactacac ccagaagagc   1380
ctctccctgt ctcccggcaa a                                             1401
```

<210> SEQ ID NO 121
<211> LENGTH: 467
<212> TYPE: PRT
<213> ORGANISM: Artificial
<220> FEATURE:
<223> OTHER INFORMATION: amino acid sequence of humanized hA2-25C-H3

<400> SEQUENCE: 121

```
Met Lys His Leu Trp Phe Phe Leu Leu Leu Val Ala Ala Pro Arg Trp
1               5                   10                  15

Val Leu Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Tyr Tyr Ala Met Ser Trp Val Arg Gln Ala Pro Gly Lys Gly Leu
    50                  55                  60

Glu Trp Val Ala Ser Ile Ser Arg Gly Gly Asp Asn Thr Tyr Tyr Arg
65                  70                  75                  80

Asp Ser Val Lys Gly Arg Phe Thr Thr Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Leu Asn Tyr Asn Asn Tyr Phe Asp Tyr Trp Gly
        115                 120                 125

Gln Gly Thr Leu Val Thr Val Ser Ser Ala Ser Thr Lys Gly Pro Ser
```

```
                130              135              140
Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Arg Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
450                 455                 460

Pro Gly Lys
465

<210> SEQ ID NO 122
<211> LENGTH: 1401
<212> TYPE: DNA
<213> ORGANISM: Artificial
<220> FEATURE:
<223> OTHER INFORMATION: nucleotide sequence of humanized hA2-25C-H4

<400> SEQUENCE: 122
atgaaacacc tgtggttctt cctcctgctg gtggcagctc ccagatgggt gctgagcgaa    60
gtgcagctgg tggaatctgg cggcggactg gtgcagcctg gcggatctct gagactgagc   120
```

```
tgtgccgcca gcggcttcac cttcagctac tacgccatga gctgggtgcg ccaggcccct    180
ggaaaaggcc tggaatgggt ggccagcatc agcagaggcg gcgacaacac ctactaccgg    240
gacagcgtga agggccggtt caccaccagc cgggacaaca gcaagaacac cctgtacctg    300
cagatgaaca gcctgcgggc cgaggacacc gccacctact attgcgccag actgaactac    360
aacaactact cgactactg gggccagggc gtgctcgtga ccgtcagctc agcctccacc    420
aagggcccaa gcgtcttccc cctggcaccc tcctccaaga gcacctctgg cggcacagcc    480
gccctgggct gcctggtcaa ggactacttc cccgaacccg tgaccgtgag ctggaactca    540
ggcgccctga ccagcggcgt gcacaccttc ccgctgtcc tgcagtcctc aggactctac    600
tccctcagca gcgtggtgac cgtgccctcc agcagcttgg gcacccagac ctacatctgc    660
aacgtgaatc acaagcccag caacaccaag gtggacaaga gagttgagcc caaatcttgt    720
gacaaaactc acacatgccc accctgccca gcacctgaac tcctgggggg accctcagtc    780
ttcctcttcc ccccaaaacc caaggacacc ctcatgatct cccggacccc tgaggtcaca    840
tgcgtggtgg tggacgtgag ccacgaagac cctgaggtca agttcaactg gtacgtggac    900
ggcgtggagg tgcataatgc caagacaaag ccccgggagg agcagtacaa cagcacgtac    960
cgggtggtca gcgtcctcac cgtcctgcac caggactggc tgaatggcaa ggagtacaag    1020
tgcaaggtct ccaacaaagc cctcccagcc cccatcgaga aaccatctc caaagccaaa    1080 ggccagcccc gggaaccaca ggtgtacacc ctgcccccat cccgggagga tgaccaag    1140 aaccaggtca gcctgacctg cctggtcaaa ggcttctatc ccagcgacat cgccgtggag    1200
tgggagagca atggccagcc cgagaacaac tacaagacca cccctcccgt gctggactcc    1260
gacggctcct tcttcctcta cagcaagctc accgtggaca gagcaggtg gcagcagggc    1320 aacgtcttct catgctccgt gatgcatgag gctctgcaca accactacac ccagaagagc    1380
ctctccctgt ctcccggcaa a                                               1401
```

<210> SEQ ID NO 123
<211> LENGTH: 467
<212> TYPE: PRT
<213> ORGANISM: Artificial
<220> FEATURE:
<223> OTHER INFORMATION: amino acid sequence of humanized hA2-25C-H4

<400> SEQUENCE: 123

```
Met Lys His Leu Trp Phe Phe Leu Leu Leu Val Ala Ala Pro Arg Trp
1               5                   10                  15

Val Leu Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Tyr Tyr Ala Met Ser Trp Val Arg Gln Ala Pro Gly Lys Gly Leu
    50                  55                  60

Glu Trp Val Ala Ser Ile Ser Arg Gly Gly Asp Asn Thr Tyr Tyr Arg
65                  70                  75                  80

Asp Ser Val Lys Gly Arg Phe Thr Thr Ser Arg Asp Asn Ser Lys Asn
                85                  90                  95

Thr Leu Tyr Leu Gln Met Asn Ser Leu Arg Ala Glu Asp Thr Ala Thr
            100                 105                 110

Tyr Tyr Cys Ala Arg Leu Asn Tyr Asn Asn Tyr Phe Asp Tyr Trp Gly
        115                 120                 125

Gln Gly Val Leu Val Thr Val Ser Ser Ala Ser Thr Lys Gly Pro Ser
```

| | | | | | | | | | | | |
|---|---|---|---|---|---|---|---|---|---|---|---|
| | | | 130 | | | 135 | | | 140 | | |
| Val | Phe | Pro | Leu | Ala | Pro | Ser | Ser | Lys | Ser | Thr | Ser | Gly | Gly | Thr | Ala |
| 145 | | | | 150 | | | | 155 | | | | | | 160 | |
| Ala | Leu | Gly | Cys | Leu | Val | Lys | Asp | Tyr | Phe | Pro | Glu | Pro | Val | Thr | Val |
| | | | | 165 | | | | | 170 | | | | | 175 | |
| Ser | Trp | Asn | Ser | Gly | Ala | Leu | Thr | Ser | Gly | Val | His | Thr | Phe | Pro | Ala |
| | | | 180 | | | | | 185 | | | | | 190 | | |
| Val | Leu | Gln | Ser | Ser | Gly | Leu | Tyr | Ser | Leu | Ser | Ser | Val | Val | Thr | Val |
| | | | 195 | | | | | 200 | | | | | 205 | | |
| Pro | Ser | Ser | Ser | Leu | Gly | Thr | Gln | Thr | Tyr | Ile | Cys | Asn | Val | Asn | His |
| | 210 | | | | | 215 | | | | | 220 | | | | |
| Lys | Pro | Ser | Asn | Thr | Lys | Val | Asp | Lys | Arg | Val | Glu | Pro | Lys | Ser | Cys |
| 225 | | | | | 230 | | | | | 235 | | | | | 240 |
| Asp | Lys | Thr | His | Thr | Cys | Pro | Pro | Cys | Pro | Ala | Pro | Glu | Leu | Leu | Gly |
| | | | | 245 | | | | | 250 | | | | | 255 | |
| Gly | Pro | Ser | Val | Phe | Leu | Phe | Pro | Pro | Lys | Pro | Lys | Asp | Thr | Leu | Met |
| | | | 260 | | | | | 265 | | | | | 270 | | |
| Ile | Ser | Arg | Thr | Pro | Glu | Val | Thr | Cys | Val | Val | Val | Asp | Val | Ser | His |
| | | 275 | | | | | 280 | | | | | 285 | | | |
| Glu | Asp | Pro | Glu | Val | Lys | Phe | Asn | Trp | Tyr | Val | Asp | Gly | Val | Glu | Val |
| 290 | | | | | 295 | | | | | 300 | | | | | |
| His | Asn | Ala | Lys | Thr | Lys | Pro | Arg | Glu | Glu | Gln | Tyr | Asn | Ser | Thr | Tyr |
| 305 | | | | | 310 | | | | | 315 | | | | | 320 |
| Arg | Val | Val | Ser | Val | Leu | Thr | Val | Leu | His | Gln | Asp | Trp | Leu | Asn | Gly |
| | | | | 325 | | | | | 330 | | | | | 335 | |
| Lys | Glu | Tyr | Lys | Cys | Lys | Val | Ser | Asn | Lys | Ala | Leu | Pro | Ala | Pro | Ile |
| | | | 340 | | | | | 345 | | | | | 350 | | |
| Glu | Lys | Thr | Ile | Ser | Lys | Ala | Lys | Gly | Gln | Pro | Arg | Glu | Pro | Gln | Val |
| | | | 355 | | | | | 360 | | | | | 365 | | |
| Tyr | Thr | Leu | Pro | Pro | Ser | Arg | Glu | Glu | Met | Thr | Lys | Asn | Gln | Val | Ser |
| | 370 | | | | | 375 | | | | | 380 | | | | |
| Leu | Thr | Cys | Leu | Val | Lys | Gly | Phe | Tyr | Pro | Ser | Asp | Ile | Ala | Val | Glu |
| 385 | | | | | 390 | | | | | 395 | | | | | 400 |
| Trp | Glu | Ser | Asn | Gly | Gln | Pro | Glu | Asn | Asn | Tyr | Lys | Thr | Thr | Pro | Pro |
| | | | | 405 | | | | | 410 | | | | | 415 | |
| Val | Leu | Asp | Ser | Asp | Gly | Ser | Phe | Phe | Leu | Tyr | Ser | Lys | Leu | Thr | Val |
| | | | 420 | | | | | 425 | | | | | 430 | | |
| Asp | Lys | Ser | Arg | Trp | Gln | Gln | Gly | Asn | Val | Phe | Ser | Cys | Ser | Val | Met |
| | | 435 | | | | | 440 | | | | | 445 | | | |
| His | Glu | Ala | Leu | His | Asn | His | Tyr | Thr | Gln | Lys | Ser | Leu | Ser | Leu | Ser |
| 450 | | | | | 455 | | | | | 460 | | | | | |
| Pro | Gly | Lys | | | | | | | | | | | | | |
| 465 | | | | | | | | | | | | | | | |

<210> SEQ ID NO 124
<211> LENGTH: 702
<212> TYPE: DNA
<213> ORGANISM: Artificial
<220> FEATURE:
<223> OTHER INFORMATION: nucleotide sequence of humanized hA2-25C-L1

<400> SEQUENCE: 124

```
atggtgctgc agacccaggt gttcatctcc ctgctgctgt ggatctccgg cgcgtacggc    60
gacatccaga tgacccagag ccctagcagc ctgagcgcca gcgtgggcga cagagtgacc   120
```

```
attacctgtc aggccagcca ggacatcggc aactggctga gctggtatca gcagaagccc    180
ggcaaggccc ccaagctgct gatctacggc gccacatctc tggccgatgg cgtgcccagc    240 agatttctg gcagcggctc cggcaccgac ttcaccctga caatcagcag cctgcagccc    300
gaggacttcg ccacctacta ctgtctgcaa gcctacagcg ccccttcac ctttggccag    360 ggcaccaagg tggaaatcaa gcgtacggtg gccgccccct ccgtgttcat cttcccccc    420 tccgacgagc agctgaagtc cggcaccgcc tccgtggtgt gcctgctgaa taacttctac    480
cccagagagg ccaaggtgca gtggaaggtg acaacgccc tgcagtccgg gaactcccag    540
gagagcgtga ccgagcagga cagcaaggac agcacctaca gcctgagcag caccctgacc    600
ctgagcaaag ccgactacga aagcacaag gtgtacgcct gcgaggtgac ccaccagggc    660
ctgagctccc ccgtcaccaa gagcttcaac agggggagt gt                       702
```

<210> SEQ ID NO 125
<211> LENGTH: 234
<212> TYPE: PRT
<213> ORGANISM: Artificial
<220> FEATURE:
<223> OTHER INFORMATION: amino acid sequence of humanized hA2-25C-L1

<400> SEQUENCE: 125

```
Met Val Leu Gln Thr Gln Val Phe Ile Ser Leu Leu Leu Trp Ile Ser
1               5                   10                  15

Gly Ala Tyr Gly Asp Ile Gln Met Thr Gln Ser Pro Ser Ser Leu Ser
            20                  25                  30

Ala Ser Val Gly Asp Arg Val Thr Ile Thr Cys Gln Ala Ser Gln Asp
        35                  40                  45

Ile Gly Asn Trp Leu Ser Trp Tyr Gln Gln Lys Pro Gly Lys Ala Pro
    50                  55                  60

Lys Leu Leu Ile Tyr Gly Ala Thr Ser Leu Ala Asp Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Leu Gln Ala Tyr
            100                 105                 110

Ser Ala Pro Phe Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 126
<211> LENGTH: 702
<212> TYPE: DNA

<213> ORGANISM: Artificial
<220> FEATURE:
<223> OTHER INFORMATION: nucleotide sequence of humanized hA2-25C-L2

<400> SEQUENCE: 126

```
atggtgctgc agacccaggt gttcatctcc ctgctgctgt ggatctccgg cgcgtacggc    60
gacatccaga tgacccagag ccctagcagc ctgagcgcca gcgtgggcga cagagtgacc   120
attacctgtc aggccagcca ggacatcggc aactggctga gctggtatca gcagaagccc   180
ggcaaggccc ccaagctgct gatctacggc gccacatctc tggccgatgg cgtgcccagc   240
agattcagcg gcagcagatc cggcaccgac tacaccctga ccatcagcag cctgcagccc   300
gaggacttcg ccacctacta ctgtctgcaa gcctacagcg cccccttcac ctttggccag   360
ggcaccaagg tggaaatcaa agcgtacggtg ccgcccccct ccgtgttcat cttccccccc   420
tccgacgagc agctgaagtc cggcaccgcc tccgtggtgt gcctgctgaa taacttctac   480
cccagagagg ccaaggtgca gtggaaggtg gacaacgccc tgcagtccgg gaactcccag   540
gagagcgtga ccgagcagga cagcaaggac agcacctaca gcctgagcag cacccctgacc   600
ctgagcaaag ccgactacga gaagcacaag gtgtacgcct gcgaggtgac ccaccagggc   660
ctgagctccc ccgtcaccaa gagcttcaac aggggggagt gt                       702
```

<210> SEQ ID NO 127
<211> LENGTH: 234
<212> TYPE: PRT
<213> ORGANISM: Artificial
<220> FEATURE:
<223> OTHER INFORMATION: amino acid sequence of humanized hA2-25C-L2

<400> SEQUENCE: 127

```
Met Val Leu Gln Thr Gln Val Phe Ile Ser Leu Leu Leu Trp Ile Ser
1               5                   10                  15

Gly Ala Tyr Gly Asp Ile Gln Met Thr Gln Ser Pro Ser Ser Leu Ser
            20                  25                  30

Ala Ser Val Gly Asp Arg Val Thr Ile Thr Cys Gln Ala Ser Gln Asp
        35                  40                  45

Ile Gly Asn Trp Leu Ser Trp Tyr Gln Gln Lys Pro Gly Lys Ala Pro
    50                  55                  60

Lys Leu Leu Ile Tyr Gly Ala Thr Ser Leu Ala Asp Gly Val Pro Ser
65                  70                  75                  80

Arg Phe Ser Gly Ser Arg Ser Gly Thr Asp Tyr Thr Leu Thr Ile Ser
                85                  90                  95

Ser Leu Gln Pro Glu Asp Phe Ala Thr Tyr Tyr Cys Leu Gln Ala Tyr
            100                 105                 110

Ser Ala Pro Phe Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205
```

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 128
<211> LENGTH: 702
<212> TYPE: DNA
<213> ORGANISM: Artificial
<220> FEATURE:
<223> OTHER INFORMATION: nucleotide sequence of humanized hA2-25C-L3

<400> SEQUENCE: 128
atggtgctgc agacccaggt gttcatctcc ctgctgctgt ggatctccgg cgcgtacggc      60
gacatccaga tgacccagag ccctagcagc ctgagcgcca gcgtgggcga cagagtgacc     120
attacctgtc aggccagcca ggacatcggc aactggctga gctggtatca gcagaagccc     180
ggcaagagcc ccaagctgct gatctacggc gccacctctc tggccgatgg cgtgccaagc     240
agattcagcg gcagcagatc cggcacccag tacaccctga ccatcagcag cctgcagccc     300
gaggacttcg ccacctacta ctgtctgcaa gcctacagcg ccccccttcac ctttggcagc     360 ggcaccaagg tggaaatcaa gcgtacggtg gccgcccccct ccgtgttcat cttccccccc     420
tccgacgagc agctgaagtc cggcaccgcc tccgtggtgt gcctgctgaa taacttctac     480
cccagagagg ccaaggtgca gtggaaggtg gacaacgccc tgcagtccgg aactcccag      540 gagagcgtga ccgagcagga cagcaaggac agcacctaca gcctgagcag caccctgacc     600
ctgagcaaag ccgactacga aagcacaaag gtgtacgcct gcgaggtgac ccaccagggc     660
ctgagctccc ccgtcaccaa gagcttcaac aggggggagt gt                        702

<210> SEQ ID NO 129
<211> LENGTH: 234
<212> TYPE: PRT
<213> ORGANISM: Artificial
<220> FEATURE:
<223> OTHER INFORMATION: amino acid sequence of humanized hA2-25C-L3

<400> SEQUENCE: 129

Met Val Leu Gln Thr Gln Val Phe Ile Ser Leu Leu Leu Trp Ile Ser
1               5                   10                  15

Gly Ala Tyr Gly Asp Ile Gln Met Thr Gln Ser Pro Ser Ser Leu Ser
            20                  25                  30

Ala Ser Val Gly Asp Arg Val Thr Ile Thr Cys Gln Ala Ser Gln Asp
        35                  40                  45

Ile Gly Asn Trp Leu Ser Trp Tyr Gln Gln Lys Pro Gly Lys Ser Pro
    50                  55                  60

Lys Leu Leu Ile Tyr Gly Ala Thr Ser Leu Ala Asp Gly Val Pro Ser
65                  70                  75                  80

Arg Phe Ser Gly Ser Arg Ser Gly Thr Gln Tyr Thr Leu Thr Ile Ser
                85                  90                  95

Ser Leu Gln Pro Glu Asp Phe Ala Thr Tyr Tyr Cys Leu Gln Ala Tyr
            100                 105                 110

Ser Ala Pro Phe Thr Phe Gly Ser Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

```
Pro Arg Glu Ala Lys Val Gln Trp Lys Val Asp Asn Ala Leu Gln Ser
            165                 170                 175

Gly Asn Ser Gln Glu Ser Val Thr Glu Gln Asp Ser Lys Asp Ser Thr
        180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 130
<211> LENGTH: 40
<212> TYPE: DNA
<213> ORGANISM: Artificial
<220> FEATURE:
<223> OTHER INFORMATION: primer

<400> SEQUENCE: 130
cagatgggtg ctgagcgaag tgcagctggt ggaatctggc                 40

<210> SEQ ID NO 131
<211> LENGTH: 36
<212> TYPE: DNA
<213> ORGANISM: Artificial
<220> FEATURE:
<223> OTHER INFORMATION: primer

<400> SEQUENCE: 131
cttggtgctg gctgagctga cggtcacgag ggtgcc                     36

<210> SEQ ID NO 132
<211> LENGTH: 30
<212> TYPE: DNA
<213> ORGANISM: Artificial
<220> FEATURE:
<223> OTHER INFORMATION: primer

<400> SEQUENCE: 132
gcggggggac cctcagtctt cctcttcccc                            30

<210> SEQ ID NO 133
<211> LENGTH: 31
<212> TYPE: DNA
<213> ORGANISM: Artificial
<220> FEATURE:
<223> OTHER INFORMATION: primer

<400> SEQUENCE: 133
ggcttcaggt gctgggcagg gtgggcatgt g                          31

<210> SEQ ID NO 134
<211> LENGTH: 24
<212> TYPE: DNA
<213> ORGANISM: Artificial
<220> FEATURE:
<223> OTHER INFORMATION: primer

<400> SEQUENCE: 134
ctgtggatct ccggcgcgta cggc                                  24

<210> SEQ ID NO 135
<211> LENGTH: 21
```

-continued

```
<212> TYPE: DNA
<213> ORGANISM: Artificial
<220> FEATURE:
<223> OTHER INFORMATION: primer

<400> SEQUENCE: 135 ggaggggggcg gccaccgtac g                                              21
```